United States Patent
Taveras et al.

(10) Patent No.: US 6,372,747 B1
(45) Date of Patent: Apr. 16, 2002

(54) FARNESYL PROTEIN TRANSFERASE INHIBITORS

(75) Inventors: Arthur G. Taveras, Denville; Ronald J. Doll, Maplewood; Alan B. Cooper, West Caldwell, all of NJ (US); Johan A. Ferreira, Bensalem, PA (US); Timothy Guzi, Chatham, NJ (US); Dinanath F. Rane, Morganville, NJ (US); Viyyoor M. Girijavallabhan, Parsippany, NJ (US); Cynthia J. Aki, Rutherford, NJ (US); Jianping Chao, Summit, NJ (US); Carmen Alvarez, Roselle Park, NJ (US); Joseph M. Kelly, Parlin, NJ (US); Tarik Lalwani, Philadelphia, PA (US); Jagdish A. Desai, Spotswood; James J-S Wang, Westfield, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/465,553

(22) Filed: Dec. 16, 1999

Related U.S. Application Data

(60) Provisional application No. 60/113,141, filed on Dec. 18, 1998.

(51) Int. Cl.$^7$ .................. A61K 31/496; C07D 403/14; C07D 403/12; A61P 35/00
(52) U.S. Cl. ................... 514/253.03; 514/254.05; 514/255.01; 514/252; 514/290; 514/326; 544/361; 544/370; 546/93; 546/210
(58) Field of Search ................... 514/254, 255, 514/290, 252, 326, 253.03, 255.01, 254.05; 544/361, 370; 546/93, 210

(56) References Cited

U.S. PATENT DOCUMENTS

| 5,416,087 A | 5/1995 | Wong et al. | 514/252 |
| 5,719,148 A | * 2/1998 | Bishop | 514/228.2 |
| 5,801,175 A | * 9/1998 | Afonso | 514/254 |

FOREIGN PATENT DOCUMENTS

| EP | 0157399 | 9/1985 | ......... C07D/211/14 |
| WO | WO 95/10515 | 4/1995 | ......... C07D/401/04 |
| WO | WO 95/10516 | 4/1995 | ......... C07D/401/04 |
| WO | WO 96/31477 | 10/1996 | ......... C07D/221/16 |
| WO | WO 96/31478 | 10/1996 | ......... C07D/221/16 |
| WO | WO 96/31505 | 10/1996 | ......... C07D/401/14 |
| WO | WO 98/57960 | 12/1998 | ......... C07D/401/14 |

OTHER PUBLICATIONS

Khosravi–Far R. et al. Cell Growth & Differentiation. 3, 461–469, Jul. 1992.*
J.E. Buss et al., "Farnesyl Transferase Inhibitors: The Successes and Surprises of a New Class of Potential Cancer Chemotherapies," *Chemistry & Biology*, vol. 118, No. 2, pp. 787–791 (1995).

W.R. Bishop et al., "Novel Tricyclic Inhibitors of Farnesyl Protein Transferase Biochemical Characterization and Inhibition of Ras Modification in Transfected Cos Cells," *The Journal of Biological Chemistry*, vol. 270, No. 51, pp. 30611–30618 (1995).

F.G. Njoroge et al., "Novel Tricyclic Aminoacetyl and Sulfonamide Inhibitors of Ras Farnesyl Protein Transferase," *Bioorganic & Medicinal Chemistry Letters*, vol. 6, No. 24, pp. 2977–2982 (1996).

F.G. Njoroge et al., "Discovery of Novel Nonpeptide Tricyclic Inhibitors of Ras Farnesyl Protein Transferase," *Bioorganic & Medicinal Chemistry*, vol. 5, No. 1, pp. 101–113 (1997).

* cited by examiner

*Primary Examiner*—Evelyn Mei Huang
(74) *Attorney, Agent, or Firm*—Henry C. Jeanette

(57) ABSTRACT

Disclosed are compounds of the formula:

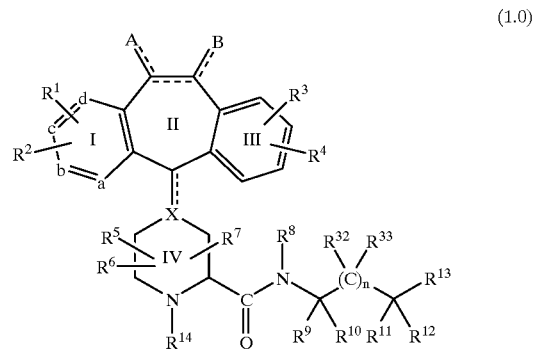

(1.0)

wherein $R^{13}$ represents an imidazole ring; $R^{14}$ represents a carbamate, urea, amide or sulfonamide group; $R^8$ represents H when the alkyl chain between the amide group and the $R^{13}$ imidazole group is substituted, or $R^8$ represents a substituent such as arylalkyl, heteroarylalkyl or cycloalkyl; and the remaining substituents are as defined herein. Also disclosed are compounds wherein $R^8$ is H, and the alkyl chain between the amide group and the $R^{13}$ imidazole group is unsubstituted. Also disclosed is a method of treating cancer and a method of inhibiting farnesyl protein transferase using the disclosed compounds.

20 Claims, No Drawings

FARNESYL PROTEIN TRANSFERASE INHIBITORS

REFERENCE TO RELATED APPLICATIONS

This application claims the benefit of U.S. Provisional Application Ser. No. 60/113,141 filed Dec. 18, 1998.

BACKGROUND

WO 95/10516, published Apr. 20, 1995, WO96/31478, published Oct. 10, 1996, and copending application Ser. No. 09/094,687 filed Jun. 15, 1998 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

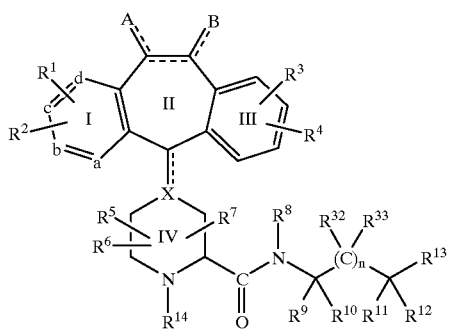

(1.0)

or a pharmaceutically acceptable salt or solvate thererof, wherein:

one of a, b, c and d represents N or $N^+O^-$, and the remaining a, b, c and d groups represent $CR^1$ or $CR^2$; or each of a, b, c, and d are independently selected from $CR^1$ or $CR^2$;

X represents N or CH when the optional bond (represented by the dotted line) is absent, and represents C when the optional bond is present;

the dotted line between carbon atoms 5 and 6 represents an optional bond, such that when a double bond is present, A and B independently represent $-R^{15}$, halo, $-OR^{16}$, $-OCO_2R^{16}$ or $-OC(O)R^{15}$, and when no double bond is present between carbon atoms 5 and 6, A and B each independently represent $H_2$, $-(OR^{16})_2$, H and halo, dihalo, alkyl and H, (alkyl)$_2$, $-H$ and $-OC(O)R^{15}$, H and $-OR^{15}$, =O, aryl and H, =$NOR^{15}$ or $-O-(CH_2)_p-O-$ wherein p is 2, 3 or 4;

each $R^1$ and each $R^2$ is independently selected from H, halo, $-CF_3$, $-OR^{15}$ (e.g., $-OCH_3$), $-COR^{15}$, $-SR^{15}$ (e.g., $-SCH_3$ and $-SCH_2C_6H_5$), $-S(O)_tR^{16}$ (wherein t is 0, 1 or 2, e.g., $-SOCH_3$ and $-SO_2CH_3$), $-N(R^{15})_2$, $-NO_2$, $-OC(O)R^{15}$, $-CO_2R^{15}$, $-OCO_2R^{16}$, $-CN$, $-NR^{15}COOR^{16}$, $-SR^{16}C(O)$ $OR^{16}$ (e.g., $-SCH_2CO_2CH_3$), $-SR^{16}N(R^{17})_2$ (provided that $R^{16}$ in $-SR^{16}N(R^{17})_2$ is not $-CH_2-$) wherein each $R^{17}$ is independently selected from H or $-C(O)OR^{16}$ (e.g., $-S(CH_2)_2NHC(O)O$-t-butyl and $-S(CH_2)_2NH_2$), benzotriazol-1-yloxy, tetrazol-5-ylthio, or substituted tetrazol-5-ylthio (e.g., alkyl substituted tetrazol-5-ylthio such as 1-methyl-tetrazol-5-ylthio), alkynyl, alkenyl or alkyl, said alkyl or alkenyl group optionally being substituted with halo, $-OR^{15}$ or $-CO_2R^{15}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, and $R^7$ each independently represents H, $-CF_3$, $-COR^{15}$, alkyl or aryl, said alkyl or aryl optionally being substituted with $-OR^{15}$, $-SR^{15}$, $-S(O)_tR^{16}$, $-NR^{15}COOR^{16}$, $-N(R^{15})_2$, $-NO_2$, $-COR^{15}$, $-OCOR^{15}$, $-OCO_2R^{16}$, $-CO_2R^{15}$, $OPO_3R^{15}$, or $R^5$ is combined with $R^6$ to represent =O or =S;

$R^8$ is selected from: H, $C_3$ to $C_4$ alkyl (preferably branched chain alkyl, and most preferably $C_4$ to $C_7$ branched chain alkyl), aryl, arylalkyl, heteroaryl, heteroarylalkyl, cycloalkyl, cycloalkylalkyl, substituted alkyl, substituted aryl, substituted arylalkyl, substituted heteroaryl, substituted heteroarylalkyl, substituted cycloalkyl, substituted cycloalkylalkyl;

the substutuents for the $R^8$ substituted groups being selected from: alkyl, aryl, arylalkyl, cycloalkyl, $-N(R^{18})_2$, $-OR^{18}$, cycloalkyalkyl, halo, CN, $-C(O)$ $N(R^{18})_2$, $-SO_2N(R^{18})_2$ or $-CO_2R^{18}$; provided that the $-OR^{18}$ and $-N(R^{18})_2$ substituents are not bound to the carbon that is bound to the N of the $-C(O)$ $NR^8-$ moiety;

each $R^{18}$ is independently selected from: H, alkyl, aryl, arylalkyl, heteroaryl or cycloalkyl;

$R^9$ and $R^{10}$ are independently selected from: H, alkyl, aryl, arylalkyl, heteroaryl, heteroarylalkyl, cycloalkyl or $-CON(R^{18})_2$ (wherein $R^{18}$ is as defined above); and the substitutable $R^9$ and $R^{10}$ groups are optionally substituted with one or more (e.g., 1–3) substituents selected from: alkyl (e.g., methyl, ethyl, isopropyl, and the like), cycloalkyl, arylalkyl, or heterarylalkyl (i.e., the $R^9$ and/or $R^{10}$ groups can be unsubtituted or can be substituted with 1–3 of the substitutents described above, except when $R^9$ and/or $R^{10}$ is H); or $R^9$ and $R^{10}$ together with the carbon atom to which they are bound, form a $C_3$ to $C_6$ cycloalkyl ring;

$R^{11}$ and $R^{12}$ are independently selected from: H, alkyl, aryl, arylalkyl, heteroaryl, heteroarylalkyl, cycloalkyl, $-CON(R^{18})_2-OR^{18}$ or $-N(R^{18})_2$; wherein $R^{18}$ is as defined above; provided that the $-OR^{18}$ and $-N(R^{18})_2$ groups are not bound to a carbon atom that is adjacent to a nitrogen atom; and wherein said substitutable $R^{11}$ and $R^{12}$ groups are optionally substituted with one or more (e.g., 1–3) substituents selected from: alkyl (e.g., methyl, ethyl, isopropyl, and the like), cycloalkyl, arylalkyl, or heterarylalkyl; or $R^{11}$ and $R^{12}$ together with the carbon atom to which they are bound, form a $C_3$ to $C_6$ cycloalkyl ring;

$R^{13}$ is an imidazolyl ring selected from:

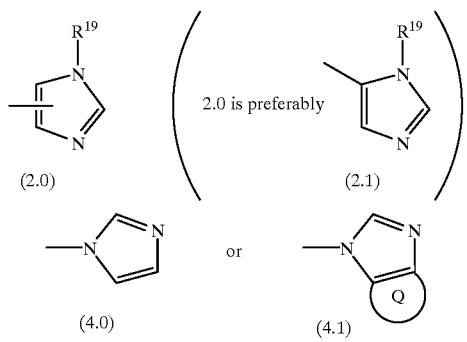

wherein $R^{19}$ is selected from: (1) H, (2) alkyl, (3) alkyl, (4) aryl, (5) arylalkyl, (6) substituted arylalkyl wherein the substituents are selected from halo (e.g., F and Cl) or CN, (7) —C(aryl)$_3$ (e.g., —C(phenyl)$_3$, i.e., trityl) or (8) cycloalkyl;

said imidazolyl ring 2.0 or 2.1 optionally being substituted with one or two substituents and said imidazole ring 4.0 optionally being substituted with 1–3 substituents and said imidazole ring 4.1 being optionally substituted with one substituent wherein said optional substituents for rings 2.0, 2.1, 4.0 and 4.1 are bound to the carbon atoms of said imidazole rings and said optional substituents are independently selected from: —NHC(O)R$^{18}$, —C(R$^{34}$)$_2$OR$^{35}$, —OR$^{18}$, —SR$^{18}$, F, Cl, Br, alkyl, aryl, arylalkyl, cycloalkyl, or —N(R$^{18}$)$_2$ (wherein each R$^{18}$ is independently selected); R$^{18}$ is as defined above; each R$^{34}$ is independently selected from H or alkyl (preferably —CH$_3$), preferably H; R$^{35}$ is selected from H, —C(O)OR$^{20}$, or —C(O)NHR$^{20}$, and R$^{20}$ is as defined below (preferably R$^{20}$ is alkyl or cycloalkyl, most preferably cyclopentyl or cyclohexyl); Q represents an aryl ring (e.g., phenyl), a cycloalkyl ring (e.g., cyclopentyl or cyclohexyl) or a heteroaryl ring (e.g., furanyl, pyrrolyl, thienyl, oxazolyl or thiazolyl), said Q is optionally substituted with 1 to 4 substituents inedependently selected from halo (e.g., F or Cl), alkyl, aryl, —OR$^{18}$, —N(R$^{18}$)$_2$ (wherein each R$^{18}$ is independently selected), —OC(O)R$^{18}$, or —C(O)N(R$^{18}$)$_2$ (wherein each R$^{18}$ is independently selected), and wherein R$^{18}$ is as defined above; (examples of the —C(R$^{34}$)$_2$OR$^{35}$ group include —CH$_2$OH, —CH$_2$OC(O)OR$^{20}$ and —CH$_2$OC(O)NHR$^{20}$);

$R^{14}$ is selected from:

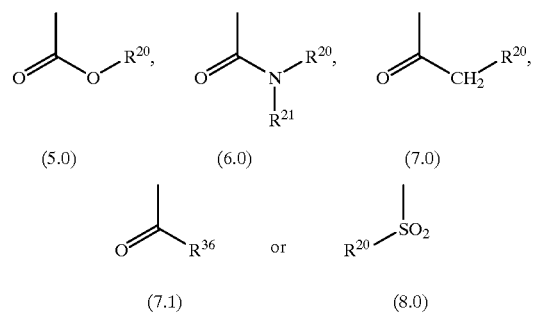

$R^{15}$ is selected from: H, alkyl, aryl or arylalkyl;

$R^{16}$ is selected from: alkyl or aryl;

$R^{20}$ is selected from: H, alkyl, alkoxy, aryl, arylalkyl, cycloalkyl, heteroaryl, heteroarylalkyl or heterocycloalkyl, provided that R$^{20}$ is not H when R$^{14}$ is group 5.0 or 8.0;

when R$^{20}$ is other than H, then said R$^{20}$ group is optionally substituted with one or more (e.g., 1–3) substituents selected from: halo, alkyl, aryl, —OC(O)R$^{18}$ (e.g., —OC(O)CH$_3$), —OR$^{18}$ or —N(R$^{18}$)$_2$, wherein each R$^{18}$ group is the same or different, and wherein R$^{18}$ is as defined above, provided that said optional substituent is not bound to a carbon atom that is adjacent to an oxygen or nitrogen atom;

$R^{21}$ is selected from: H, alkyl, aryl, arylalkyl, cycloalkyl, heteroaryl, heteroarylalkyl or heterocycloalkyl;

when R$^{21}$ is other than H, then said R$^{21}$ group is optionally substituted with one or more (e.g., 1–3) substituents selected from: halo, alkyl, aryl, —OR$^{18}$ or —N(R$^{18}$)$_2$, wherein each R$^{18}$ group is the same or different, and wherein R$^{18}$ is as defined above, provided that said optional substituent is not bound to a carbon atom that is adjacent to an oxygen or nitrogen atom;

n is 0–5;

each R$^{32}$ and R$^{33}$ for each n (i.e., for each —C(R$^{32}$)(R$^{33}$)— group), are independently selected from: H, alkyl, aryl, arylalkyl, heteroaryl, heteroarylalkyl, cycloalkyl, —CON(R$^{18}$)$_2$, —OR$^{18}$ or —N(R$^{18}$)$_2$; wherein R$^{18}$ is as defined above; and wherein said substitutable R$^{32}$ and R$^{33}$ groups are optionally substituted with one or more (e.g., 1–3) substituents selected from: alkyl (e.g., methyl, ethyl, isopropyl, and the like), cycloalkyl, arylalkyl, or heterarylalkyl; or R$^{32}$ and R$^{33}$ together with the carbon atom to which they are bound, form a C$_3$ to C$_6$ cycloalkyl ring; and R$^{36}$ is selected from branched alkyl, unbranched alkyl cycloalkyl, heterocycloalkyl, or aryl (e.g., phenyl); and provided that:

(1) when R$^{14}$ is selected from: group 6.0, 7.0, 7.1 or 8.0, and X is N, then R$^8$ is selected from: C$_3$ to C$_{10}$ alkyl, substituted C$_3$ to C$_{10}$ alkyl, arylalkyl, substituted arylalkyl, heteroarylalkyl, substituted heteroarylalkyl, cycloalkylalkyl, or substituted cycloalkylalkyl; and (2) when R$^{14}$ is selected from: group 6.0, 7.0, 7.1 or 8.0, and X is N, and R$^8$ is H, then the alkyl chain between R$^{13}$ (i.e., imidazole ring 2.0, 4.0 or 4.1) and the amide moiety (i.e., the —C(O)NR$^{18}$ group) is substituted, i.e.,: (a) at least one of R$^9$, R$^{10}$, R$^{11}$, R$^{12}$, R$^{32}$, or R$^{33}$ is other than H, and/or (b) R$^9$ and R$^{10}$, and/or R$^{11}$ and R$^{12}$, are taken together to form a cycloalkyl ring.

This invention also provides compounds of formula 1.0, as described above, wherein when R$^{14}$ is group 5.0, and X is N, and R$^8$ is H, then the alkyl chain between R$^{13}$ (i.e., imidazole ring 2.0, 4.0 or 4.1) and the amide moiety (i.e., the —C(O)NR$^{18}$ group) is substituted, i.e.,: (a) at least one of R$^9$, R$^{10}$, R$^{11}$, R$^{12}$, R$^{32}$, or R$^{33}$ is other than H, and/or (b) R$^9$ and R$^{10}$, and/or R$^{11}$ and R$^{12}$, are taken together to form a cyloalkyl ring.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricyclic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, melanoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

$MH^+$—represents the molecular ion plus hydrogen of the molecule in the mass spectrum;

BOC—represents tert-butyloxycarbonyl;

CBZ—represents —$C(O)OCH_2C_6H_5$ (i.e., benzyloxycarbonyl);

$CH_2Cl_2$—represents dichloromethane;

CIMS—represents chemical ionization mass spectrum;

DEAD—represents diethylazodicarboxylate;

DEC—represents EDCI which represents 1-(3-dimethylaminopropyl)-3-ethylcarbodiimide hydrochloride;

DMF—represents N,N-dimethylformamide;

Et—represents ethyl;

EtOAc—represents ethyl acetate;

EtOH—represents ethanol;

HOBT—represents 1-hydroxybenzotriazole hydrate;

IPA—represents isopropanol;

iPrOH—represents isopropanol;

Me—represents methyl;

MeOH—represents methanol;

MS—represents mass spectroscopy;

NMM—represents N-methylmorpholine;

Ph—represents phenyl;

Pr—represents propyl;

TBDMS—represents tert-butyldimethylsilyl;

TEA—represents triethylamine;

TFA—represents trifluoroacetic acid;

THF—represents tetrahydrofuran;

Tr—represents trityl;

alkyl—represents straight and branched carbon chains and contains from one to twenty carbon atoms, preferably one to six carbon atoms;

acyl—represents a G—C(O)— group wherein G represents alkyl, aryl, heteroaryl, cycloalkyl, heterocycloalkyl, —O—alkyl, —O—aryl, or $NR^{25}R^{26}$ wherein $R^{25}$ and $R^{26}$ are independently selected from alkyl or aryl;

arylalkyl—represents an alkyl group, as defined above, substituted with an aryl group, as defined below, such that the bond from another substituent is to the alkyl moiety;

aryl—(including the aryl portion of arylalkyl)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, —$C(O)N(R^{18})_2$, —$SO_2R^{18}$, —$SO_2N(R^{18})_2$, amino, alkylamino, dialkylamino, —$COOR^{23}$ or —$NO_2$, wherein $R^{23}$ represents alkyl or aryl; and cycloalkyl—represents saturated carbocyclic rings of from 3 to 20 carbon atoms, preferably 3 to 7 carbon atoms, said cycloalkyl ring being optionally substituted with one or more (e.g., 1, 2 or 3) alkyl groups (e.g., methyl or ethyl) and when there is more than one alkyl group each alkyl group is independently selected;

cycloalkylalkyl—represents a cycloalkyl group, as defined above, substituted with an alkyl group, as defined above, such that the bond from another substituent is to the alkyl moiety;

halo—represents fluoro, chloro, bromo and iodo;

heteroaralkyl—represents an alkyl group, as defined above, substituted with a heteroaryl group, as defined below, such that the bond from another substituent is to the alkyl moiety;

heteroaryl—represents cyclic groups, optionally substituted with $R^3$ and $R^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadizolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, triazolyl,2-, 3- or 4-pyridyl or pyridyl N-oxide (optionally substituted with $R^3$ and $R^4$), wherein pyridyl N-oxide can be represented as:

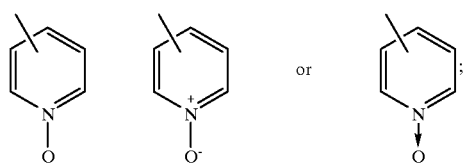

and heterocycloalkyl—represents a saturated, branched or unbranched carbocyclic ring containing from 3 to 15 carbon atoms, preferably from 4 to 6 carbon atoms, which carbocyclic ring is interrupted by 1 to 3 hetero groups selected from —O—, —S— or —$NR^{24}$, wherein $R^{24}$ represents alkyl, aryl, —$C(O)N(R^{18})_2$ wherein $R^{18}$ is as above defined (e.g., —$C(O)NH_2$) or acyl-(suitable heterocycloalkyl groups include 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, morpholinyl, etc.).

The positions in the tricyclic ring system are:

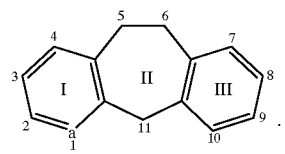

The compounds of formula 1.0 include the 2R and 2S isomers shown below (2R is preferred):

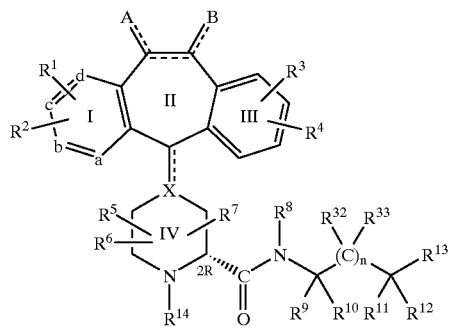

(1.0A)

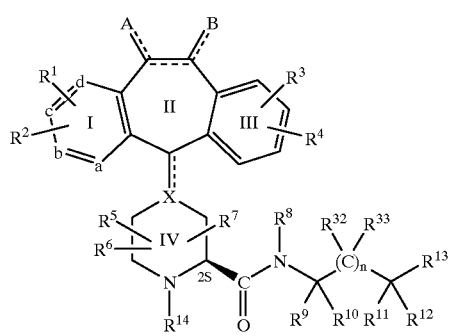

(1.0B)

Examples of $R^8$ substituents include: benzyl, —$CH_2C(CH_3)_2$, —$CH_2$-cyclohexyl, —$CH_2$-cyclopropyl —$(CH_2)_2CH_3$,

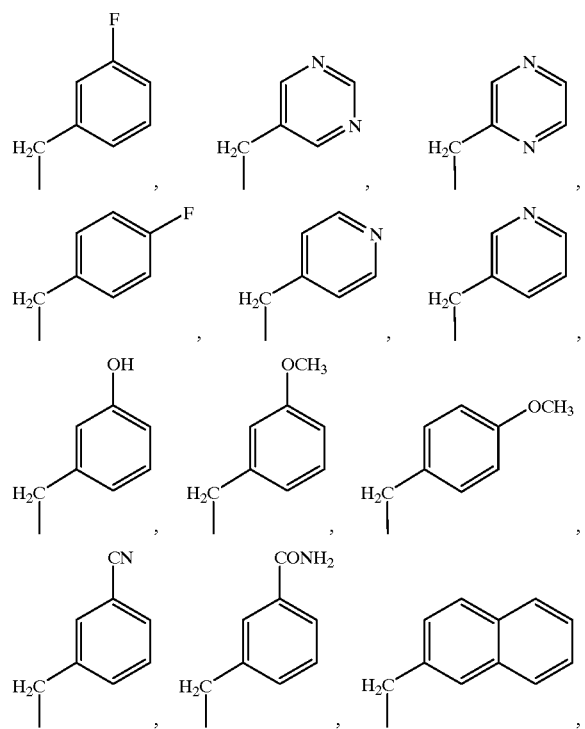

-continued

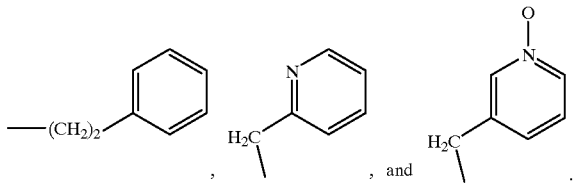

, and

Examples of $R^9$ and $R^{10}$ groups include H and benzyl

Examples of $R^{11}$ and $R^{12}$ groups include: H, —CH$_3$, —CH$_2$CH(CH$_3$)$_2$, —(CH$_2$)$_3$CH$_3$, benzyl, ethyl, p-chlorophenyl, and —OH.

Cyclopropyl is an Example of the $R^{11}$ and $R^{12}$ group being taken together with the carbon atom to which they are bound to form a cycloalkyl ring.

Examples of the optional substituents for the $R^{13}$ moiety include: —CH$_3$, —CH$_2$OH, —CH$_2$OC(O)O-cyclohexyl, —CH$_2$OC(O)O-cyclopentyl, ethyl, isopropyl, NH$_2$, and —NHC(O)CF$_3$.

Examples of $R^{19}$ include: —C(O)NH-cyclohexyl, —C(phenyl)$_3$, H, methyl or ethyl.

Examples of $R^{20}$ for group 5.0 include: t-butyl, ethyl, benzyl, —CH(CH$_3$)$_2$, —CH$_2$CH(CH$_3$)$_2$, —(CH$_2$)$_2$CH$_3$, n-butyl, n-hexyl, n-octyl, p-chlorophenyl, cyclohexyl, cyclopentyl,

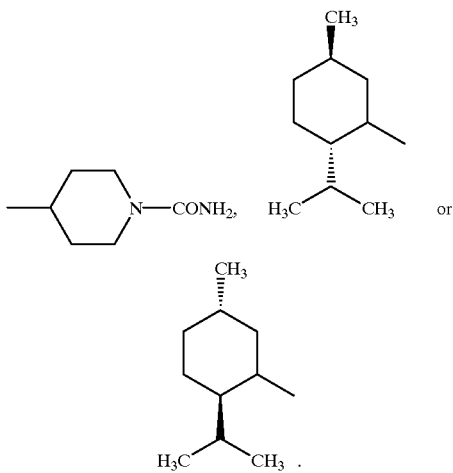

Another example of $R^{20}$ for group 5.0 is

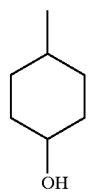

Examples of $R^{20}$ and $R^{21}$ for 6.0 include: cyclohexyl, t-butyl, H, —CH(CH$_3$)$_2$, ethyl, —(CH$_2$)$_2$CH$_3$, phenyl, benzyl, —(CH$_2$)$_2$phenyl, and —CH$_3$.

Examples of $R^{20}$ for 7.0 include: 4-pyridylNO, —OCH$_3$, —CH(CH$_3$)$_2$, -t-butyl, H, propyl, cyclohexyl and

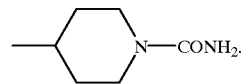

Examples for $R^{36}$ for 7.1 include: cyclohexyl, cyclopentyl, cyclobutyl, cyclopropyl,

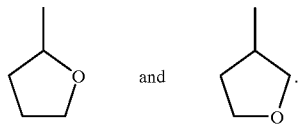

Examples for $R^{20}$ for 8.0 include: methyl, i-propyl and cyclohexylmethyl.

Examples of $R^{32}$ and $R^{33}$ include: H, phenyl, —OH and benzyl.

Compounds of this invention include compounds of formula 1.0 wherein when $R^{14}$ is selected from: group 6.0, 7.0, 7.1 or 8.0, and X is C or CH (preferably CH), then $R^8$ is selected from: $C_3$ to $C_{10}$ alkyl, substituted $C_3$ to $C_{10}$ alkyl, arylalkyl, substituted arylalkyl, heteroarylalkyl, substituted heteroarylalkyl, cycloalkylalkyl, or substituted cycloalkylalkyl.

Compounds of this invention include compounds of formula 1.0 wherein when $R^{14}$ is selected from: group 6.0, 7.0, 7.1 or 8.0, and X is C or CH (preferably CH), and $R^8$ is H, then the alkyl chain between $R^{13}$ (i.e., imidazole ring 2.0, 4.0 or 4.1) and the amide moiety (i.e., the —C(O)NR$^{18}$ group) is substituted, i.e.,: (a) at least one of $R^9$, $R^{10}$, $R^{11}$, $R^{12}$, $R^{32}$, or $R^{33}$ is other than H, and/or (b) $R^9$ and $R^{10}$, and/or $R^{11}$ and $R^{12}$, are taken together to form a cyloalkyl ring.

Compounds of this invention include compounds of formula 1.0 wherein when $R^{14}$ is group 5.0, and X is C or CH (preferably CH), and $R^8$ is H, then the alkyl chain between $R^{13}$ (i.e., imidazole ring. 2.0, 4.0 or 4.1) and the amide moiety (i.e., the —C(O)NR$^{18}$ group) is substituted, i.e.,: (a) at least one of $R^9$, $R^{10}$, $R^{11}$, $R^{12}$, $R^{32}$, or $R^{33}$ is other than H, and/or (b) $R^9$ and $R^{10}$, and/or $R^{11}$ and $R^{12}$, are taken together to form a cyloalkyl ring.

Compounds of this invention include compounds of formula 1.0 wherein when $R^{14}$ is selected from: group 6.0, 7.0, 7.1 or 8.0, and X is C or CH (preferably CH), then $R^8$ is selected from: arylalkyl, substituted arylalkyl, heteroarylalkyl, substituted heteroarylalkyl, cycloalkylalkyl, or substituted cycloalkylalkyl.

Compounds of this invention include compounds of formula 1.0 wherein when $R^{14}$ is 5.0 and X is C or CH (preferably CH), then $R^8$ is selected from: arylalkyl, substituted arylalkyl, heteroarylalkyl, substituted heteroarylalkyl, cycloalkylalkyl, or substituted cycloalkylalkyl.

Compounds of this invention include compounds of formula 1.0 wherein when $R^{14}$ is selected from: group 6.0, 7.0, 7.1 or 8.0, and X is N, then $R^8$ is selected from: arylalkyl, substituted arylalkyl, heteroarylalkyl, substituted heteroarylalkyl, cycloalkylalkyl, or substituted cycloalkylalkyl.

Compounds of this invention include compounds of formula 1.0 wherein when $R^{14}$ is 5.0 and X is N, then $R^8$ is selected from: arylalkyl, substituted arylalkyl, heteroarylalkyl, substituted heteroarylalkyl, cycloalkylalkyl, or substituted cycloalkylalkyl.

Thus, one embodiment of this invention is directed to compounds wherein $R^{14}$ is the carbamate group 5.0 and the other substituents are as defined for formula 1.0.

Another embodiment of this invention is directed to compounds wherein $R^{14}$ is the carbamate group 5.0, X is N and the other substituents are as defined for formula 1.0.

Another embodiment of this invention is directed to compounds wherein $R^{14}$ is the carbamate group 5.0, X is C or CH (preferably CH) and the other substituents are as defined for formula 1.0.

Another embodiment of this invention is directed to compounds wherein $R^{14}$ is the carbamate group 5.0, X is N, $R^8$ is arylalkyl or substituted arylalkyl (preferably arylalkyl), and the other substituents are as defined for formula 1.0.

Another embodiment of this invention is directed to compounds wherein $R^{14}$ is the carbamate group 5.0, X is N, $R^8$ is heteroarylalkyl or substituted heteroarylalkyl (preferably heteroarylalkyl), and the other substituents are as defined for formula 1.0.

Another embodiment of this invention is directed to compounds wherein $R^{14}$ is the carbamate group 5.0, X is N, $R^8$ is cycloalkylalkyl or substituted cycloalkylalkyl (preferably cycloalkylalkyl), and the other substituents are as defined for formula 1.0.

Another embodiment of this invention is directed to compounds wherein $R^{14}$ is the carbamate group 5.0, X is C or CH (preferably CH), $R^8$ is arylalkyl or substituted arylalkyl (preferably arylalkyl), and the other substituents are as defined for formula 1.0.

Another embodiment of this invention is directed to compounds wherein $R^{14}$ is the carbamate group 5.0, X is C or CH (preferably CH), $R^8$ is heteroarylalkyl or substituted heteroarylalkyl (preferably heteroarylalkyl), and the other substituents are as defined for formula 1.0.

Another embodiment of this invention is directed to compounds wherein $R^{14}$ is the carbamate group 5.0, X is C or CH (preferably CH), $R^8$ is cycloalkylalkyl or substituted cycloalkylalkyl (preferably cycloalkyalkyl), and the other substituents are as defined for formula 1.0.

Another embodiment of this invention is directed to compounds wherein when $R^{14}$ is group 5.0, and X is C or CH (preferably CH), and $R^8$ is H, then the alkyl chain between $R^{13}$ (i.e., imidazole ring 2.0, 4.0 or 4.1) and the amide moiety (i.e., the —C(O)$NR^{18}$ group) is substituted, i.e.,: (a) at least one of $R^9$, $R^{10}$, $R^{11}$, $R^{12}$, $R^{32}$, or $R^{33}$ is other than H, and/or (b) $R^9$ and $R^{10}$, and/or $R^{11}$ and $R^{12}$, are taken together to form a cyloalkyl ring, and the other substituents are as defined for formula 1.0.

Another embodiment of this invention is directed to compounds wherein when $R^{14}$ is group 5.0, and X is N, and $R^8$ is H, then the alkyl chain between $R^{13}$ (i.e., imidazole ring 2.0, 4.0 or 4.1) and the amide moiety (i.e., the —C(O)$NR^{18}$ group) is substituted, i.e.,: (a) at least one of $R^9$, $R^{10}$, $R^{11}$, $R^{12}$, $R^{32}$, or $R^{33}$ is other than H, and/or (b) $R^9$ and $R^{10}$, and/or $R^{11}$ and $R^{12}$, are taken together to form a cyloalkyl ring, and the other substituents are as defined for formula 1.0.

Another embodiment of this invention is directed to compounds wherein $R^{14}$ is a group selected from: 6.0, 7.0, 7.1 or 8.0, X is N, $R^8$ is arylalkyl or substituted arylalkyl (preferably arylalkyl) and the other substituents are as defined for formula 1.0.

Another embodiment of this invention is directed to compounds wherein $R^{14}$ is a group selected from: 6.0, 7.0, 7.1 or 8.0, X is N, $R^8$ is heteroarylalkyl or substituted heteroarylalkyl (preferably heteroarylalkyl) and the other substituents are as defined for formula 1.0.

Another embodiment of this invention is directed to compounds wherein $R^{14}$ is a group selected from: 6.0, 7.0, 7.1 or 8.0, X is N, $R^8$ is cycloalkylalkyl or substituted cycloalkylalkyl (preferably, cycloalkylalkyl) and the other substituents are as defined for formula 1.0.

Another embodiment of this invention is directed to compounds wherein $R^{14}$ is a group selected from:6.0, 7.0, 7.1 or 8.0, X is C or CH (preferably, CH), $R^8$ is arylalkyl or substituted arylalkyl (preferably arylalkyl) and the other substituents are as defined for formula 1.0.

Another embodiment of this invention is directed to compounds wherein $R^{14}$ is a group selected from: 6.0, 7.0, 7.1 or 8.0, X is C or CH (preferably, CH), $R^8$ is heteroarylalkyl or substituted heteroarylalkyl (preferably, heteroarylalkyl) and the other substituents are as defined for formula 1.0.

Another embodiment of this invention is directed to compounds wherein $R^{14}$ is a group selected from: 6.0, 7.0, 7.1 or 8.0, X is C or CH (preferably, CH), $R^8$ is cycloalkylalkyl or substituted cycloalkylalkyl (preferably, cycloalkylalkyl) and the other substituents are as defined for formula 1.0.

$R^1$, $R^2$, $R^3$, and $R^4$ are preferably selected from H or halo, and are more preferably selected from H, Br, F, or Cl, and are most preferably selected from H, Br or Cl. Representative compounds of formula 1.0 include trihalo, dihalo and monohalo substituted compounds, such as, for example: (1) 3,8, 10-trihalo; (2) 3,7,8-trihalo; (3) 3,8-dihalo; (4) 8-halo; and (5) 10-halo substituted compounds; wherein each halo is independently selected. Preferred compounds of formula 1.0 include: (1) 3-Br,8-Cl, 10-Br-substituted compounds; (2) 3-Br,7-Br,8-Cl-substituted compounds; (3) 3-Br,8-Cl-substituted compounds; (4) 8-Cl-substituted compounds; and (5) 10-Cl-substituted compounds. The 3,8-dihalo compounds are more preferred and the 8-halo compounds are most preferred. Thus, for example, 3-Br,8-Cl substituted compounds are more preferred and 8-Cl substituted compounds are most preferred.

Substituent a is preferably N or $N^+O^-$ with N being preferred.

A and B are preferably $H_2$, i.e., the optional bond is absent and the C5–C6 bridge is unsubstituted.

$R^5$, $R^6$, and $R^7$ are preferably H.

X is preferably N or CH (i.e., the optional bond is absent), and more preferably X is N.

$R^8$ is preferably selected from: arylalkyl, substituted aryl alkyl, heteroarylalkyl, substituted heteroarylalkyl, cycloalkylalkyl or substituted cycloalkylalkyl. Most preferably, $R^8$ is selected from: aryl-$(C_1-C_4)$alkyl, substituted aryl-$(C_1-C_4)$alkyl , heteroaryl-$(C_1-C_4)$alkyl, substituted heteroaryl-$(C_1-C_4)$alkyl, cycloalkyl-$(C_1-C_4)$alkyl, or substituted cycloalkyl-$(C_1-C_4)$alkyl. More preferably, $R^8$ is selected from: aryl-$CH_2$—, substituted aryl-$CH_2$—, heteroaryl-$CH_2$—, substituted heteroaryl-$CH_2$, cycloalkyl-$CH_2$— or substituted cycloalkyl-$CH_2$—. Even more preferably, $R^8$ is selected from: benzyl, 3-pyridylmethyl, 4-fluoro-benzyl or cyclopropylmethyl, and still more preferably $R^8$ is benzyl.

$R^{13}$ is preferably ring 2.0 or 4.0. When substituted on the substitutable carbon atoms of the imidazole ring, the substituents are generally selected from: —N($R^{18}$)$_2$, —NHC(O)$R^{18}$, —C($R^{34}$)$_2$O$R^{35}$, or alkyl, e.g., —$CH_3$, —$CH_2OH$, —$CH_2OC(O)$O-cyclohexyl, —$CH_2OC(O)$O-cyclopentyl, ethyl, isopropyl, $NH_2$, or —NHC(O)$CF_3$.

$R^{19}$ is preferably H or alkyl, most preferably H, methyl or ethyl, and more preferably methyl.

$R^{14}$ is preferably a carbamate group represented by substituent 5.0 described above. Preferably, $R^{20}$ for substituent 5.0 is selected from: alkyl, substituted alkyl, aryl, cycloalkyl, or cycloalkyl substituted with —OH provided that said —OH substituent is not bound to a carbon that is adjacent to an oxygen atom. More preferably $R^{20}$ for substituent 5.0 is selected from: $C_1$ to $C_4$ alkyl and $C_5$ to $C_7$ cycloalkyl. Most preferably $R^{20}$ for substituent 5.0 is selected from: t-butyl, i-propyl and cyclohexyl, with i-propyl and cyclohexyl being more preferred, and with cyclohexyl being even more preferred.

$R^{20}$ in substituent 6.0 is preferably selected from: alkyl or cycloalkyl; most preferably t-butyl, isopropyl or cyclohexyl; and more preferably cyclohexyl. $R^{21}$ is preferably selected from: H or alkyl; most preferably H, methyl or isopropyl; and more preferably H.

$R^{20}$ in substituent 7.0 is preferably selected from: cycloalkyl or alkyl; most preferably cyclohexyl, cyclopentyl, isopropyl; and more preferably cyclohexyl.

$R^{36}$ in substituent 7.1 is preferably selected from: phenyl, cyclopropyl, cyclobutyl, cyclopentyl, cyclohexyl,

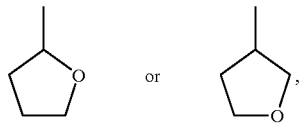

and most preferably selected from: cyclopropyl, cyclobutyl, cyclopentyl or cyclohexyl.

$R^{20}$ in substituent 8.0 is preferably selected from: alkyl or cycloalkylalkyl; most preferably methyl, isopropyl or cyclohexylmethyl; more preferably methyl or isopropyl; and even more preferably methyl.

$R^9$, $R^{10}$, $R^{11}$, and $R^{12}$ are preferably selected from: H, $C_1$ to $C_4$ alkyl (e.g., methyl or isopropyl), —CON($R^{18}$)$_2$ (e.g., —CONH$_2$), or when $R^9$ and $R^{10}$, and/or $R^{11}$ and $R^{12}$ are taken together to form a cycloalkyl ring, said ring is preferably cyclopropyl cyclopentyl or cyclohexyl.

$R^9$, $R^{10}$, $R^{11}$, and $R^{12}$ are preferably H when $R^{14}$ is the carbamate substituent 5.0 and $R^8$ is not H.

When $R^{14}$ is selected from substituents 6.0, 7.0, 7.1 and 8.0, and at least one of $R^9$, $R^{10}$, $R^{11}$, and $R^{12}$ is other than H, then at least one of $R^9$, $R^{10}$, $R^{11}$, and $R^{12}$ is:
(I) preferably selected from: (1) $C_1$ to $C_4$ alkyl (2) —CON($R^{18}$)$_2$ or (3) the cycloalkyl ring formed when $R^9$ and $R^{10}$, and/or $R^{11}$ and $R^{12}$, are taken together along with the carbon atom to which they are bound;
(II) most preferably selected from: (1) methyl, (2) isopropyl, (3) —CONH$_2$ or (4) cyclopropyl; and
(III) more preferably selected from: (1) $R^9$ and $R^{10}$ being H, and one of $R^{11}$ and $R^{12}$ being selected from: alkyl (preferably, methyl or isopropyl), and the other being selected from H or alkyl (preferably, methyl); (2) $R^9$ and $R^{10}$ being H, and $R^{11}$ and $R^{12}$ being taken together to form a cycloalkyl ring (preferably, cyclopropyl); or (3) $R^{11}$ and $R^{12}$ being H, and one of $R^9$ and $R^{10}$ being —CONH$_2$, and the other being H.

Preferred compounds, when at least one of $R^9$, $R^{10}$, $R^{11}$, and $R^{12}$ is other than H, also include compounds wherein: $R^9$ and $R^{10}$ are H, and $R^{11}$ and $R^{12}$ are the same or different alkyl, preferably the same, wherein said alkyl is more preferably methyl.

For compounds of the invention, n is preferably 0–4, more preferably 0–2, and most preferably 0 or 1.

Preferably, each $R^{32}$ and $R^{33}$ are independently selected from: H, —OR$^{18}$, aryl or arylalkyl (e.g., benzyl); most preferably H, —OH or phenyl; and more preferably H.

Compounds of formula 1.0, wherein X is N or CH, include, with reference to the C-11 bond, the R- and S-isomers:

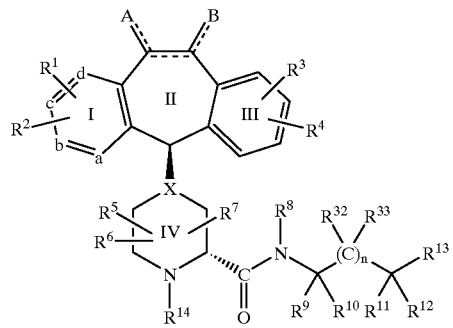

(9.0)

(R)

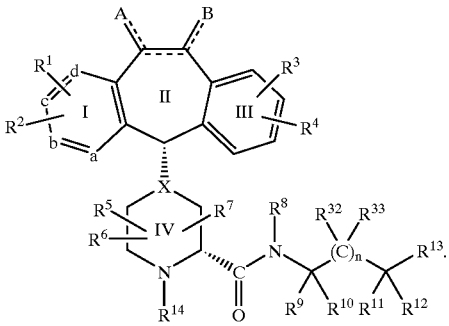

(10.0)

(S)

Compounds of formula 1.0 also include compounds having the 2S stereochemistry and the C-11 R- or C-11 S-stereochemistry.

Compounds of this invention include:

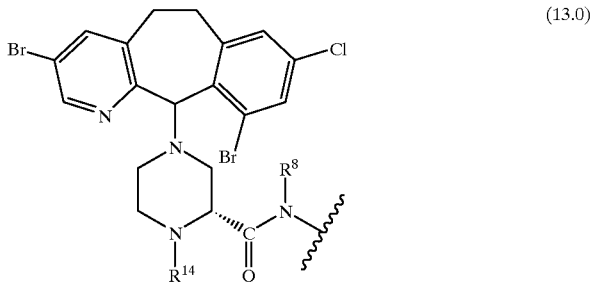

(13.0)

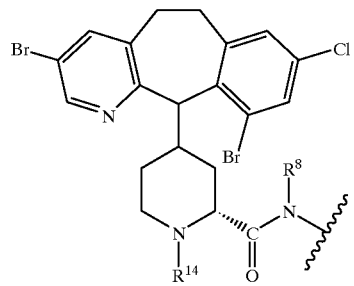

(14.0)

-continued
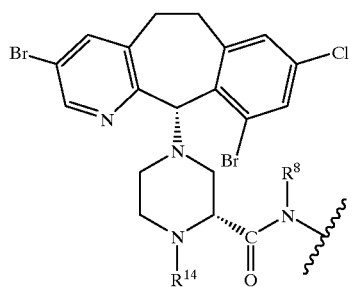 (15.0)
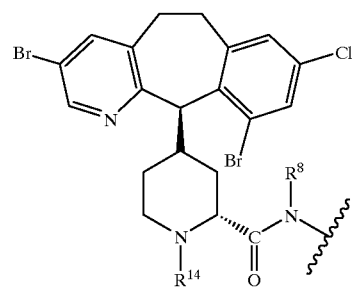 (16.0)
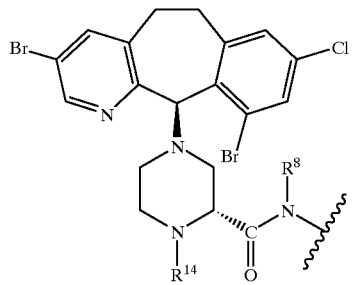 (15.1)
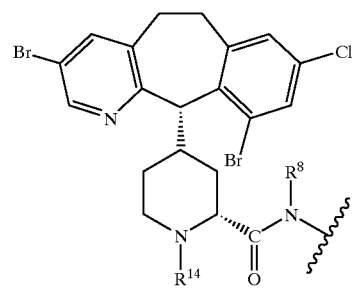 (16.1)
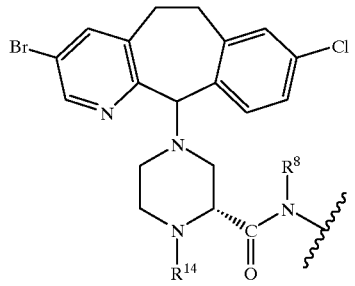 (17.0)
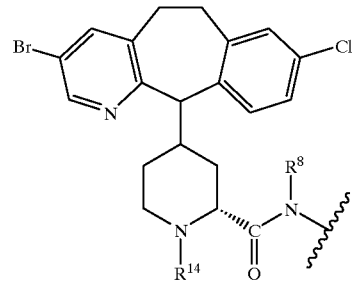 (18.0)
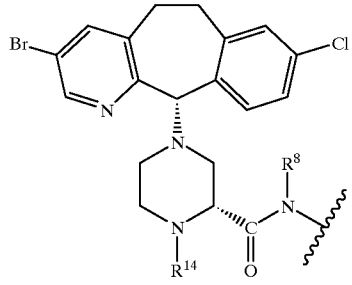 (19.0)
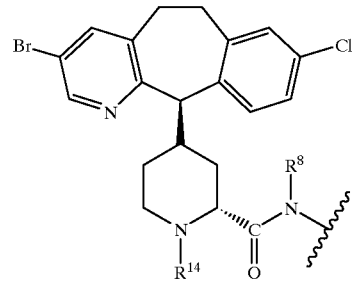 (20.0)
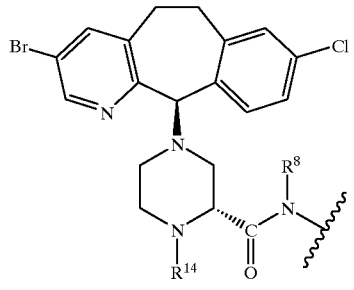 (19.1)
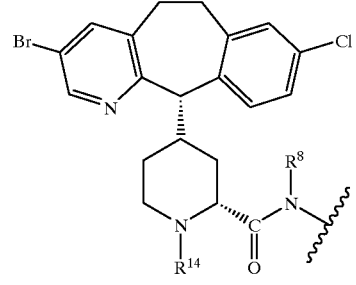 (20.1)

-continued
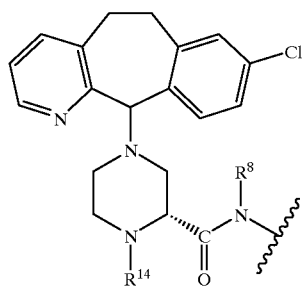 (21.0)
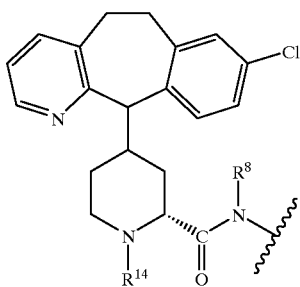 (22.0)
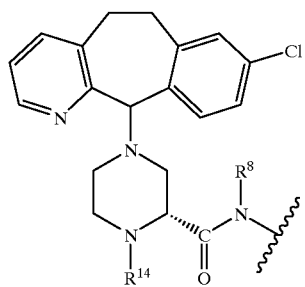 (21.0)
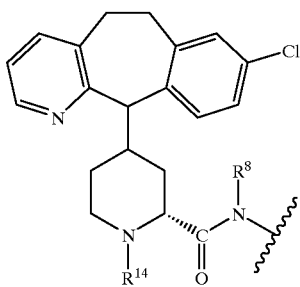 (22.0)
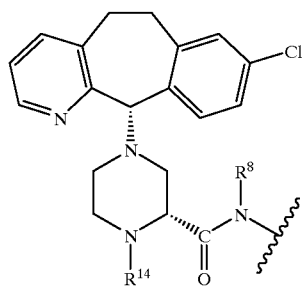 (23.0)
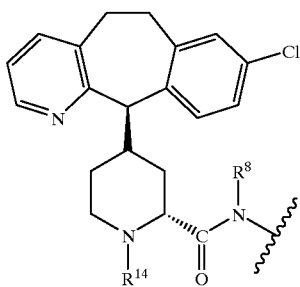 (24.0)
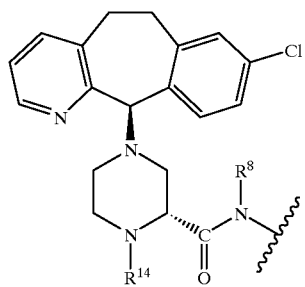 (23.1)
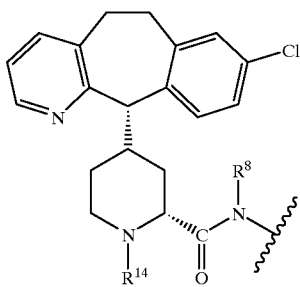 (24.1)
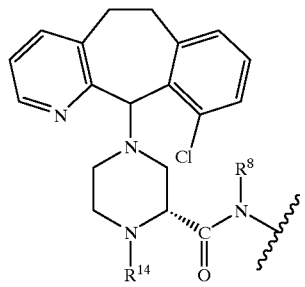 (24.2)
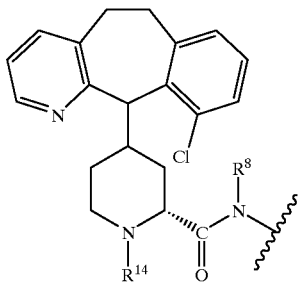 (24.3)

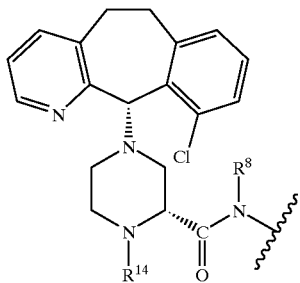

(24.4)

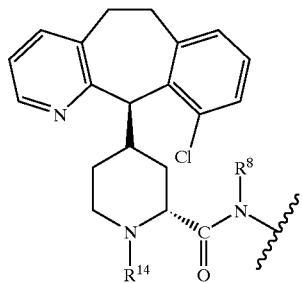

(24.5)

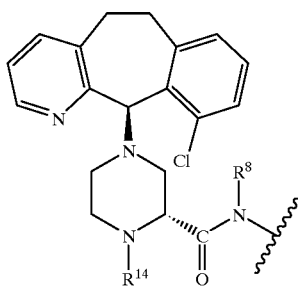

(24.6)

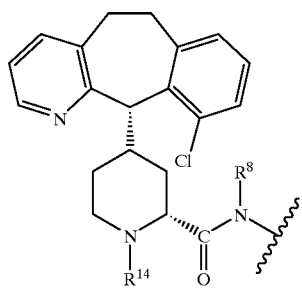

(24.7)

Compounds of the invention also include compounds corresponding to 13.0–15.0, 15.1, 16.0, 16.1, 17.0–19.0, 19.1, 20.0, 20.1, 21.0–23.0, 23.1, 24.0, and 24.1–24.7, except that the compounds have the 2S stereochemistry.

Compounds of the invention also include compounds corresponding to 13.0–15.0, 15.1, 16.0, 16.1, 17.0–19.0, 19.1, 20.0, 20.1, 21.0–23.0, 23.1, 24.0, and 24.1–24.7, except that Ring I is phenyl instead of pyridyl.

Compounds of the invention also include compounds corresponding to 13.0–15.0, 15.1, 16.0, 16.1, 17.0–19.0, 19.1, 20.0, 20.1, 21.0–23.0, 23.1, 24.0, and 24.1–24.7, except that Ring I is phenyl instead of pyridyl and the compounds have the 2S stereochemistry.

Preferred compounds of formula 1.0 include compounds of the formula:

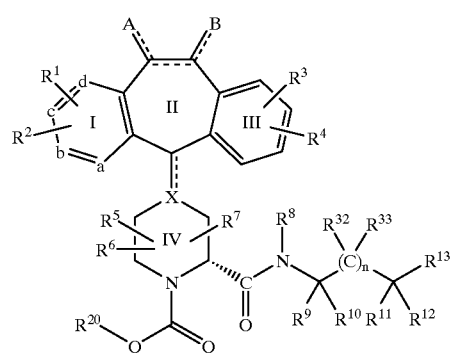

(25.0)

(i.e., wherein $R^{14}$ is the carbamate group 5.0) wherein all substituents are as above defined.

A preferred compound of formula 25.0 is:

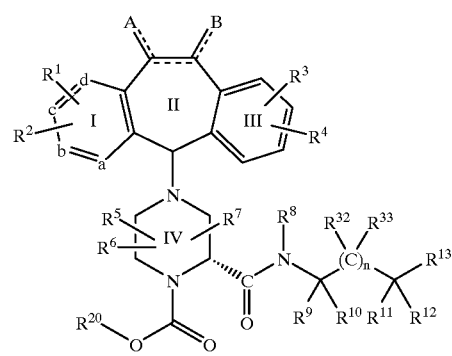

(26.0)

with formula 27.0:

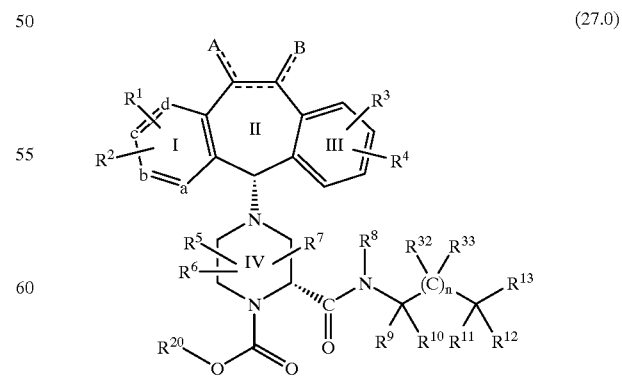

(27.0)

being most preferred (wherein all substituents are as defined above).

Compounds of formula 25.0 include:

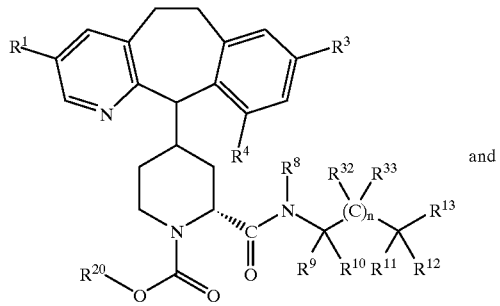

(28.0)

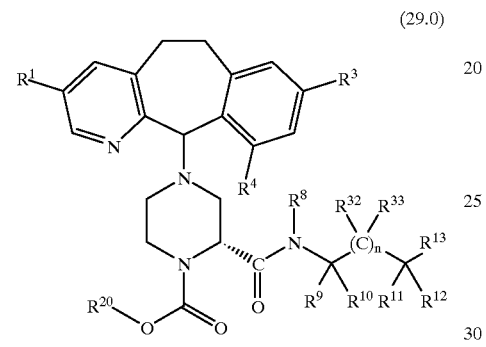

(29.0)

wherein all substituents are as defined above.

Preferred compounds of formulas 28.0 and 29.0 are those wherein the $R^1$ to $R^4$ substituents are selected to produce trihalo, dihalo and monohalo substituted compounds, as described above.

Compounds of formula 29.0 are preferred. Most preferred are compounds of formula 29.0 wherein $R^8$ is selected from: benzyl, 4-fluorobenzyl, 3-pyridylmethyl or cyclopropylmethyl; $R^{20}$ is cyclohexyl, i-propyl or t-butyl (more preferred is cyclohexyl), $R^1$ is Br or H, $R^3$ is Cl, and $R^4$ is H. More preferred are compounds of formula 29.0 wherein $R^8$ is benzyl, $R^{20}$ is cyclohexyl, i-propyl or t-butyl (even more preferred cyclohexyl), $R^1$ is H, $R^3$ is Cl, and $R^4$ is H or Cl.

Preferred compounds of this invention include:

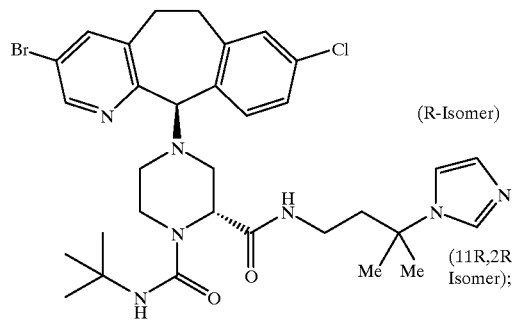

(R-Isomer)

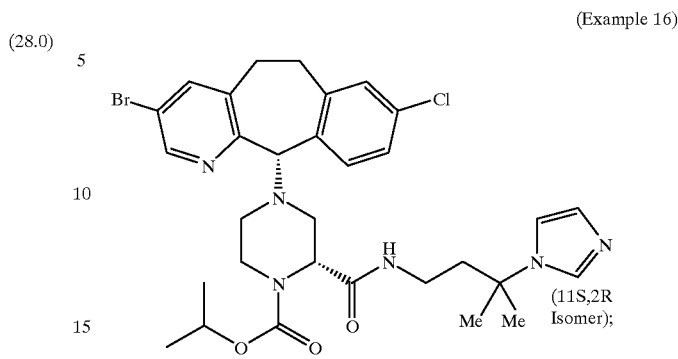

(Example 16)

(11S,2R Isomer);

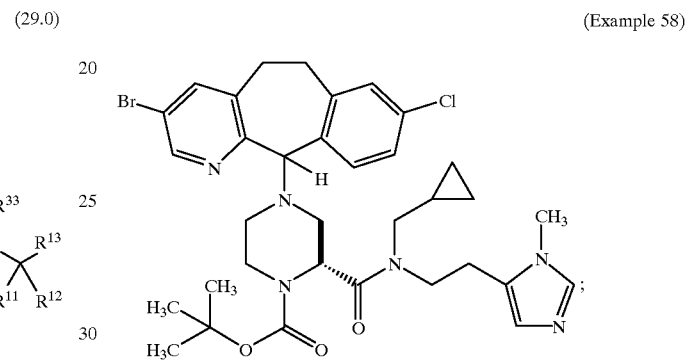

(Example 58)

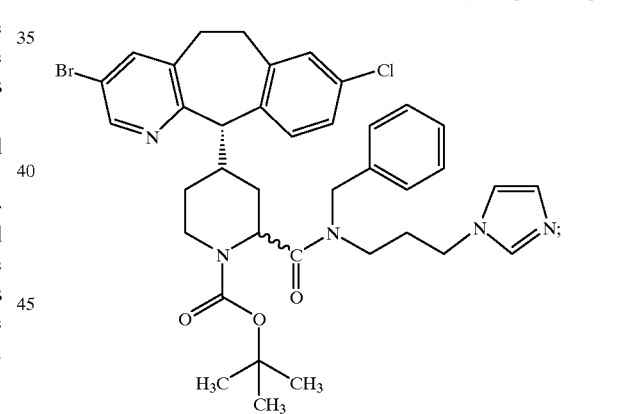

(Example 78 Step B)

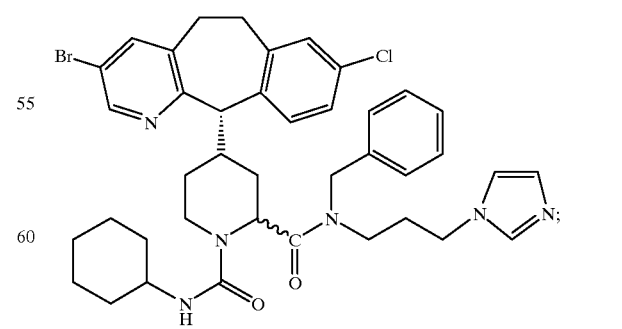

(Example 79 Step B Isomer A)

(Example 80 Isomer A)
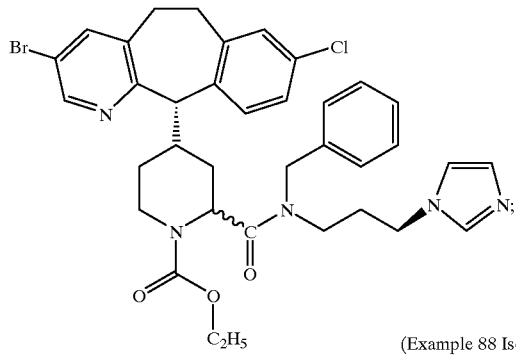
(Example 88 Isomer A)
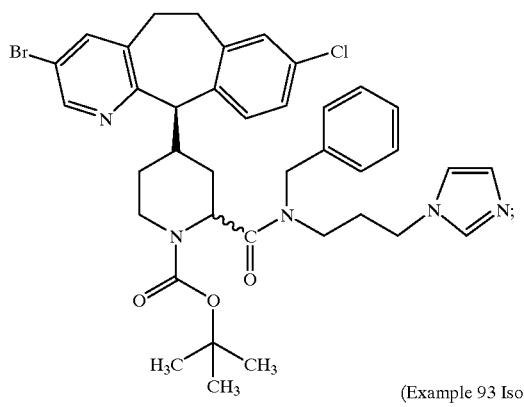
(Example 93 Isomer D)
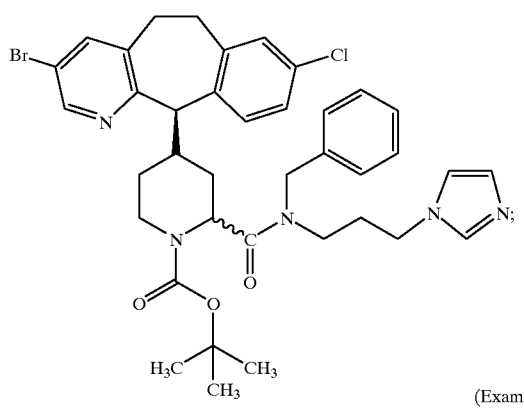
(Example 99)
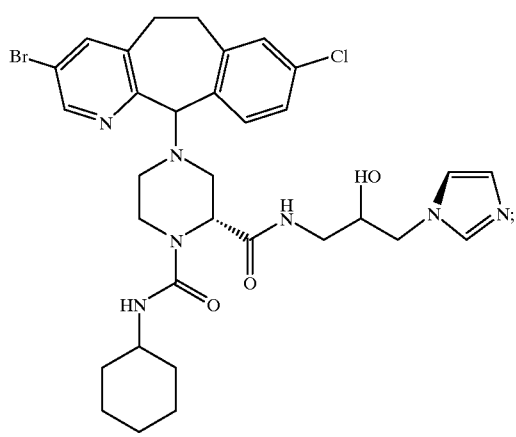
(Example 100)
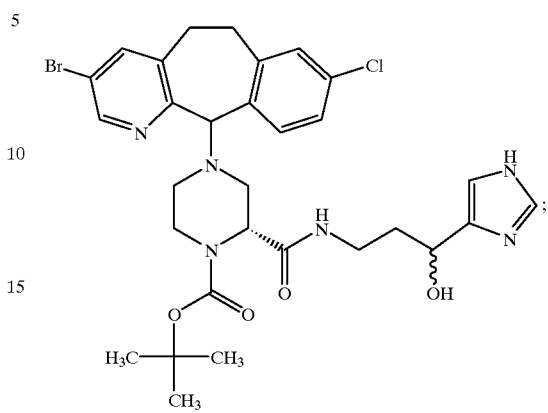
(Example 225)
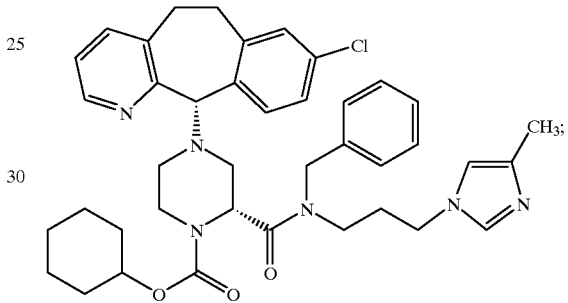
(Example 226)
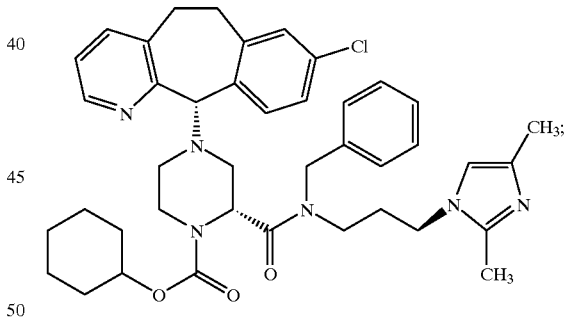
(Example 227)
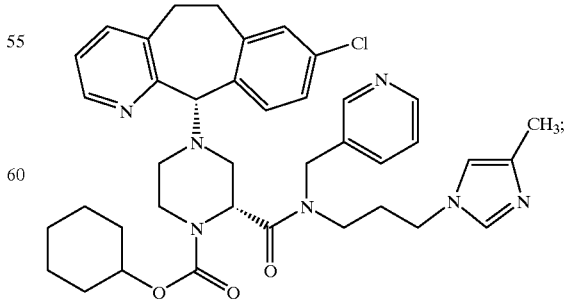

(Example 228)
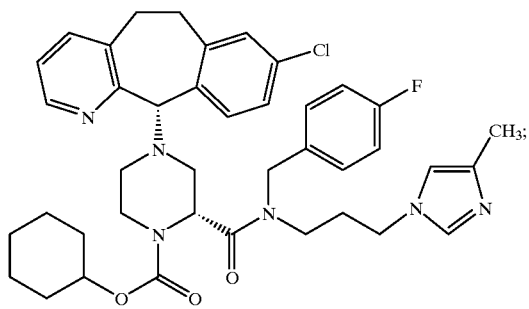
(Example 229)
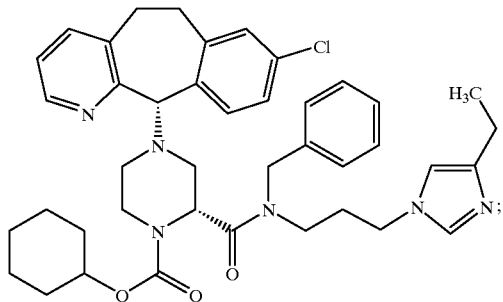
(Example 232)
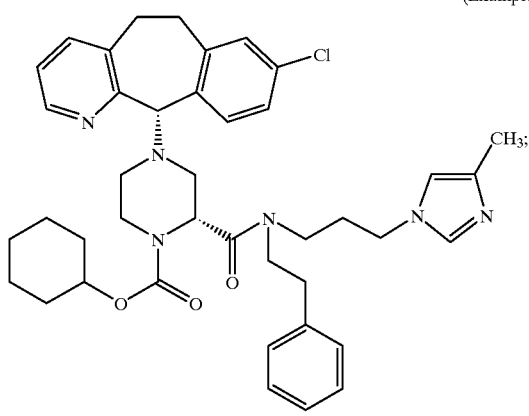
(Example 326)
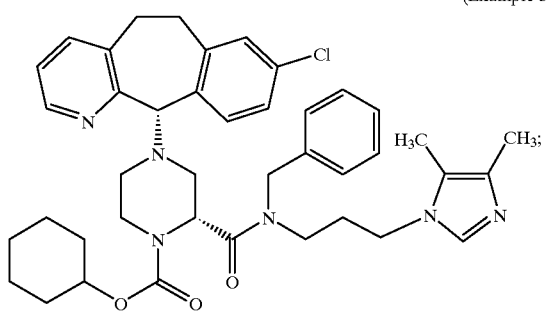
(Example 330)
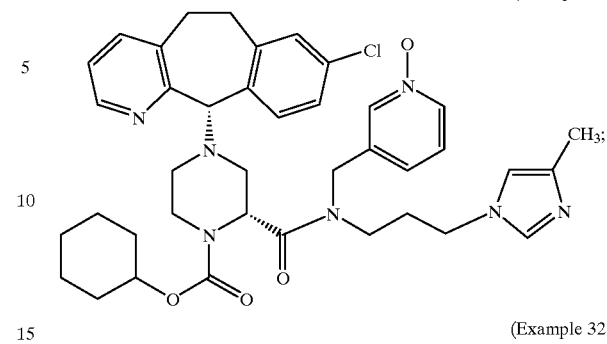
(Example 327)
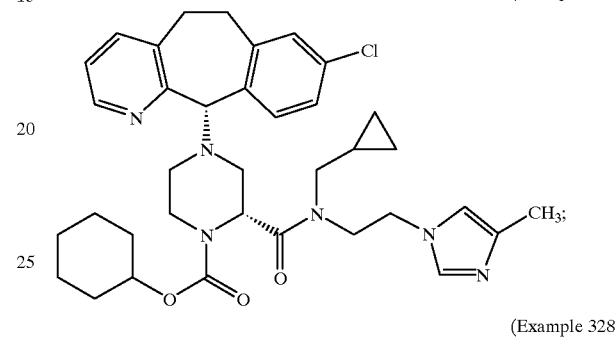
(Example 328)
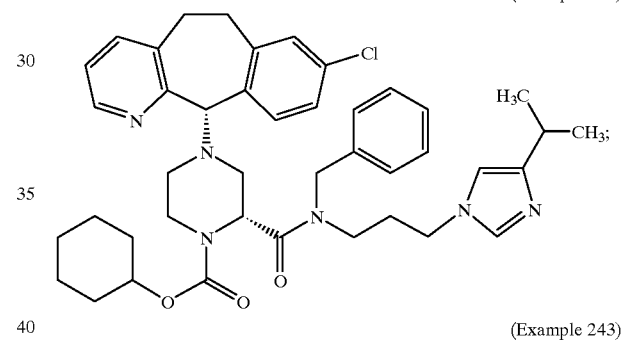
(Example 243)
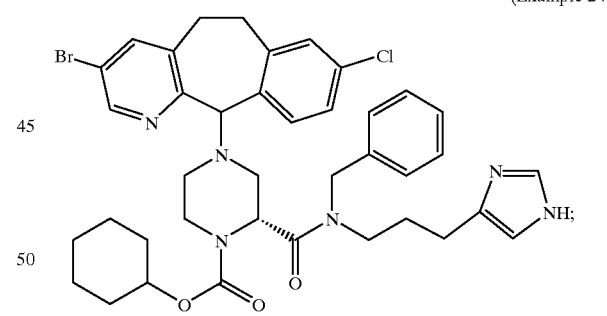
(Example 286A)
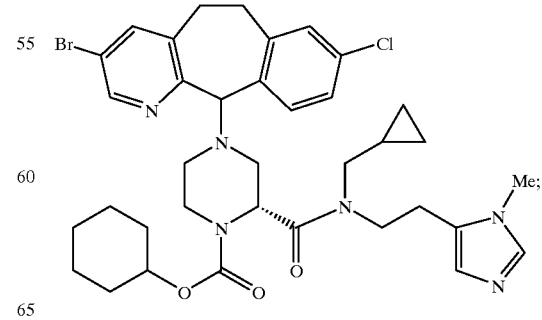

(Example 286B)
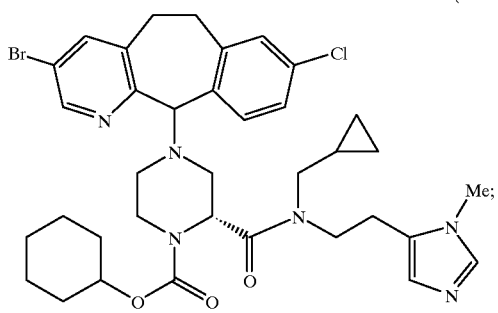
(Example 304)
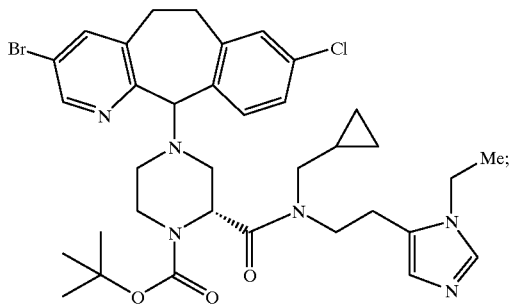
(Example 306)
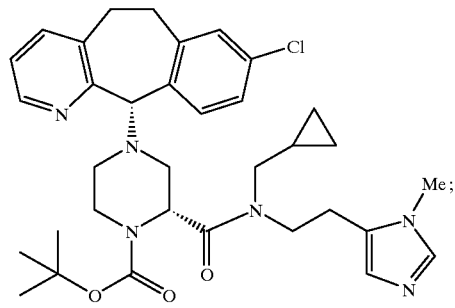
(Example 307)
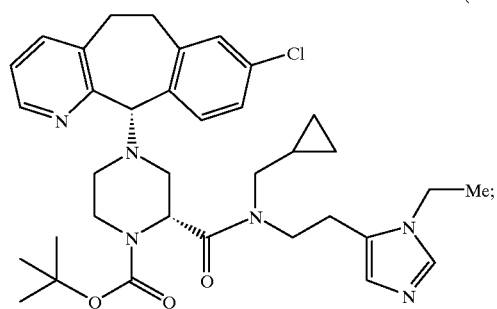
or
(Example 308)
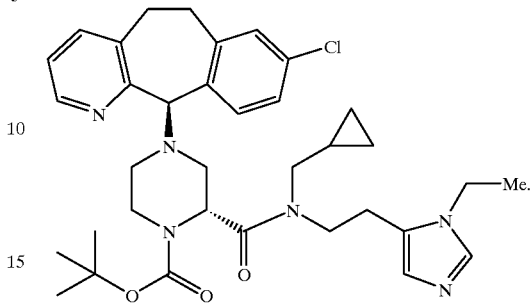
Most preferred compounds include the compounds
(Example 58)
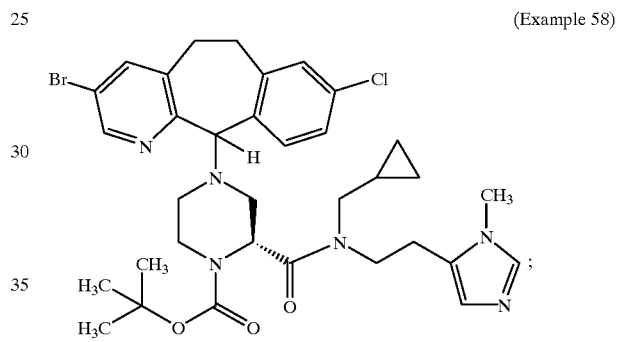
(Example 225)
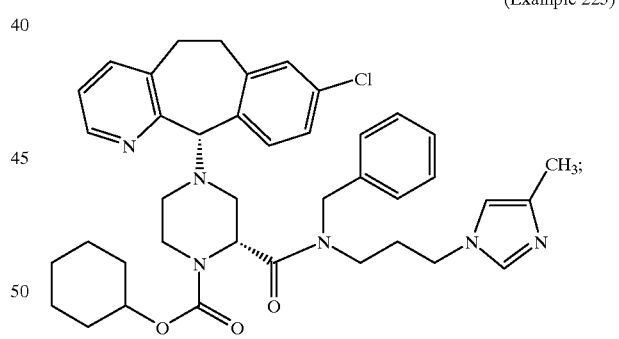
(Example 226)
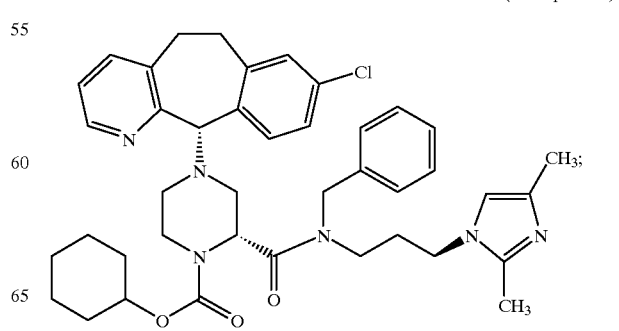

(Example 227)
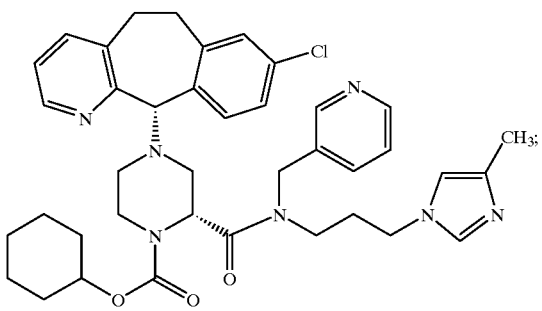

(Example 326)
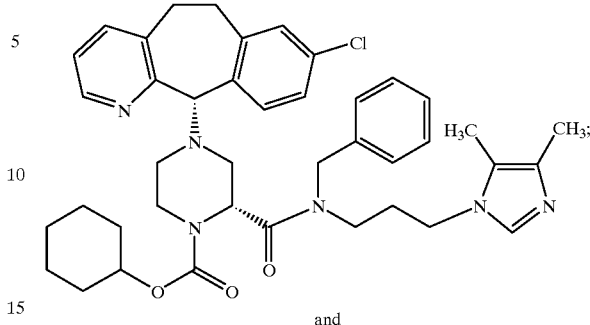

and (Example 228)
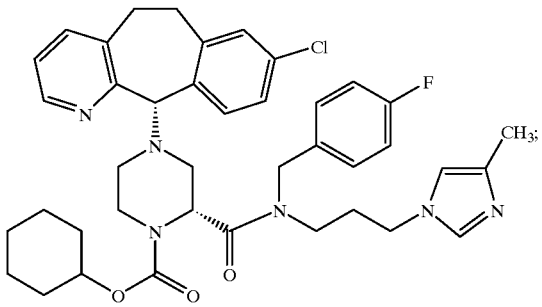

(Example 327)
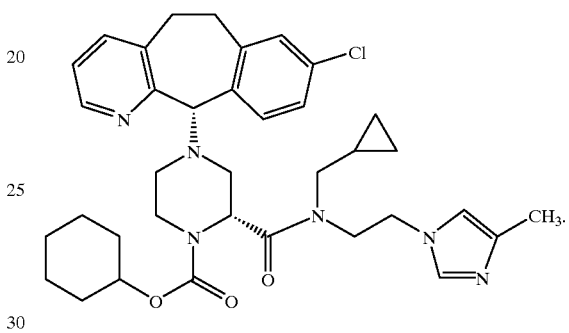

(Example 229)
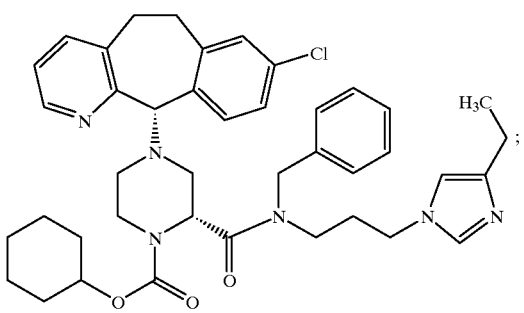

More preferred compounds include the compounds of Examples 58, 199, 225, 226, 229, 232 and 326. Compounds of Examples 58, 199, 225, 229 and 326 are even more preferred. The compound of Example 225 is even still more preferred. Preferably the compound of Examples 225, 229 and 326 are administered orally.

This invention is also directed to the compounds of Examples 26, 30, 32, 41, 42, 43, 44, 81, 105, 106, 293, and 309. The compound of Example 309 is preferred.

This invention is also directed to the compounds of Examples 31, 34, 35, 36, 37, 38, 39, 40, 67, 68, 69, 70, 73, 75, 263, 282, 283, 284, 287, and 289. The compounds of Examples 67, 68, 69, and 70 are preferred.

This invention is also directed to the compounds of Examples 27, 28, 29, 71, 72, 74, 76, 98, 101, 103, 104, 107, 108, 110, 111, 255, 256, 257, 258, 259, 260, 261, 262, 264, 265, 266, 267, 268, 269, 270, 271, 272, 273, 274, 275, 276, 277, 278, 285, 286, 286A, 290, 291, 292, 294, 295, 296, 297, 299, 300, 301, 302, and 303. Compounds of Examples 101, 103, 71, 72 Step B, 72 Step C and 259 are preferred This invention is also directed to compounds of Examples 33, 279, 280, and 281.

Lines drawn into the ring systems indicate that the indicated bond may be attached to any of the substitutable ring carbon atoms.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic (Example 232)
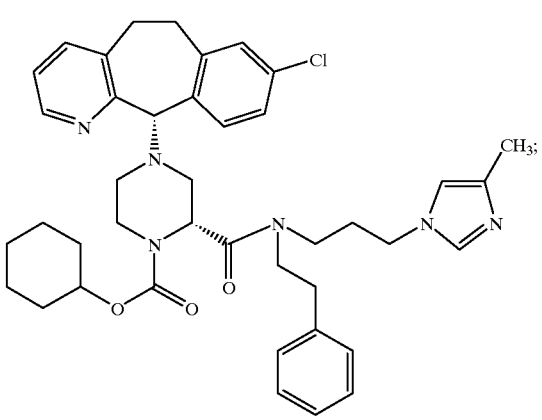

hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The compounds of formula 1.0 can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Compounds of the invention may be prepared according to the procedures described in WO 95/10516 published Apr. 20, 1995, WO 96/31478 published Oct. 10, 1996, WO 97/23478 published Jul. 3, 1997, U.S. Pat. No. 5,719,148 issued Feb. 17, 1998, and copending application Ser. No. 09/094,687 filed Jun. 15, 1998 (see also WO 98/57960 published Dec. 23, 1998); the disclosures of each being incorporated herein by reference thereto; and according to the procedures described below.

Compounds of the invention can be prepared according to the reaction schemes described below.

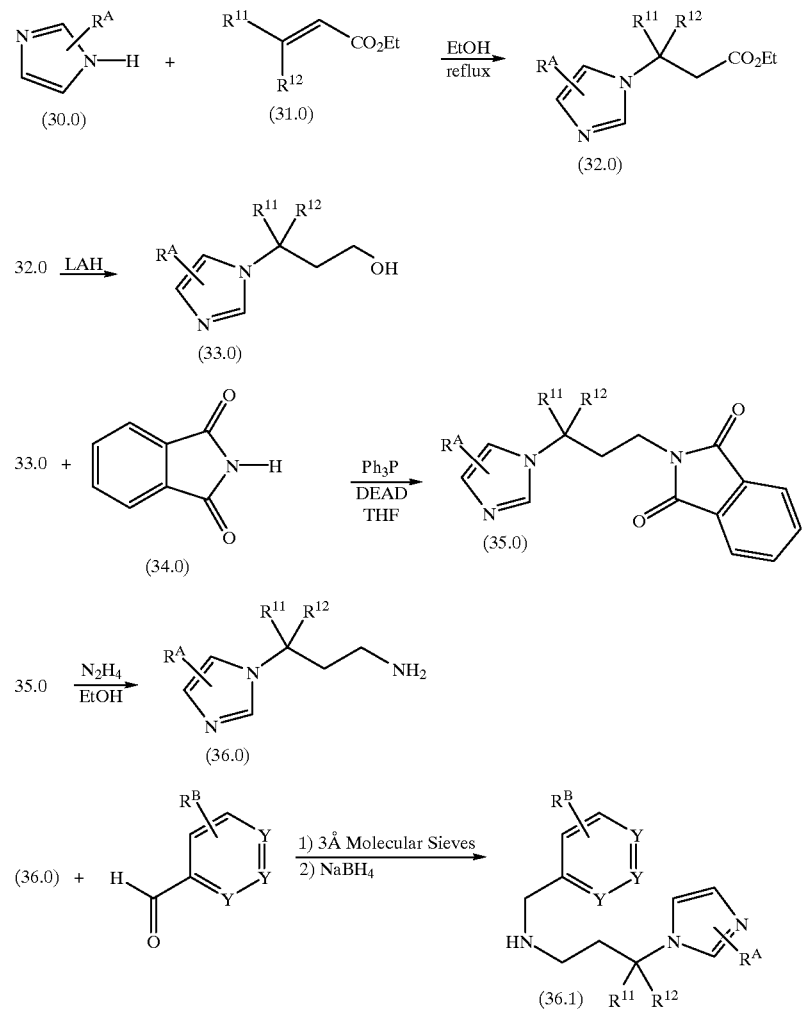

-continued
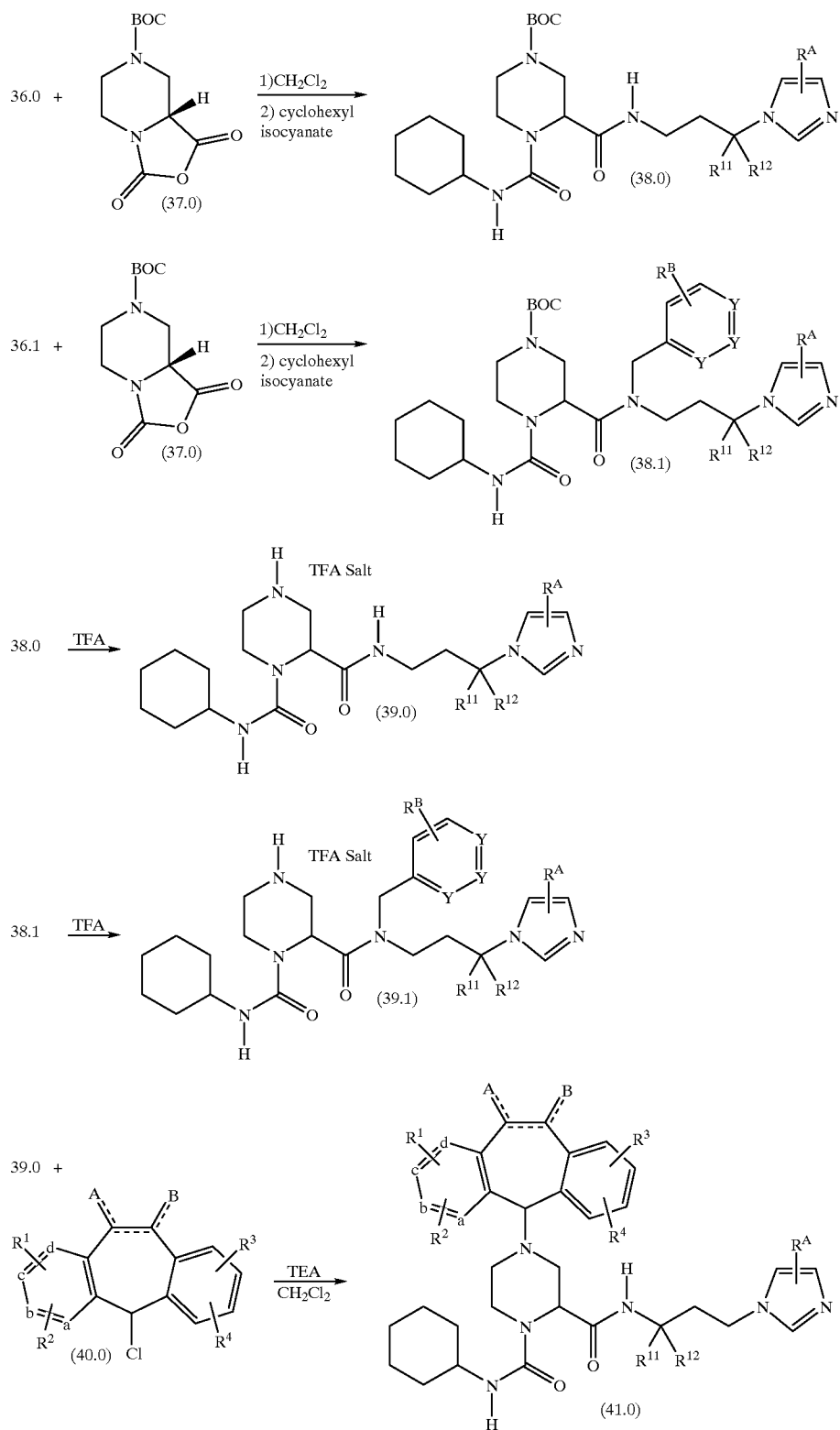

-continued

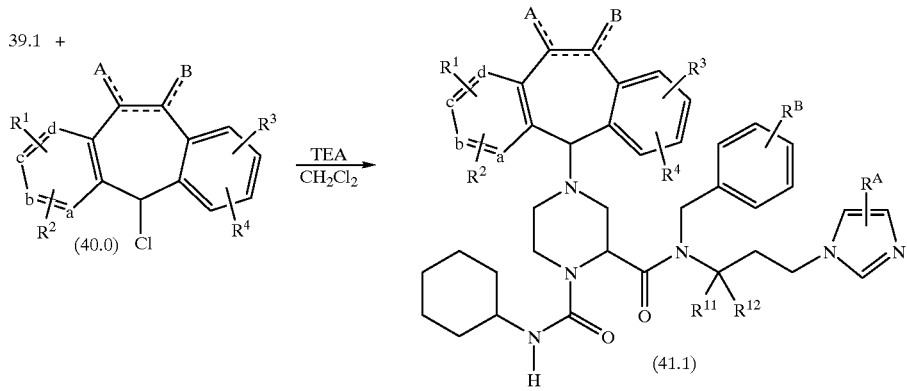

In Scheme 1, $R^{11}$ and $R^{12}$ are preferably methyl when H is bound to the amide nitrogen (i.e., when $R^8$ in formula 1.0 is H), e.g., 41.0, and are preferably H when the amide nitrogen is substituted (i.e., $R^8$ in formula 1.0 is other than H), e.g., 41.1. Those skilled in the art will appreciate that other acylating agents can be used in place of cyclohexyl isocyanate to obtain compounds having different groups bound to the carbonyl group that is bound to the piperazine nitrogen. Those skilled in the art will also appreciate that other esters can be used in place of compound 31.0 to obtain compounds having different carbon chains between the imidazole ring and the —C(O)NH-group.

Compounds of 41.0 can be prepared beginning with the conjugate addition of imidazole (2-, 4-, and/or 5-substituted) to an appropriately substituted acrylate 31.0 in EtOH at reflux or neat at 90° C. Standard LAH reduction of the ester 32.0 gives the alcohol 33.0 which can be converted to the phthalimide 35.0 via the Mitsunobu reaction. Removal of the phthalimido group with hydrazine in EtOH at reflux gives amine 36.0. This amine readily opens the piperazine anhydride 37.0 with the evolution of $CO_2$ and subsequent reaction with isocyanates gives the one pot conversion to urea 38.0. Removal of the BOC-group with 50% TFA at room temperature gives the salt 39.0, which can be readily coupled to the tricyclic chloride 40.0 to give the desired product 41.0.

In Scheme 1, and the Schemes that follow, Y represents C, N or $N^+O^-$ such that there can only be 0–2 Y substituents that are independently selected from N or $N^+O^-$. $R^A$ represents the optional substituents in the imidazole ring that are defined for imidazole ring 4.0 above. $R^B$ represents the optional substituents defined above for the aryl or heteroaryl groups for $R^8$.

For example, following Reaction Scheme 1, wherein $R^{11}$ and $R^{12}$ are methyl, and using compound 42.0 (see Preparative Example 40 in WO 95/10516 published Apr. 20, 1995)

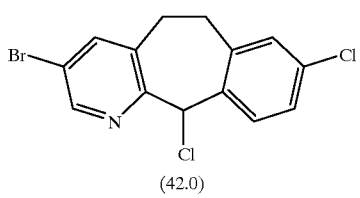

-continued compound 43.0

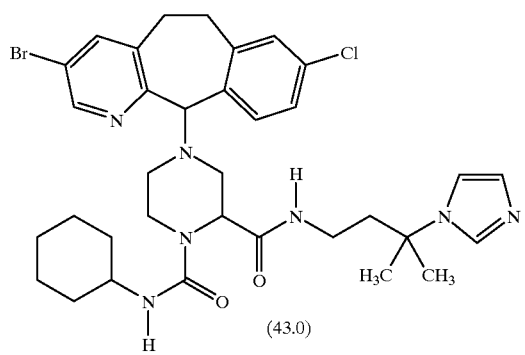

can be obtained.

Reaction Scheme 2 (n is 0)

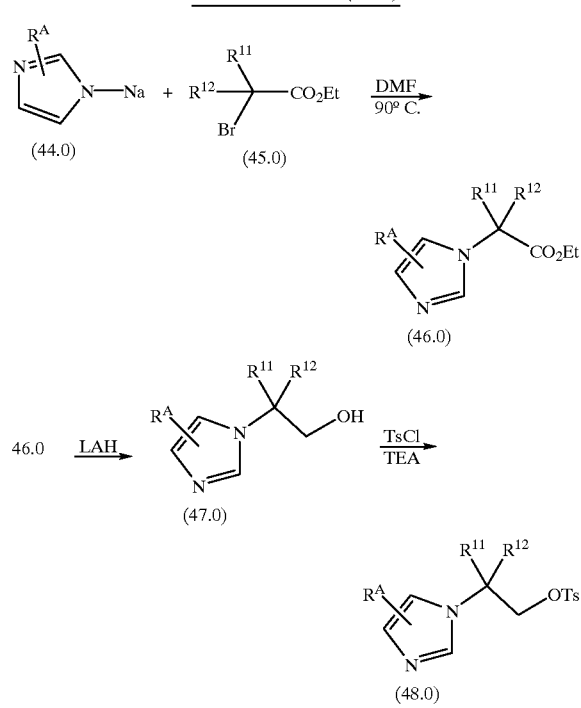

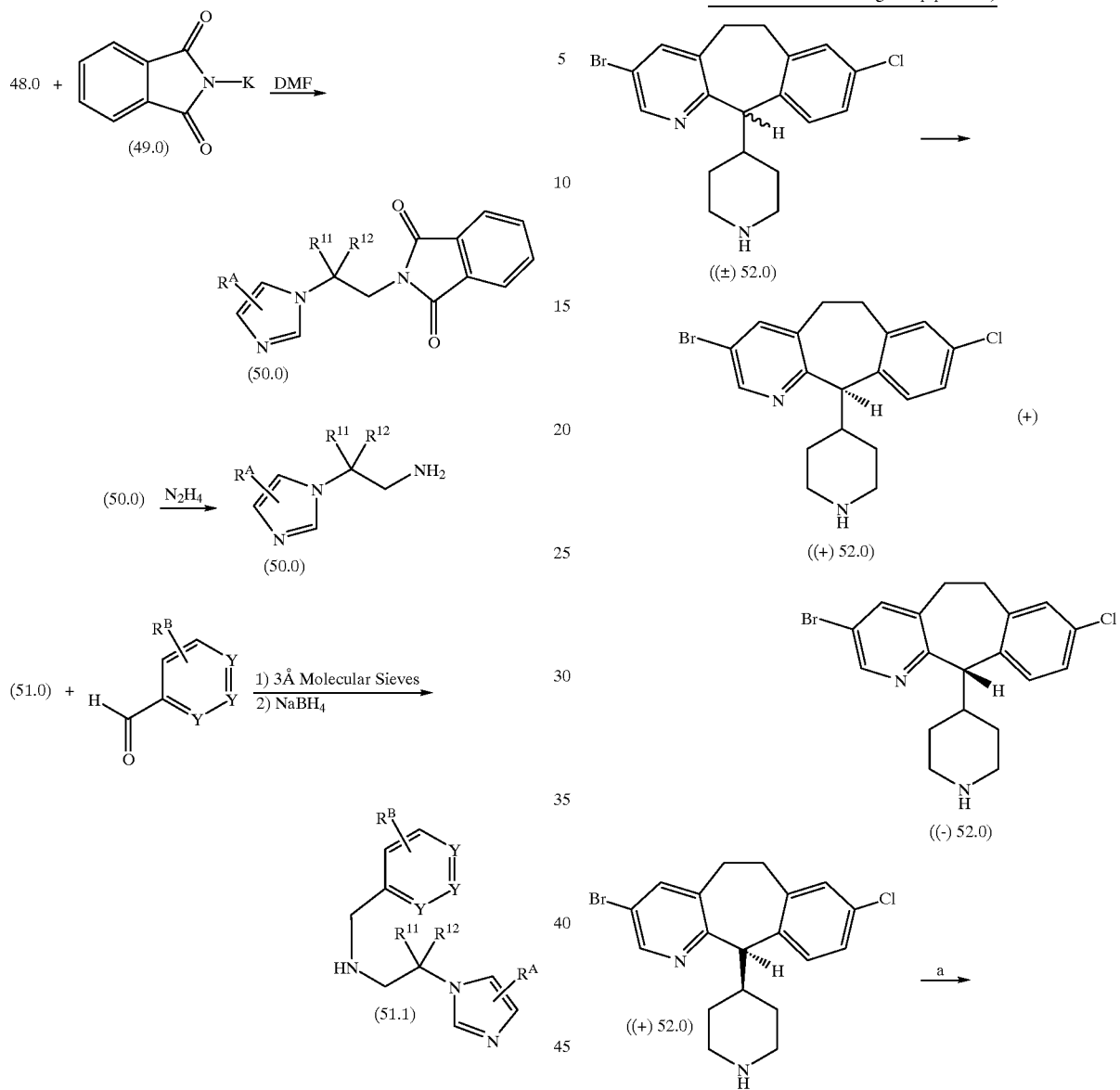

The synthesis of the intermediate amine 51.0 begins with the alkylation of the sodium salt of imidazole (or substituted imidazole) 44.0 with 45.0 at 90° C. Standard LAH reduction of the ester 46.0 gives the alcohol 47.0. Tosylation of 47.0 and displacement of tosylate with potassium phthalimide 49.0 in DMF at 90° C. gives the phthalimido derivative 50.0 which can be readily converted to the amine 51.0 with hydrazine in refluxing EtOH. Compounds wherein $R^8 \neq H$ can be prepared as described in Scheme 1.

Similar to the procedure set forth in Scheme 1 for 36.0 and 36.1, 51.0 and 51.1 in Scheme 2 are reacted to form compounds of formula 1.0. In Scheme 2, $R^{11}$ and $R^{12}$ are preferably methyl when H is bound to the amide nitrogen (i.e., when $R^8$ in formula 1.0 is H), and are preferably H when the amide nitrogen is substituted (i.e., $R^8$ in formula 1.0 is other than H).

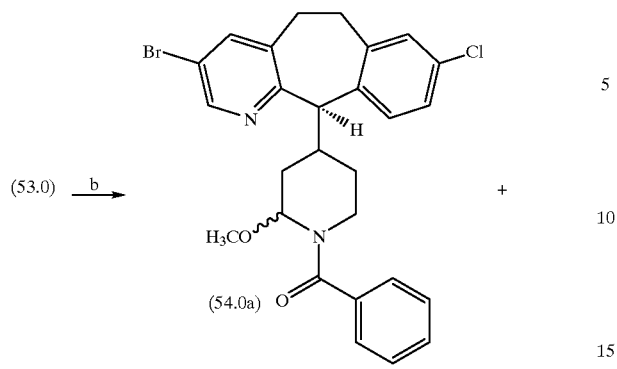
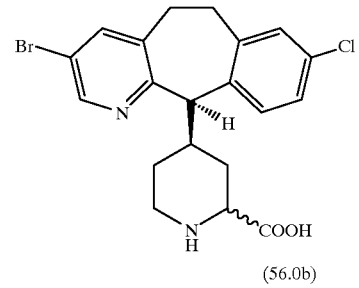
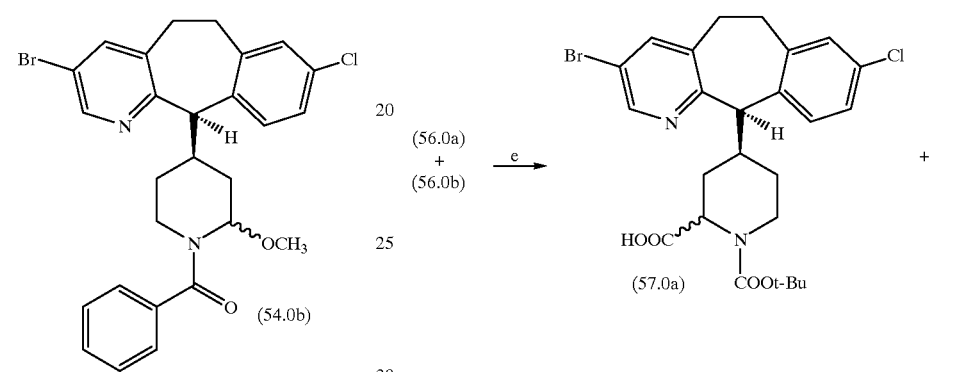
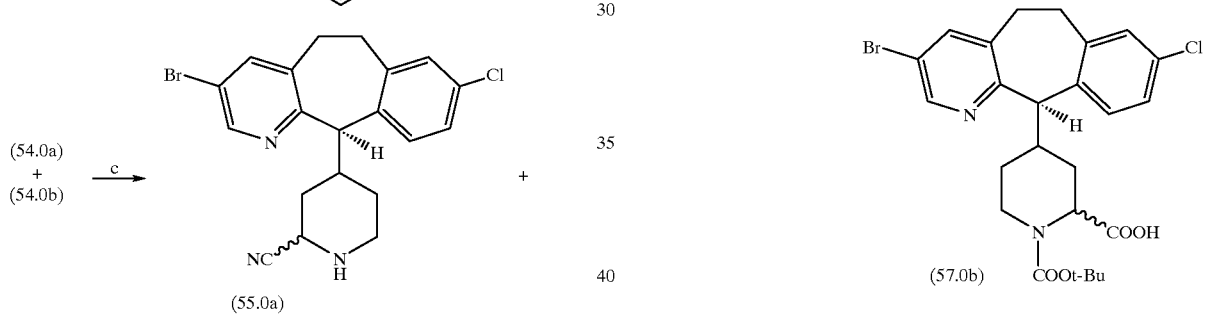
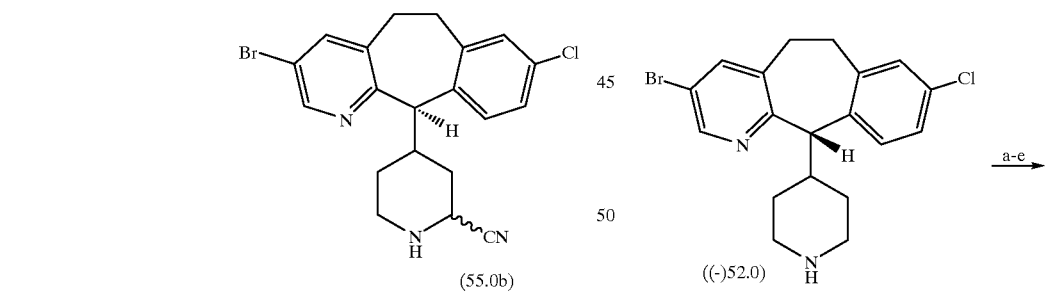
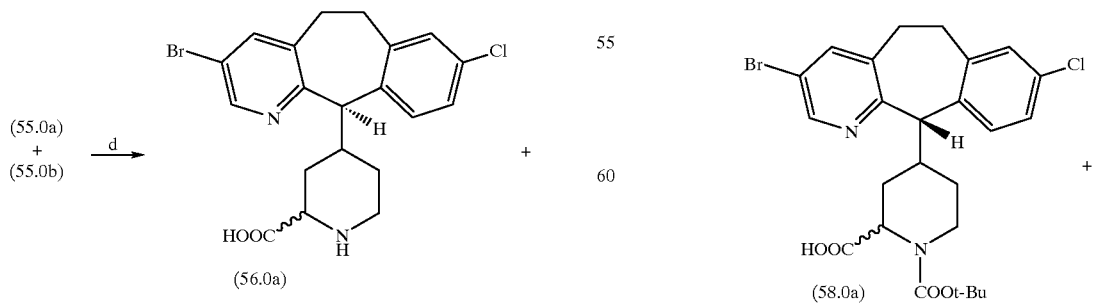

-continued

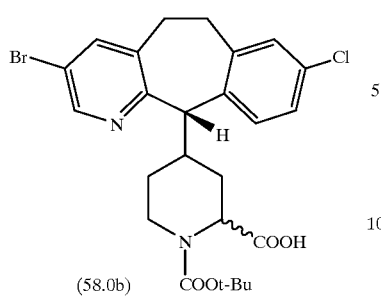

(58.0b)

Compound (±) 52.0 is resolved following procedures similar to those disclosed in WO97/23478 (published Jul. 3, 1997).

The reagents used in Reaction Scheme 3 are: Reaction Step a: Isatoic anhydride/methylene chloride; Reaction Step b: sodium nitrite/hydrochloric acid/methanol/cuprous chloride; Reaction Step c: (i) aq. hydrochloric acid/methanol/reflux (ii) sodium hydroxide/sodium cyanide; Reaction Step d: conc. hydrochloric acid/reflux.; and Reaction Step e: di-tert.butyldicarbonate/-sodium hydroxide/tetrahydrofuran.

Reaction Scheme 4 (n is 1–5)

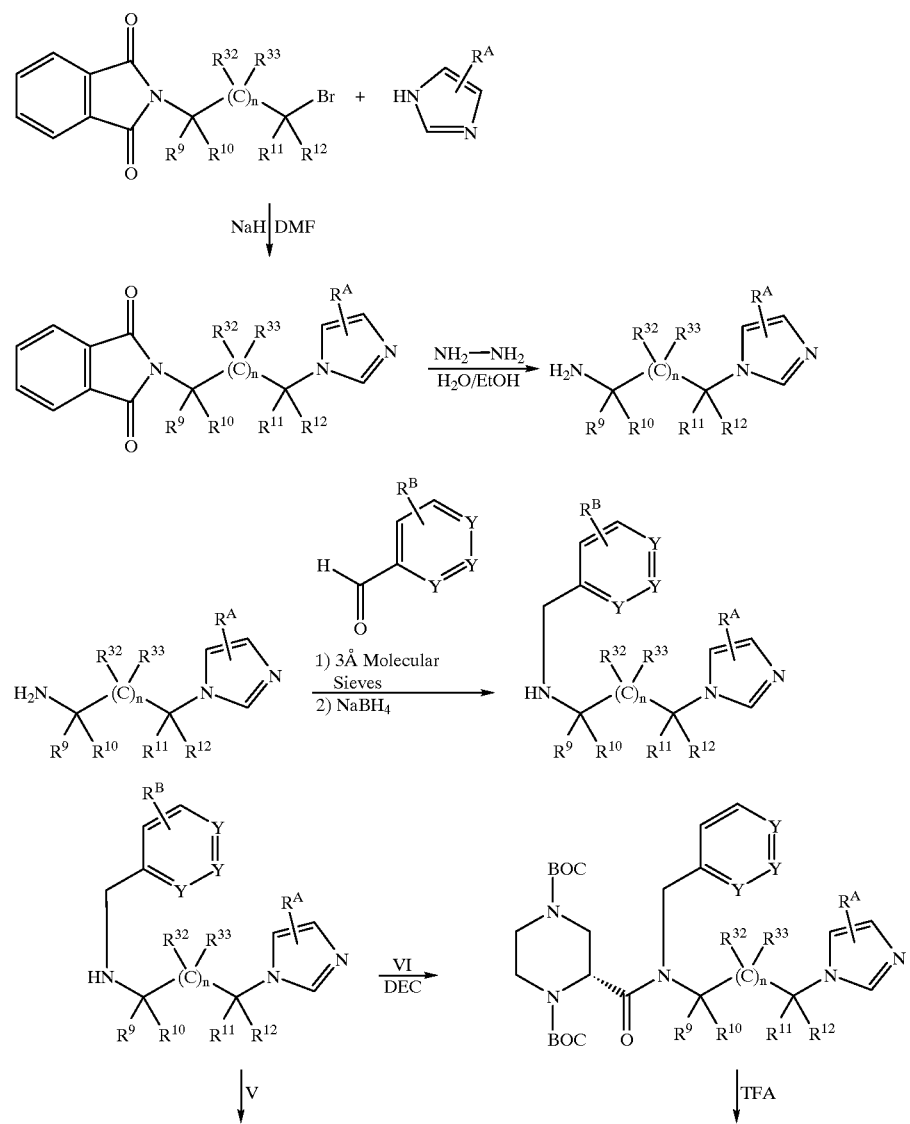

-continued
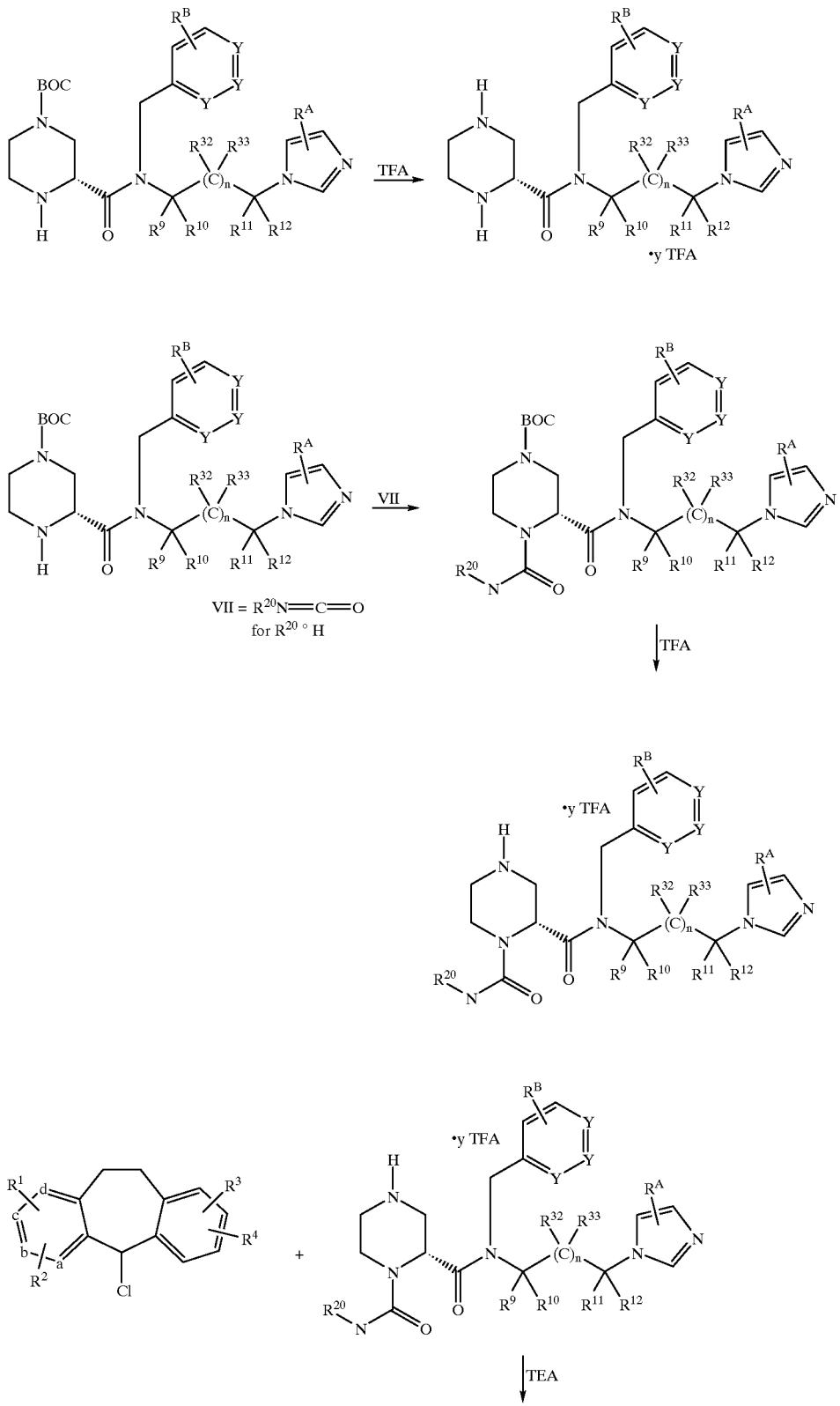

-continued
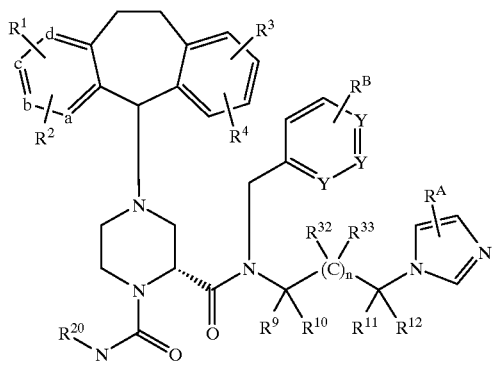
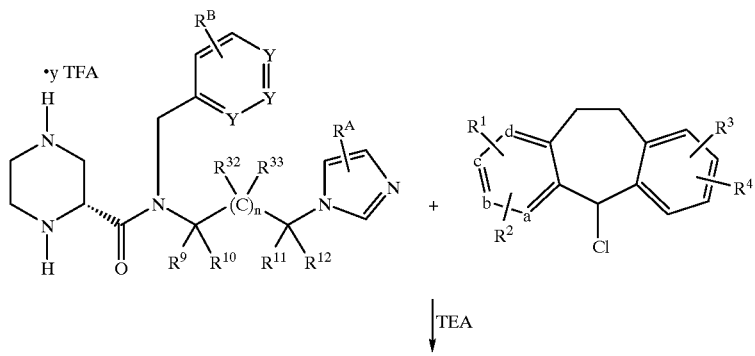
↓ TEA
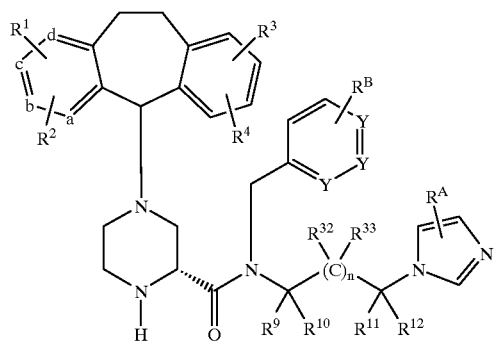
(VIII)
(VIII) + R²⁰N=C=O →
for R²⁰ ≠ H
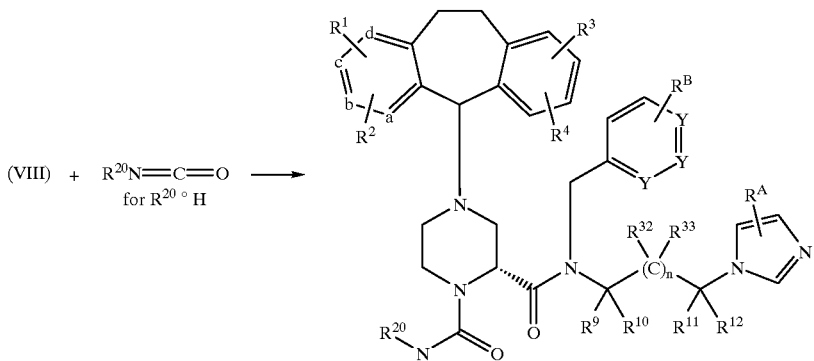

-continued
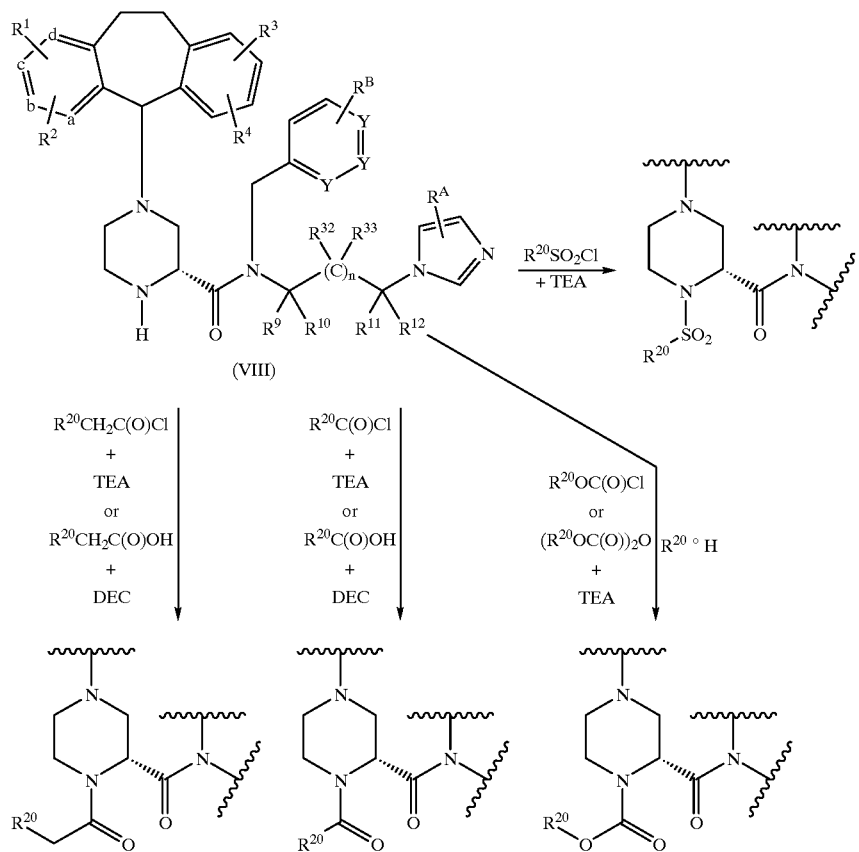
Reactants V and VI are:
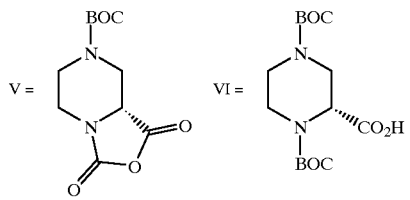
Reaction Scheme 5
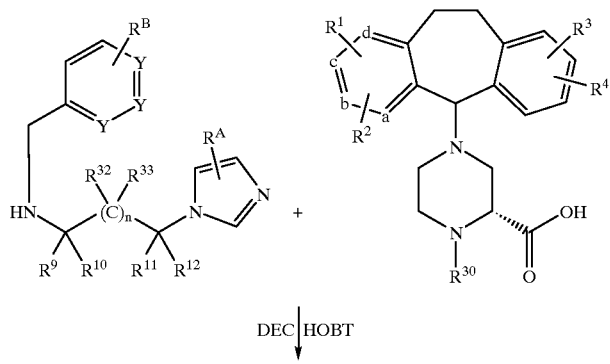
DEC | HOBT -continued
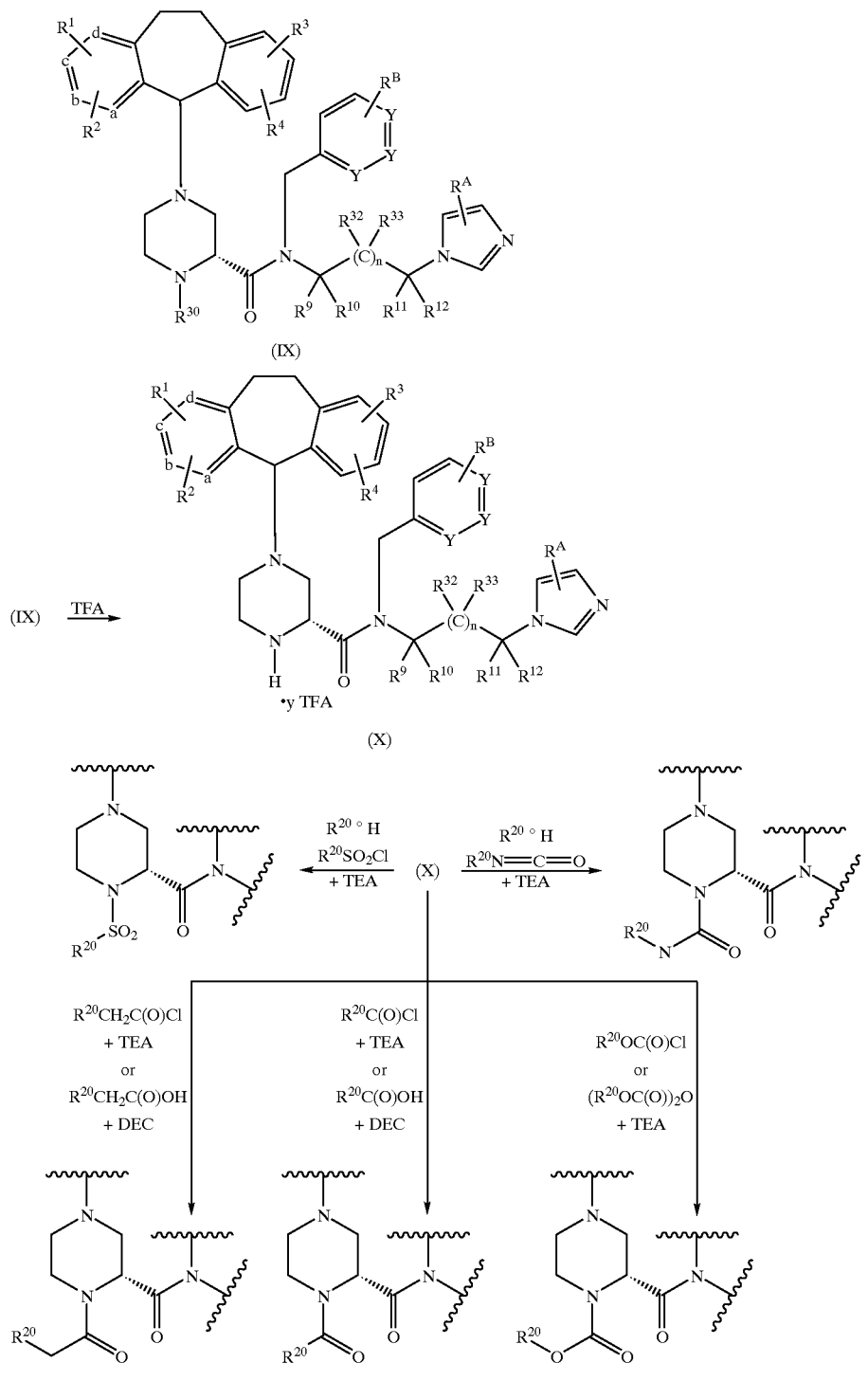
In Scheme 5, $R^{30}$ represents
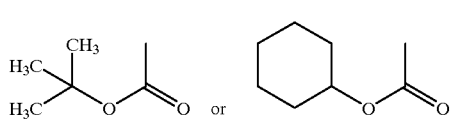
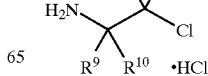
Reaction Scheme 6 - n is 0
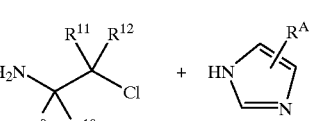

-continued

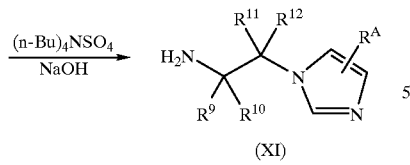 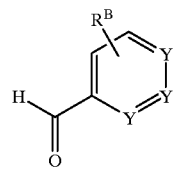

(XI)

In Scheme 6, the procedure set forth in Scheme 4 is followed, but using

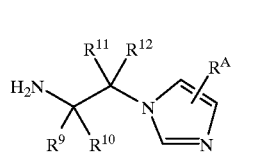

(XI)

instead of

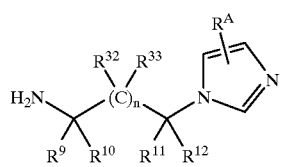

to obtain the corresponding urea (—C(O)NHR$^{20}$), amide (—C(O)CH$_2$R$^{20}$ or —C(O)R$^{20}$), sulfonamide (—SO$_2$R$^{20}$) or carbamate (—C(O)OR$^{20}$) products, wherein n is 0, can be prepared. Similarly, using

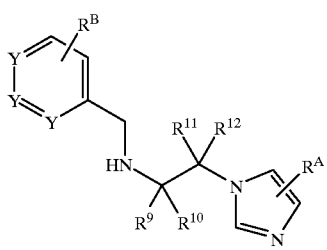

(obtained from XI following the procedures in Scheme 4), instead of

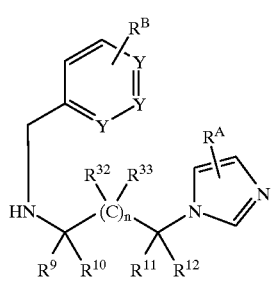

in Scheme 4 and 5 produces the corresponding ureas, amides, sulfonamides and carbamates wherein n is 0.

Those skilled in the art will appreciate that in Schemes 1, 2 and 4–6, other aldehydes can be used in place of to obtain the other substituents for R$^8$ in formula 1.0.

Those skilled in the aft will also appreciate that using

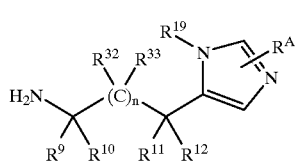

instead of

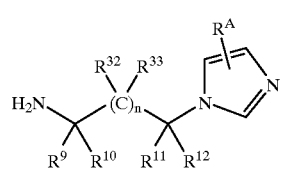

in Schemes 4 and 5, and using

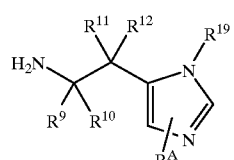

instead of

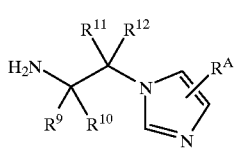

in Scheme 6 will provide the corresponding compounds wherein the imidazole is bound to the alkyl chain by a ring carbon.

Reaction Scheme 7 (R$^9$ and R$^{10}$ Are Other Than H)

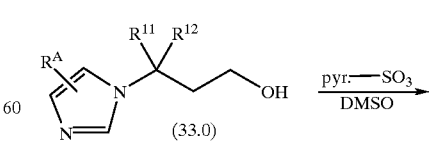

(33.0)

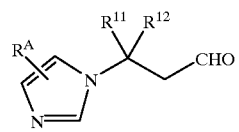

-continued

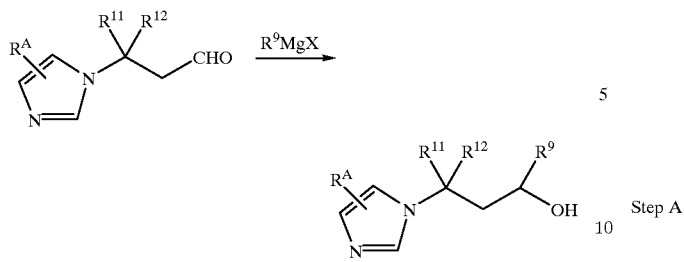

In Scheme 7, the alcohol 33.0 can be oxidized under standard conditions to give the aldehyde. Addition of the corresponding Grignard of $R^9$ gives the alcohol which can be carried on to amine as in Scheme 1 or subject to reoxidation to the ketone followed by Grignard addition of $R^{10}$. In the case where $R^9=R^{10}$, the ester 32.0 (Scheme 1) can be used as the electrophile with 2 equivalents of the appropriate Grignard reagent being added.

Reaction Scheme 8 ($R^9$ and $R^{10}$ Are Other Than H, C-Linked Imidazole)

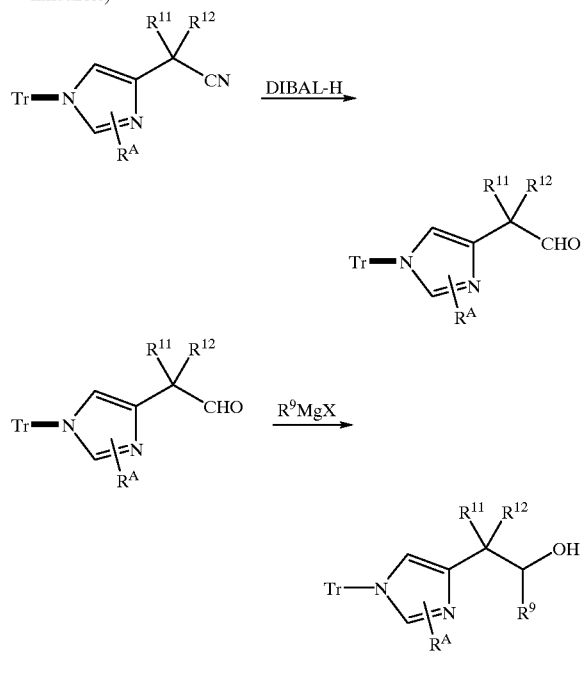

In Scheme 8, the nitrile may be reduced with DIBAL-H to the aldehyde. Similar to the procedure in Scheme 7, the aldehyde can then be treated with the appropriate Grignard reagent to give the alcohol. There can be an additional round of oxidation and Grignard addition to give the $R^9$, $R^{10}$ disubstituted derivatives with either $R^9=R^{10}$ or $R^9.R^{10}$. The resulting alcohol may be converted to the amine by the methodology shown in either Schemes 1 or 2.

Compounds useful in this invention are exemplified by the following examples, which examples should not be construed as limiting the scope of the disclosure.

PREPARATIVE EXAMPLE 1

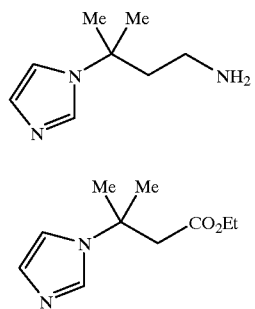

Step A

Ethyl 2,2-dimethyl acrylate (50.0 g, 2.0 eq.) was stirred with imidazole (13.28 g, 200 mmol) at 90° C. for 48 hours. The resulting solution was cooled, diluted with water (150 mL) and $CH_2Cl_2$(150 mL) and separated. The aqueous layer was washed with $CH_2Cl_2$(2×75 mL) and the combined organics were dried over $Na_2SO_4$ and concentrated in vacuo. The crude mixture was purified by flash chromatography using a 10% MeOH in $CH_2Cl_2$ solution as eluent to give the pure product as a clear oil (11.27 g, 29% yield). CIMS: $MH^+$=197.

Step B

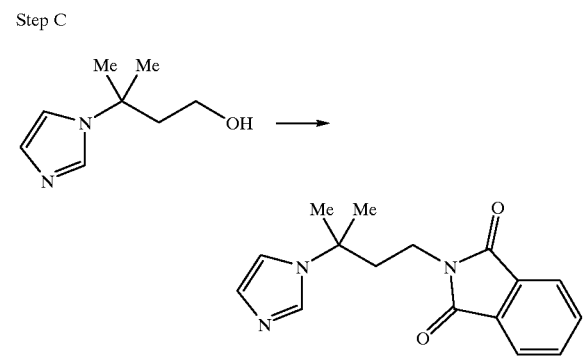

A solution of the title compound from Step A (10.0 g, 50.96 mmol) was treated with $LiAlH_4$ (51 mL, 1M solution in ether, 1.0 eq.). The reaction mixture was stirred one hour at room temperature before quenching by the dropwise addition of saturated $Na_2SO_4$ (~3.0 mL). The resulting slurry was dried with $Na_2SO_4$ (solid), diluted with EtOAc (100 mL) and filtered through a plug of Celite. The filtrate was concentrated to give a yellow oil (6.87, 87% yield) which was used without further purification. CIMS: $MH^+$= 155.

Step C

To a solution of the title compound Step B (6.85 g, 44.42 mmol), phthalimide (7.19 g, 1.1 eq.), and $Ph_3P$ (12.82 g, 1.1 eq.) in THF (200 mL) at 0° C. was added DEAD (7.69 mL, 1.1 eq.) over 10 minutes. The resulting solution was warmed to room temperature and stirred 48 hours. The reaction mixture was concentrated under reduced pressure and the product isolated by crystallization from CH$_2$Cl$_2$/Et$_2$O to give a white solid (10.03 g, 79% yield). CIMS: MH$^+$=284

Step D

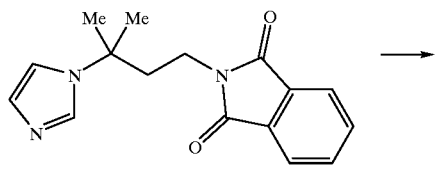

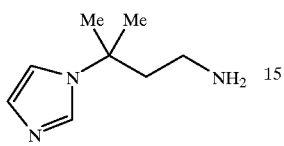

A solution of the title compound from Step C (9.50 g, 33.53 mmol) and N$_2$H$_4$ (1.25 mL, 1.2 eq.) in EtOH (100 mL) was heated at reflux 4 hours. The resulting slurry was cooled, filtered, and the filtrate concentrated under reduced pressure. The crude product was purified by flash chromatography using a 15% (10% NH$_4$OH in MeOH) solution in CH$_2$Cl$_2$ as eluent to give a pale yellow oil (2.80 g, 53% yield). LCMS: MH$^+$=154

Preparative Examples 2–4

By essentially the same procedure as that set forth in Example 1, the amines in Column 3 of Table 1 were synthesized from the esters in Column 2. "No." represents "Preparative Example Number".

TABLE 1

| No. | ESTER | AMINE | Mass Spec |
|---|---|---|---|
| 2 | cyclopropylidene-CO$_2$Et | 1-(1-(2-aminoethyl)cyclopropyl)imidazole | CIMS: MH$^+$ = 152 |
| 3 | 4-Cl-C$_6$H$_4$-CH=CH-CO$_2$Et | 4-Cl-phenyl-CH(imidazolyl)-CH$_2$CH$_2$NH$_2$ | CIMS: MH$^+$ = 236 |
| 4 | Me$_2$CH-CH=CH-CO$_2$Et | Me$_2$CH-CH(imidazolyl)-CH$_2$CH$_2$NH$_2$ variant | MH$^+$ = 168 |

PREPARATIVE EXAMPLE 5

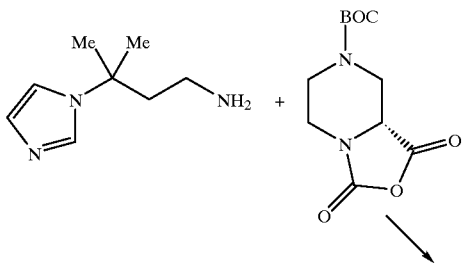

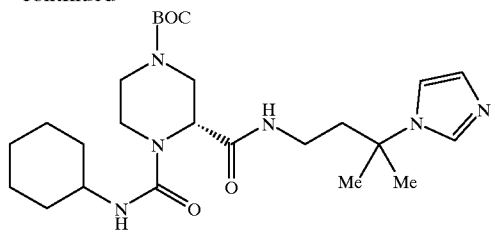

Piperazine anhydride (Preparative Example 44) (0.28 g, 1.0 eq.) was added portionwise to a solution of the title compound from Example 1 (0.17 g, 1.2 mmol) in $CH_2Cl_2$ (5.0 mL) and the resulting solution stirred 10 minutes at room temperature before adding cyclohexyl isocyanate (0.21 mL, 1.5 eq.). After stirring at room temperature 15 minutes, the reaction mixture was quenched by the addition of MeOH (1 mL), concentrated in vacuo, and purified by flash chromatography using a 10% MeOH in $CH_2Cl_2$ solution as eluent to yield a white solid (0.46 g, 85% yield). FABMS: $MH^+$=491.

PREPARATIVE EXAMPLE 6

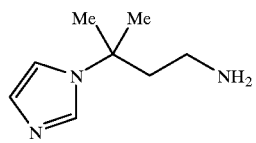

+

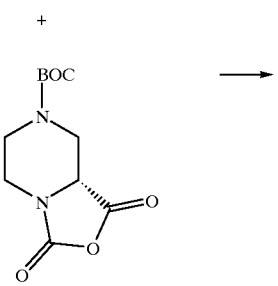

→

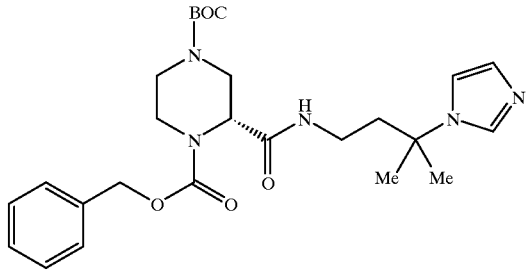

By the essentially the same procedure as that set forth in Preparative Example 5, except using ═N-(benzyloxycarbonyloxy)-succinimide (CBZ-OSuc) instead of cyclohexyl isocyanate, the title compound was prepared (0.16 g, 84% yield).

Preparative Example 6.1

By essentially the same procedure as set forth in Preparative Example 6, except instead of the amine

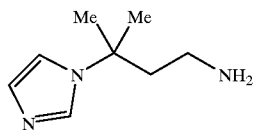

use the amine from Preparative Example 2

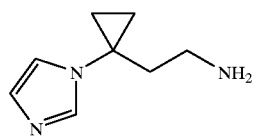

to obtain

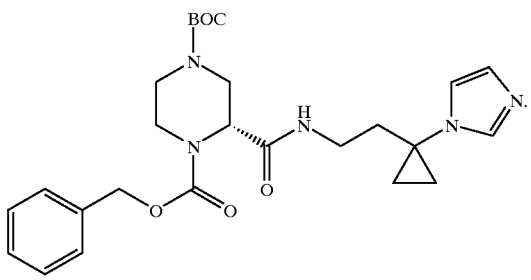

PREPARATIVE EXAMPLE 7

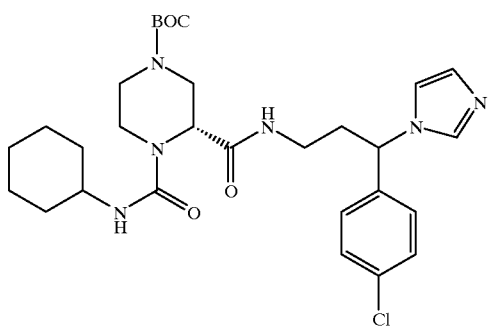

By essentially the same procedure as that set forth in Preparative Example 5, except using the title compound from Preparative Example 3 (Table 1), the title compound was prepared. LCMS: $MH^+$=573.

PREPARATIVE EXAMPLE 7.1

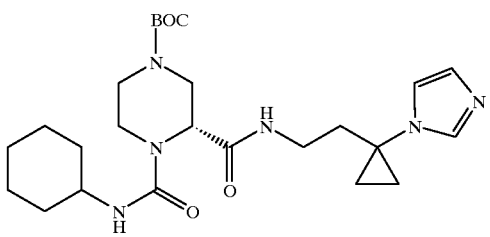

Follow the same procedure as that set forth in Preparative Example 5, except use the amine from Preparative Example 2 to obtain the title compound.

PREPARATIVE EXAMPLE 7.2

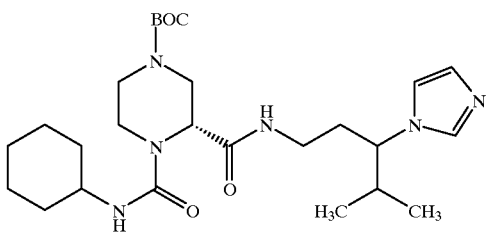

Follow the same procedure as that set forth in Preparative Example 5, except use the amine from Preparative Example 4 to obtain the title compound.

PREPARATIVE EXAMPLE 7.3

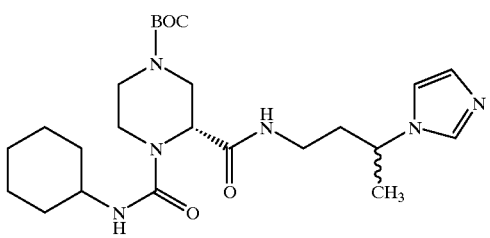

Follow the same procedure as that set forth in Preparative Example 5, except use the amine from Preparative Example 10 to obtain the title compound.

PREPARATIVE EXAMPLE 8

Step A

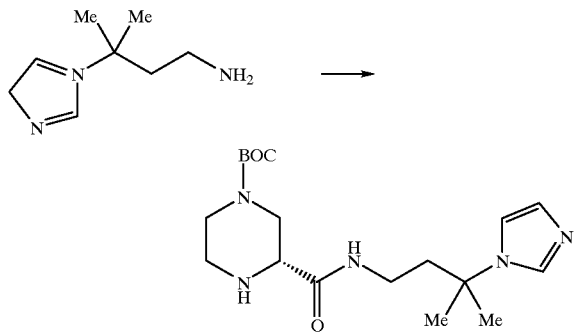

To the title compound from Preparative Example 1, Step D, (0.82 g, 5.35 mmol) in $CH_2Cl_2$ (10 mL) and TEA (0.75 mL, 1.0 eq) was added piperazine anhydride (1.65 g, 1.2 eq.) (prepared as described in Preparative Example 44) portionwise and the resulting solution was stirred at room temperature. When the reaction was complete (TLC), the solution was concentrated in vacuo and the crude product was purified by flash chromatography using a 10% (10% $NH_4OH$ in MeOH) in $CH_2Cl_2$ then 20% (10% $NH_4OH$ in MeOH) in $CH_2Cl_2$ as eluent. CIMS: $MH^+=366$.

Step B

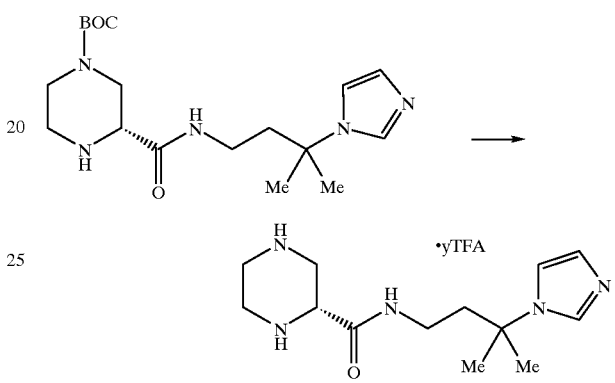

The title compound from Step A was stirred at room temperature in a 50% solution of TFA in $CH_2Cl_2$ (25 mL) for 2 hours. The resulting solution was concentrated under reduced pressure. Any residual TFA was removed by azeotroping with toluene to give the crude product which was used without further purification. CIMS: $MH^+=266$.

Step C

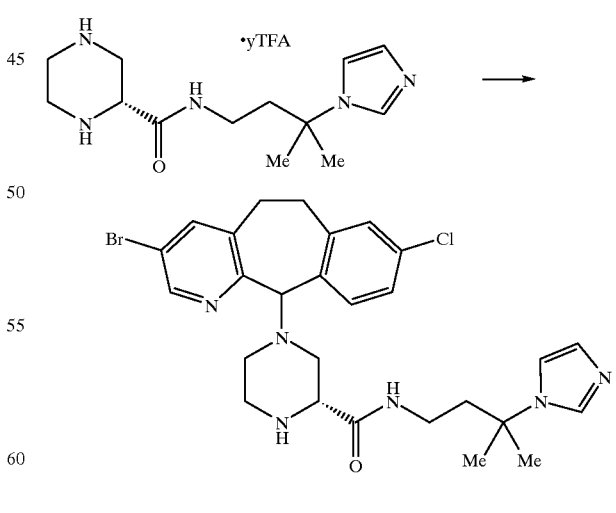

The title compound from Step B was dissolved in $CH_2Cl_2$ (30 mL) and TEA (7.62 mL, 10 eq.) was added. The reaction mixture was stirred 5 minutes before adding chloride (42.0)

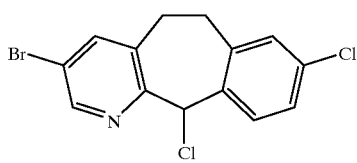

(0.908 g, 0.5 eq.). The resulting solution was stirred at room temperature for 96 hours. The reaction mixture was diluted with water (50 mL), separated and the aqueous layer extracted with CH$_2$Cl$_2$ (2×200 mL). The combined organics were dried over MgSO$_4$, filtered, and concentrated under reduced pressure. The crude product was purified by flash chromatography using a 5%, 7.5%, and then 10% (10% NH$_4$OH in MeOH) in CH$_2$Cl$_2$ solution as eluent (0.926 g, 30% yield). CIMS: MH$^+$=571.

Step D

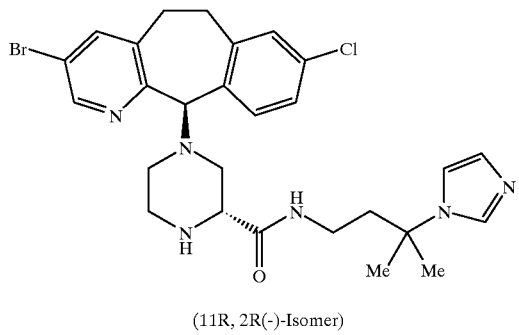

(11R, 2R(-)-Isomer)

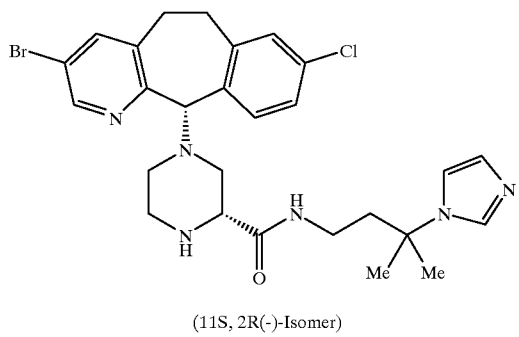

(11S, 2R(-)-Isomer)

The title compound from Step C was separated into individual diasteromers by Preparative HPLC using a ChiralPak AD column using a 20% IPA in hexanes with 0.2% diethylamine solution as, eluent:

Isomer A (11S,2R(-)-Isomer): retention time=18.2 minutes; $[\alpha]^{20}_D$=-31.7 (3.0 mg in 2.0 mL MeOH).

Isomer B (11R,2R(-)-Isomer): retention time=30.3 minutes; $[\alpha]^{20}_D$=-6.2 (2.4 mg in 2.0 mL MeOH).

PREPARATIVE EXAMPLE 9

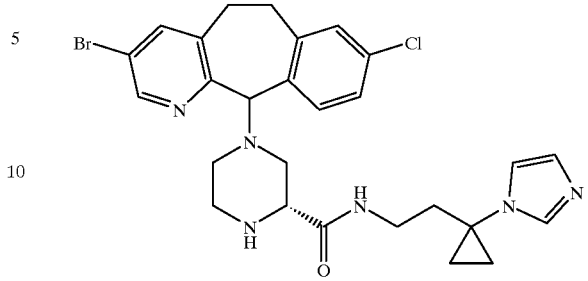

By essentially the same procedure as described in Preparative Example 8, except using the title compound from Preparative Example 2 (Table 1), the title compound was prepared.

The 11(S)- and 11(R)-isomers

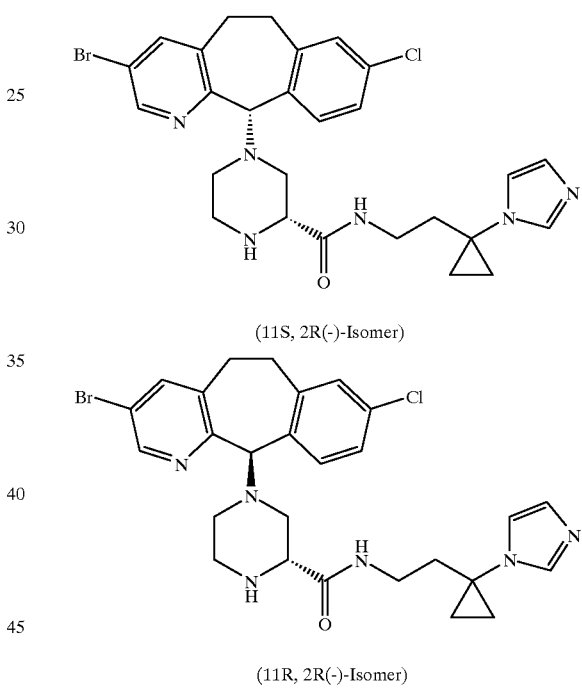

(11S, 2R(-)-Isomer)

(11R, 2R(-)-Isomer)

were separated by Preparative HPLC using a CHIRALPAK AD column using a 30% IPA in hexanes containing 0.2% diethylamine solution as eluent.

11S,2R(-)-isomer: retention time=10.2 minutes; MH$^+$=569; $[\alpha]^{20}_D$=-32.7 (4.04 mg in 2.0 mL MeOH).

11R,2R(-)-isomer: retention time=22.8 minutes; MH$^+$=569; $[\alpha]^{20}_D$=-1.2 (3.40 mg in 2.0 mL MeOH).

Preparative Example 9.1

Follow the procedure set forth in Preparative Example 8, except use the amine

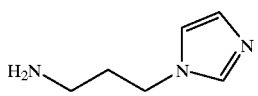

in Step A instead of

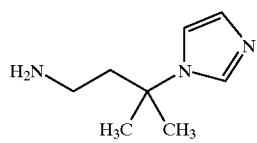

and use the 10-Cl tricycle chloride

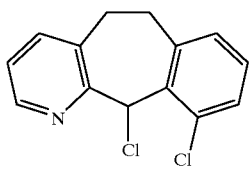

in Step C instead of the 3-Br-8-Cl-tricycle chloride (Compound 42.0) to obtain the compounds

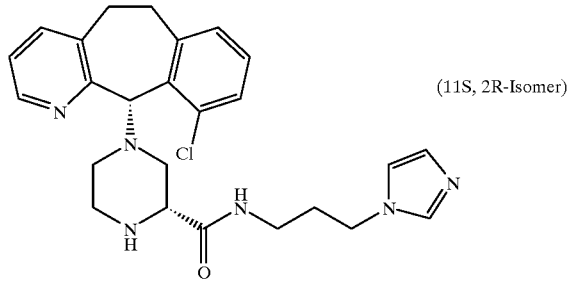

(11S, 2R-Isomer)

and

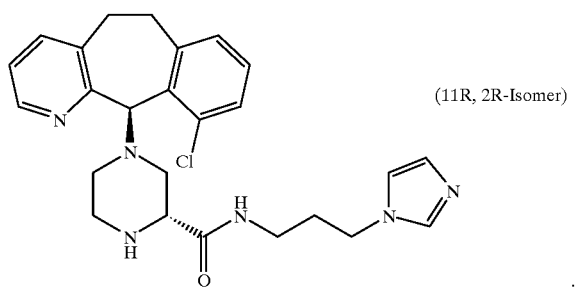

(11R, 2R-Isomer)

Obtain the 10-Cl tricycle chloride (10,11-diChloro-6,11-dihydro-5H-benzo[5,6]cyclohepta[1,2-B]pyridine) as follows:

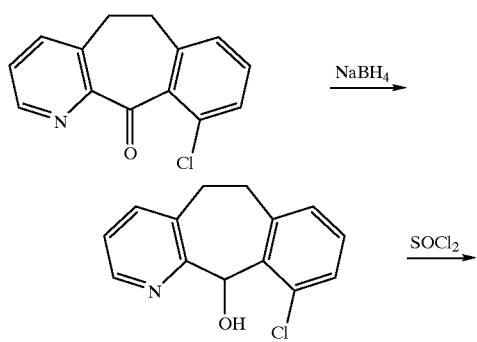

-continued

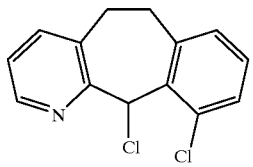

The ketone (starting material) 5,6-dihydro-10-Chloro-11H-benzo[5,6]cyclohepta[1,2-c]pyridine-11-one, can be prepared following the procedure described by Villani et al., J. Het. Chem. 8, 73–81 (1971). The product was prepared substituting the 10-Chloro, for the 10H tricycle and following the procedure described in Preparative Example 169.

1H NMR (CDCl$_3$δ) 2.97 (m, 2H), 3.55 (m, 1H), 4.03 (m, 1H), 7.11 (s, 1H), 7.13 (d, 1H), 7.22 (m, 2H), 7.31 (d, 1H), 7.53 (d, 1H), 8.49 (d, 1H).

PREPARATIVE EXAMPLE 10

Step A

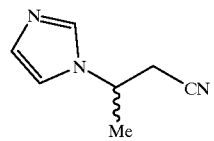

Imidazole (2.73 g, 40.1 mmol) in crotonitrile (10 mL) was heated to reflux overnight. The resulting solution was concentrated in vacuo, the residue diluted with Et$_2$O (50 mL) and washed with water (2×100 mL) and brine (1×25 mL). The combined organics were dried over Na$_2$SO$_4$ and concentrated under reduced pressure. The crude product was purified by flash chromatography using a 15% MeOH in CH$_2$Cl$_2$ solution as eluent (2.13 g, 39% yield). FABMS: MH$^+$=136.

Step B

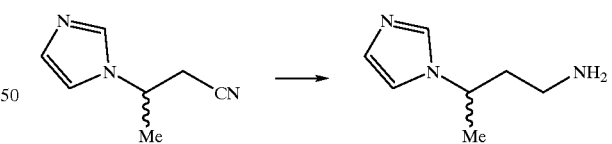

A solution of the title compound from Step A (0.50 g, 0.0037 mmol) in THF (10 mL) was treated with. LAH (5.5 mL, 1.0 M in Et$_2$O, 1.1 eq.). The reaction mixture was stirred at room temperature 3 hours and quenched by the dropwise addition of saturated Na$_2$SO$_4$. The resulting slurry was dried by the addition of solid Na$_2$SO$_4$ and filtered through a plug of Celite. The filtrate was concentrated under reduced pressure and the crude residue purified by flash chromatography using a 20% (10% NH$_4$OH in MeOH) solution as eluent (0.03 g, 6% yield).

PREPARATIVE EXAMPLE 11

Step A

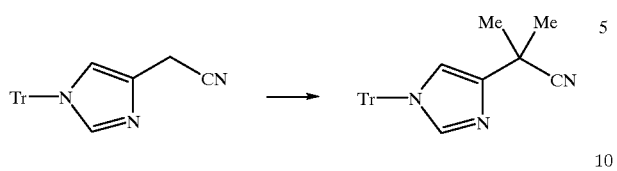

nBuLi (2.5 mL; 2.5M in hexanes; 2.1 eq.) was added to iPr$_2$NH (0.87 mL, 2.1 eq.) in THF (8.0 mL) at 0° C. The resulting solution was stirred 45 minutes before adding the nitrile (1.0 g, 2.97 mmol) in THF (7.0 mL). The reaction mixture was stirred at 0° C. for 30 minutes before adding MeI (0.37 mL, 2.0 eq.). The resulting solution was warmed to room temperature and stirred one hour. The reaction was quenched by the addition of 1N HCl until acidic, diluted with water (40 mL) and extracted with EtOAc (2×200 mL). The combined organics were dried over Na$_2$SO$_4$ and concentrated under reduced pressure. The crude product was purified by flash chromatography using a 40% EtOAc solution in hexanes as eluent (0.37 g, 33% yield). MH$^+$=378.

Step B

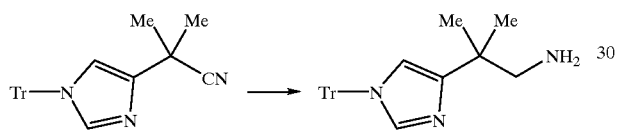

LiAlH$_4$ (2.7 mL; 1.0 M solution in THF; 1.5 eq.) was added to the title compound from Step A (0.68 g, 1.80 mmol) in THF (5.0 mmol). The resulting solution was stirred at room temperature 1.5 hours and quenched by the dropwise addition of saturated NA$_2$SO$_4$ (10 mL). The solution was extracted with Et$_2$O(2×200 mL), the combined organics dried over MgSO$_4$ and concentrated under reduced pressure (0.6 g, 88% yield).

Step C

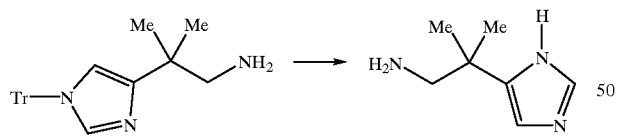

Following the same procedure as set forth in Preparative Example 27 Step C, the title compound was prepared.

PREPARATIVE EXAMPLE 12

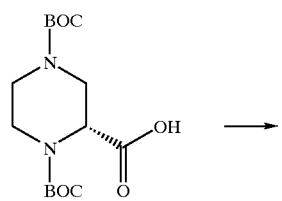

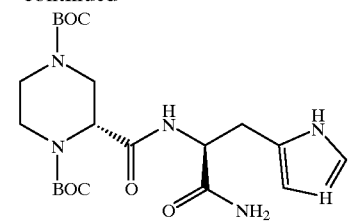

A solution of the piperazine carboxylic acid (0.29 g, 0.881 mmol) prepared as described in Preparative Example 43, L-histidinamide dihydrochloride (0.20 g, 1.0 eq.), DEC (0.25 g, 1.5 eq.), HOBT (0.18 g, 1.5 eq.), and NMM (0.48 mL, 1.5 eq.) in DMF (5 mL) was stirred at room temperature overnight. The reaction mixture was diluted with water (25 mL) and CH$_2$Cl$_2$ (50 mL), separated, and the aqueous layer extracted with CH$_2$Cl$_2$ (2×50 mL). The combined organics were dried over NA$_2$SO$_4$ and concentrated under reduced pressure. The crude product was purified by flash chromatography using a 15% MeOH in CH$_2$Cl$_2$ solution as eluent (0.24 g, 59% yield). FABMS: MH$^+$=467.

Preparative Examples 13–17

Following the procedures found in J. Chem. Soc. Perkin I (1979), 1341–1344, the following N-substituted histamines were prepared:

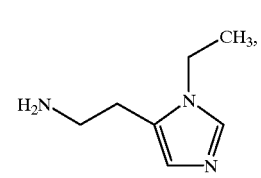

Preparative Example 13

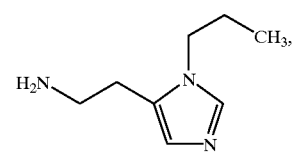

Preparative Example 14

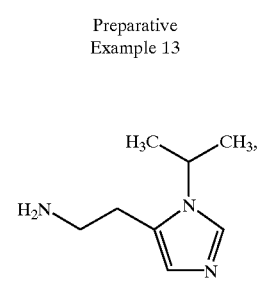

Preparative Example 15

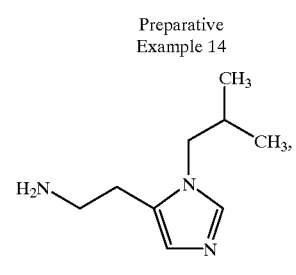

Preparative Example 16 and

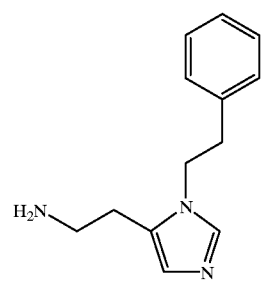

Preparative Example 17

Preparative Examples 18–26

By essentially the same procedure as that set forth in Preparative Example 74, and using the aldehydes and amines set forth in Table 2, one can obtain the intermediate products shown in Table 2.

TABLE 2

| Prep Ex. | Aldehyde | Amine | Product |
|---|---|---|---|
| 18 | benzaldehyde | 2-(1H-imidazol-5-yl)ethylamine | N-benzyl-2-(1H-imidazol-5-yl)ethylamine |
| 19 | benzaldehyde | 2-(1-methyl-1H-imidazol-5-yl)ethylamine | N-benzyl-2-(1-methyl-1H-imidazol-5-yl)ethylamine |
| 20 | pivaldehyde (2,2-dimethylpropanal) | 2-(1-methyl-1H-imidazol-5-yl)ethylamine | N-(2,2-dimethylpropyl)-2-(1-methyl-1H-imidazol-5-yl)ethylamine |
| 21 | isobutyraldehyde | 2-(1-methyl-1H-imidazol-5-yl)ethylamine | N-isobutyl-2-(1-methyl-1H-imidazol-5-yl)ethylamine |
| 22 | isobutyraldehyde | 2-(1H-imidazol-5-yl)ethylamine | N-isobutyl-2-(1H-imidazol-5-yl)ethylamine |
| 23 | cyclohexanecarboxaldehyde | 2-(1-methyl-1H-imidazol-5-yl)ethylamine | N-(cyclohexylmethyl)-2-(1-methyl-1H-imidazol-5-yl)ethylamine |

TABLE 2-continued

| Prep Ex. | Aldehyde | Amine | Product |
|---|---|---|---|
| 24 | | | |
| 25 | | | |
| 26 | | | |

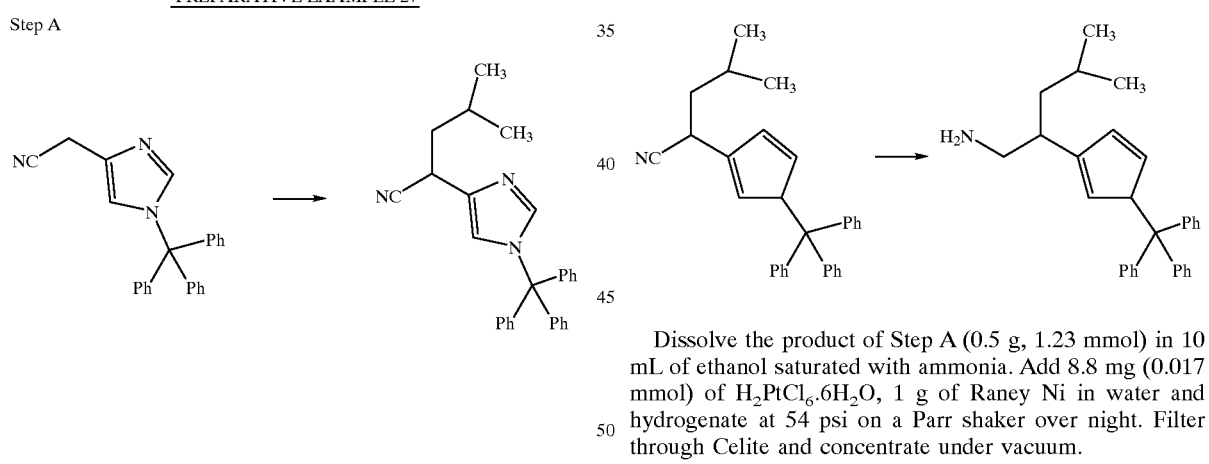

PREPARATIVE EXAMPLE 27

Step A

Dissolve the nitrile (1.5 g, 4.29 mmol) in 10 mL of THF and cool to −78° C. under nitrogen. Add 20 mL of a 1.5 M LDA solution (in cyclohexane). Then add dropwise over 2 hr. a solution of 790 mg (4.293 mmol) of 2-methylpropyliodide in 10 mL of THF. Allow to warm to room temperature and stir overnight. Add 10 mL of water followed by 1N HCl until pH of 10–11. Dilute with 100 mL of methylene chloride followed by 20 mL of sat. aqueous $Na_2SO_4$. Add $MgSO_4$ until solution is clear. Separate the organic layer and dry over $MgSO_4$. Concentrate under vacuum and flash chromatograph on silica gel using ethyl acetate-hexane (1–3) to give the product as a tan semi-solid.

Step B

Dissolve the product of Step A (0.5 g, 1.23 mmol) in 10 mL of ethanol saturated with ammonia. Add 8.8 mg (0.017 mmol) of $H_2PtCl_6 \cdot 6H_2O$, 1 g of Raney Ni in water and hydrogenate at 54 psi on a Parr shaker over night. Filter through Celite and concentrate under vacuum.

Step C

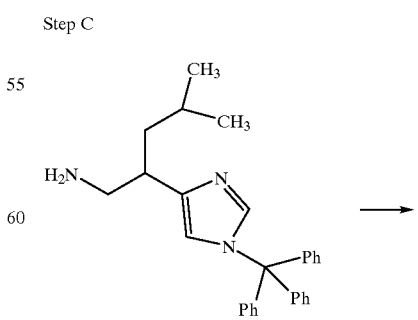

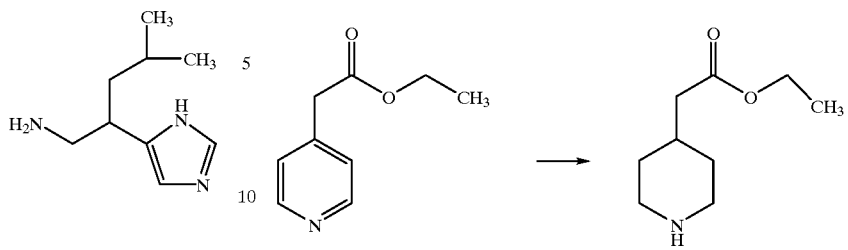

Dissolve the product of Step B (0.165 g, 0.403 mmol) in 4 mL of 2M HCl and 2 mL of methanol. Reflux for 100 min. then concentrate under vacuum. Triturate the residue with ether to give the product hydrochloride as a white solid.

Preparative Examples 28 –29, 29.1 and 30

Following the procedure set forth in Preparative Example 27, but using the indicated alkyl or benzyl halide in place of 2-methyl propyl iodide, the substituted histamines shown were prepared.

Preparative Example 28

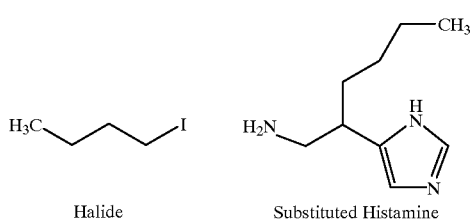

Halide     Substituted Histamine

Preparative Example 29

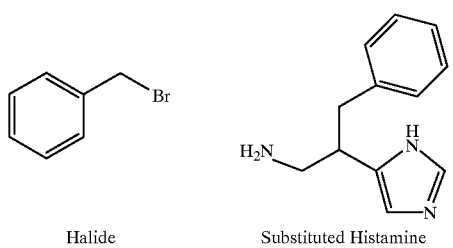

Halide     Substituted Histamine

Preparative Example 29.1

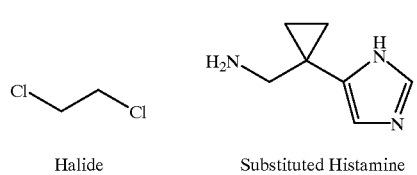

Halide     Substituted Histamine

Preparative Example 30

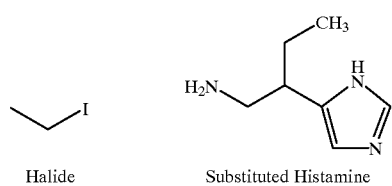

Halide     Substituted Histamine

PREPARATIVE EXAMPLE 31

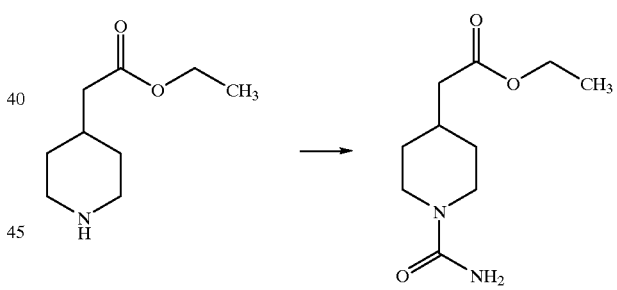

Ethyl 4-pyridyl acetate (4.5 g, 27.24 mmoles) was placed in a 500 mL Parr bottle and dissolved in anhydrous EtOH (70 mL). To the bottle was added 10% Palladium on charcoal (1.0 g). The bottle was put on a hydrogenator and the contents shaken under 55 psi hydrogen pressure at 25° C. for 94 h. The mixture was filtered through Celite® and washed with 4×40 mL anhydrous EtOH. The filtrate was rotovapped down and the residue chromatographed on silica gel using 3% (10% conc. $NH_4OH$ in methanol) dichloromethane as the eluant to give the title compound (Yield: 2.944 g, 63%): FABMS: m/z 172.2($MH^+$); $\delta_C$ ($CDCl_3$) $CH_3$: 14.3; $CH_2$: 33.2, 33.2, 41.9, 46.5, 46.5 60.2; CH: 33.4; C: 172.7; $\delta_H$ ($CDCl_3$) 1.18 (m,1H,H), 1.26 (t,3H,$CH_3$), 1.71(2H) , 1.90(1H), 1.96(1H), 2.22(d,2H), 2.63 (2H), 3.07(2H), 4.13(q,2H,$CH_3\underline{CH_2}$—).

PREPARATIVE EXAMPLE 32

Ethyl 4-piperidinyl acetate from Preparative Example 31 (500 mg; 2.92 mmoles) was dissolved in anhydrous $CH_2Cl_2$ (25 mL). To the stirring solution was added trimethylsilyl isocyanate (5.9 mL; 43.8 mmoles) and the solution was stirred at 25° C. for 17 h. The solution was worked up in $CH_2Cl_2$-saturated $NaHCO_3$ and the product chromatographed on silica gel using 2→3%(conc. $NH_4OH$ in methanol)dichloro-methane as the eluant to give the title compound, (Yield: 622 mg, 99%): CIMS: m/z 215.3 ($MH^+$); $\delta_C$ ($CDCl_3$): $CH_3$: 14.2; $CH_2$: 31.6, 31.6, 41.0, 44.2, 44.2, 60.4; CH: 32.9; C: 158.2, 172.4; $\delta_H$ ($CDCl_3$): 1.23 (m,1H, $H_4$), 1.27 (t,3H,$CH_3$), 1.75 (d,2H), 1.98 (m,1H), 2.26 (d,2H), 2.85 (t,2H), 3.94 (d, 2H), 4.15 (q,2H,$CH_3\underline{CH_2}$), 4.56 (bs, 2H).

PREPARATIVE EXAMPLE 33

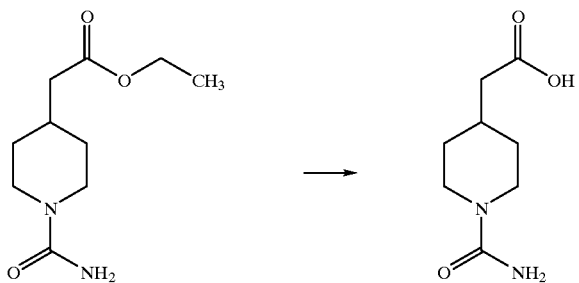

Ethyl 1-aminocarbonyl-4-piperidinyl acetate from Preparative Example 32 (153.6 mg, 0.717 mmoles) was dissolved in anhydrous $CH_2Cl_2$ (3.58 mL) and EtOH (3.58 mL). To the solution was added 1.0M LiOH (1.73 mL, 1.73 mmoles) and the mixture was stirred at 50° C. for 5.5 h. The mixture was cooled quickly to 25° C. and 1.0N HCl (2.02 mL, 2.02 mmoles) was added and the mixture stirred for 5 minutes and then rotovapped to dryness to give the title compound which was used without further purification.

PREPARATIVE EXAMPLE 34

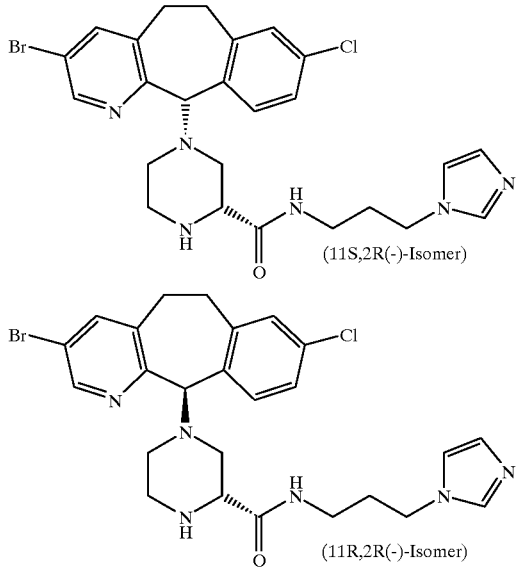

The $C_{11}$-racemate of the above isomers (Preparative Example 141) (62% pure) was subjected to preparative HPLC on a Chiralpak AD® column (50×5 cm) using 75% hexane—25% isopropyl alcohol—0.2% diethylamine as the eluant to give, in the order of elution, the 11-S(−)-isomer and the 11-R(−)-isomer.

11S2R(−)-isomer: (Yield: 0.8756 g, 55%): LCMS: m/z 543.1 (MH⁺); $\delta_C$ (CDCl$_3$) CH$_2$: 30.3, 30.4, 31.0, 36.3, 44.3, 44.7, 52.0, 54.5; CH: 58.7, 79.4, 118.8, 126.0, 129.6, 130.4, 132.3, 137.1, 141.3, 147.0; C: 120.0, 134.0, 135.4, 136.7, 140.9, 155.4, 172.2; $\delta_H$ (CDCl$_3$) 2.02 (2H, m, 2"-CH$_2$), 3.32 (2H, m, 3"-CH$_2$), 3.98 (2H, dd, 1"—CH$_2$), 4.30 (1H, s, H$_{11}$), 6.93 (1H, s, Im-H$_5$), 6.97 (1H, t, CONHCH$_2$), 7.06 (1H, s, Im-H$_4$), 7.11 (1H, s, Ar—H), 7.13 (2H, s, Ar—H), 7.16 (1H, s, Ar—H), 7.49 (1H, s, Ar—H$_{10}$), 7.57 (1H, d, Im-H$_2$) and 8.33 ppm (1H, s, Ar—H$_2$); $[a]_D^{20°\ C.}$-45.0° (MeOH, c=9.32 mg/2 mL).

11R,2R(−)-isomer: (Yield: 0.5979 g, 38%): LCMS: m/z 543.1 (MH⁺); $\delta_C$ (CDCl$_3$) CH$_2$: 30.2, 30.3, 31.1, 36.4, 44.1, 44.7, 52.2, 54.0; CH: 58.2, 79.4, 118.8, 126.1, 129.6, 130.7, 132.3, 137.0, 141.2, 146.8; C: 119.9, 134.0, 135.2, 136.9, 140.7, 155.7, 172.1; $\delta_H$ (CDCl$_3$) 3.34 (2H, m, 3"-CH$_2$), 3.97 (2H, dd, 1"-CH$_2$), 4.30 (1H, s, H$_{11}$), 6.93 (1H, s, Im-H$_5$), 7.06 (1H, s, Im-H$_4$), 7.08 (1H, s, Ar—H), 7.11 (2H, s, Ar—H), 7.14 (1H, s, Ar—H), 7.15 (1H, t, CONHCH$_2$), 7.50 (1H, s, Ar—H$_{10}$), 7.58 (1H, d, Im- H$_2$) and 8.35 ppm (1H, s, Ar—H$_2$); $[a]_D^{23.5°\ C.}$-12.0° (MeOH, c=10.19 mg/2 mL).

PREPARATIVE EXAMPLE 35

Step A

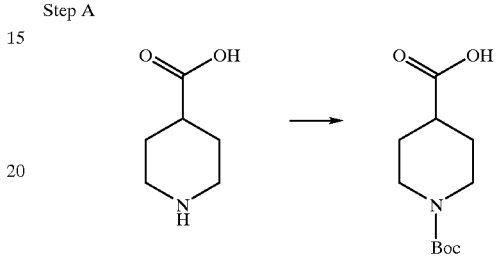

Isonipecotic acid (10 g, 77.42 mmoles) and sodium hydroxide (3.097 g, 77.42 mmoles) were dissolved in THF-water (1:1) (230 mL) and di-t-butyldicarbonate (18.59 mL, 85.17 mmoles) was added. The solution was stirred at 25° C. for 90 h. The mixture was treated with BioRad® 50W-X4 (H⁺) ion exchange resin (86.6 mL) and the resin was filtered off and washed with THF and then water. The combined filtrates were evaporated to dryness to give the title compound which was used without further purification in the next step: FABMS: m/z 229.9 (MH⁺); $\delta_c$ (d$_6$-DMSO) CH$_3$: 28.0, 28.0, 28.0; CH$_2$: 42.0–43.1((broad signal); CH: obscured; C: 78.5, 153.8, 175.6.

Step B

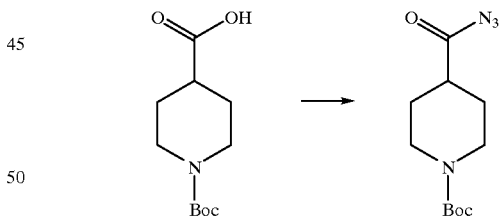

The title compound from Step A above (2 g, 8.72 mmoles) was dissolved in dry DMF (40 mL) and the solution was stirred at 0° C. under an argon atmosphere. Diphenylphosphoryl azide (2.07 mL, 9.59 mmoles) was added over 10 min followed by triethylamine (2.68 mL, 9.59 mmoles) and the mixture was stirred at 0° C. for 1 h and then at 25° C. for 19 h. Evaporation to dryness followed by chromatography on a silica gel column using 5% increasing to 7% methanol in dichloromethane afforded the title compound: (Yield: 1.57 g, 72%): $\delta_c$ (CDCl$_3$) CH$_3$: 28.5, 28.5, 28.5; CH$_2$: 32.9 (broad), 42.8 (broad); CH: 47.3; C: 79.7, 154.8, 156.5.

PREPARATIVE EXAMPLE 36

Step A

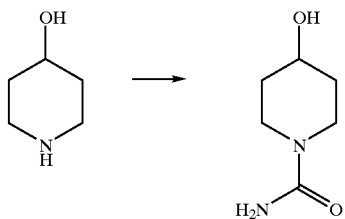

Method 1

4-Hydroxypiperidine (5 g, 49.43 mmoles) was dissolved in anhydrous dichloromethane (50 mL) and trimethylsilyl isocyanate (6.27 g, 7.36 mL, 54.38 mmoles) was added. The mixture was stirred at 25° C. under an argon atmosphere for 24 h. Water (10 mL) was added and the mixture was evaporated to dryness. The residue was chromatographed on a silica gel column using 10%(10% conc. NH$_4$OH in methanol)-dichloromethane as the eluent to give the title compound: (Yield: 6.895 g, 97%): CIMS: m/z 145.1 (MH$^+$); $\delta_C$ (d$_6$-DMSO) CH$_2$: 34.2, 34.2, 41.3, 41.3; CH: 66.1; C: 158.0; $\delta_H$ (d$_6$-DMSO) 1.22 (2H, m, 3/5-CH$_2$), 1.68 (2H, m, 3/5-CH$_2$), 2.84 (2H, m, 2/6-CH$_2$), 3.60 (1H, m, 4-CH), 3.68 (2H, m, 2/6-CH$_2$), 4.67 (1H, d, OH) and 5.87 ppm (2H, s, NH$_2$).

Method 2

4-Hydroxypiperidine (10 g, 98.86 mmoles) and urea (59.4 g, 988.6 mmoles) were dissolved in distilled water (100 mL) and the solution was heated at 100° C. for 67 h. The solution was evaporated to dryness and the product was chromatographed on a silica gel column using 10%(10% conc. NH$_4$OH in methanol)-dichloromethane as the eluent to give the title compound: (Yield: 8.3 g, 58%).

Step B

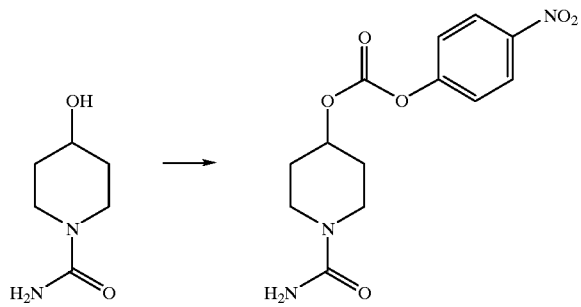

The title compound from Step A above (1 g, 6.94 mmoles) and 4-nitrophenyl chloroformate (1.54 g, 7.63 mmoles) were dissolved in anhydrous pyridine (10 mL) and the mixture was stirred at 25° C. for 24 h. The mixture was evaporated to dryness and the residue was azeotroped with toluene. The resulting product was chromatographed on a silica gel column using 3% methanol in dichloromethane as the eluant to give the title compound: (1.35 g, 63%): CIMS: m/z 310.05 (MH$^+$); $\delta_C$ (CDCl$_3$) CH$_2$: 29.9, 29.9, 40.7, 40.7; CH: 74.9, 121.7, 121.7, 125.2, 125.2; C: 145.2, 151.7, 155.3, 158.7; $\delta_H$ (CDCl$_3$) 1.82 (2H, m, 3/5-CH$_2$), 2.01 (2H, m, 3/5-CH$_2$), 3.06 (2H, s, NH$_2$), 3.31 (2H, m, 2/6-CH$_2$), 3.68 (2H, m, 2/6-CH$_2$), 4.98 (1H, m, 4-CH), 7.39 (2H, d, Ar—H1/6) and 8.28 ppm (2H, d, Ar—H3/5).

PREPARATIVE EXAMPLE 37

Step A

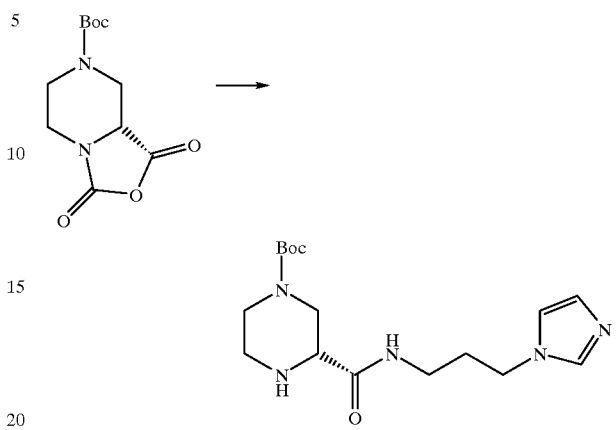

The anhydride (0.5088 g, 1.99 mmoles) (prepared as described in Preparative Example 44) and 1-(3-aminopropyl)-imidazole (0.260 mL, 2.18 mmoles) were dissolved in anhydrous dichloromethane (10 mL) and the mixture was stirred under argon at 25° C. for 5 min. The mixture was diluted with dichloromethane and extracted with saturated aqueous sodium bicarbonate. The dichloromethane layer was dried (MgSO$_4$), filtered and evaporated to dryness. The resulting product was chromatographed on a silica gel column using 10% (conc, NH$_4$OH in methanol)-dichloromethane as the eluent to give the title compound: (Yield: 0.4955 g, 74%); LCMS: m/z 338.1 (MH$^+$); $\delta_C$ (CDCl$_3$) CH$_3$: 28.4, 28.4, 28.4; CH$_2$: 31.1, 36.5, ~43.5 (broad), 44.8, ~46.(broad),; CH: 58.2, ~119.0(broad), ~129.7(broad), ~137.3(broad); C: 80.2, 154.7, 171.5; $\delta_H$ (CDCl$_3$) 1.47 (9H, s, CH$_3$), 6.96 (1H, s, Im-H$_5$), 7.08 (1H, s, Im-H$_4$) and 7.52 ppm (1H, s, Im-H$_2$).

Step B

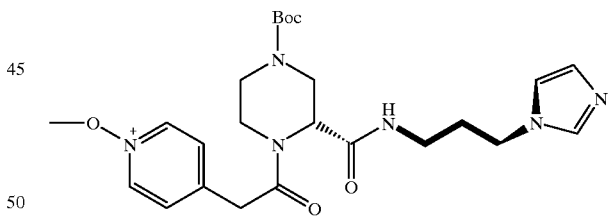

The title compound from Step A above (0.3248 g, 0.96 mmoles), 4-pyridylacetic acid N1-oxide (0.1916 g, 1.25 mmoles), 1[3-(dimethylamino)propyl]-3-ethylcarbodimide hydrochloride (0.24 g, 1.25 mmoles), 1-hydroxybenzotriazole (0.169 g, 1.25 mmoles) and 4-methylmorpholine (0.1376 mL, 1.25 mmoles) were dissolved in anhydrous DMF (11 mL) and the mixture was stirred under argon at 25° C. for 18 h. The mixture was evaporated to dryness and the residue was dissolved in dichloromethane and washed with saturated aqueous sodium bicarbonate. The organic layer was dried (MgSO$_4$), filtered and evaporated to dryness. The product was chromatographed on a silica gel column using 5% (10% conc. NH$_4$OH in methanol)-dichloromethane as the eluent to give the title compound: (Yield: 0.4333 g, 95%); LCMS: m/z 473.1 (MH$^+$); $\delta_C$ (CDCl$_3$) CH$_3$: 28.3, 28.3, 28.3; CH$_2$: 30.8, 36.5, 38.7, 43.2, ~43.5 (broad), ~44.5 (broad); CH: 53.8, ~119.2 (broad), 127.4, 127.6, ~129.3 (broad), ~137.5 (broad), 138.7, 138.9; C: 80.7, 134.5, 154.4, 169.6, 169.6; $\delta_H$ (CDCl$_3$) 1.44 (9H, s, CH$_3$), 6.97 (1H, broad s, Im-H$_5$), 7.09 (1H, broad s, Im-H$_4$), 7.20 (2H, m, Ar—H), 7.53 (1H, broad s, Im-H$_2$) and 8.14 ppm (2H, d, Ar—H).

Step C

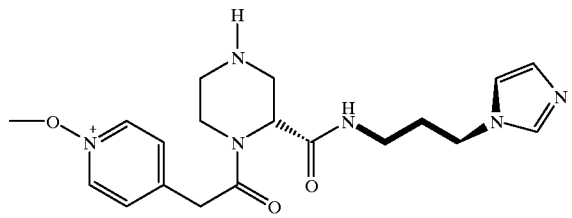

The title compound from Step B above (0.289 g, 0.612 mmoles) was dissolved in anhydrous dichloromethane (7.8 mL) and trifluoroacetic acid (2.026 mL, 26.3 mmoles) was added. The mixture was stirred at 25° C. for 1.25 h under argon and then evaporated to dryness. The product was chromatographed on a silica gel column using 5% increasing to 10% (10% conc. NH$_4$OH in methanol)dichloromethane as the eluant to give the title compound: (Yield: 0.208 g, 91%); LCMS: m/z 373.1 (MH$^+$); $\delta_C$(CDCl$_3$-CD$_3$OD) CH$_2$: 30.4, 36.2, 38.2, 43.9, 44.5, 46.2, 46.7; CH: 52.3, ~119.2 (broad), 127.7, 127.7, ~128.3 (broad), 137.4 (broad), 138.4, 138.5, 138.5; C: 137.3, 169.8, 170.6; $\delta_H$(CDCl$_3$-CD$_3$OD) 6.90 (1H, broad s, Im-H$_5$), 6.94 (1H, broad s, Im-H$_4$), 7.22 (2H, m, Ar—H), 7.47 (1H, broad s, Im-H$_2$) and 8.12 ppm (2H, d, Ar—H); $[\alpha]_D^{26.3°}$+81.1° (c=10.43 mg/2 mL, methanol).

PREPARATIVE EXAMPLE 38

Step A

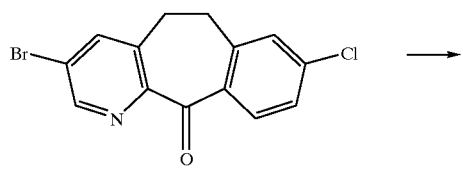

To a solution of 3-bromo-8-chloro-5,6-dihydro-11H-benzo[5,6]cyclohepta[1,2-b]pyridin-11-one (2 g) (6.2 mmoles) in anhydrous dichloromethane (14 ml) at 0° C. and under an argon atmosphere, was added a solution of 3-chloroperbenzoic acid (1.76 g) (10.4 mmoles) in anhydrous dichloromethane (35 ml) dropwise over a period of 30 minutes. The mixture was allowed to warm to room temperature and after 18 h additional 3-chloro-perbenzoic acid (0.88 g) (5.2 mmoles) in anhydrous dichloro-methane (25 ml) was added and the mixture was stirred for a total of 42 h. The mixture was diluted with dichloromethane and washed with 1N NaOH (200 ml). The aqueous layer was extracted with additional dichloromethane (2×200 ml) and the combined organic layers were dried over magnesium sulfate, filtered and evaporated to dryness. The product was chromatographed on silica gel using 0.25%–0.5%–1% (10% conc. NH$_4$OH in methanol)dichloromethane as the eluant to give the title compound (Yield: 1.386 g, 66%): ESIMS; m/z 338.1 (MH$^+$); $\delta_C$ (CDCl$_3$) CH$_2$: 30.5, 34.0; CH: 126.9, 127.6, 130.3, 132.5, 140.4; C: 121.0, 135.1, 138.3, 139.7, 141.6, 145.3, 188.0 ppm.

Step B

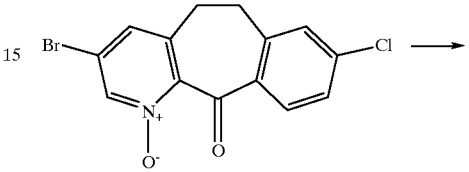

The title compound of Step A (1.3422 g) (3.96 mmoles) was dissolved in methanol (18 ml) and dichloromethane (20 ml) and sodium borohydride (0.219 g) (5.79 mmoles) was added. The mixture was stirred under argon at 0° C. for 1 h and then allowed to warm up to 25° C. over a period of 1 h. The mixture was diluted with dichloromethane (800 ml) and washed with 1N NaOH (150 ml). The aqueous layer was extracted with dichloromethane (2×100 ml) and the combined organic layers were dried over magnesium sulfate, filtered and evaporated to dryness. The product was chromatographed on silica gel using 1% (10% conc. NH$_4$OH in methanol)dichloro-methane as the eluant to give the title compound (Yield: 1.24 g, 92%): ESIMS: m/z 340.1 (MH$^+$); $\delta_C$ (CDCl$_3$) CH$_2$: 31.2, 32.0; CH: 69.1, 126.8, 129.5, 131.7, 131.7, 136.7; C: 118.3, 134.7, 135.2, 139.7, 141.0, 148.9 ppm.

Step C

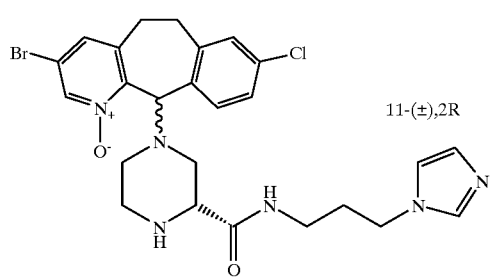

The title compound from Step B (0.552 g, 1.62 mmoles) and triethylamine (1.19 mL, 8.52 mmoles) were dissolved in anhydrous dichloromethane (8.5 mL) and the solution was cooled to 0° C. Methanesulfonyl chloride (0.4 mL, 5.16 mmoles) was added over 30 min and the mixture was stirred at 0° C. for a total of 1.25 h. The solution was evaporated to dryness to give the 11-mesyl derivative which was used without further purification. The latter was dissolved in anhydrous dichloromethane (40 mL) and the solution was stirred at 0° C. N-[3-(1H-Imidazol-1-yl)propyl]-2(R)-piperazinecarboxamide (Preparative Example 136) (0.5 g, 2.11 mmoles) dissolved in anhydrous dichloromethane (20 mL) and anhydrous DMF (20 mL) was added at 0° C. and the solution was stirred and allowed to warm up to 25° C. over 2 h. The reaction was allowed to proceed at 25° C. for 18 h and was then diluted with dichloromethane and washed with saturated aqueous sodium bicarbonate, dried (MgSO$_4$), filtered and evaporated to dryness. The product was chromatographed on a silica gel column using 4% (10% conc. NH$_4$OH in methanol)-dichloro-methane as the eluant to give the title racemic compound: Yield: 0.399 g, 44%); FABMS: m/z 559.3 (MH$^+$).

Step D

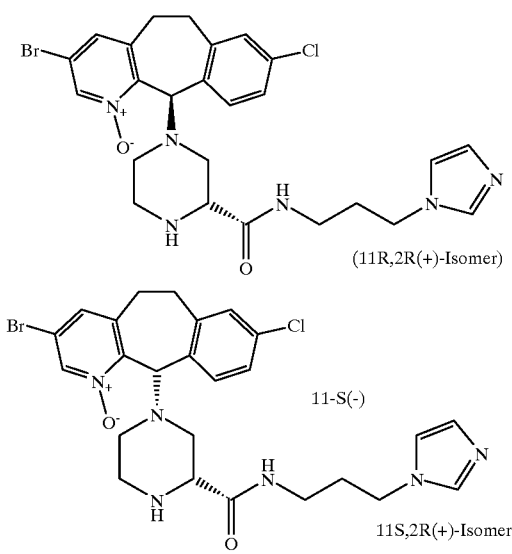

The title racemic compound from Step C above (0.395 g) was subjected to preparative HPLC on a Chiralpak AD® column (50×5 cm) using 65% hexane—35% isopropyl alcohol—0.2% diethylamine as the eluant to give in the order of elution the 11-R(+)-diastereoisomer of the title compound followed by the 11-S(−)-diastereoisomer of the title compound.

11R,2R(+)-diastereoisomer: (Yield: 0.1854 g); FABMS: m/z 559.2 (MH$^+$); $\delta_C$ (CDCl$_3$) CH$_2$: 30.1, 30.3, 31.2, 36.4, 43.9, 44.7, 51.6, 52.8; CH: 57.8, 64.3, 118.9, 126.3, 129.6, 130.6, 130.7, 133.4, 137.3, 138.4; C: 118.2, 133.6, 134.6, 140.1, 141.0, 148.1, 172.0; $\delta_H$ (CDCl$_3$) 5.70 (1H, s, H$_{11}$), 6.95 (1H, broad s, Im-H$_5$), 7.04 (1H, broad s, Im-H$_4$), 7.51 (1H, broad s, Im-H$_2$) and 8.22 ppm (1H, s, Ar—H$_2$); $[\alpha]_D^{20°}$ +41.2° (c=11.08 mg/2 mL, methanol).

11S,2R(−)-diastereoisomer: (Yield: 0.18 g); FABMS: m/z 559.2 (MH$^+$); $\delta_C$ (CDCl$_3$) CH$_2$: 30.1, 30.3, 31.1, 36.5, 44.4, 44.8, 51.6, 53.4; CH: 58.9, 64.4, ~119.2, 126.3, 129.5, 130.6, 130.7, 133.4, ~137.3, 138.5; C: 118.3, 133.7, 134.6, 139.9, 141.0, 148.1, 172.1; $\delta_H$ (CDCl$_3$) 5.69 (1H, s, H$_{11}$), 6.94 (1H, broad s, Im-H$_5$), 7.07 (1H, broad s, Im-H$_4$), 7.51 (1H, broad s, Im-H$_2$) and 8.26 ppm (1H, s, Ar—H$_2$); $[\alpha]_D^{19.9°}$ −71.0° (c=10.32 mg/2 mL, methanol).

PREPARATIVE EXAMPLE 39

Step A

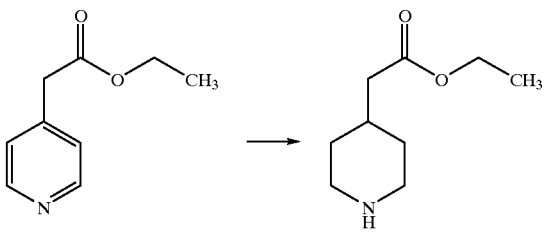

Ethyl 4-pyridyl acetate (4.5 g, 27.24 mmoles) was placed in a 500 mL Parr bottle and dissolved in anhydrous EtOH (70 mL). 10% Palladium on charcoal (1.0 g) was added and the contents shaken under 55 psi hydrogen pressure at 25° C. for 94 h. The mixture was filtered through Celite® and washed with 4×40 mL anhydrous EtOH. The filtrate was evaporated to dryness and the residue was chromatographed on silica gel using 3% (10% conc. NH$_4$OH in methanol)-dichloromethane as the eluant to give the title compound: (Yield: 2.944 g, 63%): FABMS: m/z 172.2 (MH$^+$); $\delta$C (CDCl$_3$) CH$_3$: 14.3; CH$_2$: 33.2, 33.2, 41.9, 46.5, 46.5 60.2; CH: 33.4; C: 172.7; $\delta$H (CDCl$_3$) 1.18 (1H, m, H$_4$, 1.26 (3H, t,CH$_3$), 1.71(2H), 1.90(1H), 1.96(1H), 2.22(2H, d), 2.63 (2H), 3.07(2H), 4.13 ppm (2H, q, CH$_3$CH$_2$—).

Step B

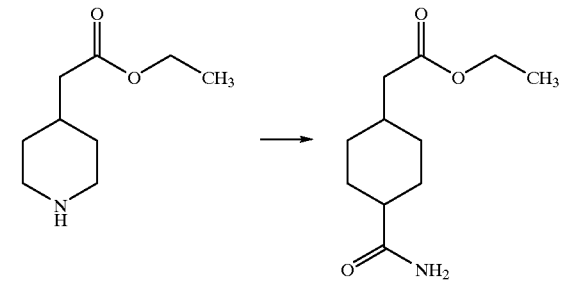

Ethyl 4-piperidinyl acetate (500 mg; 2.92 mmoles) from Step A above was dissolved in anhydrous dichloromethane (25 mL). To the stirred solution was added trimethylsilyl isocyanate (5.9 mL; 43.8 mmoles) and the solution was stirred at 25° C. for 17 h. The solution was diluted with dichloromethane and washed with saturated aqueous sodium bicarbonate. The dichloromethane layer was dried (MgSO$_4$), filtered and evaporated to dryness. The product was chromatographed on silica gel using 2% increasing to 3%(10% conc. NH$_4$OH in methanol)-dichloromethane as the eluant to give the title compound: (Yield: 622 mg, 99%): CIMS: m/z 215.3 (MH$^+$); $\delta_c$(CDCl$_3$): CH$_3$: 14.2; CH$_2$: 31.6, 31.6, 41.0, 44.2, 44.2, 60.4; CH: 32.9; C: 158.2, 172.4; $\delta_H$ (CDCl$_3$): 1.23 (1H, m, H$_4$), 1.27 (3H, t, CH$_3$), 1.75 (2H, d), 1.98 (1H, m), 2.26 (2H, d), 2.85 (2H, t), 3.94 (2H, d), 4.15 (2H, q, CH$_3$CH$_2$—), 4.56 (2H, bs).

Step C

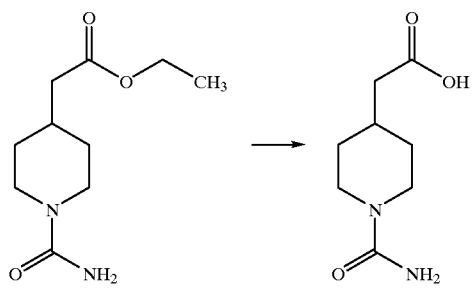

Ethyl 1-aminocarbonyl-4-piperidinyl acetate (153.6 mg, 0.717 mmoles) from Step B above was dissolved in anhydrous dichloromethane (3.58 mL) and ethanol (3.58 mL). To the solution was added 1.0M LiOH (1.73 mL, 1.73 mmoles) and the mixture was stirred at 50° C. for 5.5 h. The mixture was cooled quickly to 25° C. and 1.0N HCl (2.02 mL, 2.02 mmoles) was added and the mixture stirred for 5 minutes and then evaporated to dryness to give the title compound, which was used without further purification.

PREPARATIVE EXAMPLE 40

Step A

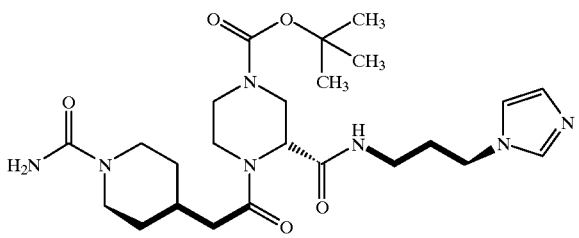

The title compound from Preparative Example 37, Step A above (0.45 g, 1.33 mmoles), 1[3-(dimethylamino)propyl]-3-ethylcarbodiimide hydrochloride (0.332 g, 1.73 mmoles), 1-hydroxybenzotriazole (0.234 g, 1.73 mmoles) and 4-methylmorpholine (0.382 mL, 3.46 mmoles) were dissolved in anhydrous DMF (7 mL). The title compound from Preparative Example 33, Step C above (0.3228 g, 1.73 mmoles) dissolved in anhydrous DMF (8 mL) was added and the mixture was stirred at 25° C. for 22 h. The solution was evaporated to dryness and the residue was taken up in dichloromethane and washed with saturated aqueous sodium bicarbonate, dried (MgSO$_4$), filtered and evaporated to dryness. The residue was chromatographed on a silica gel column using 5% (10% conc. NH$_4$OH in methanol)-dichloromethane as the eluant to give the title compound: (Yield: 0.3553 g, 53%).

Step B

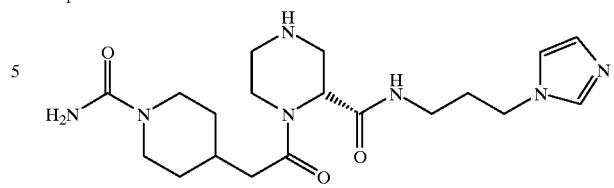

The title compound from Step A above (0.45 g, 0.9 mmoles) was dissolved in methanol (5.625 mL). A 10% (v/v) solution of conc. H$_2$SO$_4$ in dioxane (13.5 ml) was added and the mixture was stirred at 25° C. for 2 h. Anhydrous methanol (200 mL) was added followed by BioRad® AG1-X8 (OH$^-$) resin until the solution was neutral to pH paper. The resin was filtered off and washed with methanol and the combined filtrates were evaporated to dryness. The residue was chromatographed on a silica gel column using 5% increasing to 6.5% (10% conc. NH$_4$OH in methanol)dichloro-methane as the eluant to give the title compound: (Yield: 0.317 g, 96%); FABMS: m/:z 406.2 (MH$^+$); δ$_C$ (CDCl$_3$-~5% CD$_3$OD) CH$_2$: 30.8, 31.9, 31.9, 36.2/36.3/36.6, 39.1/39.3/39.5, 44.1/44.2, 44.4, 44.4, 44.8, 44.8; CH: 51.2/56.3, 119.0, 128.8, 137.0; C: 158.7, 171.0/171.1, 171.9/172.6; δ$_H$ (CDCl$_3$- 2.86% CD$_3$OD) 4.84 (1H, d, H$_2$), 6.96 (1H, broad s, Im-H$_5$), 7.04 (1H, broad s, Im-H$_4$) and 7.53 ppm (1H, broad s, Im-H$_2$).

PREPARATIVE EXAMPLE 40A

Step A

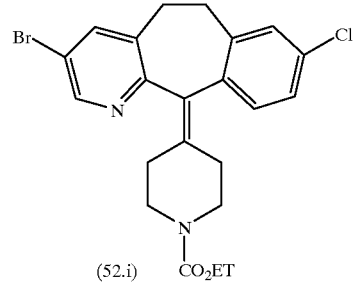

(52.i)

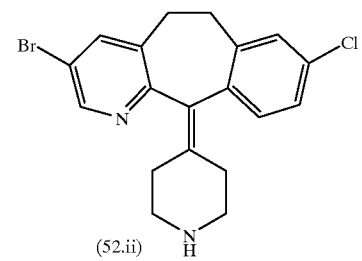

(52.ii)

A solution of 52.i (J. Med. Chem. 4890–4902 (1988))(205 g) in conc. HCl (1 L) and water (100 mL) is refluxed for 18 h, then poured into ice (3 Kg). Aq. 50% NaOH is added to pH 12 followed by extraction with EtOAc (3×4 L), the extracts are washed with brine, dried and evaporated to afford 52.ii (166 g).

Step B

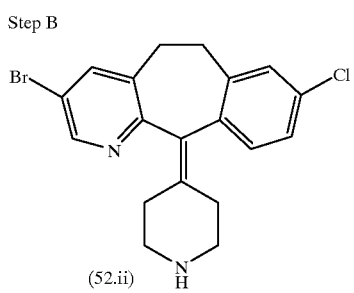

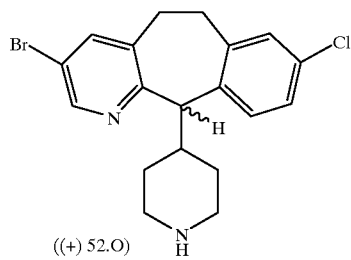

A 1M solution of DIBAL in toluene (908 mL) is added dropwise during 2 h to a solution of 52.ii (166 g) in toluene (4 L) at rt. followed by stirring for 18 h. The mixture is cooled to 0–5° C. and stirred for 1 h and extracted with 1N HCl (2 L). The aqueous extract is basified to pH 10 with 50% NaOH and extracted with EtOAc (3×2 L). The extracts are evaporated and chromatographed on silica-gel (1 Kg). Elution with 10% MeOH/CH$_2$Cl$_2$ affords the title compound (±) 52.0 (104 g): HRMS (FAB) calcd for C$_{19}$H$_{21}$N$_2$$^{79}$BrCl 393.0556, found 393.0554.

Step C

The racemate (±) 52.0 (96 g) is resolved by HPLC on a 8×30 cm CHIRALPAK AD column at 25° C. with the UV detector set at 290 nm. Elution with 0.05% diethylamine-methanol affords: Peak 1 (–) 52.0 (40 g): [α]$_D^{20}$ –28.4° (c 0.3, MeOH); Further elution with the same solvent affords: Peak 2 (+) 52.0 (42 g): [α]$_D^{20}$ +27.5° (c 0.3, MeOH).

PREPARATIVE EXAMPLE 41

Step A

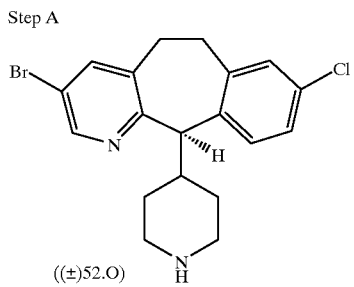

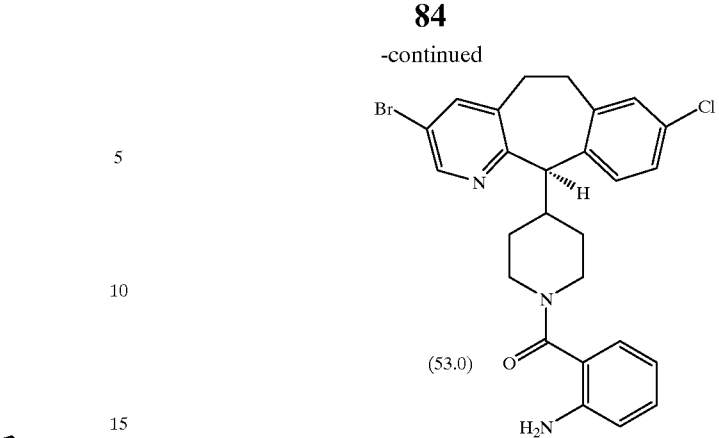

A solution of (+)-52.0 (2.3 g) in dimethylformamide (30 ml) is reacted with isatoic anhydride (1.25 g) in the presence of DMAP (0.1 g) at r.t. for 3 hrs and is then evaporated under reduced pressure and residual dimethylformamide is azeotroped with toluene. The residue is dissolved in ethylacetate (50 ml) and the solution is extracted with 10% sodium carbonate (3×100 ml). The organic layer is filtered through silica-gel (100 ml) followed by elution with ethylacetate. The filtrate is evaporated under reduced pressure to afford the title compound 53.0 as an amorphous solid (3.68 g). MS(FAB): m/z 510 (MH)$^+$.

Step B

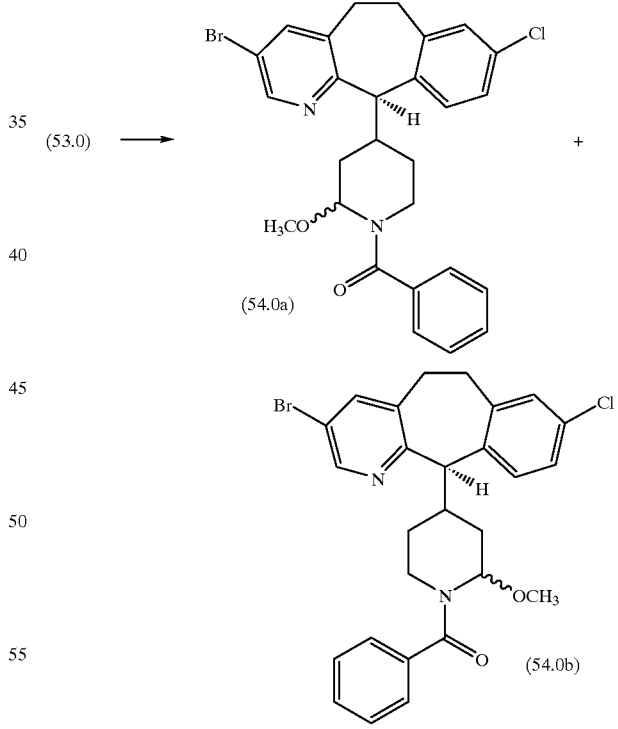

A solution of 53.0 (3.1 g) and sodium nitrite (0.8 g) in methanol (500 ml) is stirred at r.t. under nitrogen with cuprous chloride (0.15 g) while adding dropwise over 10 minutes a 4M hydrochloric acid/dioxane solution (3.9 ml). The reaction mixture is stirred for 24 hrs followed by the addition of 10% sodium carbonate to pH 8, concentrated under reduced pressure, diluted with water (200 ml) and extracted with dichloromethane (4×100 ml). The combined extract is evaporated under reduced pressure and the crude reaction product is flash chromatographed on silica-gel (400 ml). Elution with 25% ethylacetate-hexane affords after evaporation the title compound 54.0a and 54.0b as an off-white amorphous solid (2.97 g). $^1$H NMR (CDCl$_3$, 300 MHz) d 3.30 (s, 3H); MS (FAB) m/e 525 (MH)$^+$.

Steps C–E

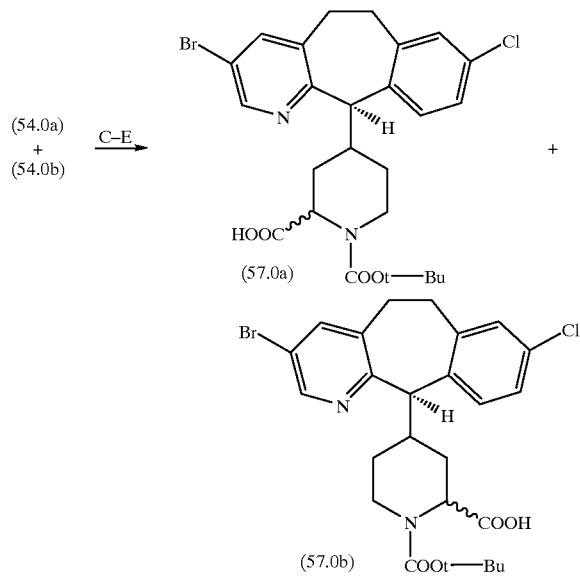

A solution of 54.0a and 54.0b (17 g) in methanol (150 ml) and 2N hydrochloric acid (170 ml) and conc. HCl (60 ml) is heated under reflux for 17 hrs, followed by evaporation under reduced pressure. The resulting amorphous solid is dissolved in methanol (160 ml) and sodium cyanide (15 g) is added with stirring until the reaction is basic (pH 8). The reaction is stirred for 2 h, diluted with dichloromethane (300 ml) and filtered. The filtrate is evaporated and the residue is dissolved in conc HCl (150 ml) and the mixture is heated in an oil bath (120° C.) for 4 h and is then evaporated under reduced pressure. The residue is dissolved in THF (100 ml) and 10% NaOH (30 ml) is added to pH>8 followed by the dropwise addition of a solution of (BOC)$_2$O (9 g) in THF (50 ml) with vigorous stirring for 24 h. The solution is concentrated to a low volume, stirred with hexane (2×120 ml) and ice-water followed by acidification of the aqueous layer with citric acid and extraction with EtOAc. The crude product obtained by evaporating the extract is purified by flash chromatography to afford the mixture of 57.0a and 57.0b as light tan solid that appears as a single tlc spot (16 g). $^1$H NMR (CDCl$_3$, 300 MHz) d 1.40 (s, 9H); MS (FAB) m/z 535 (MH)$^+$.

The single tlc spot is a mixture of four isomers which are separated after derivatization into the compounds of Examples 77 to 79 and 87 to 97 below.

Following the above procedure (Steps A–E), except using Compound (−)-52.0 (17 g), a mixture of 58.0a and 58.0b is obtained as a light solid that appears as a single tlc spot (17 g). MS(ES) m/z 535 (MH$^+$).

PREPARATIVE EXAMPLE 42

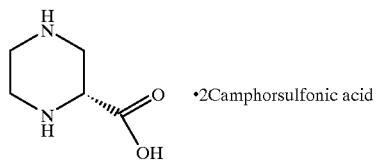

•2Camphorsulfonic acid

To 2.5 kg of (R)-(−)-camphorsulfonic acid stirring at 60° C. in 1250 ml of distilled water was added a soution of the potassium salt of 2-carboxyl-piperazine (565 gm, 3.35 mol). The mixture was allowed to stir at 95° C. until completely dissolved. The solution was allowed to stand at ambient temperature for 48 hrs. The resulting precipitate was filtered to obtain 1444 gm of damp solid. The solids were then dissolved in 1200 ml of distilled water and heated on a steam bath until all solids dissolved. The hot solution was then set aside to cool slowly for 72 hrs. The crystalline solids were filtered to give 362 gm of the pure 2-R-enantiomeric product as a white crystalline solid. [α]$_D$=−14.9°.

PREPARATIVE EXAMPLE 43

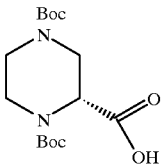

2-R-carboxy-piperazine-di-(R)-(−)-camphorsulfonic acid (Preparative Example 42) (362 gm, 0.608 mol) was dissolved in 1.4 L of distilled water and 1.4 L of methanol. 75 ml of 50% NaOH was dripped in to the stirred reaction mixture to obtain a ~pH 9.5 solution. To this solution was added di-tert-butyl-dicarbonate (336 gm, 1.54 mol) as a solid. The pH dropped to ~7.0. The pH of the reaction mixture was maintained at 9.5 with 50% NaOH (total of 175 ml), and the reaction mixture stirred for 2.5 hours to obtain a white precipitate. The reaction mixture was diluted to 9 L with ice/water followed by washing with 2 L of ether. The ether was discarded and the pH of the aqueous layer adjusted to pH 3.0 by the portionwise addition of solid citric acid. The acidified aqueous layer was then extracted with dichloromethane 3× with 2 L. The organic layers were combined, dried over sodium sulfate, filtered and evaporated to obtain 201.6 gm of title compound as a white glassy solid. FABMS (M+1)=331.

PREPARATIVE EXAMPLE 44

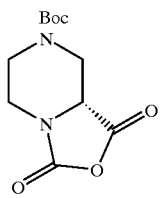

To an ice cold solution N,N-dimethylformamide (49.6 ml) was added, dropwise, thionylchloride (46.7 ml) over a period of 5 minutes in a 5 L round bottom flask under a nitrogen atmosphere. The reaction mixture was allowed to stir for 5 min. and the ice bath removed and the reaction mixture allowed to stir at ambient temperature for 30 min. The reaction mixture was cooled again in an ice bath and a solution of of N,N-di-tert-butoxycarbonyl-2-R-carboxyl-piperazine (Preparative Example 43) (201.6 gm, 0.61 mmol) in 51.7 ml of pyridine and 1.9 L of acetonitrile was cannulated into the reaction mixture. The reaction mixture was allowed to warm to ambient temperature to obtain a yellowish turbid solution. After stirring at ambient temperature for 18 hours, the reaction mixture was filtered and the filtrate poured into ice water (7L) and then extracted with 4×2 L of ethyl acetate, dried over sodium sulfate, filtered and evaporated to dryness under vacuo to obtain 115.6 gm (73%) of the title product as a white solid.

PREPARATIVE EXAMPLE 45

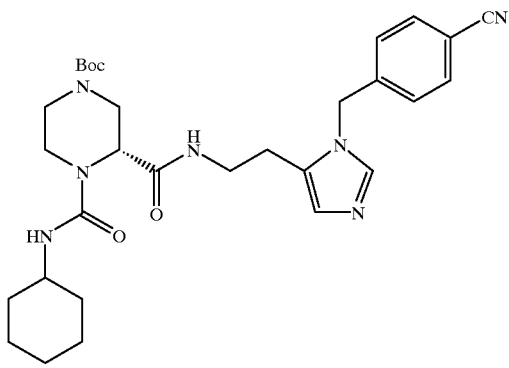

1N-p-Cyanobenzyl histamine (0.34, 1.5 mmol) (prepared as described in Preparative Example 163) was added to a solution of the Boc-anhydride (Preparative Example 44) (0.38 gm, 1.5 mmol) in 10 ml of dichloromethane and stirred under a nitrogen. After 1 hr, 0.15 gm more of the Boc-anhydride was added and the reaction monitored for completion by normal phase tlc using 10% methanol/dichloromethane as the eluent. After the reaction went to completion (~1 hour), 0.25 ml (2 mmol) of cyclohexyl isocyanate was added to the reaction mixture and stirred for 1 hour. The reaction mixture was poured into brine and extracted with dichloromethane (3x). The dichloromethane layers were combined, dried over MgSO$_4$, filtered and evaporated to dryness. The residue was chromatographed on a flash column of silica gel using 5% methanol/dichloromethane to obtain 0.714 gm of pure title compound as a solid. FABMS (M+1)=564.

PREPARATIVE EXAMPLE 46

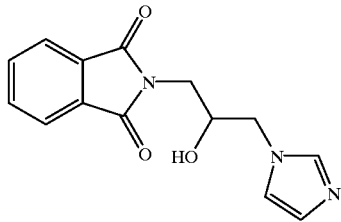

N-(2,3-Epoxypropyl)phthalimide (2.3 gm, 11.3 mmol) was dissolved in N,N-dimethylformamide and imidazole (1.53 gm, 1.5 eq.) was added and the reaction mixture stirred at 90° C. for 5 hours. Brine was added and the product extracted with ethylacetate to obtain the title product (0.67 gm).

PREPARATIVE EXAMPLE 47

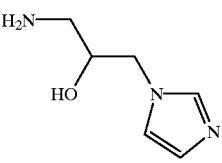

1-Phthalamido-2-hydroxy-3-1-H-imidazole-propane (from Preparative Example 46) (0.6 gm) was dissolved in ethanol and 5 ml of hydrazine hydrate added. The reaction mixture was refluxed for 3 hours. The reaction mixture was cooled to ambient temperature and the resulting precipitate filtered. The filtrate was evaporated to dryness to obtain the title product which was used without further purification.

PREPARATIVE EXAMPLE 48

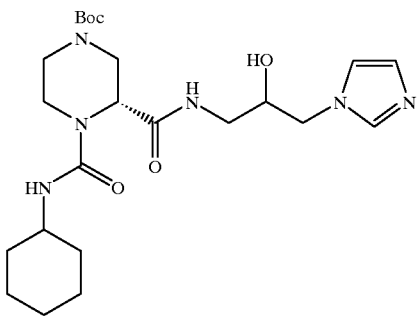

1-Amino-2-hydroxy-3-1-H-imidazole-propane (from Preparative Example 47) (2.2 mmol) was added to a solution of the Boc-anhydride (Preparative Example 44) (0.57 gm, 2.2 mmol) in 10 ml of dichloromethane and stirred under nitrogen. After 1 hr, 0.15 gm more of the Boc-anhydride was added and the reaction monitored for completion by normal phase tlc using 10% methanol/dichloromethane as the eluent. After the reaction went to completion (~1 hour), 0.85 ml (6.6 mmol) of cyclohexyl-isocyanate was added to the reaction mixture and stirred for 1 hour. The reaction mixture was poured into brine and extracted with dichloromethane (3x). The dichloromethane layers were combined, dried over MgSO$_4$, filtered and evaporated to dryness. The residue was chromatographed on a flash column of silica gel using 5% methanol/dichloromethane to obtain 0.487 gm of pure title compound as a solid.

PREPARATIVE EXAMPLE 49

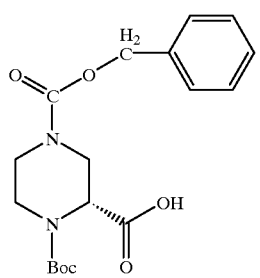

2-Carboxy-piperazine-dicamphorsulfonic acid salt (Preparative Example 42) (17.85 gm, 30 mmole) was dissolved in 180 ml of distilled water. Dioxane (180 mL) was added and the pH adjusted to 11.0 with 50% NaOH. The reaction mixture was cooled to 0–5° C. in an ice-MeOH bath and a solution of benzyl-chloroformate (4.28 mL, 30 mmol) in 80 mL of dioxane was added over a period of 30–45 minutes while stirring at 0–5° C. and keeping the pH at 10.5 to 11.0 with 50% NaOH. After the addition was complete, stirring was continued for 1 hr. The reaction mixture was then evaporated to dryness (to get rid of the dioxane for extraction). The residue was dissolved in 180 mL of dist. water and the pH adjusted slowly to 4.0 with 1N HCl. The aqueous solution was washed with 3×180 mL of ethyl acetate (The ethyl acetate was dried over MgSO₄, filtered, and evaporated to obtain N,N-di-CBZ-2-carboxy-piperazine and saved). The pH of the aqueous layer, which contains the desired product, was adjusted to 10.5 to 11.0 with 50% NaOH and solid di-tert-butyl-dicarbonate (7.86 gm, 36 mmol) was added and the mixture was stirred while keeping the pH at 10.5 to 11.0 with 50% NaOH. After 1 hr. the pH stabilized. When reaction was complete, the reaction mixture was washed with 2×180 mL of Et₂O. The aqueous layer was cooled in an ice bath and adjusted pH to 2.0 with 1N HCl (slowly). Extract the product with 3×200 mL of ethyl acetate. Dry over MgSO₄, filter and evaporate to obtain 9.68 gm (88%) of pure product as a white solid.

PREPARATIVE EXAMPLE 50

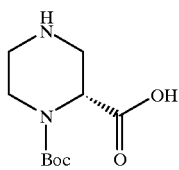

4-N-CBZ-1N-Boc-2-carboxy-piperazine (Preparative Example 49) (9.6 gm, 26.3 mmol) was dissolved in 100 mL of absolute ethanol in a hydrogenation vessel. The vessel was flushed with nitrogen and 3 gm of 10% Pd/C (50% by weight with water) was added. The mixture was hydrogenated at 55 psi of H₂ for 18 hours. After 18 hrs, the reaction mixture had a precipitate. The tlc was checked (30% MeOH/NH₃/CH₂Cl₂). The reaction mixture was filtered on a pad of Celite, and the pad washed with EtOH followed by distilled water. The filtrate was evaporated to ~⅓ the volume (to get rid of the EtOH) and 200 mL of distilled water was added. The aqueous layer was extracted with ethyl acetate three times (the ethyl acetate layer contained pure N,N-Di-Boc-2-carboxy-piperazine which was saved). The water layer was evporated to dryness and evaporated from methanol two times to obtain 3.98 (17.37 gm, mmol) of pure product.

PREPARATIVE EXAMPLE 51

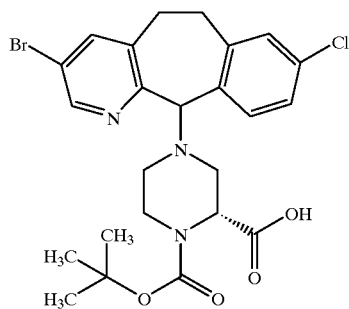

The tricyclic alcohol (Preparative Example 40 in WO 95/10516)

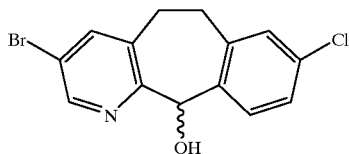

(5.6 gm, 17.33 mmol) was dissolved in 56 ml of dichloromethane and 2.46 ml of thionyl chloride was added while stirring under a dry nitrogen atmosphere. After 5 hrs. the tlc was checked (by adding an aliquot of the reaction mixture to 1N NaOH and shaking with dichloromethane and checking the dichloromethane layer by tlc using 50% EtOAc/Hexanes as the eluent). The mixture was evaporated to give a gum which was evaporated from dry toluene twice and once from dichloro-methane to give the 11-chloro derivative as a foamy solid which was used without further purification. The resulting 11-chloro-tricyclic compound was dissolved in 100 ml of dry DMF, 1N-Boc-2-carboxy-piperazine (Preparative Example 50) (3.98 gm) was added followed by 12.11 ml of triethylamine and the mixture stirred at ambient temperature under a nitrogen atmosphere. After 24 hours the DMF was evaporated and the residue dissolved in 200 ml of ethyl acetate and washed with brine. The brine layer was washed with ethyl acetate two more times and the ethyl acetate layers combined, dried over magnesium sulfate, filtered, and evaporated to give a foamy solid. The solid was chromatographed on a 1½"×14" column of silica gel eluting with 2 L of 0.4% 7N MeOH/NH₃:CH₂Cl₂, 6 L of 0.5% 7N MeOH/—NH₃:CH₂Cl₂, 2 L of 0.65% 7N MeOH/NH₃:CH₂Cl₂, 2 L of 0.8% 7N MeOH/NH₃:CH₂Cl₂, 4 L of 1% 7N MeOH/NH₃:CH₂Cl₂, 2 L of 3% 2N MeOH/NH₃:CH₂Cl₂, 2 L of 5% 2N MeOH/NH₃:CH₂Cl₂, 2 L of 10% 2N MeOH/NH₃:CH₂Cl₂, 2 L of 15% 2N MeOH/NH₃:CH₂Cl₂, 4 L of 20% 2N MeOH/NH₃:CH₂Cl₂ to obtain 4.63 gm of final product.

PREPARATIVE EXAMPLE 52

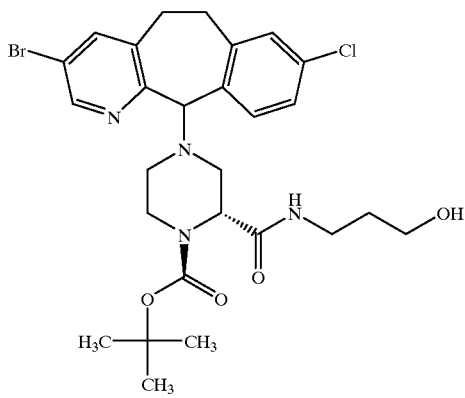

The title compound from Preparative Example 51 (1 gm, 1.86 mmol) was dissolved in 50 ml of DMF and 1-amino-3-propanol (0.214 ml, 1.5 eq.), DEC (0.71 gm, 2 eq.), HOBT (0.5 gm, 2 eq.), and N-methyl-morpholine (1.02 ml, 5 eq.) was added and the reaction mixture stirred for 18 hours. The reaction mixture was added to brine and the product extracted with ethyl acetate 3 times to obtain a crude oil, after the solvent was evaporated under reduced pressure, which was purified by chromatography on a silica gel column 20%–50% ethyl acetate/hexanes as the eluent. The product containing fractions were pooled to obtain 0.67 gm (60%) of pure title compound.

PREPARATIVE EXAMPLE 53

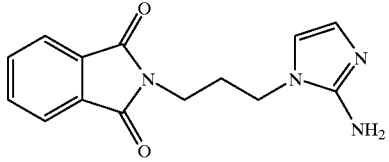

2-Aminoimidazole (8 g, 60 mmol) was dissolved in 200 ml of DMF and cooled in an ice bath. Sodium hydride 60% oil dispersion (2.4 g, 60 mmol) was added portionwise and the reaction mixture stirred for 1 hour. N-(3-Bromopropyl)-phthalimide (16 g, 74 mmol) was added and the reaction mixture stirred for ½ hour at 0° C., 1 hour at ambient temperature, and then 1 hour at 85° C. The reaction mixture was then cooled to ambient temperature and added to brine and extracted with ethyl acetate to obtain the crude product which was purified by column chromatography using 2% methanol/methylene chloride to obtain 4.88 gm of title compound.

PREPARATIVE EXAMPLE 54

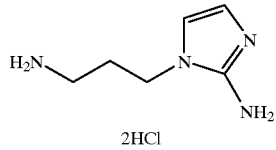

2HCl 0.5 gm of 1-phthalimidopropyl-2-aminoimidazole (from Preparative Example 53) was refluxed in 20 ml of 6N HCl for 6 hours. The mixture was washed with ethyl acetate and the aqueous layer evaporated to dryness to obtain 0.45 g of the title product.

PREPARATIVE EXAMPLE 55

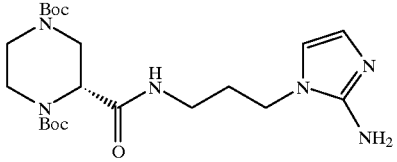

1-Aminopropyl-2-aminoimidazole (Preparative Example 54)0.25 gm) and N,N-di-butoxycarbonyl-2-R-carboxyl-piperazine (from Preparative Example 43) (0.32 gm) was dissolved in 10 ml of DMF. DEC (0.2 gm.), 1-hydroxybenzotriazole (0.135 gm), and N-methyl-morpholine (0.54 ml) was added and the reaction mixture stirred for 5 hours. The reaction was poured into brine and extracted with dichloromethane to obtain 0.43 gm of the title product after chromatography on silica gel using 2% methanol/-dichloromethane up to 10%. FABMS M+1= 453.3.

PREPARATIVE EXAMPLE 56

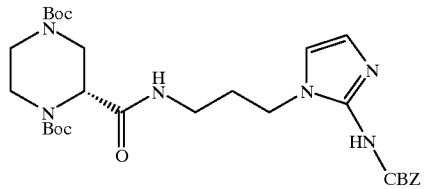

1-Aminopropyl-2-aminoimidazolyl-N 1,N4-di-tert.butyl-1,2(R)-piperazinedicarboxamide (Preparative Example 55) (0.38 gm) was dissolved in 20 mL of dichloromethane and 0.24 ml of triethylamine. Benzyloxycarbonyl-N-hydroxysuccinimide (0.22 gm) was added and the reaction mixture stirred for 18 hours at ambient temperature. The reaction mixture was washed with brine and chromatographed on a silica gel column using ethyl acetate as the eluent to obtain 0.39 gm of title product. FABMS M+1= 587.3.

PREPARATIVE EXAMPLE 57

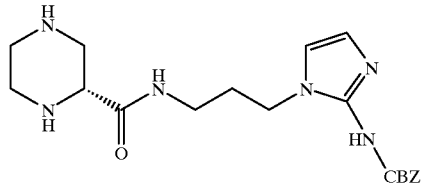

2 TFA 1-benzyloxycarbonylaminopropyl-2-aminoimidazolyl-N1,N4-di-tert.butyl-1,2(R)-piperazinedicarboxamide (Preparative Example 56) (0.4 gm) was dissolved in 3 ml of dichloromethane and 1 ml of trifluoroacetic acid was added and the reaction mixture stirred for 3 hours at ambient temperature. The reaction mixture was then evaporated to dryness to obtain the pure title product.

PREPARTIVE EXAMPLE 58

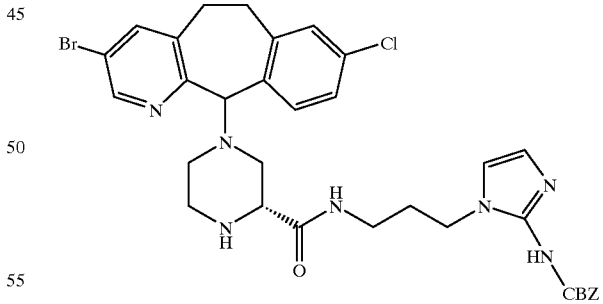

1-benzyloxycarbonylaminopropyl-2-aminoimidazolyl-1,2(R)-piperazinedicarboxamide (Preparative Example 57) was dissolved in 50 ml of DMF and 0.46 ml of triethylamine. 3-Bromo-8,11-dichloro-6,11-dihydro-5H-benzo[5,6]cyclohepta[1,2-b]pyridine (171 mg) was added and the reaction mixture stirred for 24 hours. The reaction mixture was added to brine and extracted with dichloromethane to obtain 82 mg of pure title product after silica gel chromatography using methanol/dichloro-methane as the eluent.
FABMS (M+1)=694.

PREPARATIVE EXAMPLE 59

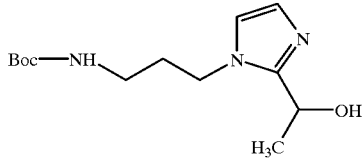

1-tert-Butoxycarbonylaminopropyl-imidazole (0.991 gm, 4.4 mmol) was dissolved in 25 mol of dry THF and cooled to −78° C. A 2.5M solution of n-butyllithium (3.88 ml, 9.68 mmol) in cyclohexanes was added dropwise and the reaaction stirred for ½ hour. Acetaldehyde (0.49 ml, 8.8 mmol) was added and the reaction stirred for ½ hour. The reaction mixture was allowed to warm to ambient temperature. The reaction was diluted with ethyl acetate and washed with brine. The ethyl acetate layer was evaporated to obtain a gum which was chromatographed on silica gel to obtain 0.54 gm of title product. ($MH^+$=170).

PREPARATIVE EXAMPLE 60

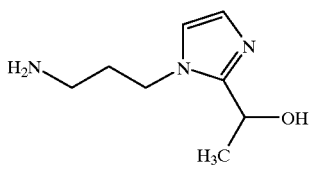

1-tert-Butoxycarbonylaminopropyl-2-hydroxyethyl-imidazole (Preparative Example 59) (0.51 gm) was dissolved in trifluoroacetic acid and stirred for 3–4 hours. The mixture was evaporated to dryness to obtain the pure TFA salt of the title compound.

PREPARATIVE EXAMPLE 61

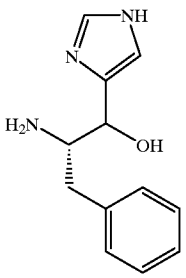

1-N-Trityl-4-iodoimidazole (1.91 gm) was dissolved in 20 ml of dichloromethane and 1.46 ml of ethyl magnesium-bromide was added while stirring. After 15 min. N-Boc-phenylalanine aldehyde (0.5 gm) was added and the reaction mixture was stirred for 18 hours. The reaction mixture was washed with saturated ammonium chloride, dried over magnesium sulfate, and chromatographed on silica gel to obtain 0.8 gm of the intermediate blocked product. FABMS (M+1)=561. This was then treated with 4M HCl/dioxane for 18 hours. The mixture was evaporated to dryness and dissolved in distilled water and washed with ethyl acetate. The aqueous layer was evaporated to obtain pure title product. ($MH^+$=218).

PREPARATIVE EXAMPLE 62

Step A

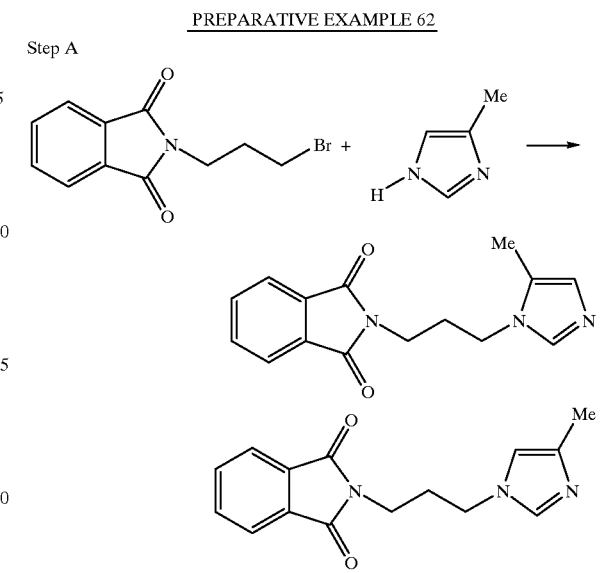

A mixture of N-(3-bromopropyl)phthalimide (12.3 g, 46 mmol), 4-methylimidazole (3.78 g, 46 mmol), sodium hydride (60% in mineral oil, 1.84 g, 46 mmol) and anhydrous DMF (50 mL) was stirred at 25–70° C. under $N_2$ overnight. The mixture was concentrated in vacuo to give a residue which was diluted with dichloromethane, filtered, concentrated in vacuo and purified by flash column chromatography (silica gel) using 1% MeOH—$CH_2Cl_2$ saturated with aqueous ammonium hydroxide to give the title compound as an oil (8.04 g, 65%, $MH^+$=270).

Step B

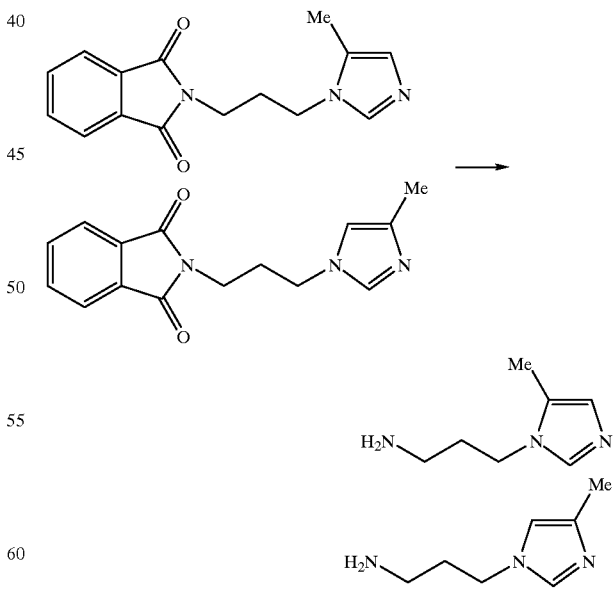

To a solution of the title compound from Step A (8.02 g, 29.8 mmol) dissolved in absolute EtOH (150 mL) was added hydrazine-mono hydrate (15 mL) and the mixture was stirred at reflux for 12 h under $N_2$. The mixture was diluted with dichloromethane, filtered and concentrated in vacuo. The residue was purified by flash column chromatography (silica gel) using 5% MeOH—$CH_2Cl_2$ saturated with aqueous ammonium hydroxide to give the title compound as an oil (2.95 g, 71%, $MH^+$=140).

Preparative Examples 63–67

Following the procedure set forth in Preparative Example 62, but using the substituted imidazole in Table 3 below instead of 4-methylimidazole in Step A, the amines (Product) listed in Table 3 were prepared.

TABLE 3

| Prep. Ex. | Imidazole | Product | $MH^+$ | Yield (%) |
|---|---|---|---|---|
| 63 | | | 154 | 70 |
| 64 | | | 154 | 60 |
| 65 | | | 154 | 68 |
| 66 | | | 140 | 46 |
| 66.1 | | | — | 88 |

$MH^+$ 266.1657

$MH^+$ 266.1657

Preparative Example 67

If the procedure set forth in Preparative Example 62 were followed, except the imidazole

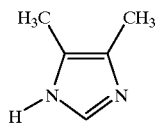

would be used instead of 4-methylimidazole in Step A, the amine

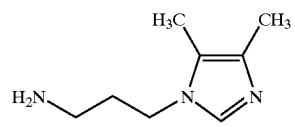

would be obtained.

Preparative Example 67.1

If the procedure set forth in Preparative Example 62 were followed, except the imidazole

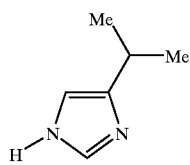

would be used instead of 4-methylimidazole in Step A, the amine

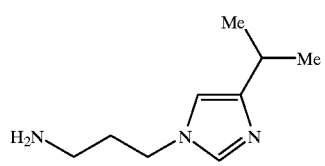

would be obtained.

PREPARATIVE EXAMPLE 68

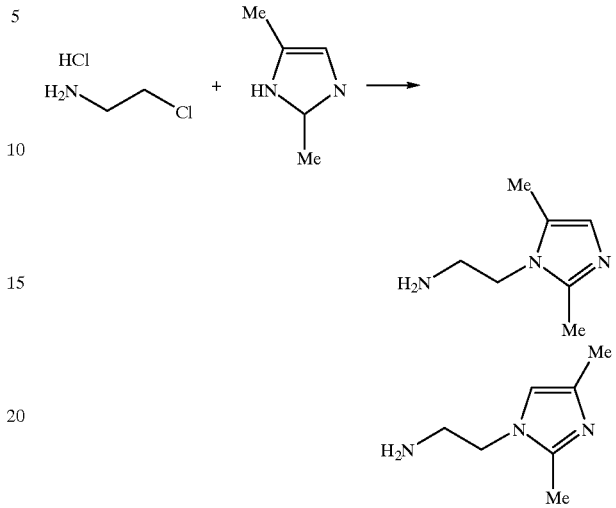

A mixture of 2-chloroethylamine hydrochloride (7.66 g, 66 mmol), 2,4-dimethylimidazole (5.88 g, 61 mmol), tetrabutyl ammonium sulfate (0.83 g, 2.5 mmol), solid NaOH (8.81 g, 220 mmol) and anhydrous acetonitrile (80 mL) was stirred at reflux for 48 h under $N_2$. The mixture was filtered, concentrated in vacuo and purified by flash column chromatography (silica gel) using 2% MeOH—$CH_2Cl_2$ saturated with aqueous ammonium hydroxide to give the title compound as an oil (10.7 g, 100%, $MH^+$=140).

Preparative Examples 69–73

Following the procedure set forth in Preparative Example 68, but using the substituted imidazole or triazole in Table 4 below instead of 2,4-dimethylimidazole, the amines (Product) listed in Table 4 were prepared.

TABLE 4

| Prep. Ex. | Imidazole | Product | $MH^+$ | Yield (%) |
|---|---|---|---|---|
| 69 | ![imidazole] | ![product] | 126 | 75 |

TABLE 4-continued

| Prep. Ex. | Imidazole | Product | MH+ | Yield (%) |
|---|---|---|---|---|
| 70 | (imidazole) | H₂N-CH₂CH₂-imidazole | 112 | 65 |
| 71 | 2-unsubstituted benzimidazole | N-(2-aminoethyl)benzimidazole | 176 | 55 |
| 72 | 2-methylimidazole | 1-(2-aminoethyl)-2-methylimidazole | 126 | 53 |
| 73 | benzotriazole | (A) 1-(2-aminoethyl)benzotriazole | (A): 163 | (A): 60 |
|  |  | (B) 2-(2-aminoethyl)benzotriazole | (B): 163 | (B): 40 |

PREPARATIVE EXAMPLE 74

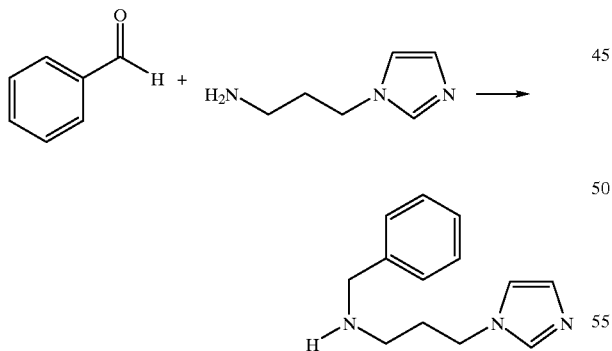

A mixture of 1-(3-aminopropyl)imidazole (37.1 g, 297 mmol), benzaldehyde (30 g, 283 mmol), 3 Å molecular sieves (50 g), sodium acetate (24.1 g, 283 mmol) and anhydrous methanol (700 mL) was stirred at room temperature under $N_2$ overnight. The mixture was cooled to 0° C. and sodium borohydride (10.9 g, 288 mmol) was added portionwise over 1 hour. The mixture was stirred at room temperature for 3 hours. The mixture was filtered through celite, washed with methanol, and concentrated in vacuo to give a residue which was diluted with dichloro-methane and washed with 10% aqueous sodium hydroxide. The organic phases were washed with brine, dried over anhydrous magnesium sulfate, filtered and concentrated in vacuo to give the title compound as a pale yellow oil (56.3 g, 92%, MH+= 216).

Preparative Examples 75–95

Following the procedure set forth in Preparative Example 74, but using the aldehyde and imidazolylalkyl amine (Imidazole) in Table 5, the amines (Product) in Table 5 were obtained.

TABLE 5

| Prep Ex. | Aldehyde | Imidazole | Product | % Yield (MH⁺) |
|---|---|---|---|---|
| 75 | 3-fluorobenzaldehyde | 1-(3-aminopropyl)imidazole | N-(3-fluorobenzyl)-3-(1-imidazolyl)propylamine | 46 (234) |
| 76 | N-(4-fluorobenzyl)-3-(1-imidazolyl)propylamine | 1-(3-aminopropyl)imidazole | N-(3-fluorobenzyl)-3-(1-imidazolyl)propylamine | 91 (234) |
| 77 | isonicotinaldehyde | 1-(3-aminopropyl)imidazole | N-(4-pyridylmethyl)-3-(1-imidazolyl)propylamine | 74 (217) |
| 78 | nicotinaldehyde | 1-(3-aminopropyl)imidazole | N-(3-pyridylmethyl)-3-(1-imidazolyl)propylamine | 92 (217) |
| 79 | 3-hydroxybenzaldehyde | 1-(3-aminopropyl)imidazole | N-(3-hydroxybenzyl)-3-(1-imidazolyl)propylamine | 98 (232) |
| 80 | 3-methoxybenzaldehyde | 1-(3-aminopropyl)imidazole | N-(3-methoxybenzyl)-3-(1-imidazolyl)propylamine | 97 (246) |
| 81 | 4-methoxybenzaldehyde | 1-(3-aminopropyl)imidazole | N-(4-methoxybenzyl)-3-(1-imidazolyl)propylamine | 81 (246) |

TABLE 5-continued

| Prep Ex. | Aldehyde | Imidazole | Product | % Yield (MH+) |
|---|---|---|---|---|
| 82 | 3-cyanobenzaldehyde | 1-(3-aminopropyl)imidazole | N-(3-cyanobenzyl)-3-(imidazol-1-yl)propylamine | 68 (241) |
| 83 | 2-naphthaldehyde | 1-(3-aminopropyl)imidazole | N-(naphth-2-ylmethyl)-3-(imidazol-1-yl)propylamine | 87 (266) |
| 84 | cyclohexanecarboxaldehyde | 1-(3-aminopropyl)imidazole | N-(cyclohexylmethyl)-3-(imidazol-1-yl)propylamine | 84 (222) |
| 85 | benzaldehyde | 1-(3-aminopropyl)-4-methylimidazole (A) and 1-(3-aminopropyl)-5-methylimidazole (B) | (A) N-benzyl-3-(4-methylimidazol-1-yl)propylamine; (B) N-benzyl-3-(5-methylimidazol-1-yl)propylamine | (A): 45 (230); (B): 21 (230) |
| 86 | pyridine-3-carboxaldehyde | 1-(3-aminopropyl)-4-methylimidazole and 1-(3-aminopropyl)-5-methylimidazole | N-(pyridin-3-ylmethyl)-3-(4-methylimidazol-1-yl)propylamine and N-benzyl-3-(5-methylimidazol-1-yl)propylamine | 62 (239) |

TABLE 5-continued

| Prep Ex. | Aldehyde | Imidazole | Product | % Yield (MH+) |
|---|---|---|---|---|
| 87 | benzaldehyde | 1-(2-aminoethyl)imidazole | N-benzyl-2-(imidazol-1-yl)ethylamine | 80 (202) |
| 88 | benzaldehyde | 1-(3-aminopropyl)-2-ethylimidazole | N-benzyl-3-(2-ethylimidazol-1-yl)propylamine | 63 (244) |
| 89 | benzaldehyde | 1-(3-aminopropyl)-2,4-dimethylimidazole | N-benzyl-3-(2,4-dimethylimidazol-1-yl)propylamine | 86 (244) |
|  | benzaldehyde | 1-(3-aminopropyl)-2,5-dimethylimidazole | N-benzyl-3-(2,5-dimethylimidazol-1-yl)propylamine |  |
| 90 | 4-fluorobenzaldehyde | 1-(3-aminopropyl)-4-methylimidazole | N-(4-fluorobenzyl)-3-(4-methylimidazol-1-yl)propylamine | 83 (248) |
|  | | 1-(3-aminopropyl)-5-methylimidazole | N-(4-fluorobenzyl)-3-(5-methylimidazol-1-yl)propylamine | |
| 91 | benzaldehyde | 1-(3-aminopropyl)-4-ethylimidazole | N-benzyl-3-(4-ethylimidazol-1-yl)propylamine | 20 (244) |

TABLE 5-continued

| Prep Ex. | Aldehyde | Imidazole | Product | % Yield (MH+) |
|---|---|---|---|---|
| 93 | | | | 44 (216) |
| 94 | | | | 95 (230) |
| 95 | | | | 68 (217) |

PREPARATIVE EXAMPLE 95.1

Step A

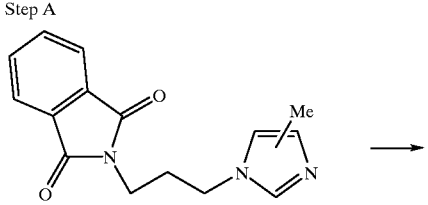

To a CH$_2$Cl$_2$ (500 mL) solution of the title compound from Preparative Example 62 Step A (65.7 g) cooled to 0° C. was added trityl choride (27.2 g). The resulting mixture was warmed to and stirred at room temperature for 1.5 hr, then concentrated in vacuo without heating. Purification by flash column chromatography (silica, 1:1 Acetone-EtOAc) afforded the pure 4-methyl isomer (35.02 g, MH+=270).

Step B

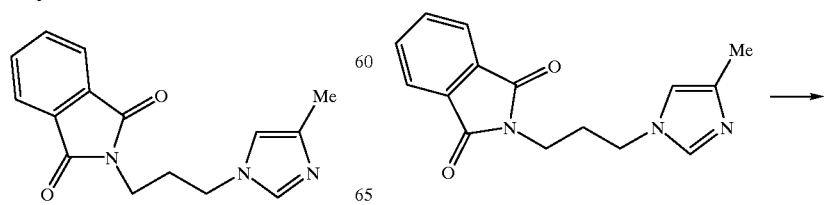

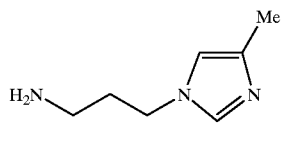

Following essentially the same procedure as that described in Preparative Example 62 Step B except using the pure 4-methylimidazole product from Preparative Example 95.1 Step A (35.02 g), the title compound was afforded (16.12 g, MH⁺=140).

Step C

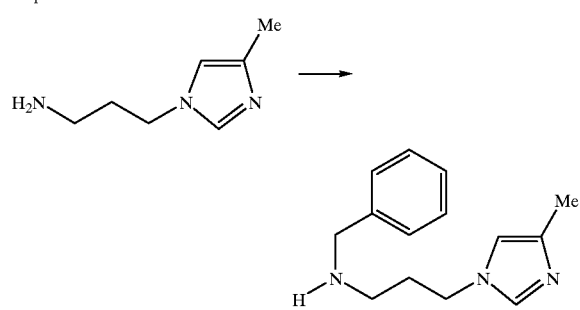

Following essentially the same procedure as that described in Preparative Example 74 except using the pure 4-methylimidazolepropylamine product from Preparative Example 95.1 Step B above (16.12 g) instead of 1-(3-aminopropyl)imidazole, the title compound was afforded (18.03 g, MH⁺=230).

PREPARATIVE EXAMPLE 97

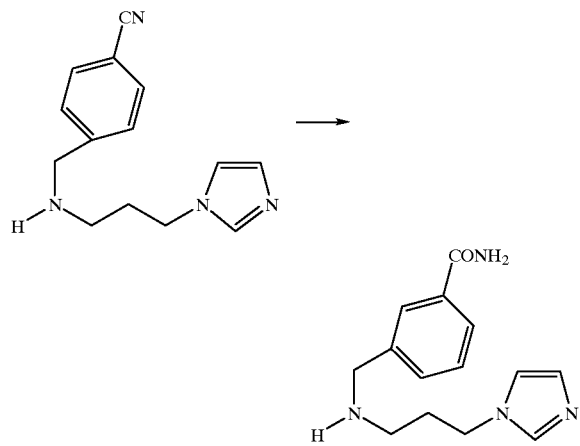

A mixture of the title compound from Preparative Example 82 (0.50 g, 2.1 mmol), absolute EtOH (50 mL), 30% hydrogen peroxide (aq) (0.45 mL, 4.4 mmol) and 1M NaOH (aq) (4.4 mL, 4.4 mmol) was stirred at 50° C. for 12 h. The mixture was concentrated in vacuo and purified by flash column chromatography (silica gel) using 10% MeOH—CH₂Cl₂ saturated with aqueous ammonium hydroxide to give the title compound as an oil (0.33 g, 61%, MH⁺=259).

PREPARATIVE EXAMPLE 98

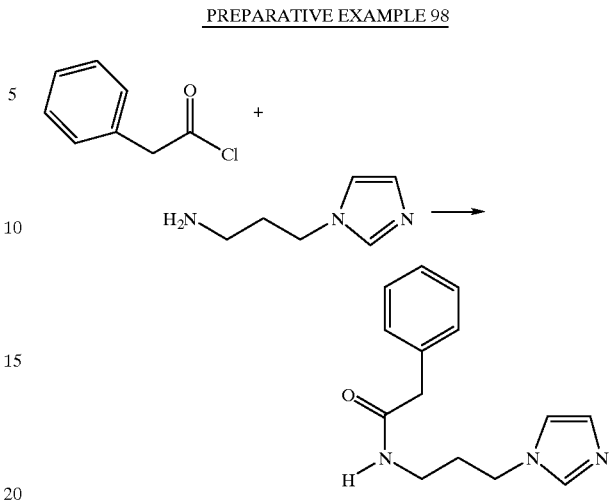

To a cooled (0° C.) solution of 1-(3-aminopropyl)imidazole (Aldrich, 1.9 mL, 16 mmol) and triethylamine (5.6 mL, 40 mmol) dissolved in anhydrous CH₂Cl₂ (20 mL) was added phenylacetyl chloride (2.12 mL, 16 mmol). The mixture was warmed to and stirred at room temperature overnight. The mixture was washed with 1N aqueous NaOH, dried over anhydrous MgSO₄ and filtered. The solution was concentrated in vacuo and purified by flash column chromatography (silica gel) using 2% MeOH—98% CH₂Cl₂ saturated with aqueous ammonium hydroxide to give the title compound as an oil (1.8 g, 45%, MH⁺=244).

PREPARATION EXAMPLE 99

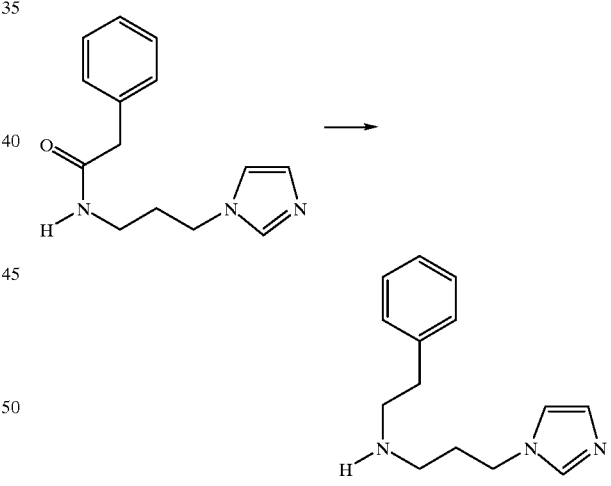

To a refluxing solution of the title compound from Preparative Example 98 (0.51 g, 2.1 mmol) dissolved in anhydrous THF (5 mL) was added borane dimethylsulfide complex (6.3 mL, 2M in THF, 13 mmol). After 1 hr, the mixture was cooled to room temperature and stirred overnight. Hydrochloric acid (1N) was added dropwise until the reaction mixture was determined to be acidic (pH paper). The mixture was basified with 1N aqueous NaOH, extracted with CH₂Cl₂, dried over anhydrous MgSO₄ and filtered. The solution was concentrated in vacuo and purified by flash column chromatography (silica gel) using 2% MeOH-98% CH₂Cl₂ saturated with aqueous ammonium hydroxide to give the title compound as an oil (0.25 g, 52%, MH⁺=230).

PREPARATIVE EXAMPLE 100

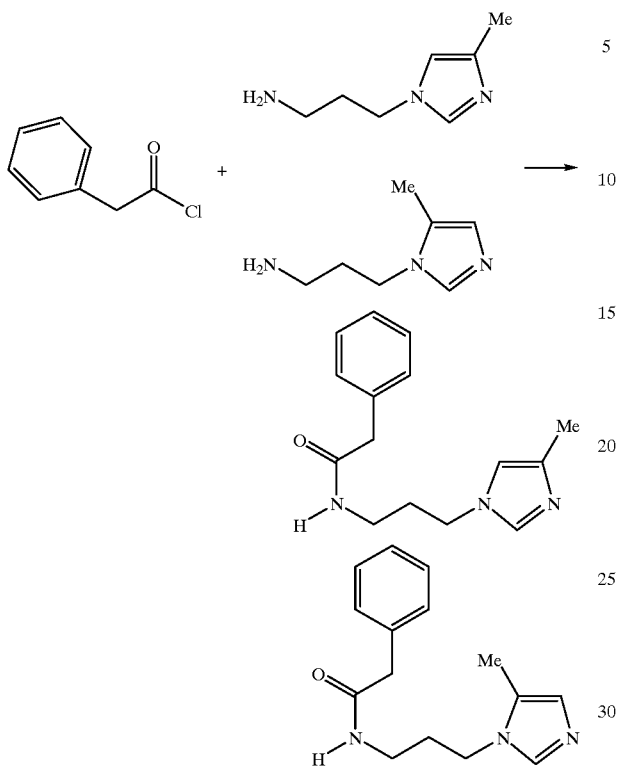

To a cooled (0° C.) solution of the title compound from Preparative Example 62 Step B (0.7 g, 5 mmol) and triethylamine (1.7 mL, 12.5 mmol) dissolved in anhydrous CH$_2$Cl$_2$ (10 mL) was added phenylacetyl chloride (0.67 mL, 5 mmol). The mixture was warmed to and stirred at room temperature overnight. The mixture was washed with 1M HCl (aq) and the aqueous phase was basified with 1N aqueous NaOH. This phase was extracted with CH$_2$Cl$_2$ and dried over anhydrous MgSO$_4$ and filtered. The solution was concentrated in vacuo to give the title compound as an oil (0.72 g, 56%, MH$^+$=258).

PREPARATIVE EXAMPLE 101

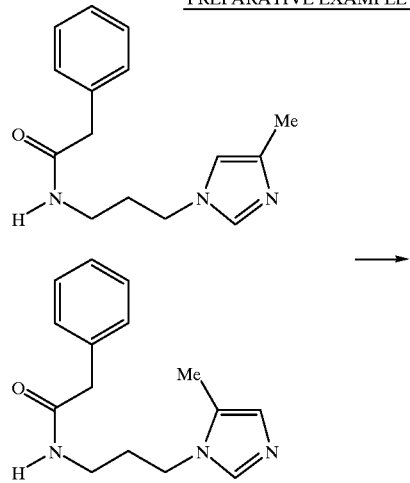

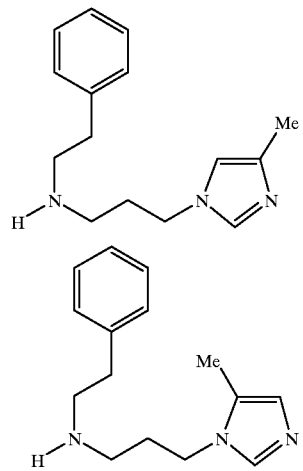

To a refluxing solution of the title compound from Preparative Example 100 (0.66 g, 2.5 mmol) dissolved in anhydrous THF (15 mL) was added borane-THF complex (5 mL, 1M in THF, 5 mmol). The mixture was refluxed for 12 h, then cooled to room temperature and concentrated in vacuo. The residue was diluted with 1M HCl and washed with CH$_2$Cl$_2$ then the aqueous phase was basified with 50% aqueous NaOH and extracted with CH$_2$Cl$_2$ and dried over anhydrous MgSO$_4$ and filtered. The solution was concentrated in vacuo and purified by preparative plate chromatography (silica gel) using 3% MeOH—CH$_2$Cl$_2$ saturated with aqueous ammonium hydroxide to give the title compound as an oil (0.21 g, 35%, MH$^+$=244) which was purified by preparative chiral chromatography (Chiralpack AD, 5 cm×50 cm column, flow rate 80 mL/min, 5–8% IPA-Hexane+0.2% diethylamine).

Preparative Example 101.1

If the procedure of Preparative Example 100 were followed, but the compound

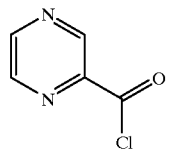

was to be reacted with the title compound from Preparative Example 62 Step B, then the Product

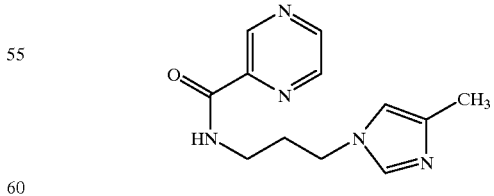

would be obtained.

Preparative Example 101.2

If the procedure of Preparative Example 101 were followed, but the Product from Preparative Example 101.1 was to be used, then the Product

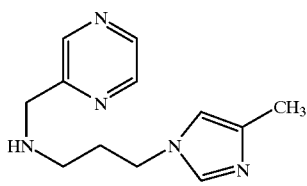

would be obtained=.

PREPARATIVE EXAMPLE 102

Step A

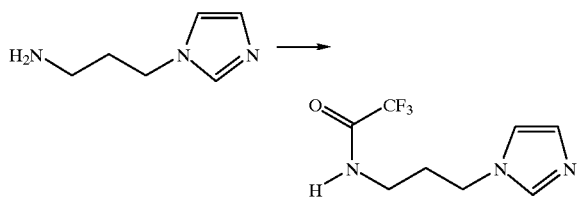

To a cooled (0° C.) solution of 1-(3-aminopropyl) imidazole (10 g, 80 mmol) and triethylamine (17.1 mL, 120 mmol) dissolved in anhydrous $CH_2Cl_2$ (50 mL) was added trifluoroacetic anhydride (12.4 mL, 88 mmol). The mixture was warmed to and stirred at room temperature overnight. The mixture was washed with water, dried over anhydrous $MgSO_4$, filtered and concentrated in vacuo to give the title compound as an oil (15.7 g, 88%, $MH^+=222$).

Step B

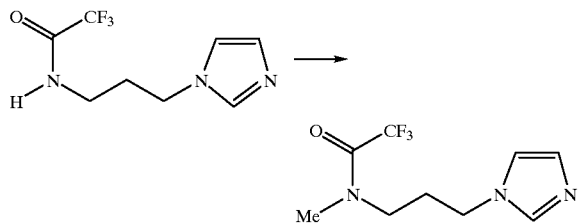

To the title compound from Step A (0.24 g, 1.1 mmol) dissolved in anhydrous DMF (10 mL) was added solid sodium hydride (85 mg, 2.1 mmol, 60% dispersion in mineral oil). When gas evolution ceased, methyl iodide (0.1 mL, 1.1 mmol) was added and the mixture was stirred at 70° C. for 40 min. The resulting mixture was cooled to room temperature, concentrated in vacuo, diluted with $CH_2Cl_2$ and washed with water. The solution was dried over anhydrous $MgSO_4$, filtered and concentrated in vacuo to give an oil (0.28 g). Purification by preparative plate chromatography (silica gel) using 2% MeOH-98% $CH_2Cl_2$ saturated with aqueous ammonium hydroxide gave the title compound as a yellow oil (78 mg, 30%, $MH^+=236$).

Step C

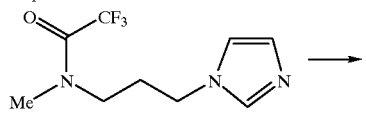

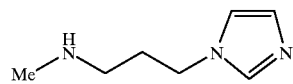

A mixture of the title compound from Step B (74 mg, 0.3 mmol) and 20% KOH in $H_2O$ (0.6 mL) was stirred at room temperature for 15 min. The resulting mixture was concentrated in vacuo and purified by flash column chromatography (silica gel) using 10% MeOH-90% $CH_2Cl_2$ saturated with aqueous ammonium hydroxide to gave the title compound as an oil (65 mg, 100%, $MH^+=140$).

PREPARATIVE EXAMPLE 103

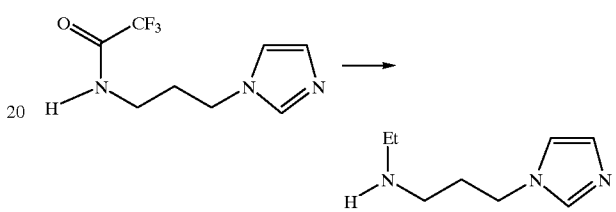

Following a similar procedure as that used for the preparation of the title compounds from Preparative Example 102 Steps B–C, but using ethyl iodide instead of methyl iodide, the ethyl amine was obtained as an oil (893 mg, 43%, $MH^+=154$).

PREPARATIVE EXAMPLE 104

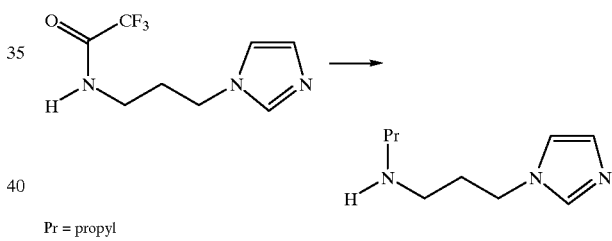

Pr = propyl

Following a similar procedure as that used for the preparation of the title compounds from Preparative Example 102 Steps B–C, but using propyl iodide instead of methyl iodide, the propyl amine was obtained as an oil (649 mg, 29%, $MH^+=168$).

PREPARATIVE EXAMPLE 105
(Alternative Procedure to Preparative Example 74)

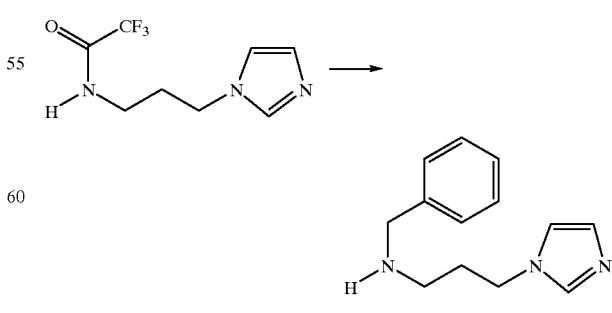

Following a similar procedure as that used for the preparation of the title compounds from Preparative Example 102

Steps B–C, but using benzyl bromide instead of methyl iodide), the benzyl amine was obtained as an oil (1.64 g, 56%, MH⁺=216).

PREPARATIVE EXAMPLE 106

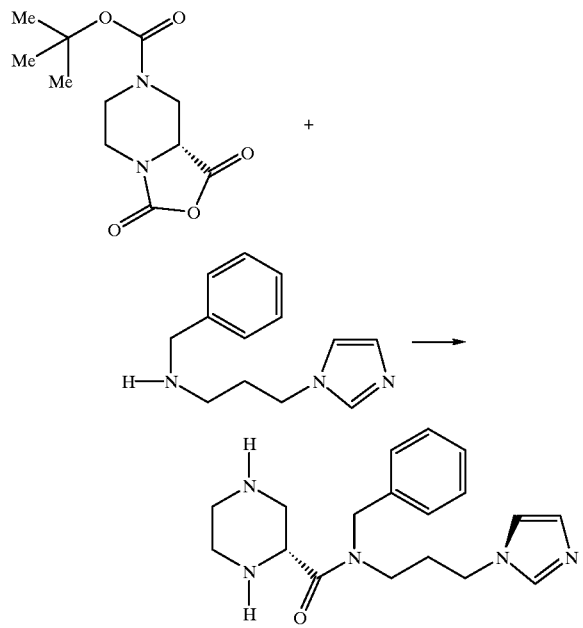

A mixture of the title compound from Preparative Example 74 (1.34 g, 6.2 mmol), the title compound from Preparative Example 44 (1.6 g, 6.2 mmol), triethyl amine (1.3 mL, 9.3 mmol) and anhydrous CH$_2$Cl$_2$ (10 mL) was stirred at room temperature for 48 hrs. Trifluoroacetic acid (10 mL) was added and the resulting mixture was stirred for an additional 1.5 hrs. Aqueous NaOH (1N) was added dropwise to neutralize the reaction mixture and the resulting mixture was extracted with CH$_2$Cl$_2$. The organic phase was dried over anhydrous MgSO$_4$, filtered and concentrated in vacuo to give a residue which was purified by flash column chromatography (silica gel) using 1% MeOH-99% CH$_2$Cl$_2$ saturated with aqueous ammonium hydroxide to give the title compound as an oil (520 mg, 26%, MH⁺=328).

PREPARATIVE EXAMPLE 107

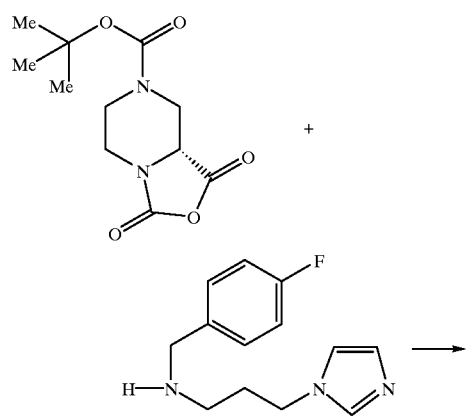

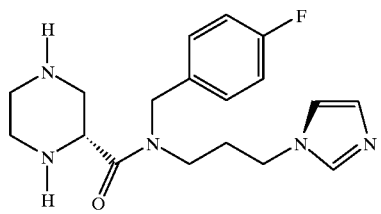

Using the procedure described for Preparative Example 106, but using the title compound from Preparative Example 76, the title compound was prepared: 0.16 g, 10%, MH⁺= 346).

PREPARATIVE EXAMPLE 108

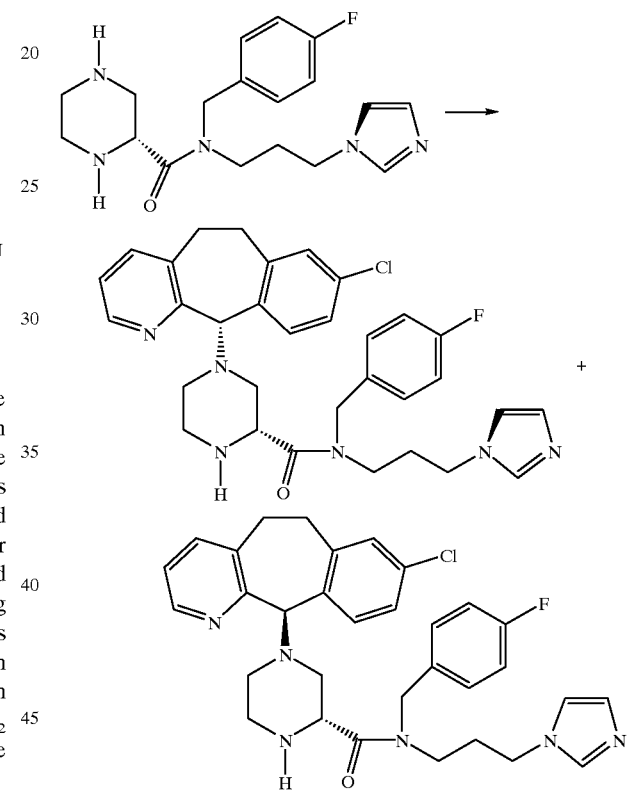

Using the procedure described for Preparative Example 110 (below), but using the title compound from Preparative Example 107 (146 mg, 0.55 mmol), and the 8-Cl-tricyclic chloride (see Preparative Example 7 in WO 95/10516)

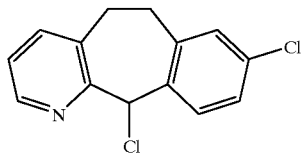

(159 mg, 0.46 mmol), the title compounds were prepared and separated by preparative plate chromatography (silica gel) using 2% MeOH—CH$_2$Cl$_2$ saturated with aqueous ammonium hydroxide: diastereomer A (45, 17.1%, MH⁺= 573); diastereomer B (43 mg, 16.3%, MH⁺=573).

PREPARATIVE EXAMPLE 109

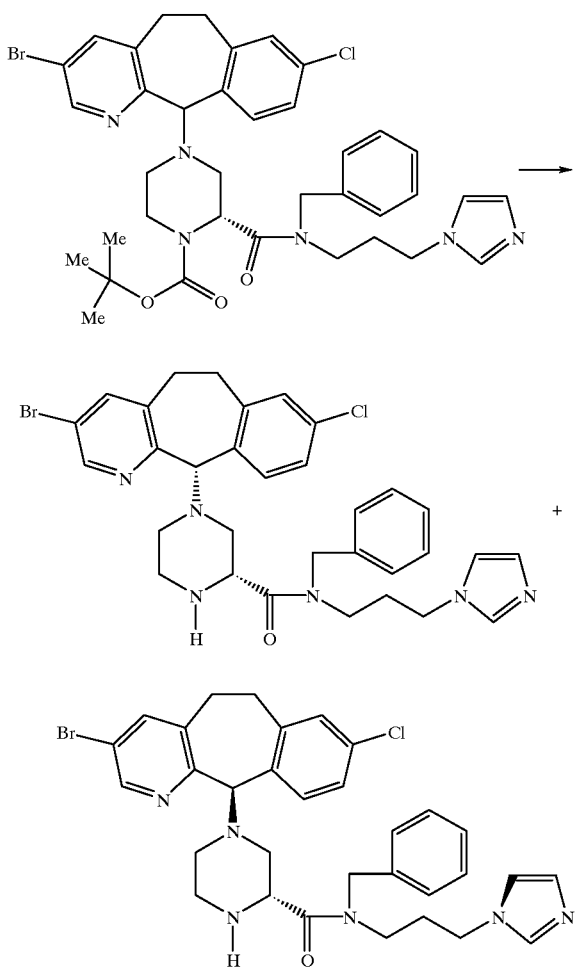

To a solution of the title compound from Example 113 (below) (4.90, 6.7 mmol) dissolved in anhydrous $CH_2Cl_2$ (25 mL) was added TFA (15 mL). The solution was stirred at room temperature under $N_2$ for 2 hrs, then concentrated in vacuo, diluted with $CH_2Cl_2$, washed with a saturated aqueous solution of $NaHCO_3$ and dried over anhydrous $MgSO_4$. The mixture was filtered concentrated in vacuo and purified by flash column chromatography (silica gel) using 2% MeOH-98% $CH_2Cl_2$ saturated with aqueous ammonium hydroxide to give the title compound as a mixture of diastereomers (3.66 g, quantitative). The diastereomers were separated by preparative chiral chromatography (Chiralpack AD, 5 cm×50 cm column, flow rate 80 mL/min., 99.8% MeOH +0.2% diethylamine) to give 1.62 g of the 11S,2R diastereomer A and 1.97 g of the 11R,2R diastereomer B.

Physical chemical data 11S,2R diastereomer A: mp=109.3° C.; $MH^+$=633; $[\alpha]^{20}_D$=−66.2° (3.93 mg/2 mL MeOH).

Physical chemical data 11R,2R diastereomer B: mp=64.5° C.; $MH^+$=633; $[\alpha]^{20}_D$=−41.80° (4.69 mg/2 mL MeOH).

PREPARATIVE EXAMPLE 110
(Alternative procedure to Preparative Example 109)

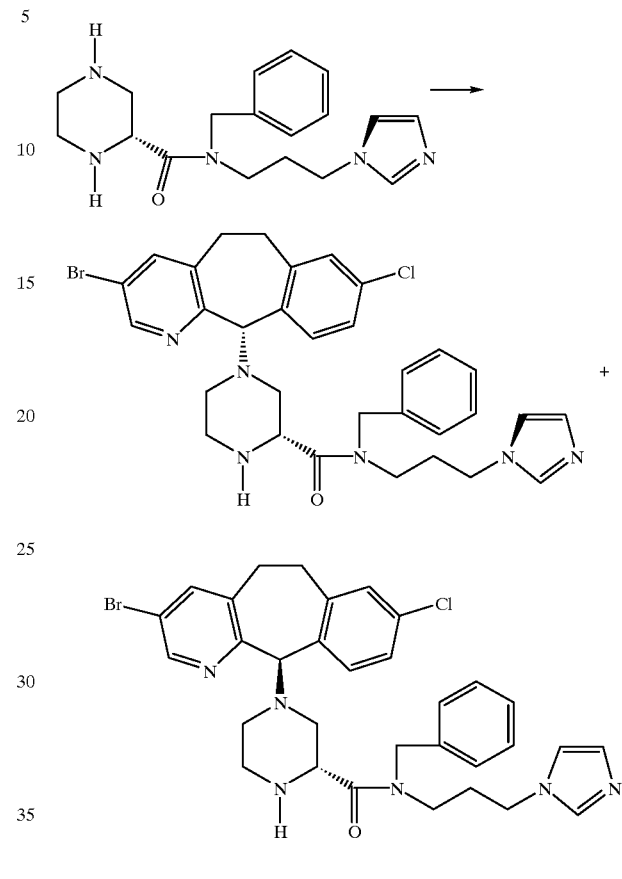

A mixture of the title compound from Preparative Example 106 (510 mg, 1.6 mmol), the tricyclic chloride (Compound No. 42.0) (534 mg, 1.6 mmol), triethylamine (1.1 mL, 7.8 mmol) and $CH_2Cl_2$ (10 mL) was stirred at room temperature overnight. The reaction mixture was concentrated in vacuo and purified by flash colunm chromatography (silica gel) using 2% MeOH-98% $CH_2Cl_2$ saturated with aqueous ammonium hydroxide to give the title compound as a light yellow solid (420 mg, 42%, $MH^+$=633). The diastereomers were separated by preparative chiral chromatography (Chiralpack AD, 5 cm×50 cm column, flow rate 80 mL/min., 99.8% MeOH +0.2% diethylamine) to give 182 mg of diastereomer A and 126 mg of diastereomer B.

PREPARATIVE EXAMPLE 111

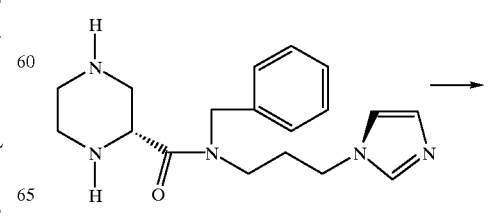

-continued

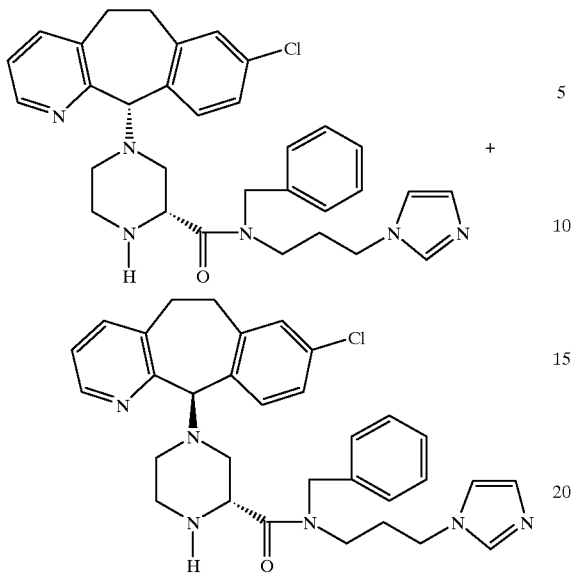

A mixture of the title compound from Preparative Example 106 (1.93 g, 5.9 mmol), the 8-Cl-tricyclic chloride (see Preparative Example 7 in WO95/10516) (1.56 g, 5.9 mmol), triethylamine (4.1 mL, 29.5 mmol) and $CH_2Cl_2$ (10 mL) was stirred at room temperature for 48 h. The reaction mixture was concentrated in vacuo and purified by flash column chromatography (silica gel) using 2% MeOH-98% $CH_2Cl_2$ saturated with aqueous ammonium hydroxide to give the title compound as a light yellow solid (1.56 g, 49%, $MH^+=555$). The diastereomers were separated by preparative chiral chromatography (Chiralpack AD, 5 cm×50 cm column, flow rate 80 mL/min., 30% IPA+70% Hexane +0.2% diethylamine) to give 0.72 g of the 11S,2R diastereomer A and 0.57 g of the 11R,2R diastereomer B.

Preparative Example 111.1

Follow the procedure of Preparative Example 111, but use the 10-Cl-tricycle chloride

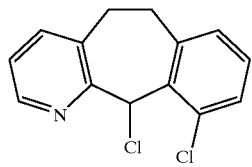

to obtain

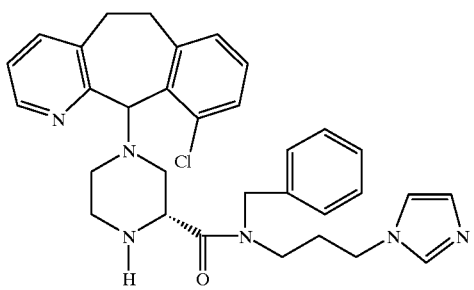

-continued
PREPARATIVE EXAMPLE 112

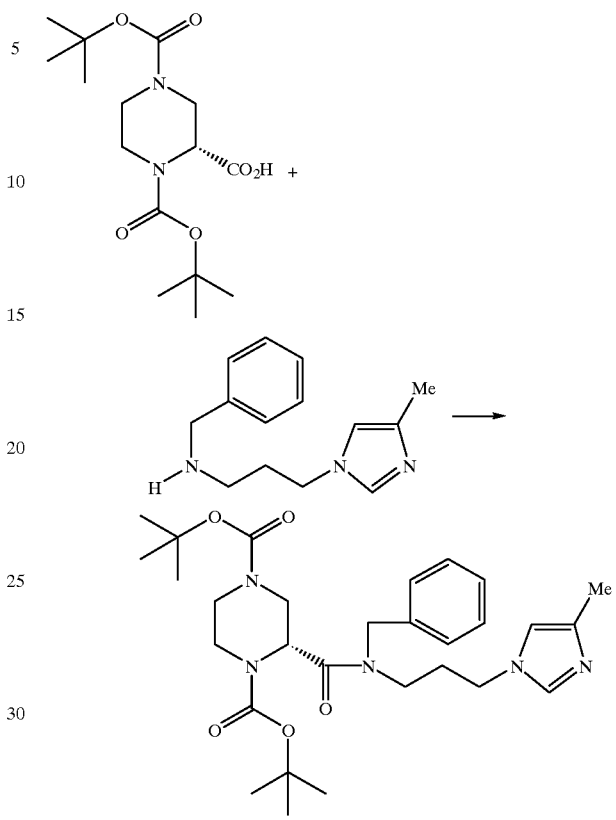

To the carboxylic acid from Preparative Example 43 (2 g, 6 mmol) were added HOBT (0.82 g, 6.1 mmol), DEC (1.2 g, 6.0 mmol), the title compound from Preparative Example 85 (1.39 g, 6.1 mmol, isolated by preparative chiral chromatography (Chiralpack AD, 5 cm×50 cm column, flow rate 80 mL/min., 8% IPA+92% Hexane+0.2% diethylamine), NMM (1.7 mL, 15.5 mmol) and anhydrous DMF (60 mL). The mixture was stirred at room temperature under $N_2$ overnight. The mixture was concentrated in vacuo, diluted with $CH_2Cl_2$ and washed with NaOH (aq). The organic phase was dried over anhydrous $Na_2SO_4$, filtered and concentrated in vacuo. The residue was purified by flash column chromatography (silica gel) using 2–15% MeOH—$CH_2Cl_2$ saturated with aqueous ammonium hydroxide to give the title compound (1.8 g, 55%, $MH^+=542$).

PREPARATIVE EXAMPLE 113

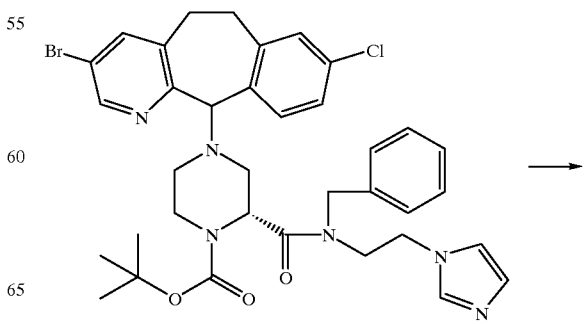

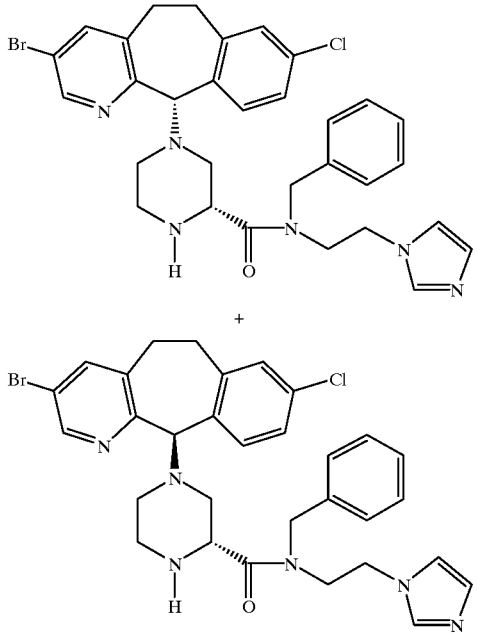

Using the procedure described for Preparative Example 109, but using the title compound from Example 126 below, the title compounds were prepared and separated: 11S,2R (−)-diastereomer A: 25.4% yield, MH⁺=619; [α]²⁰_D=−46.7° (1.86 mg/2 mL MeOH); 11R,2R(−)-diastereomer B: 21.1% yield, MH⁺=619; [α]²⁰_D=−23.0° (2.6 mg/2 mL MeOH).

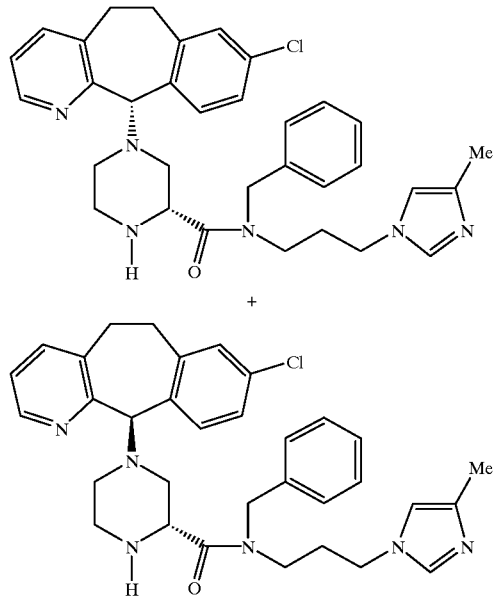

To a solution of the title compound from Preparative Example 112 (1.8, 3.33 mmol) dissolved in anhydrous CH₂Cl₂ (5 mL) was added TFA (5 mL). The solution was stirred at room temperature under N₂ overnight, concentrated in vacuo and diluted with DMF (10 mL). To this was added the 8-Cl-tricyclic chloride (562 mg, 1.1 mmol) and triethylanline (10 mL) and allowed to stir at room temperature for 48 h. The reaction mixture was concentrated in vacuo, diluted with CH₂Cl₂, washed with a saturated aqueous solution of NaHCO₃ and dried over anhydrous MgSO₄. After filtration and concentration in vacuo, the residue was purified by flash column chromatography (silica gel) using 3–10% MeOH-98% CH₂Cl₂ saturated with aqueous ammonium hydroxide to give the title compounds (11S,2R diastereomer A, 152 mg, 27%, MH⁺=569; and 11R,2R diastereomer B, 316 mg, 56%, MH⁺=569).

PREPARATIVE EXAMPLE 114

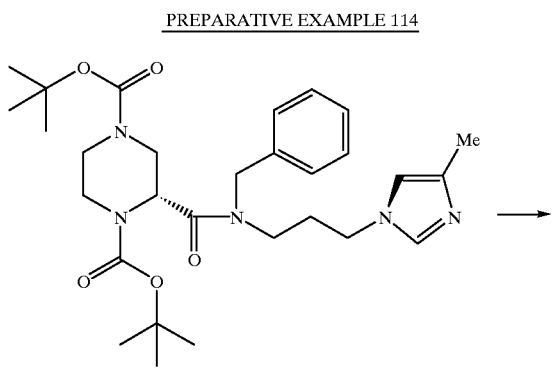

PREPARATIVE EXAMPLE 115

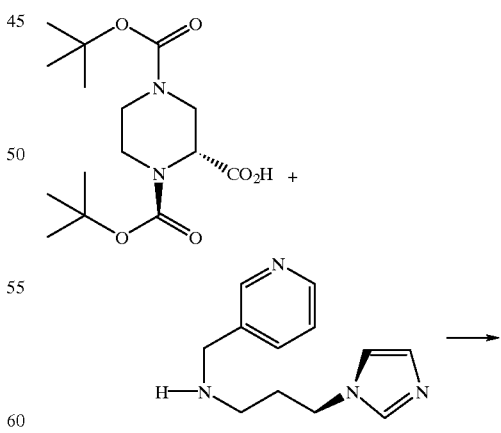

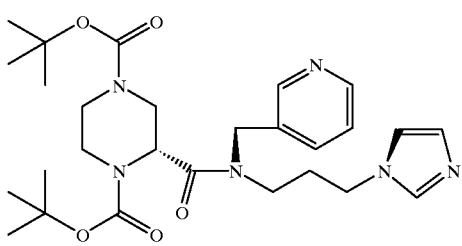

To title compound from Preparative Example 43 (2.64 g, 8.0 mmol) were added HOBT (1.26 g, 9.3 mmol), DEC (1.79 g, 9.3 mmol), the title compound from Preparative Example 78 (1.44 g, 6.7 mmol), NMM (1.5 mL, 13.6 mmol) and anhydrous DMF (10 mL). The mixture was stirred at room temperature under $N_2$ overnight. The mixture was concentrated in vacuo, diluted with $CH_2Cl_2$ and washed with NaOH (aq). The organic phase was dried over anhydrous $Na_2SO_4$, filtered and concentrated in vacuo. The residue was purified by flash column chromatography (silica gel) using 1% MeOH—$CH_2Cl_2$ saturated with aqueous ammonium hydroxide to give the title compound (0.94 g, 27%, $MH^+$=529).

PREPARATIVE EXAMPLE 116

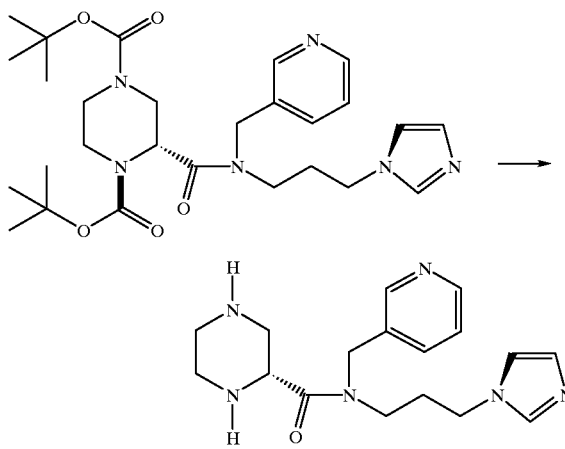

The title compound from Preparative Example 115 (0.73 g, 1.38 mmol) and anhydrous $CH_2Cl_2$ (5 mL) was stirred at room temperature for 48 hrs. Trifluoroacetic acid (2 mL) was added and the resulting mixture was stirred for an additional 1.5 hrs. Aqueous NaOH (1N) was added dropwise to neutralize the reaction mixture and the resulting mixture was extracted with $CH_2Cl_2$. The organic phase was dried over anhydrous $MgSO_4$, filtered and concentrated in vacuo to give a residue which was purified by flash column chromatography (silica gel) using 5–15% MeOH—CH2Cl2 saturated with aqueous ammonium hydroxide to give the title compound as an oil (346 mg, 76%, $MH^+$=329).

PREPARATIVE EXAMPLE 117

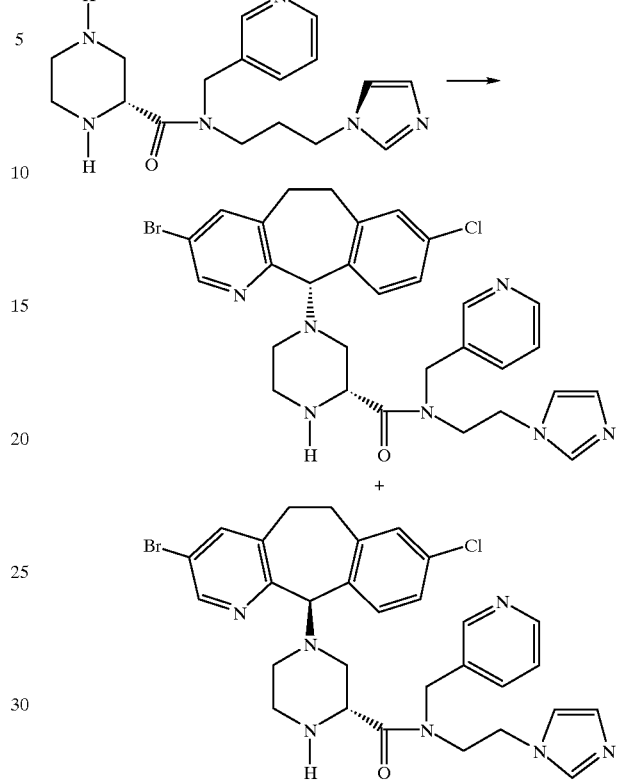

Using the procedure described for Preparative Example 110, but using the title compound from Preparative Example 116 (343 mg, 1 mmol) and the tricyclic chloride (Compound No. 42.0) (718 mg, 2 mmol), the title compounds were prepared and separated: 11S,2R diastereomer A: 135 mg, 29%, $MH^+$=634; 11R,2R diastereomer B: 126 mg, 27%, $MH^+$=634.

PREPARATIVE EXAMPLE 118

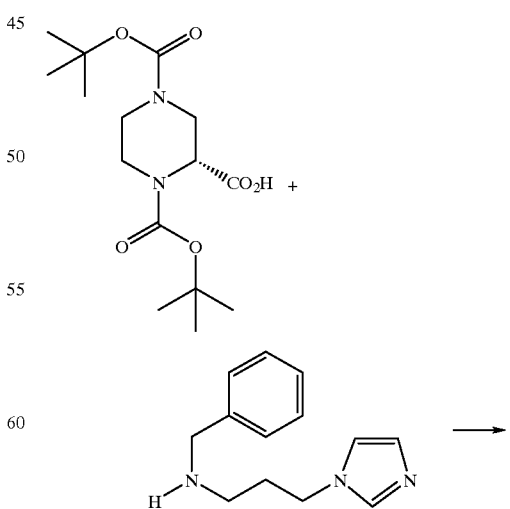

-continued

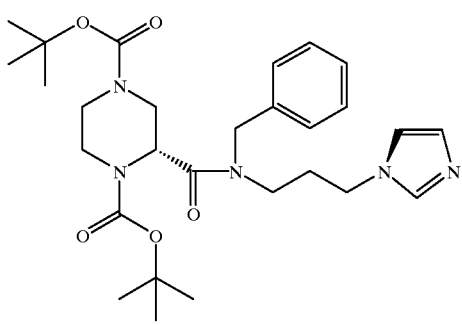

To the carboxylic acid from Preparative Example 43 (7.26 g, 22 mmol) were added HOBt (3.92 g, 29 mmol), DEC (5.49 g, 29 mmol), the title compound from Preparative Example 74 (4.73 g, 22 mmol), NMM (4.84 mL, 44 mmol) and anhydrous DMF (35 mL). The mixture was stirred at room temperature under $N_2$ overnight. The mixture was concentrated in vacuo, diluted with $CH_2Cl_2$ and washed with NaOH (aq). The organic phase was dried over anhydrous $Na_2SO_4$, filtered and concentrated in vacuo. The residue was purified by flash column chromatography (silica gel) using 1% MeOH—$CH_2Cl_2$ saturated with aqueous ammonium hydroxide to give the title compound (1.71 g, 15%, $MH^+$=528).

PREPARATIVE EXAMPLE 119

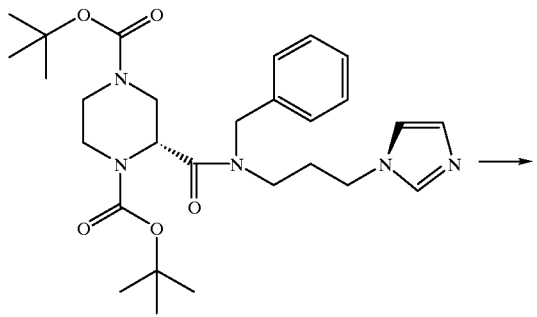

The title compound from Preparative Example 118 (1.4 g, 2.7 mmol) and paraformaldehyde (solid, 2.8 g) were heated at 130° C. in a sealed tube for 12 h. The mixture was diluted with $CH_2Cl_2$ and filtered. The organic phase was concentrated in vacuo and purified by flash column chromatography (silica gel) using 1% MeOH—$CH_2C_2$ saturated with aqueous ammonium hydroxide to give the title compound (0.89 g, 59%, $MH^+$=558).

PREPARATIVE EXAMPLE 120

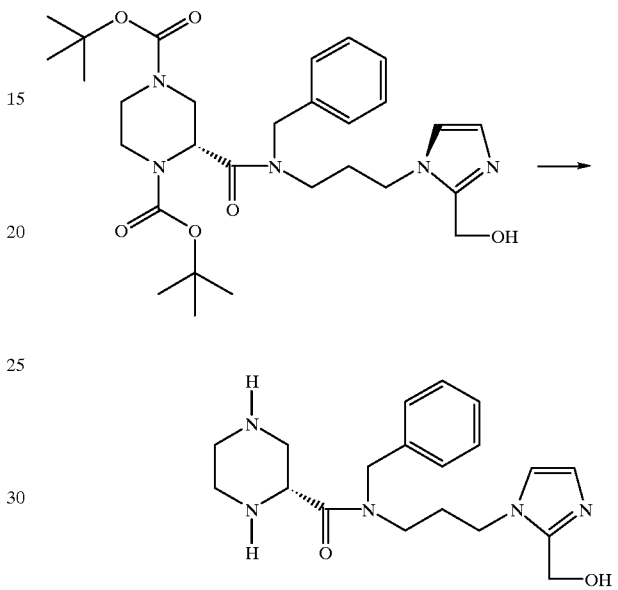

The title compound from Preparative Example 119 (0.88 g, 1.6 mmol), anhydrous $CH_2Cl_2$ (10 mL) and trifluoroacetic acid (10 mL) were stirred at room temperature for 1.5 hrs. Aqueous NaOH (1N) was added dropwise to neutralize the reaction mixture followed by concentration in vacuo and purification by flash column chromatography (silica gel) using 5–12% MeOH—$CH_2Cl_2$ saturated with aqueous ammonium hydroxide to give the title compound as an oil (503 mg, 88%, $MH^+$=358).

PREPARATIVE EXAMPLE 121

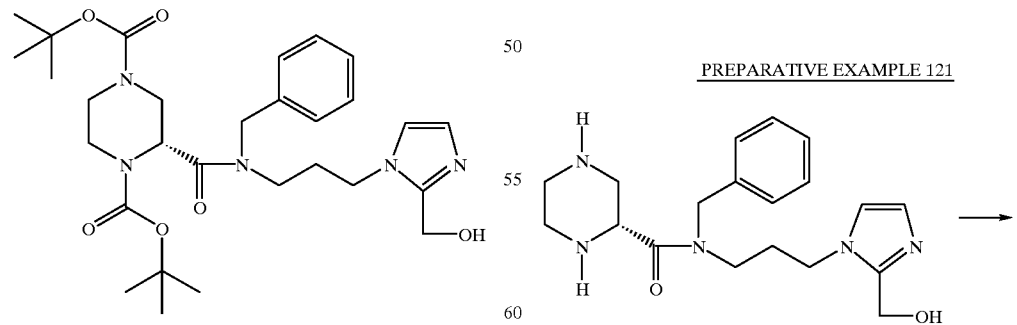

127

-continued

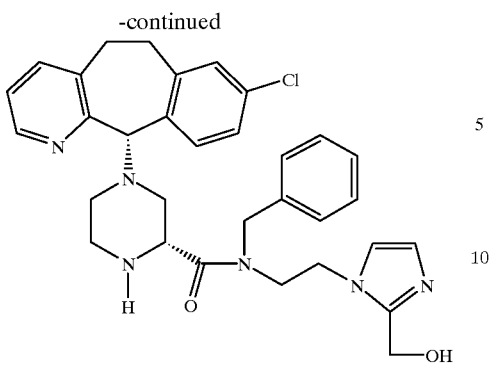

+

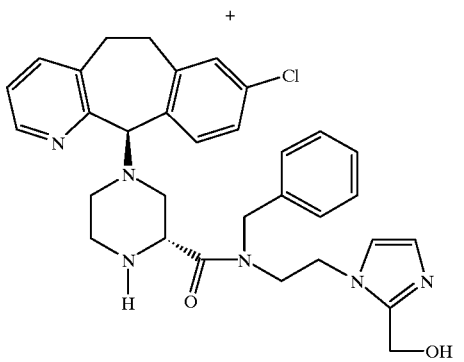

The title compound from Preparative Example 120 (498 mg, 1.4 mmol) was dissolved in anhydrous $CH_2Cl_2$ (10 mL). To this was added the 8-Cl-tricyclic chloride (370 mg, 1.4 mmol) and triethylamine (0.6 mL) and allowed to stir at room temperature for 24 h. The reaction mixture was concentrated in vacuo and diluted with $CH_2Cl_2$, purified by flash column chromatography (silica gel) using 3% MeOH—$CH_2Cl_2$ saturated with aqueous ammonium hydroxide to give the title compounds as a mixture of diastereomers (38% yield) which were separated by preparative chiral chromatography (Chiralpack AD, 5 cm×50 cm column, flow rate 80 mL/min, 30% IPA-Hexane +0.2% diethylamine). (diastereomer A: 178 mg, $MH^+$=585; and diastereomer B: 130 mg, $MH^+$=585).

PREPARATIVE EXAMPLE 122

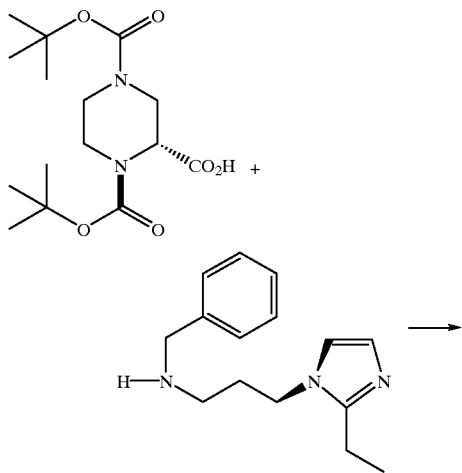

128

-continued

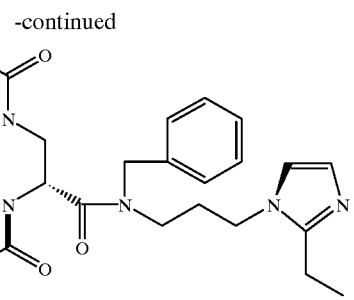

To the carboxylic acid from Preparative Example 43 (8.11 g, 25 mmol) were added HOBT (4.39 g, 33 mmol), DEC (6.33 g, 33 mmol), the title compound from Preparative Example 88 (5.97 g, 25 mmol), NMM (5.5 mL, 50 mmol) and anhydrous DMF (40 mL). The mixture was stirred at room temperature under $N_2$ for 48 h. The mixture was concentrated in vacuo, diluted with $CH_2Cl_2$ and washed with NaOH (aq). The organic phase was dried over anhydrous $Na_2SO_4$, filtered and concentrated in vacuo. The residue was purified by flash column chromatography (silica gel) using 1% MeOH—$CH_2Cl_2$ saturated with aqueous ammonium hydroxide to give the title compound (5.24 g, 38%, $MH^+$=556).

PREPARATIVE EXAMPLE 123

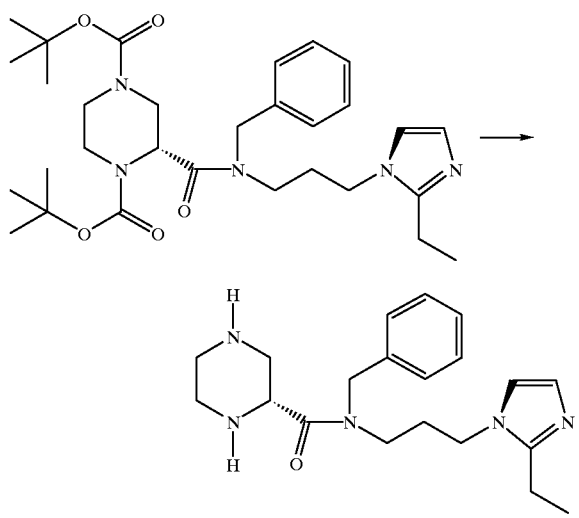

The title compound from Preparative Example 122 (5.23 g, 9.4 mmol), anhydrous $CH_2Cl_2$ (10 mL) and trifluoroacetic acid (10 mL) were stirred overnight. Aqueous NaOH (1N) was added dropwise to neutralize the reaction mixture, concentrated in vacuo, and purified by flash column chromatography (silica gel) using 5–9% MeOH—$CH_2Cl_2$ saturated with aqueous ammonium hydroxide to give the title compound as an oil (2.69 mg, 81%, $MH^+$=356).

PREPARATIVE EXAMPLE 124

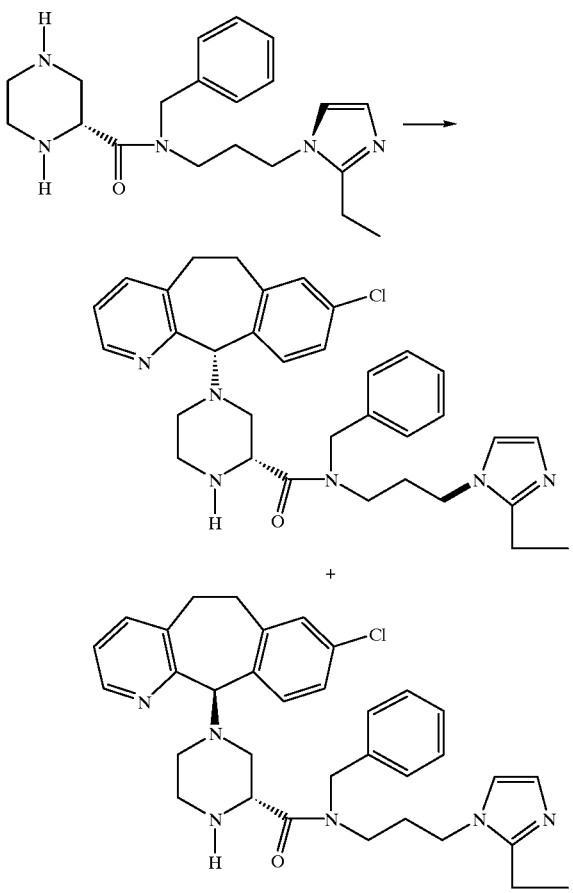

The title compound from Preparative Example 123 (2.67, 7.5 mmol) was dissolved in anhydrous $CH_2Cl_2$ (40 mL). To this was added the 8-Cl-tricyclic chloride (1.98 g, 7.5 mmol) and triethylamine (3.14 mL) and allowed to stir at room temperature for 12 h. The reaction mixture was concentrated in vacuo, diluted with $CH_2Cl_2$, washed with a saturated aqueous solution of $NaHCO_3$ and dried over anhydrous $MgSO_4$. After filtration and concentration in vacuo, the residue was purified by flash column chromatography (silica gel) using 1–2% MeOH—$CH_2Cl_2$ saturated with aqueous ammonium hydroxide to give the title compounds in 43% yield (diastereomer A, 1.2 g, $MH^+$=583; and diastereomer B, 681 mg, $MH^+$=583).

PREPARATIVE EXAMPLE 125

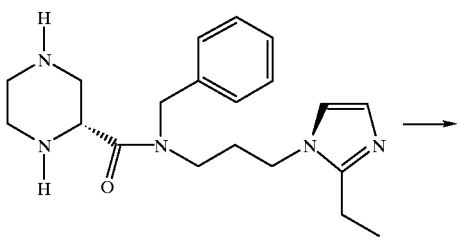

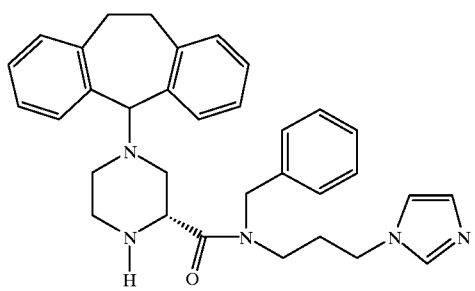

A mixture of the title compound from Preparative Example 106 (200 mg, 0.61 mmol), chlorobenzosuberane (140 mg, 0.61 mmol), triethylamine (0.43 mL, 3.1 mmol) and $CH_2Cl_2$ (10 mL) was stirred at room temperature overnight. The reaction mixture was concentrated in vacuo and purified by preparative plate chromatography (silica gel) using 2% MeOH—$CH_2Cl_2$ saturated with aqueous ammonium hydroxide to give the title compound as a light yellow solid (63 mg, 20%, $MH^+$=520).

PREPARATIVE EXAMPLE 126

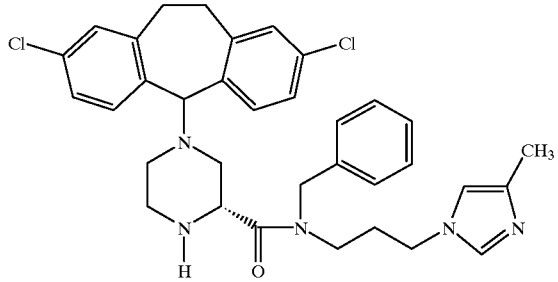

If the procedure of Preparative Example 114 is followed, except the 3,8-dichloro tricyclic compound

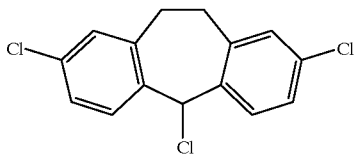

is used instead of the 8-Cl-tricycle chloride, the title compound would be obtained.

PREPARATIVE EXAMPLE 127

Step A

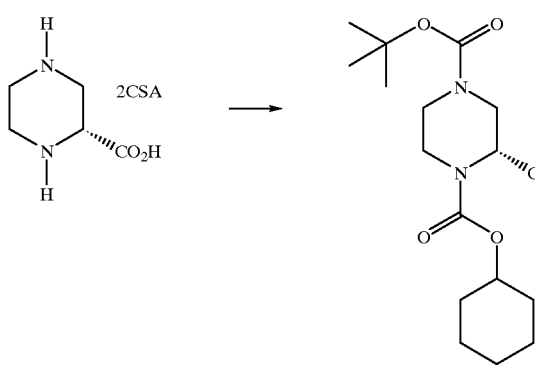

To the piperazine carboxylic acid dicamphorsulfonic acid salt (Preparative Example 42) (14.63 g, 24.6 mmol) dissolved in water (80 mL) and dioxane (80 mL) was added 50% NaOH (aq) until pH 11. BOC-ON (6.65 g, 27.04 mmol) was added while stirring at room temperature for 6.5 hrs and while maintaining the pH at 11 with 50% NaOH. The pH was lowered to 9.5 using 10% HCl (aq) and cyclohexyl chloroformate (4.0 g, 24.6 mmol) was added dropwise while maintaining the pH at 9.5 with a slow addition of 50% NaOH (aq) with stirring at 25° C. for an additional 12 h. The mixture was extracted with Et$_2$O and the aqueous phase was acidified to pH 3 with 6M HCl (aq). This aqueous phase was extracted with EtOAc and the organic phase was dried over anhydrous MgSO$_4$, filtered and concentrated in vacuo, and purified by flash chromatography (silica gel) using 25–50% EtOAc-hexane to give the title compound (6.65 g, 76%, MH$^+$=357).

Step B

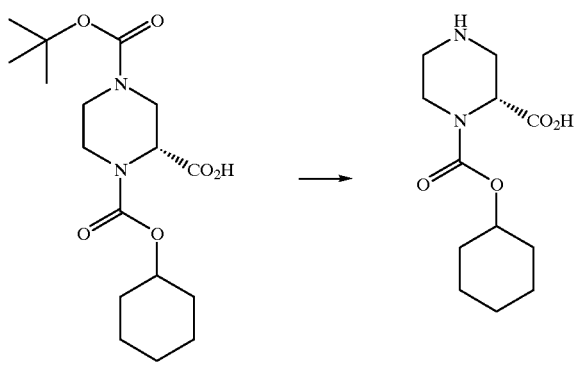

The title compound from Step A (6.65 g, 18.7 mmol) and trifluoroacetic acid (20 mL) dissolved in anhydrous CH$_2$Cl$_2$ (50 mL) were stirred at room temperature for 1 hr. The organic phase was concentrated in vacuo to give a residue.

Step C

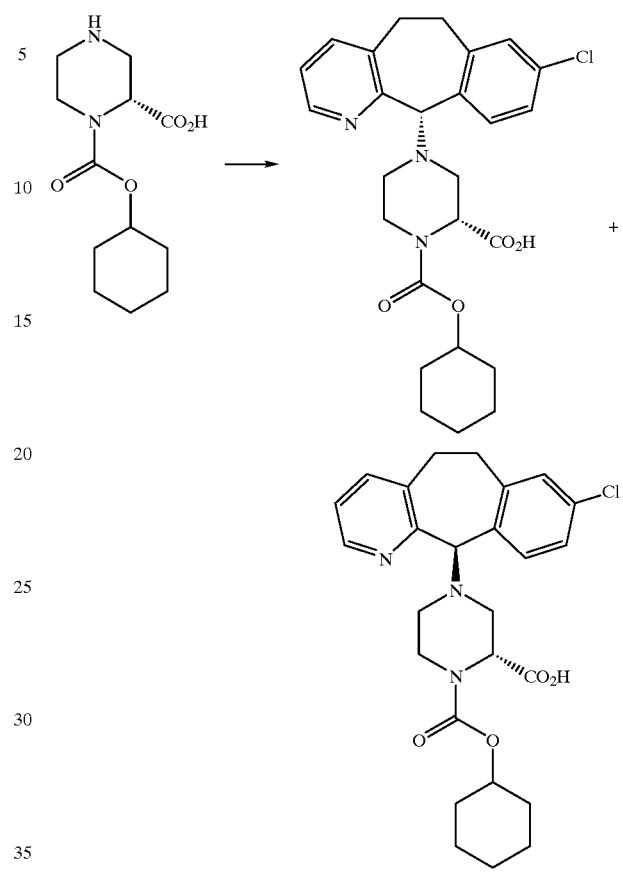

The title compound from Step B was dissolved in anhydrous CH$_2$Cl$_2$ (50 mL) and DMF (50 mL). To this was added the 8-Cl-tricyclic chloride (8.42 g, 31.8 mmol) and triethylamine (3 mL) and allowed to stir at room temperature for 48 h. The reaction mixture was concentrated in vacuo, diluted with EtOAc, washed with 3N NaOH and the organic phase was neutralized with 50% citric acid and dried over anhydrous Na$_2$SO$_4$. After filtration and concentration in vacuo, the residue was purified by flash column chromatography (silica gel) using 2–5% MeOH—CH$_2$Cl$_2$ to give the title compounds (11S,2R diastereomer A, 2.43 g, 27%, MH$^+$=485; and 11R,2R diastereomer B, 2.5 g, 30%, MH$^+$=484).

PREPARATIVE EXAMPLE 128

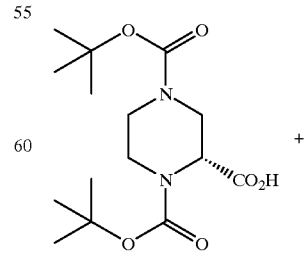

-continued

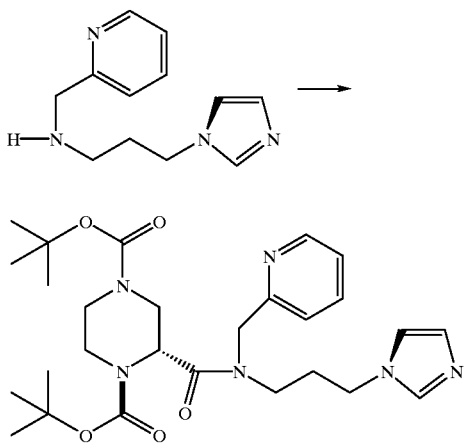

To the title compound from Preparative Example 43 (1.83 g, 5.6 mmol) were added HOBT (0.88 g, 6.5 mmol), DEC (1.24 g, 6.5 mmol), the title compound from Preparative Example 95 (1 g, 4.6 mmol), NMM (1.0 mL, 9.25 mmol) and anhydrous DMF (10 mL). The mixture was stirred at room temperature under $N_2$ overnight. The mixture was concentrated in vacuo, diluted with $CH_2Cl_2$ and washed with NaOH (aq). The organic phase was dried over anhydrous $Na_2SO_4$, filtered and concentrated in vacuo. The residue was purified by flash column chromatography (silica gel) using 10% MeOH—$CH_2Cl_2$ saturated with aqueous ammonium hydroxide to give the title compound (0.70 g, 24%, $MH^+$=529).

PREPARATIVE EXAMPLE 129

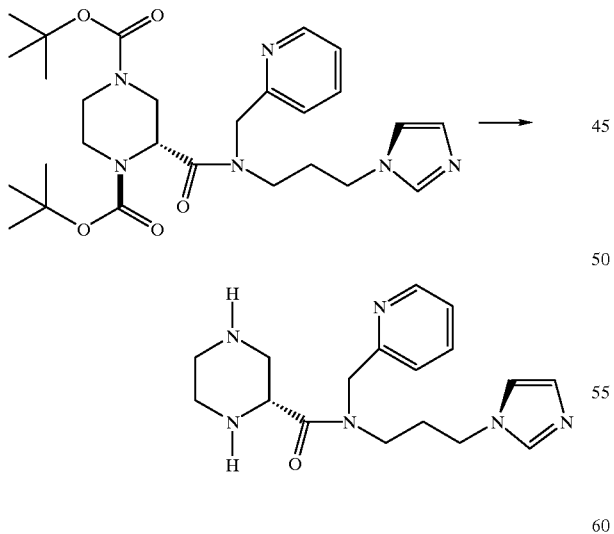

The title compound from Preparative Example 128 (0.70 g, 1.3 mmol), anhydrous $CH_2Cl_2$ (10 mL) and trifluoroacetic acid (10 mL) were stirred at room temperature for 12 h, then concentrated in vacuo. Aqueous NaOH (1N) was added dropwise to neutralize the reaction mixture and the resulting mixture was extracted with $CH_2Cl_2$. The organic phase was dried over anhydrous $Na_2SO_4$, filtered and concentrated in vacuo to give a residue which was purified by flash column chromatography (silica gel) using 10% MeOH—$CH_2Cl_2$ saturated with aqueous ammonium hydroxide to give the title compound as a brown oil (232 mg, 53%, $MH^+$=329).

PREPARATIVE EXAMPLE 130

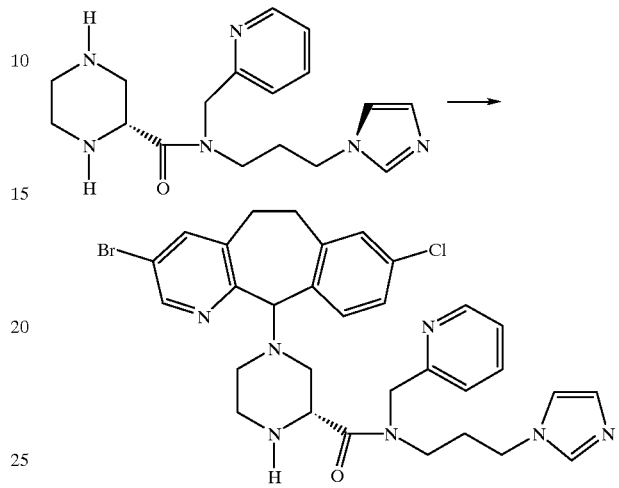

The title compound from Preparative Example 129 (0.20 g, 0.61 mmol) was dissolved in anhydrous DMF (5 mL). To this was added the tricyclic chloride (Compound No. 42.0) (0.2 g, 0.58 mmol) and triethylamine (0.43 mL, 3.0 mmol) and allowed to stir at room temperature for 12 h. The reaction mixture was poured into brine and extracted with EtOAc. The organic extract was dried over anhydrous $Na_2SO_4$, filtered and concentrated in vacuo. Purification by flash column chromatography (silica gel) using 10% MeOH—$CH_2Cl_2$ saturated with aqueous ammonium hydroxide afforded the title compound (100 mg, 27%, $MH^+$=634).

PREPARATIVE EXAMPLE 131

Step A

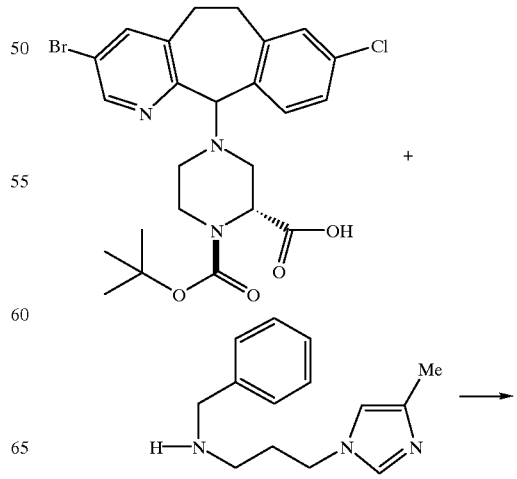

135
-continued

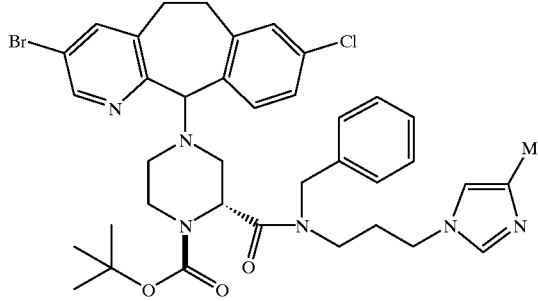

To the title compound from Preparative Example 51 (1.4 g, 70% purity, 1.8 mmol) and $CH_2Cl_2$ (10 mL) cooled to ° C. were added triethylamine (0.5 mL, 3.6 mmol) and isobutyl chloro-formate (0.25 mL, 1.9 mmol). After stirring the mixture at 0° C. for 3 h, the title compound from Preparative Example 95.1 (0.4 g, 1.7 mmol, isolated by preparative chiral chromatography (Chiralpack AD, 5 cm×50 cm column, flow rate 80 mL/min, 8% IPA+92% Hexane+0.2% diethylamine) was added and the mixture was stirred at room temperature under $N_2$ overnight. The mixture was washed with 1M NaOH(aq) and the organic phase was dried over anhydrous $Na_2SO_4$, filtered and concentrated in vacuo. The residue was purified by flash column chromatography (silica gel) using 2–5% MeOH—$CH_2Cl_2$ saturated with aqueous ammonium hydroxide to give the title. compound as a mixture of diastereomers (0.45 g, 34%, $MH^+$=747).

Step B

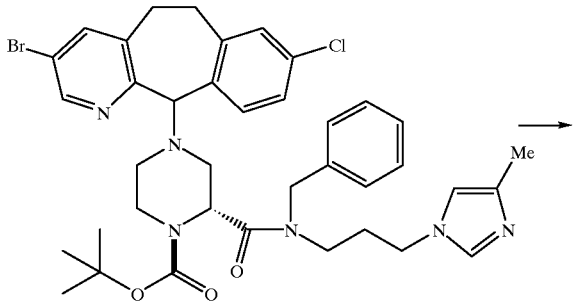

136
-continued

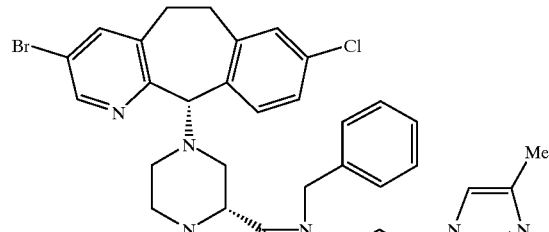

To a solution of the title compound from Step A (0.45, 0.60 mmol) dissolved in anhydrous $CH_2Cl_2$ (5 mL) was added TFA (5 mL). The solution was stirred at room temperature under $N_2$ overnight, then concentrated in vacuo, diluted with $CH_2Cl_2$, washed with 1N NaOH (aq) and dried over anhydrous $Na_2SO_4$. The mixture was filtered, concentrated in vacuo and purified by flash column chromatography (silica gel) using 2–5% MeOH—$CH_2Cl_2$ saturated with aqueous ammonium hydroxide to give the title compound as a mixture of diastereomers. The diastereomers were separated by preparative chiral chromatography (Chiralpack AD, 5 cm×50 cm column, flow rate 80 mL/min., 60% IPA+40% hexane+0.2% diethylamine) to give 0.11 g of diastereomer A and 0.23 g of diastereomer B.

Physical chemical data for the 11S,2R(−)-diastereomer A: $MH^+$=647; $[\alpha]^{20}_D$=−45.4° (2.91 mg/2 mL MeOH).

Physical chemical data for the 11R,2R(−)-diastereomer B: $MH^+$=647; $[\alpha]^{20}_D$=−23.5° (2.21 mg/2 mL MeOH).

PREPARATIVE EXAMPLE 132

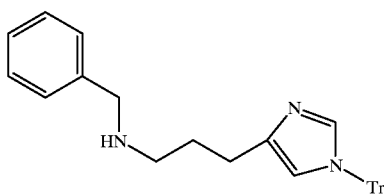

Step A

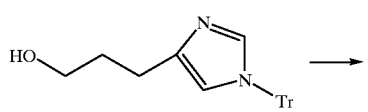

-continued

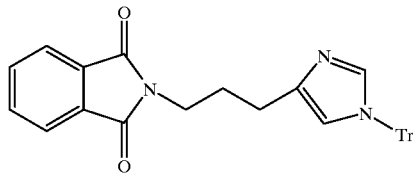

To a stirred solution of 1-(triphenylmethyl-1H-imidazol-4-yl)-3-hydroxypropane (WO 9629315) (5.04 g, 13.68 mmoles), phthalimide (2 g, 13.6 mmoles) and triphenyl phosphine (3.57 g, 13.6 mmoles) in THF (100 mL) at 0° C. was added diethyl azodicarboxylate (2.14 mL, 13.6 mmoles) dropwise. The reaction mixture stirred for 1 h at 0° C. and then at room temperature for 16 h. Filtered to give the title compound (4.6 g, 100%), CIMS: m/z (MH$^+$)=498; $\delta_H$ (CDCl$_3$) 1.72 (bs, 1H), 1.9 (m, 1H), 2.05 (m, 1H), 2.6 (m, 1H), 3.75 (m, 2H), 6.6–7.8 (m, 21H).

Step B

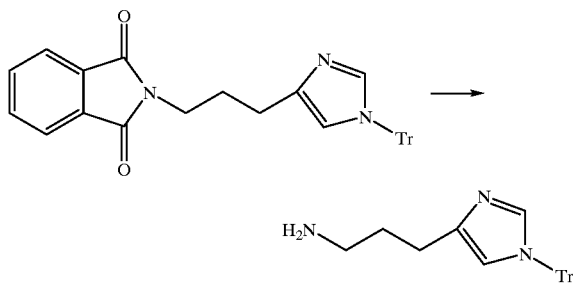

The title compound from Step A (2 g, 4.02 mmoles) and hydrazinehydrate (3.89 mL, 80.39 mmoles) were heated under reflux in ethanol (80 mL) for 16 h. The solids were filtered off and the filtrate was evaporated to give the title compound (1.35 g, 91%), CIMS: m/z (MH$^+$) 368; $\delta_H$ (CDCl$_3$) 1.8–1.85 (m, 2H), 2.6–2.62 (m, 2H), 2.8–2.83 (m, 2H), 7.1(s, 1H), 7.3 (s, 1H).

Step C

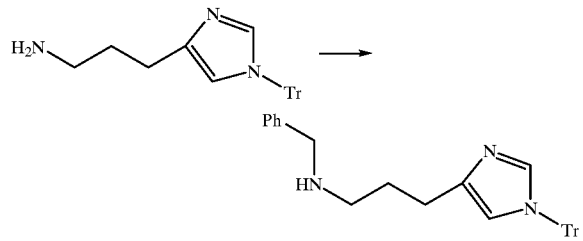

Ph = phenyl

To a stirred solution of the title compound from Step B (1.5 g, 4.08 mmoles) and benzaldehyde (0.433 g, 4.08 mmoles) was added sodium cyanoborohydride (0.256 g, 4.08 mmoles). The pH of the solution was adjusted to ~4.25 with acetic acid. The reaction mixture was then stirred for 2 h. The pH was then adjusted to 11.5 with 50% NaOH and extracted with ethyl acetate. The ethyl acetate extract was washed with water and brine and dried (MgSO$_4$) Evaporated to give a crude residue which was chromatographed on silica gel using 4% (10% conc NH$_4$OH in methanol)-CH$_2$Cl$_2$ as the eluant to give the title compound (1.04 g, 78%), CIMS: m/z (MH$^+$)=458; $\delta_H$ (CDCl$_3$) 1.8–1.82 (m, 2H), 2.58–2.64 (m, 4H), 3.6 (s, 2H), 6.5 (s, 1H), 7.15–7.4 (m, 6H).

PREPARATIVE EXAMPLE 133

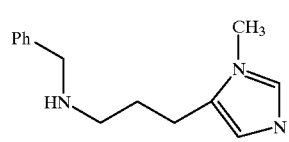

Step A

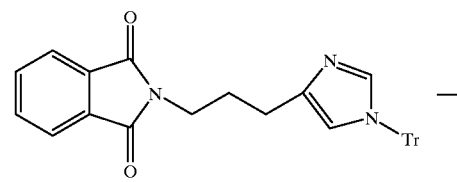

The title compound from Preparative Example 132 Step A (2 g, 4.1 mmoles) in CH$_2$Cl$_2$ (20 mL) was treated with methyl iodide (0.75 mL 12.05 mmoles) and stirred for 16 h. Evaporated to dryness to a gummy residue which was then refluxed with 6N HCl (25 mL) for 16 h. Evaporation to dryness gave a semisolid which was neutralized with aqueous NaHCO$_3$ and evaporation to dryness again gave semi-white solids. Stirred with CH$_2$Cl$_2$ (100 mL)and MeOH (50 mL) and filtered off the solids. The filtrate was evaporated to give the title compound (0.3 g), CIMS: m/z (MH$^+$) 140; $\delta_H$ (CDCl$_3$) 1.8 (m, 2H), 2.6–2.8 (m, 4H), 3.6 (s, 3H), 6.68 (s, 1H), 7.4 (s, 1H).

Step B

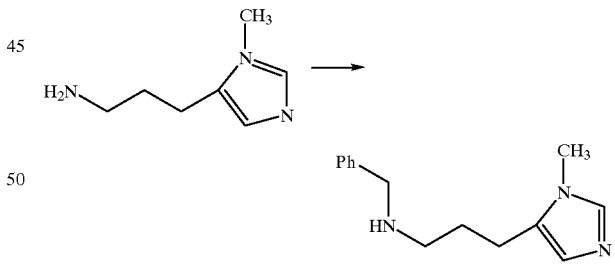

The title compound from Step A (1.97 g 14.14 mmoles), benzaldehyde (1.65 g 15.55 mmoles), sodium acetate (1.1 g, 13.42 mmoles) and 3 Å molecular sieves (2 g) in methanol were stirred for 18 h. To this sodium borohydride (0.519 g 13.72 mmoles) was added and stirred for 4 h. The solids were filtered off and the filtrate was evaporated to a residue which was chromatographed to give the title compound (0.59 g 18.5%) CIMS: m/z (MH$^+$) 230; $\delta_H$ (CDCl$_3$) 1.8 (q, 2H), 2.6 (t, 2H), 2.65 (t, 2H), 3.25 (s, 3H), 3.8 (s, 2H), 7.2–7.4 (m, 7H).

PREPARATIVE EXAMPLE 134

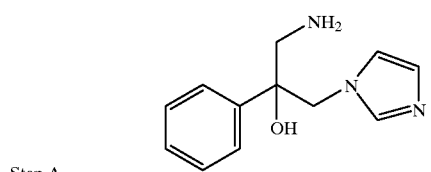

Step A

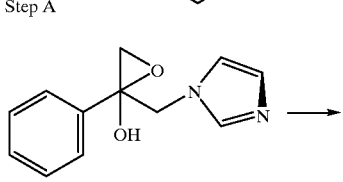

1-(2-Phenyl-2,3-epoxypropyl)-1H-imidazole (GB 2 099818 A) (2.15 g, 10.85 mmoles) and sodium azide (1.41 g, 21.71 mmoles) were heated in DMF (20 mL) at 60° C. for 16 h. Evaporated to dryness and extracted with $CH_2Cl_2$, washed with brine and dried ($MgSO_4$). Evaporated to give the title compound (0.932 g, 36%), CIMS: m/z ($MH^+$) =244; $\delta_H$ ($CDCl_3$) 3.7 (q, 2H0, 4.5 (dd, 2H, 6.6 (s, 1H), 6.95 (s, 1H), 7.3–7.45 (m, 5H), 8.2 (s, 1H).

Step B

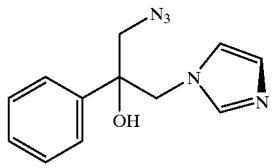

The title compound from Step A (0.8 g, 3.31 mmoles) in ethanol (15 mL) was hydrogenated over 10% Pd on carbon (0.2 g) at 50 psi overnight. The catalyst was filtered off and evaporated to give the title compound (0.71 g 98%). CIMS: m/z ($MH^+$)=218.

PREPARATIVE EXAMPLE 135

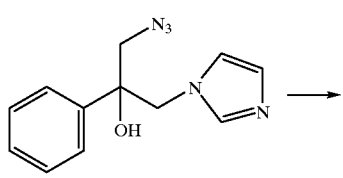

-continued

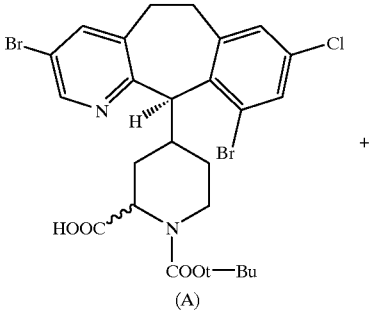

(A)

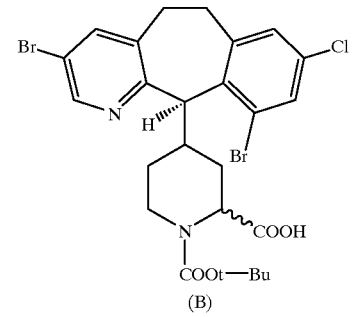

(B)

By following Steps a to e of Preparative Example 41 starting with the (+) isomer, a mixture of the title compounds A and B is obtained as a light tan solid that appears as a single tlc spot: $^1$NMR ($CDCl_3$, 300 MHz) δ1.42 (s, 9H), 4.85 (m, 2H), 7.12 (s, 1H), 7.50 (s, 1H), 7.55 (s, 1H), 8.48 (m, 1H); HRMS (FAB) calcd for $C_{25}H_{28}N_2O_4$ BrCl$^{81}$Br 615.0084, found 615.0092.

PREPARATIVE EXAMPLE 136

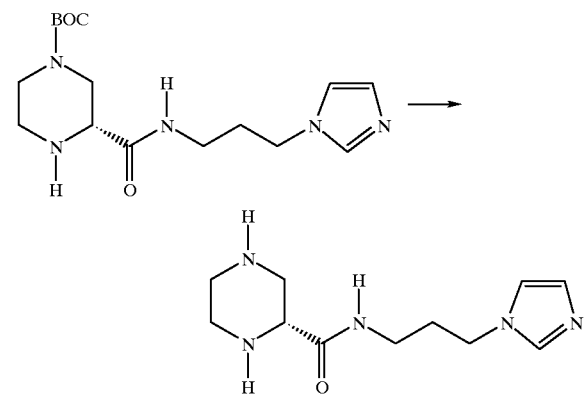

Following the procedure set forth in Preparative Example 123, but using the title compound from Preparative Example 37 Step A. the title compound was obtained (quantitative yield; $MH^+$=338).

Preparative Examples 137–138

Following the procedure described for Preparative Example 106, the piperazines listed in Table 5A below were prepared using the corresponding amines.

TABLE 5A

| Prep. Ex. | Amine | Product | yield (%) | MH+ |
|---|---|---|---|---|
| 137 | H2N-CH2CH2-N(imidazole-2-Me) | piperazine-C(O)NH-CH2CH2-N(imidazole-2-Me) | 47 | 238 |
| 138 | H2N-CH2CH2-N(4-Me-imidazole) | piperazine-C(O)NH-CH2CH2-N(4-Me-imidazole) | 100 | 238 |
|  | H2N-CH2CH2-N(5-Me-imidazole) | piperazine-C(O)NH-CH2CH2-N(5-Me-imidazole) |  |  |

Preparative Examples 139–141

Similarly, using the procedure described for Preparative Example 110 and the piperazines listed in the Table 5B below, the corresponding tricyclic amines were prepared.

TABLE 5B

| Prep. Ex. | Piperazine | Product | yield (%) | MH+ |
|---|---|---|---|---|
| 139 | piperazine-C(O)NH-CH2CH2-N(imidazole-2-Me) | Br,Cl-tricyclic-piperazine-C(O)NH-CH2CH2-N(imidazole-2-Me) | 73 | 543 |
| 140 | piperazine-C(O)NH-CH2CH2-N(4-Me-imidazole) | Br,Cl-tricyclic-piperazine-C(O)NH-CH2CH2-N(4-Me-imidazole) | 34 | 543 |

| Prep. Ex. | Piperazine | Product | yield (%) | MH+ |
|---|---|---|---|---|
| 141 | | | 31 | 543 |

PREPARATIVE EXAMPLE 142

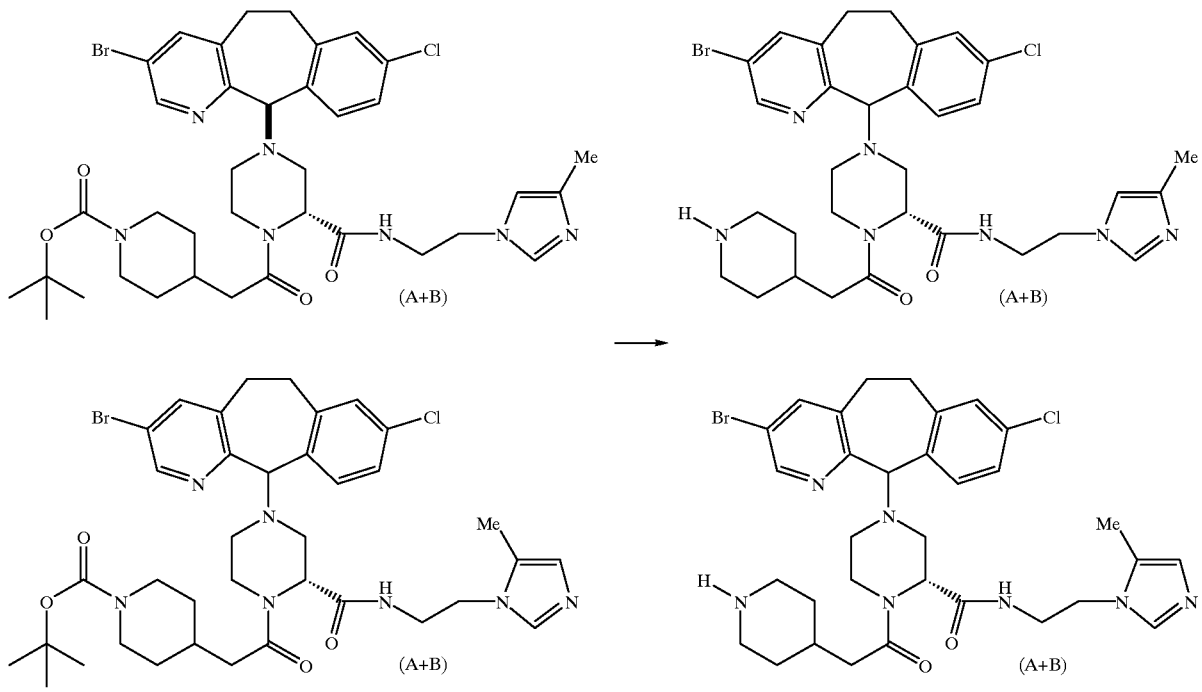

The title compound for Example 289 (0.39 g, 0.51 mmol), anhydrous CH₂Cl₂ (3 mL) and trifluoroacetic acid (3 mL) were stirred at room temperature for 2 h, then concentrated in vacuo. Aqueous NaOH (1N) was added dropwise to neutralize the reaction mixture and the resulting mixture was extracted with CH₂Cl₂. The organic phase was dried over anhydrous MgSO₄, filtered and concentrated in vacuo to give a residue which was purified by flash column chromatography (silica gel) using 5% MeOH—CH₂Cl₂ saturated with aqueous ammonium hydroxide to give the title compound as an off-white solid (52 mg, 15%, mp=150° C., MH⁺=768).

PREPARATIVE EXAMPLE 143

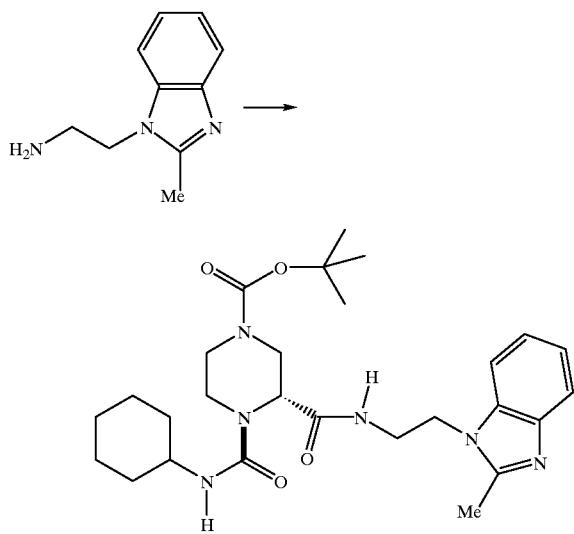

A solution of the title compound from Preparative Example 71 (0.9 g, 5.14 mmol) and the anhydride from Preparative Example 44 (1.38 g, 1.05 eq) dissolved in anhydrous dichloromethane (10 ml) was stirred at room temperature overnight. Additional anhydride (0.105 g) was added and after 1 hr cyclohexyl isocyanate (0.98 mL, 7.71 mmol) was added to the reaction mixture which was stirred for an additional 1.5 hrs. Concentration in vacuo and purification by flash column chromatography (silica gel) using 1–3% MeOH—$CH_2Cl_2$ saturated with ammonium hydroxide as eluent afforded the title compound as a white solid (1.82 g, 69%, mp=126.9–128.9° C., $MH^+$=513).

Preparative Examples 144–149

Following essentially the same procedure as that described for Preparative Example 143, the BOC-protected piperazines listed in Table 5C below were prepared using the corresponding amines.

TABLE 5C

| Prep. Ex. | Amine | Product | yield (%) | $MH^+$ |
|---|---|---|---|---|
| 144 | | | 100 | 500 |
| 145 | | | 100 | 500 |

TABLE 5C-continued

| Prep. Ex. | Amine | Product | yield (%) | MH+ |
|---|---|---|---|---|
| 146 | | | 57 | 517 |
| 147 | | | 100 | 477 |
| 148 | | | | |
| 149 | | | 58 | 465 |
| 149A | | | — | — |

TABLE 5C-continued
| Prep. Ex. | Amine | Product | yield (%) | MH+ |
|---|---|---|---|---|
| 149B | 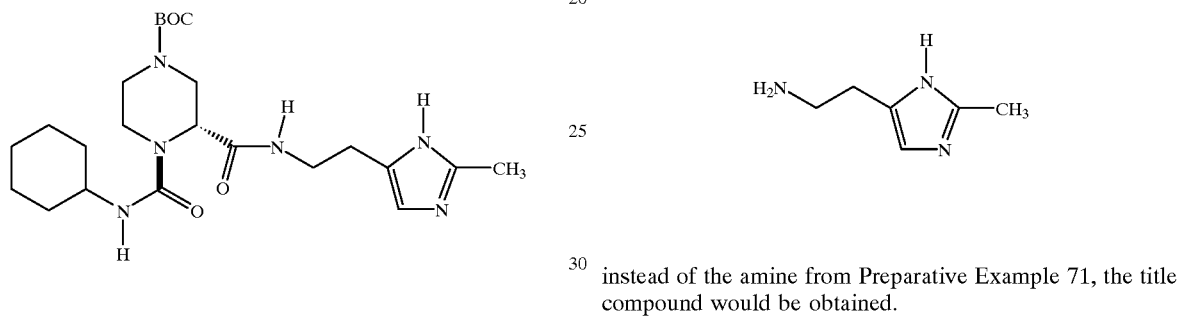 | | — | — |
PREPARATIVE EXAMPLE 150
If one were to follow essentially the same procedure as that described for Preparative Example 143, but using the amine
instead of the amine from Preparative Example 71, the title compound would be obtained.
PREPARATIVE EXAMPLE 151
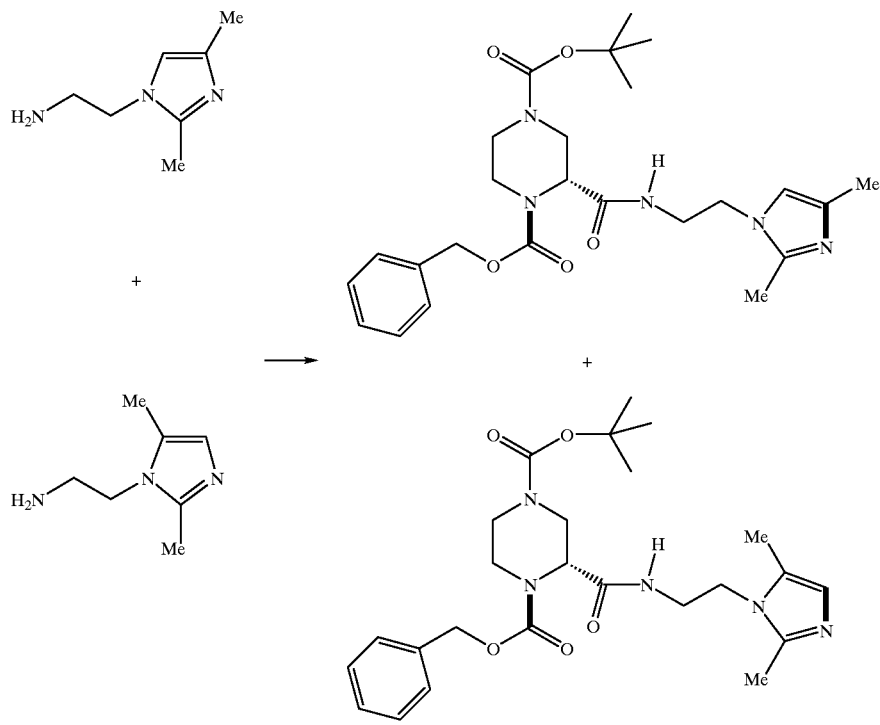

A solution of the title compound from Preparative Example 68 (2.12 g, 15.2 mmol), triethylamine (30.4 mmol) and the anhydride from Preparative Example 44 (3.89 g, 15.2 mmol) dissolved in anhydrous dichloromethane (30 ml) was stirred at room temperature for 30 min. Benzyloxycarbonylsuccinimide (4.17 g, 16.7 mmol) was added and the resulting mixture was stirred at room temperature overnight. Concentration in vacuo and purification by flash column chromatography (silica gel) using 2% MeOH—CH$_2$Cl$_2$ saturated with ammonium hydroxide as eluent afforded the title compounds (2.57 g, 35%). The regioisomers were separated by HPLC (Chiracel AD column) using 5% isopropanol—95% hexane—0.2% diethylamine to give the 2,4-dimethyl isomer (mp=64.2° C., MH$^+$=486) and the 2,5-dimethyl isomer (mp=71.5° C., MH$^+$=486).

PREPARATIVE EXAMPLE 152

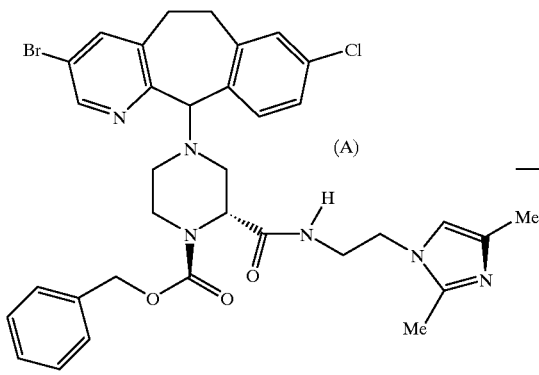

A solution of the title compound from Example 293 diastereomer A (0.386 g, 0.56 mmol), glacial acetic acid (3 mL) and 33% HBr in acetic acid (1 mL) was stirred at room for 2 hr. Diethyl ether was added and the precipitate filtered and dried under vacuo to afford the title compound (0.48 g, 100%, MH$^+$=557.

PREPARATIVE EXAMPLE 153

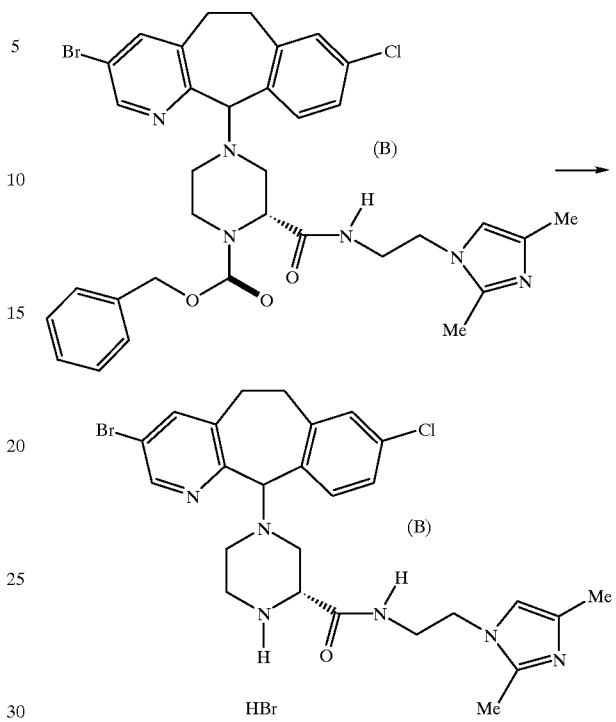

A solution of the title compound from Example 293 diastereomer B (0.372 g), glacial acetic acid (3 mL) and 33% HBr in acetic acid (1 mL) was stirred at room for 2 hr. Diethyl ether was added and the precipitate filtered and dried in vacuo to afford the title compound (0.433 g, 100%, MH$^+$=557.

PREPARATIVE EXAMPLE 154

Step A

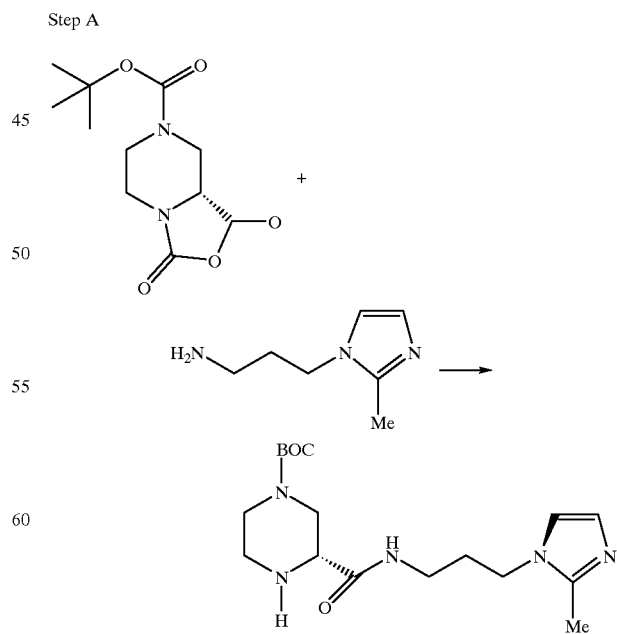

A mixture of the title compound from Preparative Example 66 (1.0 g, 7.2 mmol), the anhydride from Preparative Example 44 (2.2 g, 8.6 mmol), triethyl amine (1.5 mL, 10.8 mmol) and anhydrous $CH_2Cl_2$ (10 mL) was stirred at room temperature for 12 hrs. The mixture was concentrated in vacuo, diluted with $CH_2Cl_2$ and washed with a saturated aqueous solution of $NaHCO_3$. The organic phase was dried over anhydrous $Na_2SO_4$, filtered and concentrated in vacuo.

Step B

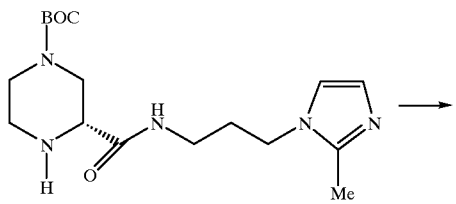

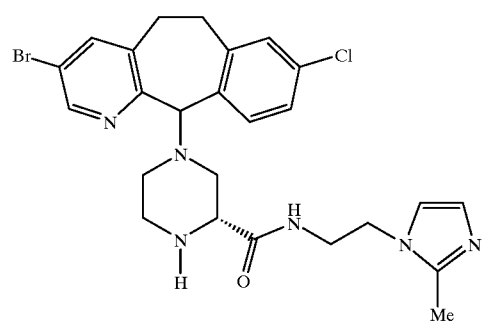

Trifluoroacetic acid (10 mL) was added to the title compound from Step A above (1.0 g, 7.2 mmol) dissolved in $CH_2Cl_2$ (10 mL) and the resulting mixture was stirred for 5 hrs at 25° C. The mixture was concentrated in vacuo, diluted with $CH_2Cl_2$ (50 mL) and combined with the tricyclic chloride (compound # 42.0) (2.7 g, 7.9 mmol) and triethylamine (5–10 mL) and stirred at room temperature overnight. The mixture was concentrated in vacuo, diluted with $CH_2Cl_2$ and washed with a saturated aqueous solution of $NaHCO_3$. The organic phase was dried over anhydrous $Na_2SO_4$, filtered, concentrated in vacuo and purified by flash column chromatography (silica gel) using 5% MeOH—$CH_2Cl_2$ saturated with aqueous ammonium hydroxide to give the title compound as a mixture of diastereomers (1.9 g, 47%, $MH^+$=557).

PREPARATIVE EXAMPLE 155

Step A

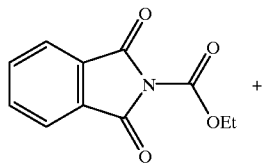 +

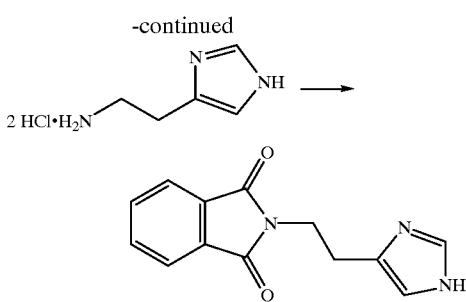

N-Carbethoxyphthalimide (62.8 g, 0.275 mol, 1.1 eq.) was added portionwise over a period of 30 minutes to a stirred solution of histamine dihydrochloride (46.7 g, 0.250 mol, 1.0 eq.) and sodium carbonate (54.3 g, 0.513 mol, 2.05 eq.) in distilled water (1250 ml) at room temperature. The resulting snow-white suspension was stirred vigorously at room temperature for 90 minutes. The solid was filtered off and thoroughly washed with ice-cold distilled water (4×50 ml). The solid was collected and dried under vacuum over $P_2O_5$ at 60° C. for 12 h to give the title compound (59.2 g, 0.245 mol, 98%, $MH^+$=242).

Step B

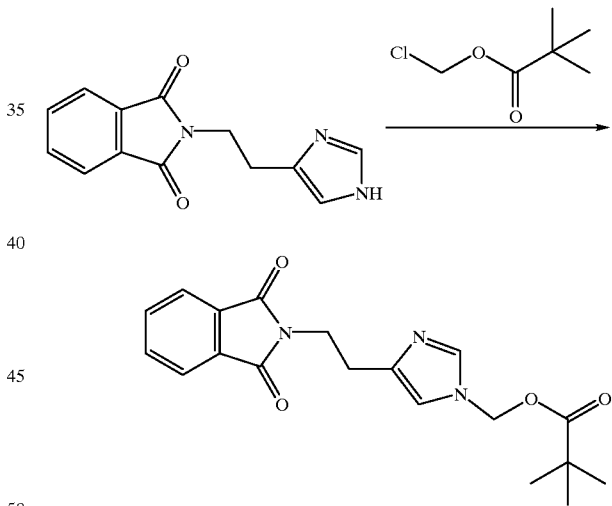

A solution of chloromethyl pivalate (18.5 ml, 0.125 mol, 1.2 eq.) in anhydrous N,N-dimethylformamide (DMF, 100 ml) was added dropwise over a period of one hour to a stirred mixture of Step A above (25.0 g, 0.104 mol, 1.0 eq.) and potassium carbonate (17.2 g, 0.125 mol, 1.2 eq.) in anhydrous DMF (500 ml) at 90° C. under a nitrogen atmosphere. The mixture was stirred at 90° C. for 12 h. The volatiles were removed under vacuum at 50° C. The residue was taken up in brine (100 ml) and extracted with ethyl acetate (4×25 ml). The combined organic extracts were dried over $NA_2SO_4$, filtered, and concentrated under vacuum at 30° C. The residual off-white solid was flash-chromatographed (hexanes: acetone=6: 4 v/v) over silica gel to give the title compound (20 g, 0.056 mol, 54%, $MH^+$= 356).

Step C

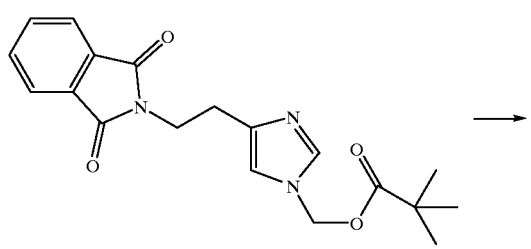

A solution of the title compound from Step B above (5 g, 14.1 mmol) and 4-chlorobenzylchloride (2.5 g, 15.5 mmol) was stirred in anhydrous acetonitrile (60 ml) at reflux under a nitrogen atmosphere for 48 h. The mixture was concentrated in vacuo and recrystallized from ethyl acetate-hexane to give the title compound as a solid (3.2 g, 47%, MH+= 480), and the filtrate which was concentrated to give additional product (3.6 g, 53%).

Step D

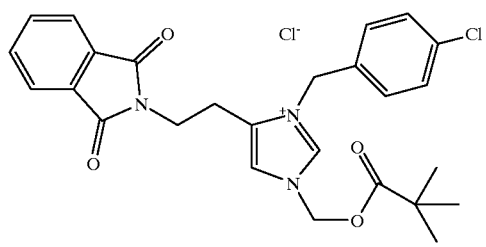

A 7 N solution of ammonia in methanol (10 ml, 0.07 mol) was added slowly to a stirred solution of the title compound from Step C above (3.2 g, 6.6 mmol) diluted with MeOH (10 mL) at −20° C. The resulting mixture was warmed to room temperature and stirred for another 12 h, then concentrated in vacuo and purified by flash column chromatography (silica gel) using 3% MeOH—$CH_2Cl_2$ saturated with ammonium hydroxide as eluent to afford the title compound as a sticky solid (1.2 g, 51%, MH+=366).

Step E

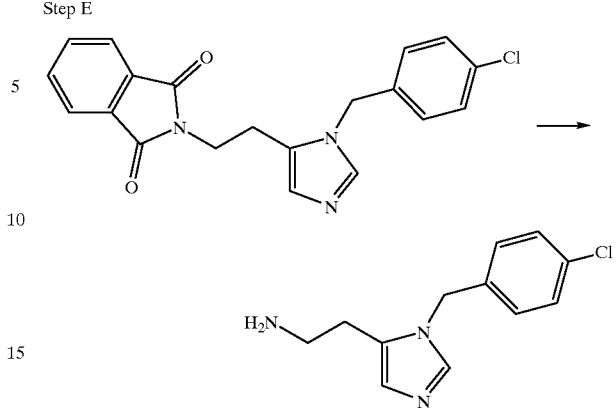

A solution of the title compound from Step D above (1.21 g, 3.3 mmol) and hydrazine monohydrate (1.7 ml, 0.033 mol, 10 eq.) in absolute ethanol (20 ml) was stirred at 50° C. under a nitrogen atmosphere for 20 min. The resulting suspension was diluted with ethanol and dichloromethane and filtered. The filtrate was concentrated in vacuo to afford the title compound as a yellow oily solid (0.7 g, 91%, MH+=236).

Step F

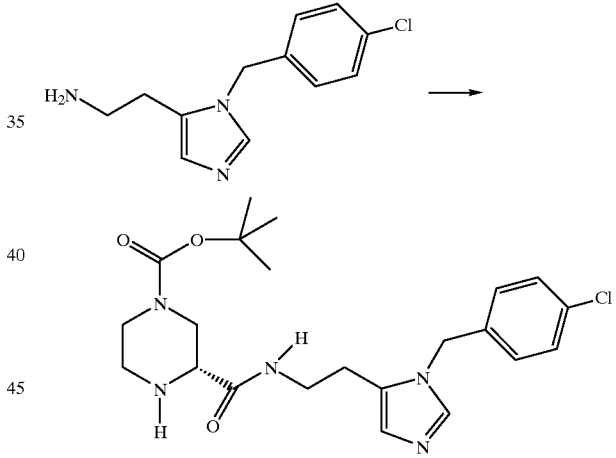

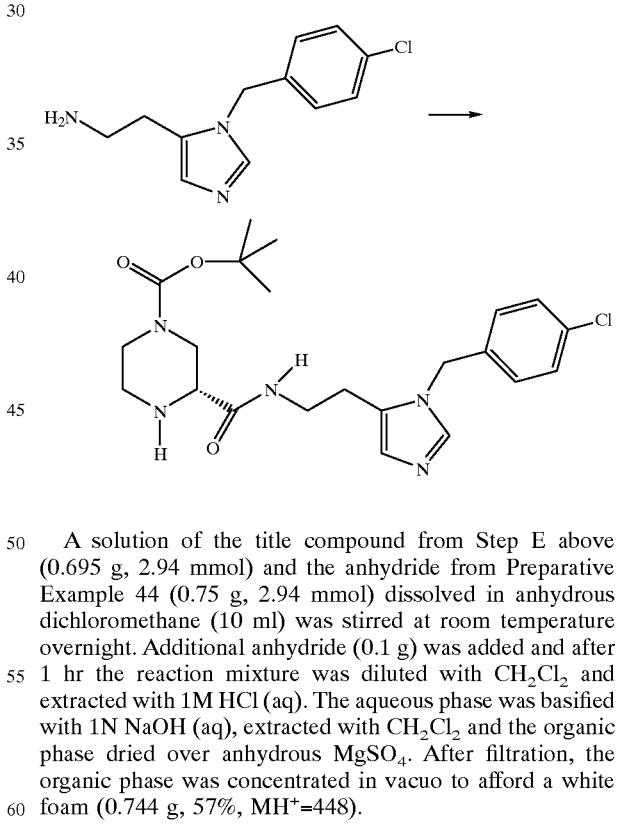

A solution of the title compound from Step E above (0.695 g, 2.94 mmol) and the anhydride from Preparative Example 44 (0.75 g, 2.94 mmol) dissolved in anhydrous dichloromethane (10 ml) was stirred at room temperature overnight. Additional anhydride (0.1 g) was added and after 1 hr the reaction mixture was diluted with $CH_2Cl_2$ and extracted with 1M HCl (aq). The aqueous phase was basified with 1N NaOH (aq), extracted with $CH_2Cl_2$ and the organic phase dried over anhydrous $MgSO_4$. After filtration, the organic phase was concentrated in vacuo to afford a white foam (0.744 g, 57%, MH+=448).

Preparative Examples 156–157

Following the procedure described for Preparative Example 155 Steps C–F, the piperazines listed in Table 5D below were prepared using the corresponding arylalkyl halides.

TABLE 5D

| Prep. Ex. | Halide | Product | MH+ |
|---|---|---|---|
| 156 | 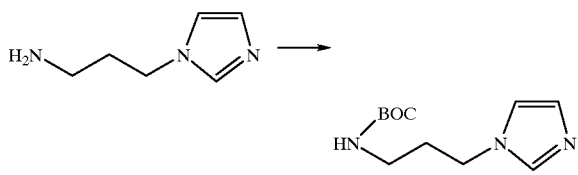 | | 428 |
| 157 | | | 441 |

PREPARATIVE EXAMPLE 158

STEP A

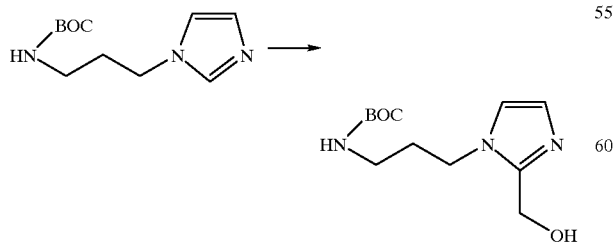

To 3-(1H-imidazol-1-yl)propylamine (20 mL, 167.6 mmol) dissolved in water (200 mL) and MeOH (200 mL) was added 50% NaOH (aq) until pH 9.5. Di-tert-butyldicarbonate (41 g, 187.9 mmol) was added while stirring at room temperature for 4 hrs and while maintaining the pH at 9.5 with 50% NaOH. The mixture was concentrated in vacuo to remove most MeOH, then extracted with $CH_2Cl_2$. The organic phase was dried over anhydrous $MgSO_4$, filtered and concentrated in vacuo to give the title compound (23.7 g, 63%, MH+=226).

Step B

To a solution of the title compound from Step A above (0.50 g, 2.22 mmol) dissolved in anhydrous THF (15 ml) and stirred at −78° C. was added n-butyllithium (2.8 mL, 1.75M in hexane) and the resulting mixture was warmed to and stirred at −20° C. for 1.5 h. The reaction mixture was recooled to −78° C. and anhydrous DMF (0.35 mL, 4.52 mmol) was added. After warming to and stirring at 25° C. for 2 h, MeOH (2 mL) and $NaBH_4$ (171 mg, 4.5 mmol) were added and the resulting mixture was stirred for 1 h at 25° C. The mixture was concentrated in vacuo, diluted with dichloromethane, washed with water, and the organic phase was dried over anhydrous $Na_2SO_4$, filtered, and concentrated in vacuo. Purification by flash column chromatography (silica gel) using 5–10% MeOH—$CH_2Cl_2$ saturated with ammonium hydroxide as eluent afforded the title compound (0.32 g, 56%, MH+=256).

Step C

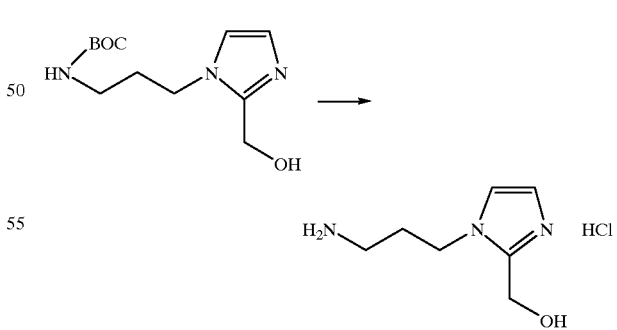

To the title compound from Step B above (0.31 g, 1.2 mmol) was added 4M HCl in dioxane (5 mL) and the mixture was stirred at 25° C. for 12 h. Concentration in vacuo afforded a residue which was used directly in Step D.

Step D

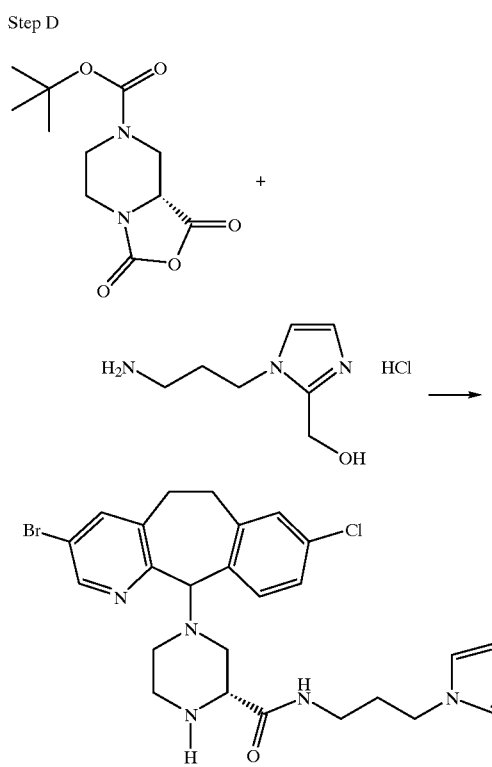

A mixture of the title compound from Step C above, triethylamine (4 mL) and the anhydride from Preparative Example 44 (0.55 g, 2.15 mmol) dissolved in anhydrous DMF (10 ml) was stirred at room temperature overnight. The mixture was concentrated in vacuo and diluted with anhydrous $CH_2Cl_2$ (5 mL), DMF (5 mL) and trifluoroacetic acid (10 mL). The resulting mixture was stirred for 12 hrs at room temperature, then concentrated in vacuo and diluted with anhydrous $CH_2Cl_2$ (5 mL) and DMF (5 mL). The tricyclic chloride (compound # 42.0) (0.75 g, 2.17 mmol) and triethylamine (3 mL) were added and the mixture was stirred at 25° C. for 48 h. The mixture was concentrated in vacuo, diluted with $CH_2Cl_2$ and washed with a saturated aqueous solution of $NaHCO_3$. The organic phase was dried over anhydrous $Na_2SO_4$, filtered, concentrated in vacuo and purified by flash column chromatography (silica gel) using 5–10% MeOH—$CH_2Cl_2$ saturated with aqueous ammonium hydroxide to give the title compound as a mixture of diastereomers (0.376 g, 33%, $MH^+$=573).

Preparative Examples 159–160

Following the procedure described for Preparative Example 158 Step D, the piperazines listed in Table 5E below were prepared using the corresponding amines or amine hydrochlorides.

TABLE 5E

| Prep. Ex. | Amine | Product | 1. yield (%) 2. $MH^+$ |
|---|---|---|---|
| 159 | 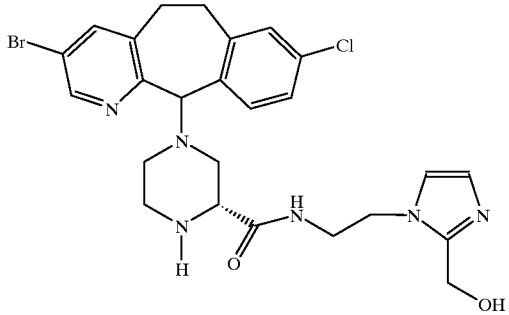 | 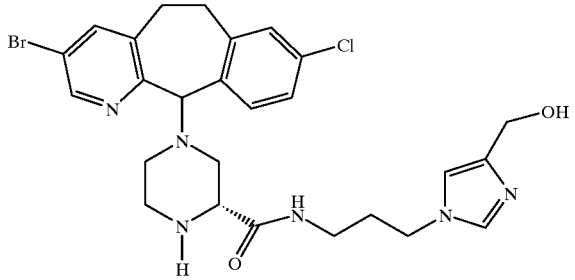 | 1. 37 2. 559 |
| 160 | | | 1. 25 2. 573 |

PREPARATIVE EXAMPLE 161

Step A

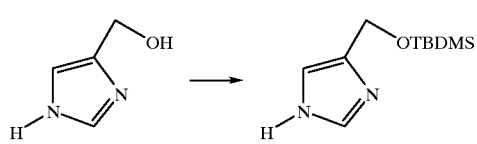

A mixture of 4-hydroxymethylimidazole (2 g, 14.9 mmol), triethylamine (5 mL) and TBDMS-Cl (2.5 g, 16.6 mmol) dissolved in anhydrous $CH_2Cl_2$ (20 ml) was stirred at room temperature overnight. The mixture was filtered, diluted with anhydrous $Et_2O$ and refiltered. The filtrate was concentrated in vacuo, diluted with $CH_2Cl_2$ and washed with a saturated aqueous solution of $NaHCO_3$. The organic phase was dried over anhydrous $Na_2SO_4$, filtered and concentrated in vacuo to give the title compound (2.22 g, 71%, $MH^+=213$).

Step B

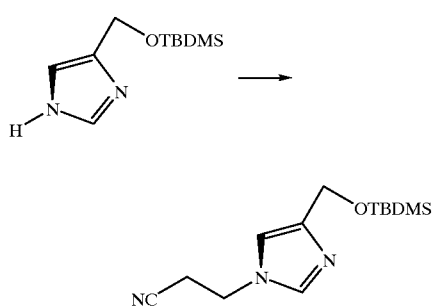

A solution of the title compound from Step A above (2.22 g, 10.5 mmol) dissolved in acrylonitrile (10 ml) was stirred at reflux for 48 h. Concentration in vacuo afforded the title compound (2.09 g, 75%, $MH^+=266$).

Step C

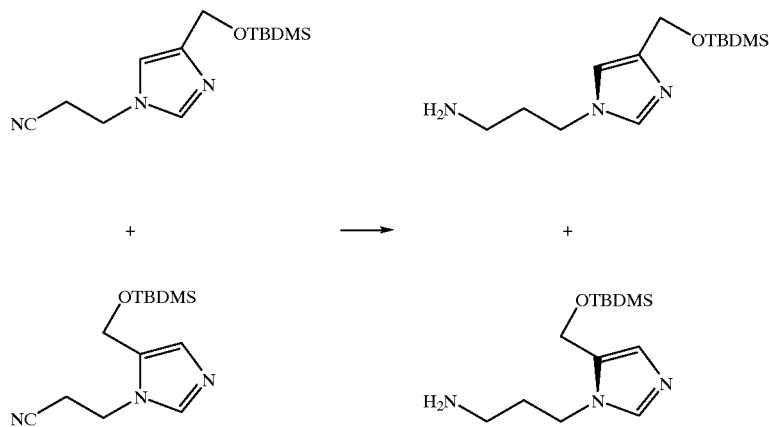

A mixture of the title compound from Step B above (2.08 g, 7.85 mmol), Raney nickel (230 mg), MeOH (20 mL) and $NH_4OH$ (7.5 mL) was stirred in a Parr hydrogenator at room temperature for 48 h. The mixture was filtered through celite, concentrated in vacuo, diluted with $CH_2Cl_2$ and washed with a saturated aqueous solution of $NaHCO_3$. The organic phase was dried over anhydrous $Na_2SO_4$, filtered, concentrated in vacuo and purified by flash column chromatography (silica gel) using 5% MeOH—$CH_2Cl_2$ saturated with aqueous ammonium hydroxide to give the title compounds [(4-substituted isomer, 465 mg, 22%, $MH^+=270$) and (5-substituted isomer, 220 mg, 10%, $MH^+=270$)].

PREPARATIVE EXAMPLE 162

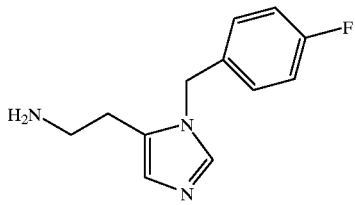

Following the procedure described for Preparative Example 155 Steps C–E, except using 4-fluorobenzyl bromide instead of 4-chlorobenzyl chloride in Preparative Example 155 Step C, the title compound was prepared (52%, MH⁺=220).

PREPARATIVE EXAMPLE 163

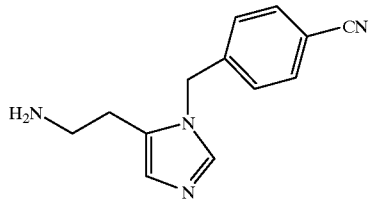

Following the procedure described for Preparative Example 155 Steps C–E, except using 4-cyanobenzyl bromide instead of 4-chlorobenzyl chloride in Preparative Example 155 Step C, the title compound was prepared (63%, MH⁺=227).

PREPARATIVE EXAMPLE 164

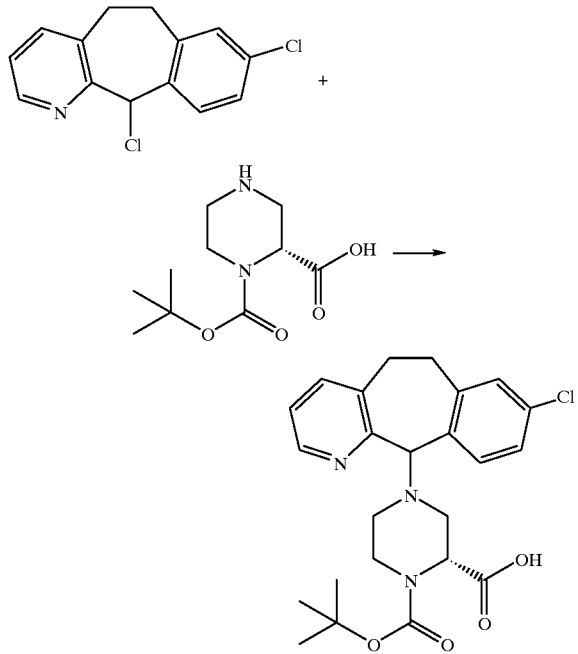

Tricyclic chloride (5.04 g, 1.1 eq.) was added to a solution of the title compound from Preparative Example 50 (4.0 g, 17.3 mmol) and TEA (12.05 mL, 5 eq.) in DMF (60 mL). The resulting solution was stirred at room temperature 72 hours at which time the reaction mixture was concentrated under reduced pressure. The residue was diluted with 3M NaOH and extracted with EtOAc. The aqueous layer was neutralized with 50% citric acid and extracted with EtOAc. The combine organics were dried over $Na_2SO_4$, filtered, and concentrated in vacuo. The crude product was purified by flash chromatography using a 12% (10% $NH_4OH$ in MeOH) solution in $CH_2Cl_2$ as eluent to give the C-11 (S)-isomer (2.13 g, 54%) as the first eluting isomer and the C-11 (R)-isomer (2.4 g, 61%) as the second 11S, 2R(+)-Isomer

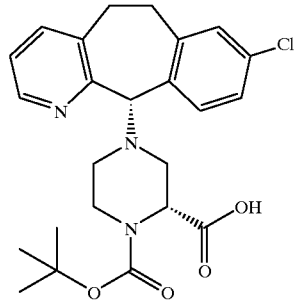

11(S),2(R)(+)-isomer (first eluting isomer): $[\alpha]^{20}_D$=+84.9 (5.18 mg in 5.0 mL MeOH); LCMS: MH⁺=458.

11R, 2R Isomer

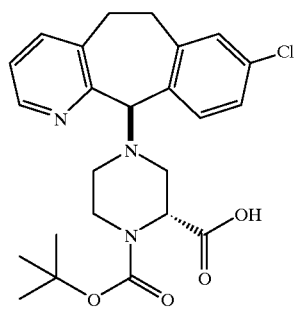

11(R),2(R)-isomer (second eluting isomer): FABMS: MH⁺=458.

PREPARATIVE EXAMPLE 165

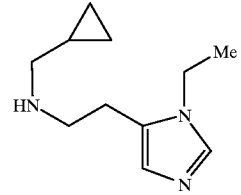

Following the procedure described for Preparative Example 25, except using the title compound from Preparative Example 13 instead of N-1-methyl histamine, the title compound was prepared (33%, MH⁺=195).

PREPARATIVE EXAMPLE 166

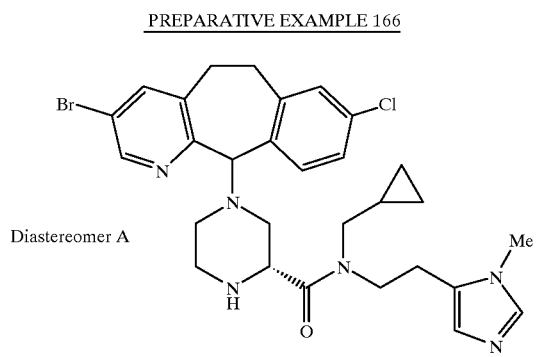

Diastereomer A

Similarly, using the procedure described for Preparative Example 142, except using the title compound from Example 305 diastereomer A instead of the title compound from Example 289, the title compound was prepared (80%, $MH^+=599$).

PREPARATIVE EXAMPLE 167

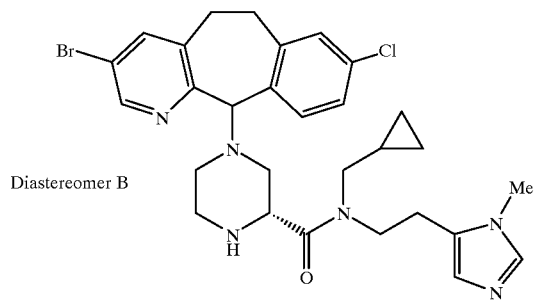

Diastereomer B

Following the procedure described for Preparative Example 142, except using the title compound from Example 305 diastereomer B instead of the title compound from Example 289, the title compound was prepared (100%, $MH^+=599$).

PREPARATIVE EXAMPLE 168

Step A

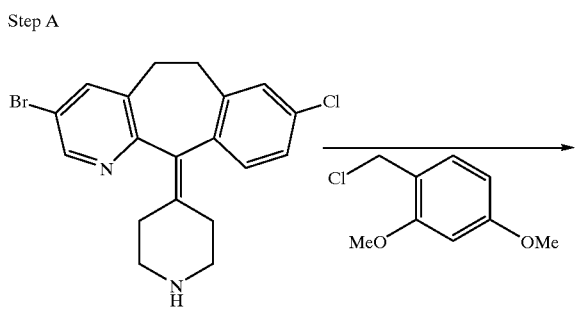

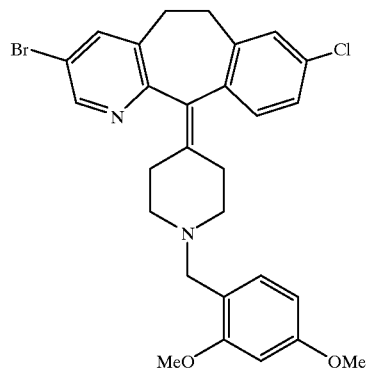

The title compound from Preparative Example 40A Step A (compound 52.ii) (5 g, 12.8 mmol) was dissolved in 2.7 ml of 2,4-dimethoxybenzaldehyde by heating to 120° C. Formic acid (1.3 mL) was dripped into the reaction mixture while the reaction mixture stirred at 120° C. for 45 min. The resulting solid mixture was dissolved in dichloromethane and dried over magnesium sulfate, filtered and evaporated to dryness to obtain a solid which was chromatographed on silica gel to obtain 5.17 g of title product. FABMS (M+1)= 463.4

Step B

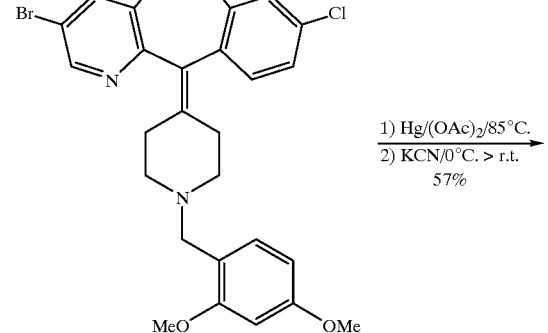

1) Hg/(OAc)$_2$/85°C.
2) KCN/0°C. > r.t.
57%

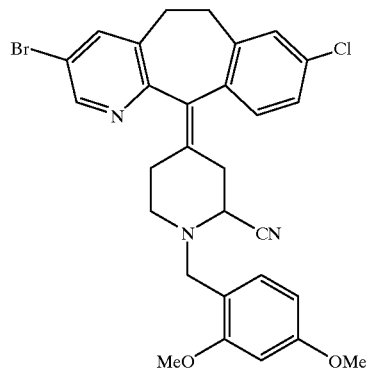

The title compound from Step A (1 gm, 1.8 mmol) was dissolved in 45 ml of 5% acetic acid/water and stirred at 85° C. Mercuric acetate (2.3 gm) was added and the reaction mixture stirred for 5 hours. After cooling in an ice bath, potassium cyanide (1.25 gm) was added and the reaction mixture stirred vigorously for 18 hours. 1N Sodium hydroxide (excess) was added and the product extracted with ethyl acetate three times. After chromatography on silica gel using ethylacetate as the eluent, 0.747 gm of title product was obtained.

Step C

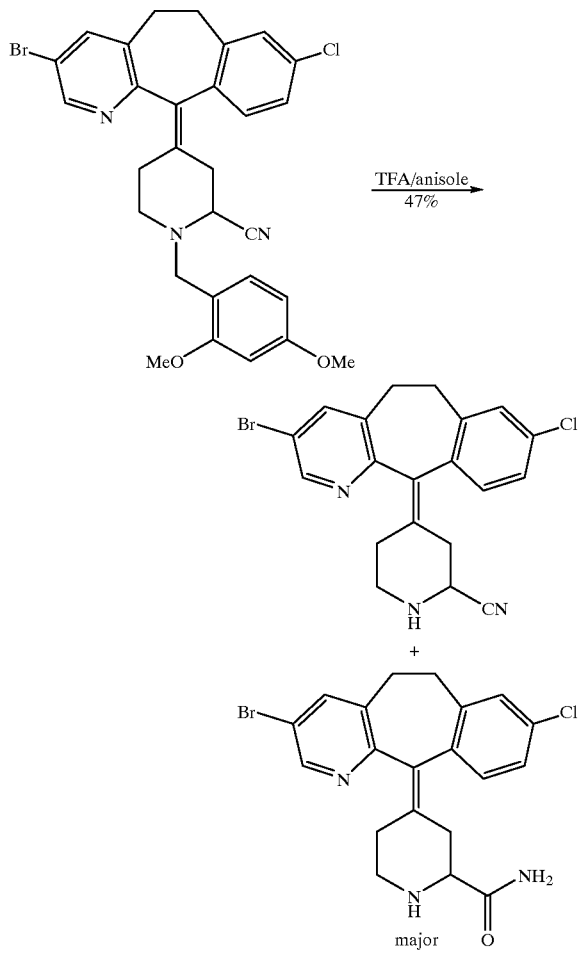

The title product from Step B (0.2 gm) was dissolved in 6 ml of trifluoroacetic acid and 0.5 ml of anisole and stirred for 1 hour at 60° C. to obtain the title carboxamide product (72 mg) after silica gel chromatography using 2% methanol/dichloro-methane as the eluent. FABMS (M+1)=432.

Step D

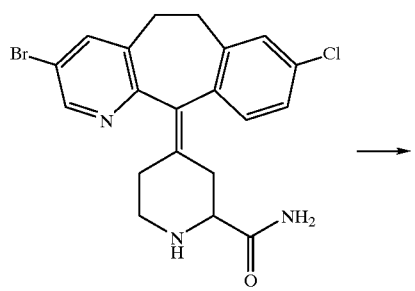

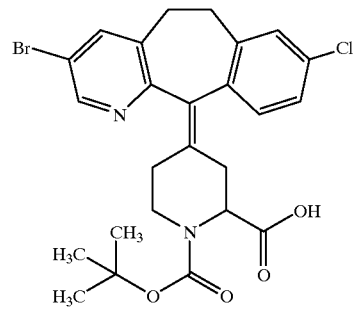

The major product (carboxamide) from Step C (0.19 gm) was dissolved in 10 ml of 6N hydrochloric acid and refluxed for 24 hours. The 6 N HCl was removed under vacuum and the residue dissolved in water (5 ml). Di-tert-butyldicarbonate (0.13 gm) was added and the pH of the reaction mixture brought to 9.0 with 1 N sodium hydroxide. After stirring 2 hours at ambient temperature, the reaction mixture was added to citric acid and extracted with dichloromethane to obtain the crude product which was chromatographed on silica gel to obtain 93 mg of title product. FABMS (M+1)=533.

Step E

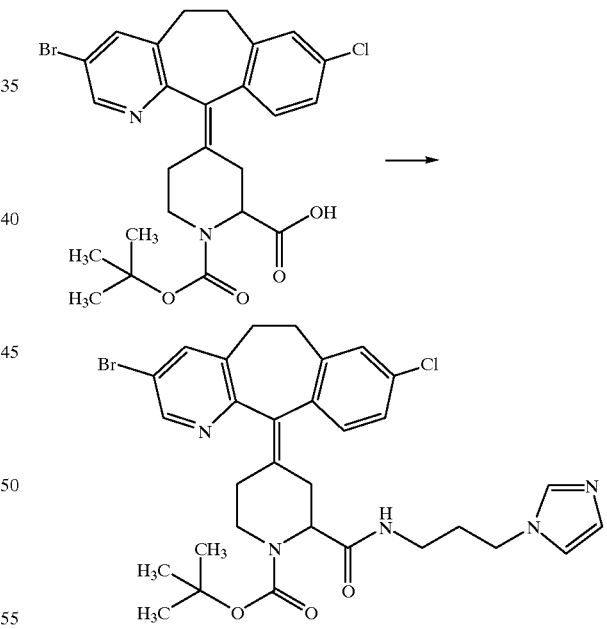

The title compound from Step D (70 mg, 0.13 mmol) was dissolved in 2 ml of DMF and DEC (37 mg, 0.19 mmol.), HOBT (26 mg, 0.19 mmol), and N-methyl-morpholine (42 uL, 0.4 mmol) were added and the reaction mixture stirred at ambient temperature for 7 hours. After addition to water and extraction with dichloromethane, the crude product was chromatographed on a silica gel column to obtain 86 mg of title product. FABMS (M+1)=640.

Preparative Example 169

11-Chloro-6,11-dihydro-5H-benzo[5,6]cyclohepta[1,2-B]pyridine

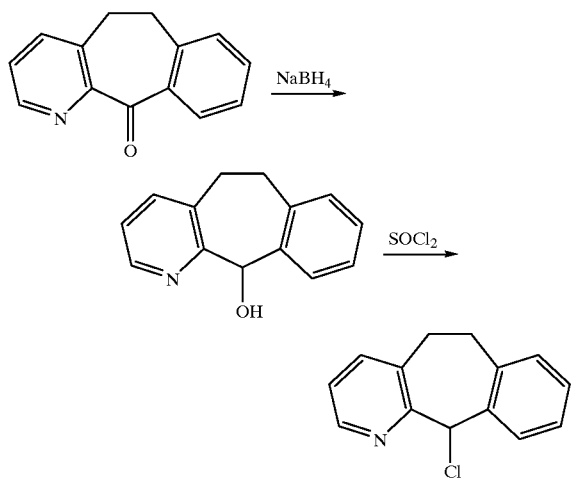

The ketone (starting material) 5,6-dihydro-11H-benzo[5,6]cyclohepta[1,2-c]pyridine-11-one, may be prepared by following the methods described in U.S. Pat. No. 3,419,565.

Sodium borohydride (2 g, 53.3 mmol) was added to a solution of the ketone (3 g, 14.35 mmol) in methanol (50 ml) at 0° C., then stirred for 2 hours at room temperature. The reaction was quenched by addition of ice (10 g) and 2N HCl (10 ml, basified with 2N NaOH (13 ml) and extracted with MeCl₂ (2×50 ml). The organic layer was separated, dried over MgSO₄, filtered and solvent evaporated yielding the alcohol (3 g, 100%).

1H NMR (DMSO, δ) 3.0–3.4(m,4H) 6.101(brs,2H) 7.0–7.3(m,4H) 7.5(m,2H) 8.314(d,1H).

Thionyl chloride (3 ml, 41.12 mmol) was added to a solution of the alcohol (2.5 g, 11.84 mmol) in MeCl₂(50 ml) at room temperature, then stirred for 1 hour. The solvent was evaporated, water 50 (ml) and 5% NaOH (10 ml) were added. The mixture was extracted with MeCl₂ (100 ml), organic layer was dried over MgSO₄, filtered, and solvent evaporated yielding a tan solid, which was triturated with ether, and filtrate concentrated yielding a white solid. (1.5 g).

1H NMR (CDCl₃, δ) 2.9–3.0 (m, 2H), 3.6 (m, 1H), 3.9 (m, 1H), 6.3 (s, 1H), 7.2 (m,3H). 7.3 (d, 1H), 7.4 (d, 1H), 7.5(d, 1H), 8.42 (d, 1H).

The filtered solid was dried yielding (0.9 g) of additional material. Total yield (2.4 g, 87%).

PREPARATIVE EXAMPLE 170

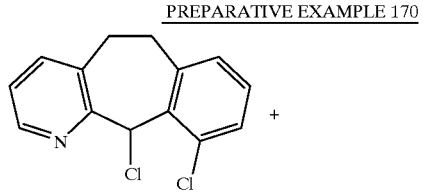

+

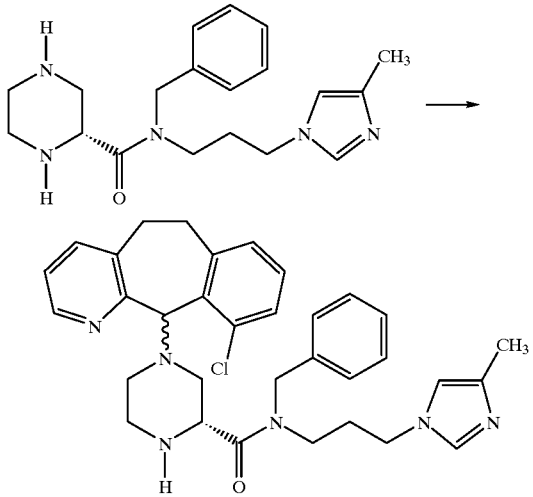

Acetonitrile (5 ml) was added to a mixture of the 10-Chloro tricycle (0.5 g, 1.90 mmol) (Preparative Example 9.1) and the substituted piperazine (0.78 g, 1.90 mmol). Triethylamine (1 ml, 7.18 mmol) was added, and the mixture stirred overnight at room temperature. Water (50 ml) and 5% NaOH were added and the mixture was extracted with MeCl₂ (2×100 ml). The organic layer was separated, dried over MgSO₄ and solvent was evaporated yielding desired product (0.7 g, 57%) as a mixture of 2 diastereomers, which were separated by column chromatography on silica gel, eluting with 5% v/vMeOH/MeCl₂ containing 2% NH₄OH. Isomer A (the less polar isomer) eluted first.

TABLE 5F

| Isomer | Mass (Fabs, MH) | $[\alpha]_D^{20}$ |
|---|---|---|
| A, B | 569.1 | — |
| A | 569.2786 | −55.9° C. = 0.1085 |
| B | 569.2816 | −27.4° C. = 0.1085 |

PREPARATIVE EXAMPLE 171

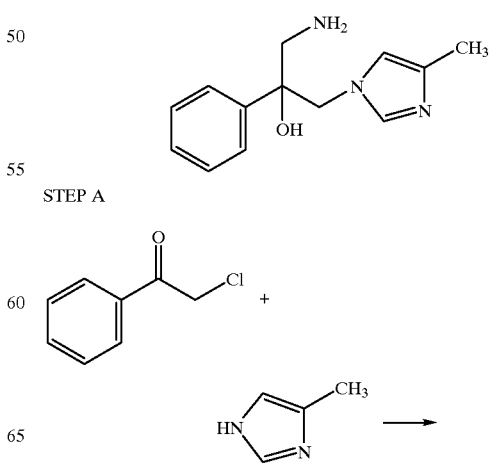

STEP A

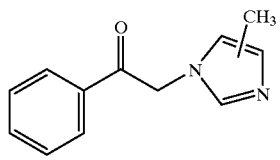

A mixture of 2-chloroacetophenone (25 g, 0.16 moles) and 4-methyl imidazole (66.1 g, 0.8 moles) was heated at 100° C. for 2 h. Cooled and the crude product chromatographed on a silica gel column eluting with $CH_2Cl_2$/3% $CH3OH$ saturated with aqueous ammonium hydroxide to give mixture of 4- and 5-methyl 1H-imidazolyl acetophenone (23 g, 73%), MS, $MH^+$=201).

STEP B

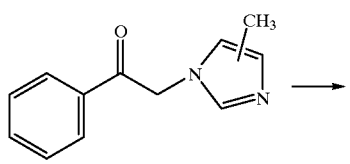

Trityl chloride (7.28 g, 0.26 moles) was added to the product from Step A in $CH_2Cl_2$ (200 mL) and stirred overnight at room temperature. The mixture was chromatographed on a silica gel column eluting with ethyl acetate/acetone (3:1) to give 4-methyl-1H-imidazolyl acetophenone (15.5 g), FabMS: $MH^+$=201.

STEP C

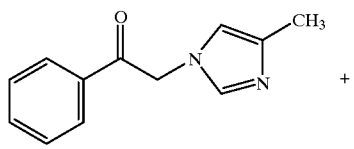

+

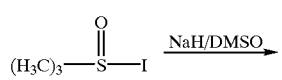

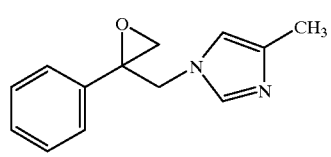

To a mixture of NaH (0.998 g, 24.97 mmoles, and trimethyl sulfoxonium iodide (5.49 g, 24.97 mmoles) in DMSO (50 mL) the product (5 g) from Step B was added and stirred for 1.5 h. Extracted the product with ethyl acetate and washed with brine, dried and solvent evaporated to give 1-(2-phenyl-2,3-epoxypropyl)-1H-4-methyl imidazole (3.44 g, 64%), FABMS: $MH^+$=215)

STEP D

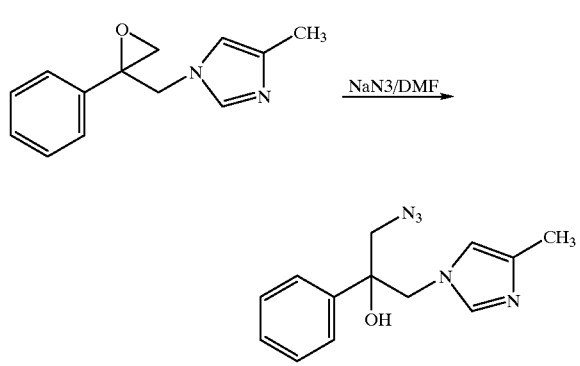

The product from Step C (3.45 g, 16.11 mmoles) and sodium azide (2.093 g, 32.21 mmoles) were heated in DMF (100 mL) at 600 C. for 12 h. Evaporated to dryness and extracted with $CH_2Cl_2$, washed with brine and dried ($MgSO_4$). Evaporated to give the title compound (3.83 g, 93%). FABMS: $MH^+$=258

STEP E

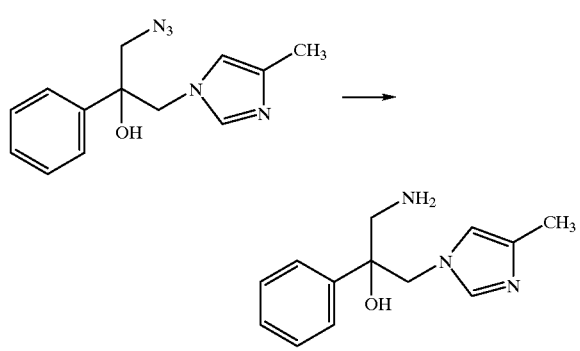

The title compound from Step D in ethanol (80 mL) was hydrogenated over 10% Pd on carbon (1.2 g) at 50 psi overnight. The catalyst was filtered off and evaporated to give the title compound (2.83 g, as yellow viscous oil).

Preparative Examples 172–188

Following the procedure set forth in Preparative Example 74 but using the aldehyde and imidazoalkyl amine (Imidazole) in Table 5G, the amines (Product) in Table 5G were obtained.

TABLE 5G

| Prep Ex. | Aldehyde | Imidazole | Product |
|---|---|---|---|
| 172 | 2-hydroxybenzaldehyde | 3-(4-methyl-1H-imidazol-1-yl)propan-1-amine | 2-((3-(4-methyl-1H-imidazol-1-yl)propylamino)methyl)phenol<br>% Yield = 60<br>MH⁺ = 246 |
| 173 | isonicotinaldehyde N-oxide | 3-(4-methyl-1H-imidazol-1-yl)propan-1-amine | 4-((3-(4-methyl-1H-imidazol-1-yl)propylamino)methyl)pyridine N-oxide<br>% Yield = 22<br>MH⁺ = 247 |
| 174 | (S)-2,3-dihydroxypropanal | 3-(4-methyl-1H-imidazol-1-yl)propan-1-amine | (S)-3-(3-(4-methyl-1H-imidazol-1-yl)propylamino)propane-1,2-diol<br>% Yield = 27<br>MH⁺ = 214 |
| 175 | 2,6-dichloroisonicotinaldehyde | 3-(4-methyl-1H-imidazol-1-yl)propan-1-amine | N-((2,6-dichloropyridin-4-yl)methyl)-3-(4-methyl-1H-imidazol-1-yl)propan-1-amine<br>% Yield = 59<br>MH⁺ = 299 |
| 176 | 3-chlorobenzaldehyde | 3-(4-methyl-1H-imidazol-1-yl)propan-1-amine | N-(3-chlorobenzyl)-3-(4-methyl-1H-imidazol-1-yl)propan-1-amine<br>% Yield = 76<br>MH⁺ = 264 |

TABLE 5G-continued

| Prep Ex. | Aldehyde | Imidazole | Product |
| --- | --- | --- | --- |
| 177 | 4-chlorobenzaldehyde | 3-(4-methyl-1H-imidazol-1-yl)propan-1-amine | N-(4-chlorobenzyl)-3-(4-methyl-1H-imidazol-1-yl)propan-1-amine<br>% Yield = 77<br>MH$^+$ = 264 |
| 178 | 2-chlorobenzaldehyde | 3-(4-methyl-1H-imidazol-1-yl)propan-1-amine | N-(2-chlorobenzyl)-3-(4-methyl-1H-imidazol-1-yl)propan-1-amine<br>% Yield = 79<br>MH$^+$ = 264 |
| 179 | pyridoxal | 3-(4-methyl-1H-imidazol-1-yl)propan-1-amine | % Yield = 45<br>MH$^+$ = 291 |
| 180 | benzaldehyde | 3-(4,5-dimethyl-1H-imidazol-1-yl)propan-1-amine | % Yield = 71<br>MH$^+$ = 244 |
| 181 | benzaldehyde | 3-(4-isopropyl-1H-imidazol-1-yl)propan-1-amine | % Yield = 25<br>MH$^+$ = 258 |

TABLE 5G-continued

| Prep Ex. | Aldehyde | Imidazole | Product |
|---|---|---|---|
| 182 | | | % Yield = 89<br>MH+ = 247 |
| 183 | | | % Yield = 13<br>MH+ = 180 |
| 184 | | | % Yield = 27<br>MH+ = 232 |
| 185 | | | % Yield = 50<br>MH+ = 195 |
| 186 | | | % Yield = 12<br>MH+ = 180 |

TABLE 5G-continued

| Prep Ex. | Aldehyde | Imidazole | Product |
|---|---|---|---|
| 187 | benzaldehyde | H₂N-CH₂CH₂CH₂-N(imidazole with Me, Me, Me) | benzyl-NH-CH₂CH₂CH₂-N(imidazole with Me, Me, Me)<br>% Yield = 84<br>$MH^+$ = 258 |
| 188 | benzaldehyde | H₂N-CH₂CH₂CH₂-N(benzimidazole) | benzyl-NH-CH₂CH₂CH₂-N(benzimidazole)<br>% Yield = 88<br>$MH^+$ = 266 |

Preparative Example 190–197

Using the procedure described for Preparative Example 109, but using the title compounds from the Examples listed in the Table 5H, the Product amines were prepared.

TABLE 5H

| Prep. Ex. | BOC compound from Ex. No. | Product | 1. Yield (%)<br>2. $MH^+$ |
|---|---|---|---|
| 190 | 343 | Isomer A (structure with Br-pyridine, Cl-phenyl, piperazine, amide, benzyl, imidazole with Me, Me) | 1. 661<br>2. 87 |

TABLE 5H-continued
| Prep. Ex. | BOC compound from Ex. No. | Product | 1. Yield (%) 2. MH+ |
|---|---|---|---|
| 191 | 344 | 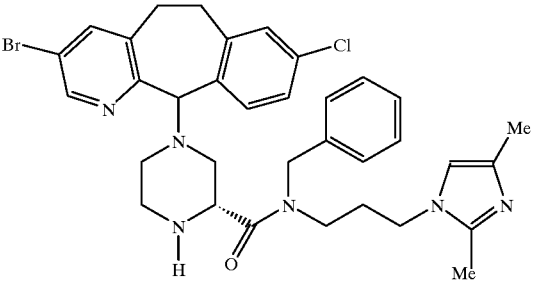<br>Isomer B | 1. 661<br>2. 80 |
| 192 | 345 | 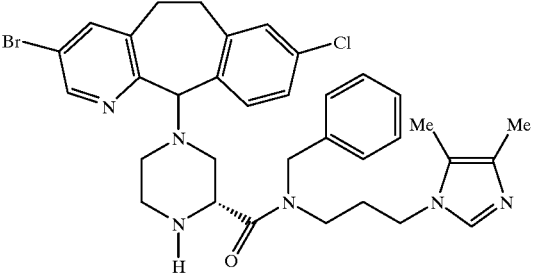<br>Isomer A | 1. 72<br>2. 661 |
| 193 | 346 | 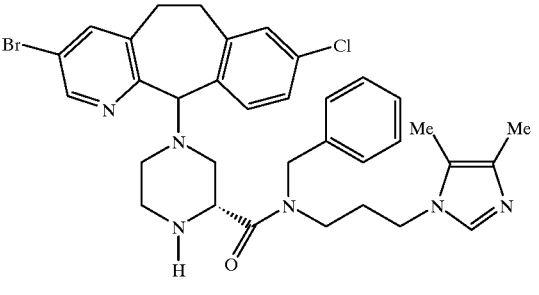<br>Isomer B | 1. 71<br>2. 661 |

TABLE 5H-continued

| Prep. Ex. | BOC compound from Ex. No. | Product | 1. Yield (%) 2. MH+ |
|---|---|---|---|
| 194 | 347 | Isomer A | 1. 93 2. 661 |
| 195 | 348 | Isomer B | 1. 92 2. 661 |
| 196 | 349 | Isomer A | 1. 85 2. 647 |
| 197 | 350 | Isomer B | 1. 87 2. 647 |

PREPARATIVE EXAMPLE 199

Step A

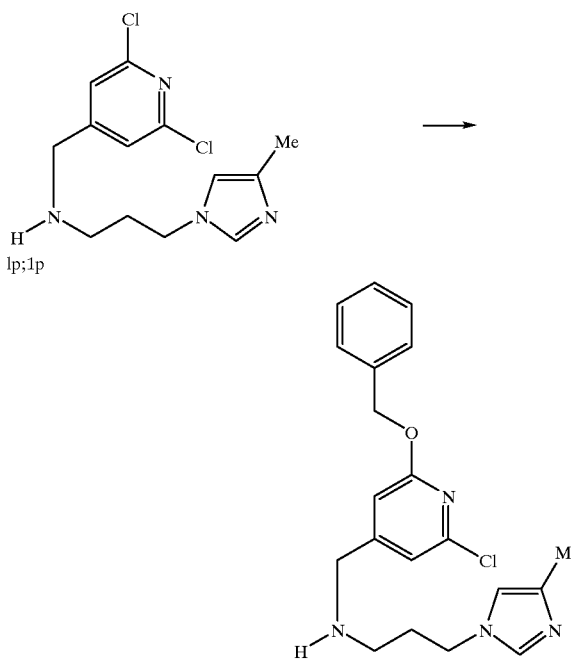

The title compound from Preparative Example 175 (0.9 g), benzyl alcohol (0.68 mL), solid potassium hydroxide (0.66 g), 18-crown-6-ether (80 mg) and anhydrous toluene (20 mL) were stirred at reflux. Purification by preparative plate chromatography (silica, 4% MeOH—$CH_2Cl_2$, $NH_4OH$ saturated) afforded the benzyl ether (0.73 g, 68%, $MH^+$=371).

Step B

The title compound from Step A above (0.72 g), methanol (60 mL) and 10% palladium on carbon (300 mg) were stirred under 50 psi hydrogen atmosphere for 3 days. Filtration through celite afforded a solution which was treated with TEA (3 equiv) and $CH_2Cl_2$. Filtration and purification by preparative plate chromatography (silica, 5% MeOH—$CH_2Cl_2$, $NH_4OH$ saturated) afforded the title compound (0.20 g, 42%, $MH^+$=247).

PREPARATIVE EXAMPLE 200
Preparation of the tricyclic N-oxide moiety

-continued

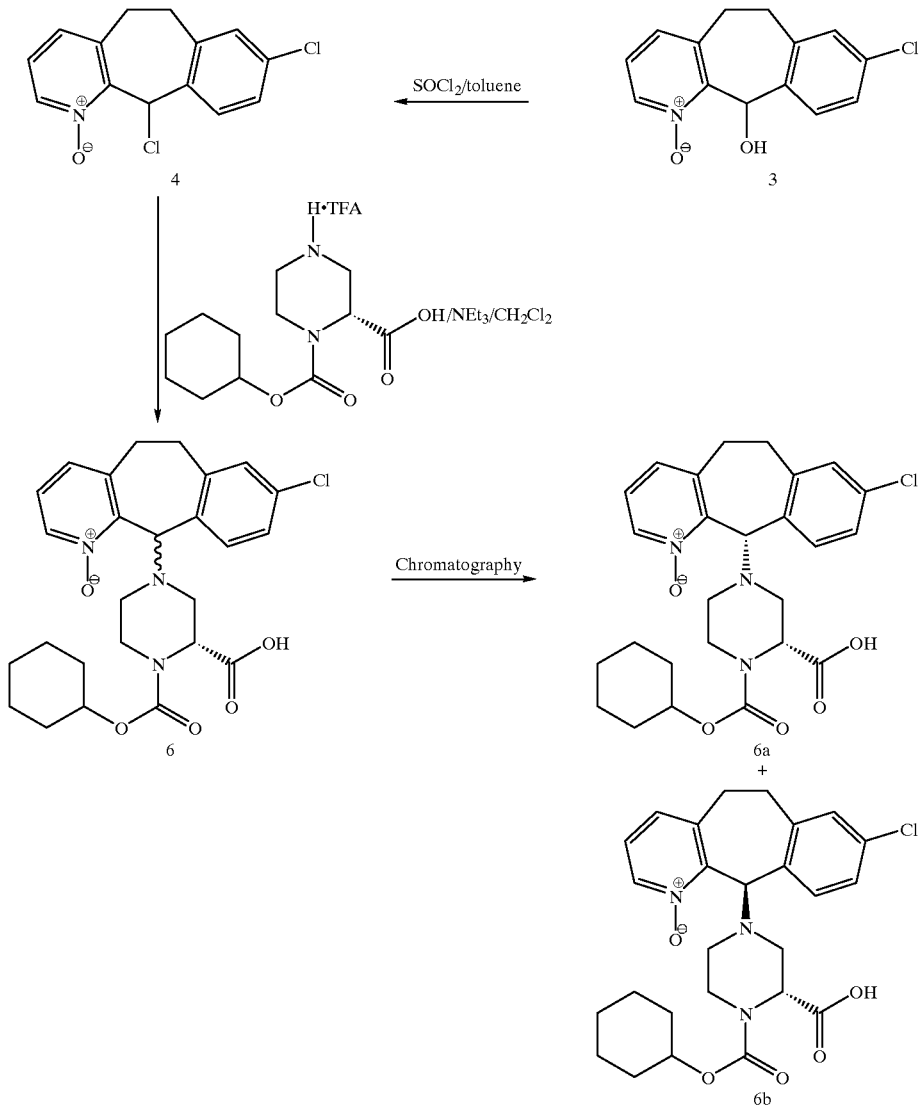

[1→2] A solution of 3-peroxybenzoic acid (25 g, 102.59 mmol, 2.5 eq.) in anhydrous dichloromethane (250 mL) was added dropwise over a period of one hour to a stirred solution of 8-chloro-4-aza-10,11-dihydro-5H-dibenzo[a,d] cyclohepten-5-one 1 (10 g, 41.04 mmol, 1.0 eq.) in anhydrous dichloromethane (100 mL) at 0° C. under a nitrogen atmosphere. The solution was slowly (3 h) warmed to room temperature and stirred for another 12 h. The solution was extracted with 1 M aqueous sodium hydroxide solution (5×100 mL), washed with brine (2×100 mL), dried over $Na_2SO_4$, filtered, and concentrated under house vacuum at 30° C. to give 2 as a canary-yellow solid. The title compound 2 was used directly without further attempts at purification.

Yield: 10 g=38.51 mmol=94%

[M+H]$^+$: 260

HRMS (FAB+): Calculated for $C_{14}H_{11}ClNO_2$ ([M+H]$^+$): 260.0475 Observed: 260.0478

[2→3] Sodium borohydride (2.21 g, 57.76 mmol, 1.5 eq.) was added portionwise over a period of 15 minutes to a solution of 2 (10 g, 38.51 mmol, 1.0 eq.) in anhydrous methanol (500 mL) at 0° C. under a nitrogen atmosphere. The resulting suspension was stirred at 0° C. for one hour and at room temperature for another hour. The volatiles were removed under house vacuum at 30° C. and the residue was taken up in 1 M aqueous NaOH solution (250 mL). The aqueous solution was extracted with dichloromethane (5×100 mL). The combined organic extracts were washed with brine (100 mL), dried over $Na_2SO_4$, filtered, and concentrated under house vacuum at 30° C. to give 3 as a lime-green solid. Compound 3 was used directly without any attempts at purification.

Yield: 9 g=34.39 mmol=89%

[M+H]$^+$: 262

HRMS (FAB+): Calculated for $C_{14}H_{13}ClNO_2$ ([M+H]$^+$): 262.0635 Observed: 262.0636

[3→4] Thionyl chloride (5 mL, 68.78 mmol, 2.0 eq.) was added dropwise over a period of 10 minutes to a stirred suspension of 3 (9 g, 34.39 mmol, 1.0 eq.) and anhydrous toluene (150 mL) at 0° C. under a nitrogen atmosphere. The cream-colored suspension was slowly (3 h) warmed to room temperature and stirred for another 12 h. The volatiles were removed under house vacuum at 30° C. The residue was taken up in dichloromethane (250 mL) and washed with ice-cold, saturated aqueous NaHCO₃ solution (5×100 mL) until the aqueous washings were moderately basic at pH 9. The organic layer was washed with brine (100 mL), dried over Na₂SO₄, filtered, and concentrated under house vacuum at 30° C. to give 4 as a cream-colored solid in essentially quantitative yield. Due to its high reactivity, compound 4 was used directly without any attempts at purification or characterization (other than ¹H NMR).

Yield: 9.55 g≡34.09 mmol≡99%

4→6 Triethylamine (18 mL, 126.65 mmol, 5.0 eq.) was added dropwise to a stirred solution of 5 (previously described in the art; 9.38 g, 25.33 mmol, 1.0 eq.) in anhydrous dichloromethane (50 mL) at room temperature under a nitrogen atmosphere. The solution was stirred at room temperature for 30 minutes and was cooled to 0° C. A solution of 4 (8.52 g, 30.39 mmol, 1.2 eq.) in anhydrous dichloromethane (50 mL) was added dropwise over a period of 25 minutes. The mixture was slowly (3 h) warmed to room temperature and stirred for another 12 h. The volatiles were removed under house vacuum at 30° C. The residue was taken up in 50% m/v aqueous citric acid solution (100 mL) and extracted with ethyl acetate (5×100 mL). The organic extracts were combined and dried over Na₂SO₄, filtered, and concentrated under house vacuum at 30° C. The residual cream-colored solid was flash-chromatographed (CH₂Cl₂:MeOH=19:1 v/v) to give the diastereomerically pure isomers 6a and 6b at C-11 of the tricycle.

For 6a:

Yield: 5.75 g≡11.50 mmol≡45%

Off-white foam; M.p.: 78–83° C.

[M+H]⁺: 500

HRMS (FAB+): Calculated for C₂₆H₃₁ClNO₃O₅ ([M+H]⁺): 500.1953 Observed: 500.1952

For 6b:

Yield: 3.00 g≡6.00 mmol≡24%

Off-white solid; M.p.: 94–99° C.

[M+H]⁺: 500

HRMS (FAB+): Calculated for C₂₆H₃₁ClN₃O₅ ([M+H]⁺): 500.1953 Observed: 500.1952

PREPARATIVE EXAMPLE 201

Step A

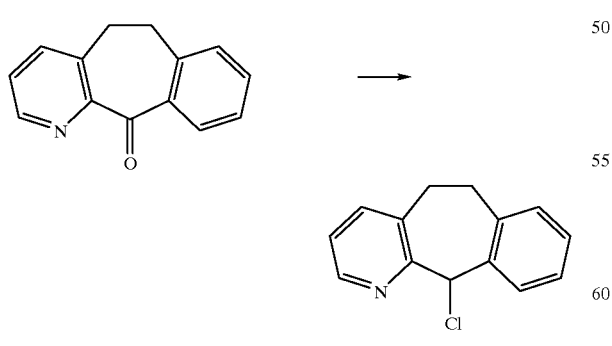

Following the procedure outlined in U.S. Pat. No. 5,151,423, except substituting the 8-chloro tricycle with the 8-H analog described in U.S. Pat. No. 3,419,565, the 8-hydrido tricyclic chloride is obtained.

Step B

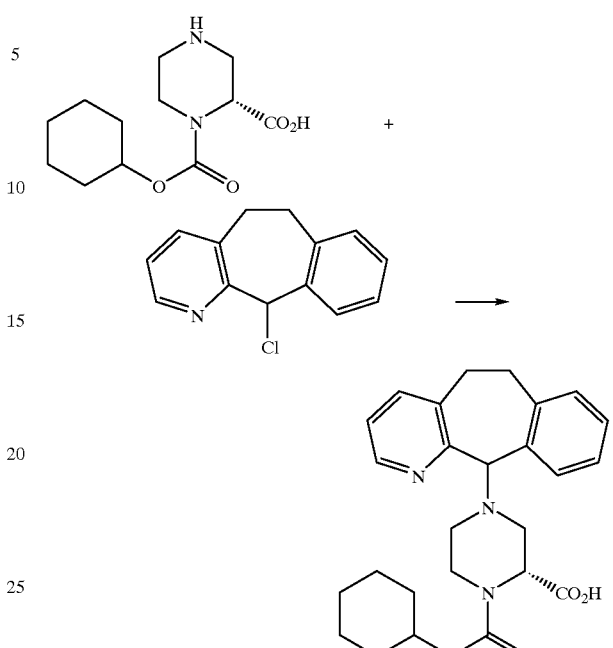

Following the procedure described for Preparative Example 127 Step C, except using the 8-hydrido tricyclic chloride from Preparative Example 201 Step A instead of the 8-chloro tricyclic chloride, the title compounds were isolated.

The isomers were separated by column chromatography (silica) using 3% MeOH/CH₂Cl₂.

Isomer A: C(11)-(S): 38%, MH⁺=450.

Isomer B: C(11)-(R): 31%, MH⁺=450.

Preparative Example 202

Step A

Following the procedure set forth in Preparative Example 127 Step C, but substituting the tricyclic chloride

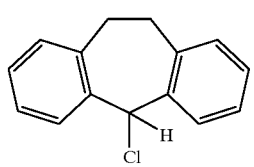

for the 8-Cl tricyclic chloride, one obtains the following acid:

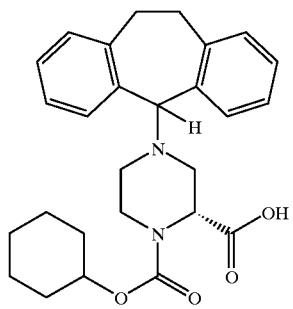

Solid, 51% yield, mp=120.5–125.1° C.

PREPARATIVE EXAMPLE 202A

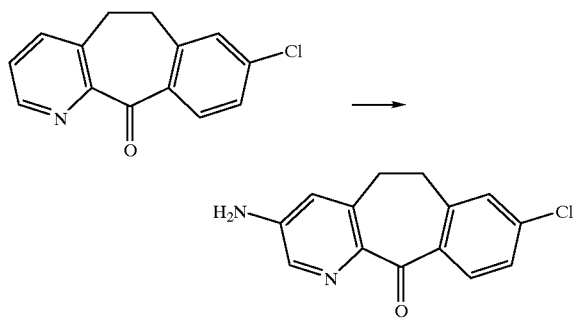

By essentially the same procedure set forth in Njoroge et. al. (J. Med. Chem. (1997),40, 4290) for the preparation of 3-aminoloratadine only substituting the 3-H ketone (J. Het. Chem (1971) 8, 73) for loratadine, the title compound was prepared.

PREPARATIVE EXAMPLE 203

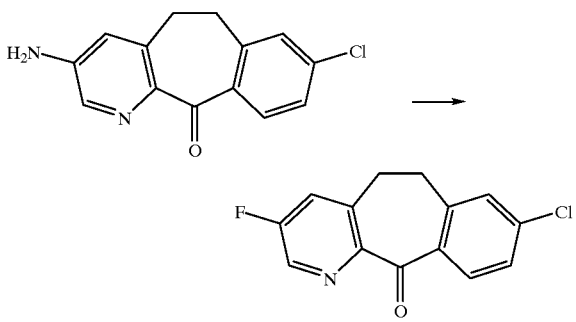

The title compound from Preparative Example 202A (1.62 g, 6.26 mmol) was added portionwise to NO$^+$BF$_4^-$ (0.81 g, 1.1 eq.) in toluene (10 mL) at 0° C. The resulting slurry was stirred at 0° C. for 2.5 hours before warming to room temperature. The reaction mixture was heated at reflux for 2 hours, cooled, neutralized with 1N NaOH and extracted with EtOAc (3×50 mL). The combined organics were washed with 1N HCl (2×25 ml), saturated NaHCO$_3$ (1×25 mL), and water (1×15 mL), dried over Na$_2$SO$_4$, filtered, and concentrated under reduced pressure. The crude product was purified by flash chromatography using a 70:30 hexanes:EtOAc mix as eluent to yield a yellow solid (0.68 g, 42% yield). LCMS: MH$^+$=262.

PREPARATIVE EXAMPLE 204

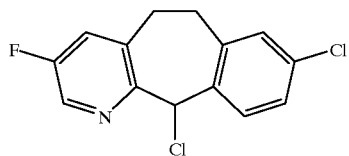

By essentially the same procedure set forth in Preparative Example 201 Step A, the title compound was prepared from the ketone of Preparative Example 203 and used without further purification (0.66 g, 100% crude yield).

PREPARATIVE EXAMPLE 205

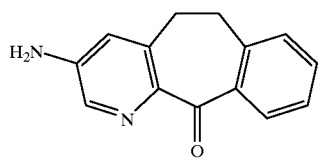

$^+$NH$_4$HCO$_2^-$ (2.44 g, 10 eq.) was added to a solution of the title compound from Preparative Example 202A (2.00 g, 7.74 mmol) and 5% Pd/C (0.50 g) in EtOH (100 mL) and the resulting solution was heated to reflux 2 hours. The reaction mixture was cooled, filtered through a plug of Celite and concentrated under reduced pressure. The residue was diluted with H$_2$O (100 mL) and extracted with CH$_2$Cl$_2$ (3×75 mL). The combined organics were dried over Na$_2$SO$_4$, filtered, and concentrated in vacuo to give a yellow solid (1.22 g, 70% yield) which was used without further purification: FABMS: MH$^+$=225.

PREPARATIVE EXAMPLE 206

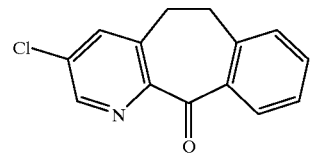

The title compound from Preparative Example 205 (1.22 g, 5.44 mmol) was added portionwise to CuCl$_2$ (0.88 g, 1.2 eq) and tBuONO (0.98 mL, 1.5 eq) in CH$_3$CN (25 mL) at 0° C. The resulting solution was warmed to RI and stirred for 72 hours. The reaction mixture was quenched by the addition of 1M HCl (10 mL), neutralized with 15% NH$_4$OH and extracted with EtOAc (3×100 mL). The combined organics were washed with 15% NH$_4$OH (1×50 mL), 1M HCl (1×50 mL) and saturated NaHCO$_3$, dried over Na$_2$SO$_4$, filtered and concentrated. The crude product was purified by flash chromatography using a 50:50 EtOAc:hexanes mixture as eluent to give a pale yellow solid (0.81 g, 61% yield): CIMS: MH$^+$=244.

PREPARATIVE EXAMPLE 207

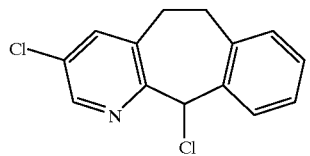

By essentially the same procedure set forth in Preparative Example 201 Step A, the title compound was prepared from the ketone of Preparative Example 206 and used without further purification.

PREPARATIVE EXAMPLE 208

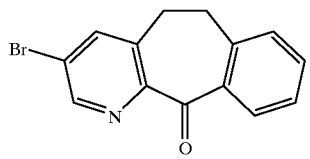

By essentially the same procedure set forth in Preparative Example 206, only substituting $CuBr_2$ for $CuCl_2$ the title compound was prepared (1.33 g, 60% yield): FABMS: $MH^+=244$.

PREPARATIVE EXAMPLE 209

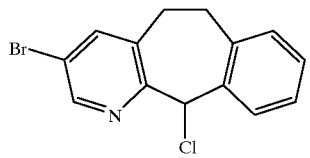

By essentially the same procedure set forth in Preparative Example 201 Step A, the title compound was prepared from the ketone of Preparative Example 208 and used without further purification.

PREPARATIVE EXAMPLE 210

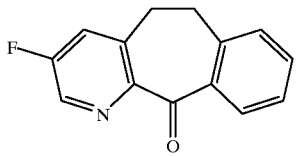

By essentially the same procedure set forth in Preparative Example 203 only substituting the title compound from Preparative Example 205, the title compound can be prepared.

PREPARATIVE EXAMPLE 211

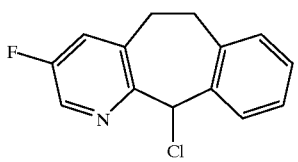

By essentially the same procedure set forth in Preparative Example 201 Step A, except starting with the ketone of Preparative Example 210, the title compound can be prepared.

PREPARATIVE EXAMPLE 212

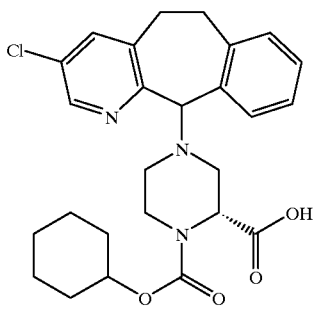

By essentially the same procedure set forth in Preparative Example 127 Step C, only substituting the 3-Cl, 8-H tricyclic chloride prepared in Preparative Example 207 for the 3-H, 8-Cl tricyclic chloride the title compound (C-11(S)- and (R)-isomers) was prepared. FABMS: $MH^+=484$.

EXAMPLE 1

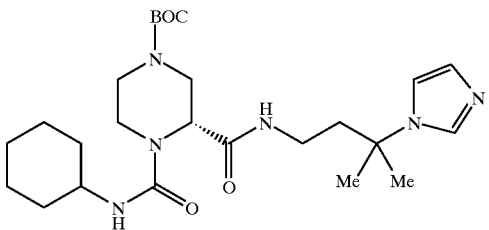

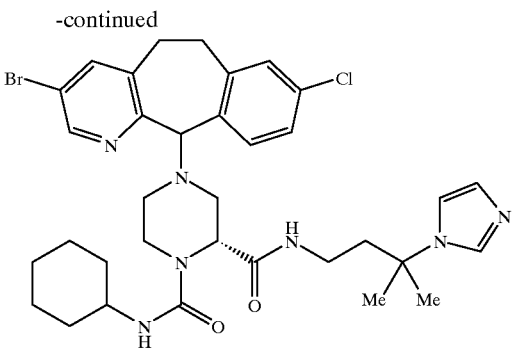

A solution of the title compound from Preparative Example 5 (0.44 g, 0.897 mmol) was stirred at room temperature in $CH_2Cl_2$ (10 mL) and TFA (4 mL) until starting material was consumed (TLC). The reaction mixture was concentrated under reduced pressure to remove any excess TFA and the compound was redissolved in $CH_2Cl_2$ (5 mL), treated with chloride (42.0)

(42.0)

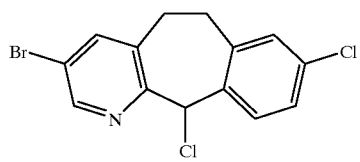

(0.37 g, 1.2 eq.) and TEA (2.5 mL, 10 eq.) and stirred at room temperature for 84 hours. The reaction mixture was diluted with saturated $NaHCO_3$ (25 mL), water (25 mL), and $CH_2Cl_2$ (25 mL) and separated. The aqueous layer was extracted with $CH_2Cl_2$ and the combined organics dried over $Na_2SO_4$ and concentrated under reduced pressure. The crude product was purified by flash chromatography using a 5% (10% $NH_4OH$ in MeOH) solution in $CH_2Cl_2$ as eluent to yield a tan solid (0.45 g, 71% yield). mp 142–144° C.: FABMS: $MH^+$=696.

EXAMPLE 2

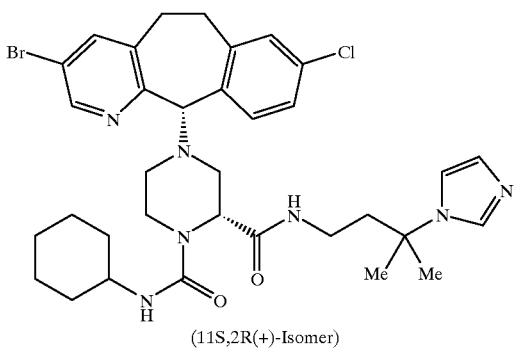

(11S,2R(+)-Isomer)

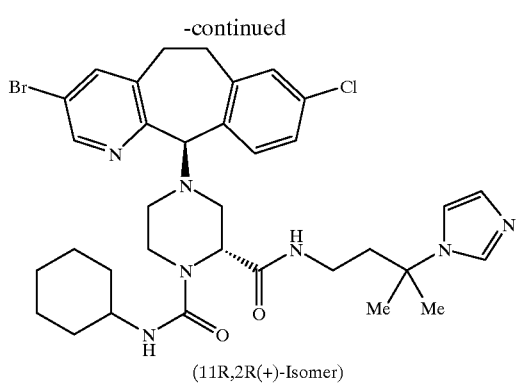

(11R,2R(+)-Isomer)

The title compound from Example 1 was separated into the 11(S)(+)- and 11(R)(+)-diastereomers by preparative HPLC using a CHIRALPAK AD column using a 12% i-PrOH in hexanes solution with 0.2% diethylamine as eluent:

11S,2R(+)-Isomer: retention time=29.21 minutes; $[\alpha]^{23.5}_D$=+19.1 (3.35 mg in 2.0 mL $CHCl_3$); mp=147–149° C.; LCMS: $MH^+$=696.

11R,2R(+)-Isomer: retention time=39.8 minutes; $[\alpha]^{24.1}_D$=+73.0 (3.07 mg in 2.0 mL $CHCl_3$); mp=128–131° C.; LCMS: $MH^+$=696.

EXAMPLE 3

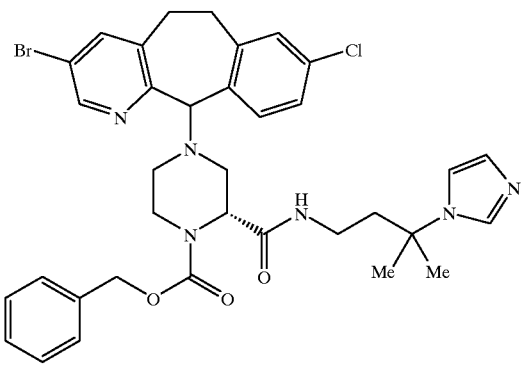

By essentially the same procedure as that set forth in Example 1, except using the title compound from Preparative Example 6, the title compound was prepared (0.085 g, 45% yield). mp 103–106° C.; LCMS: $MH^+$=705.

EXAMPLE 4

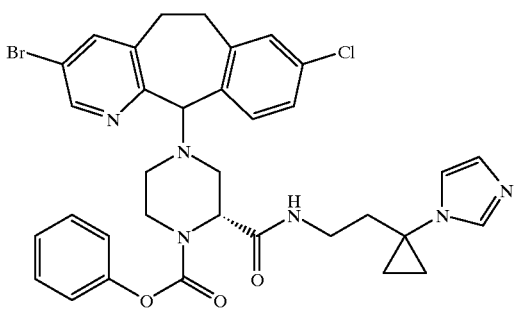

By essentially the same procedure as that set forth in Example 3, except using the title compound from Preparative Example 6.1, the title compound was prepared. mp=111–150° C.; MH$^+$=703

EXAMPLE 5

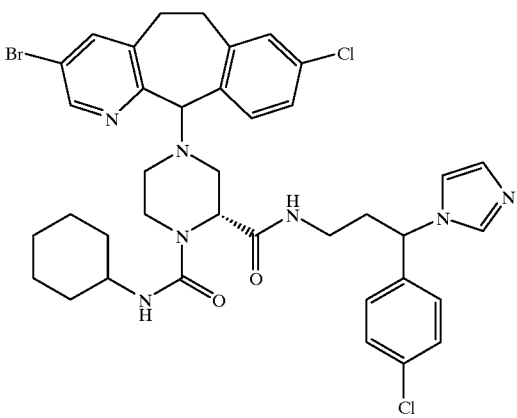

By essentially the same procedure as that set forth in Example 1, except using the title compound from Preparative Example 7, the title compound was prepared. mp 138–140° C.; LCMS: MH$^+$=778.

EXAMPLE 6

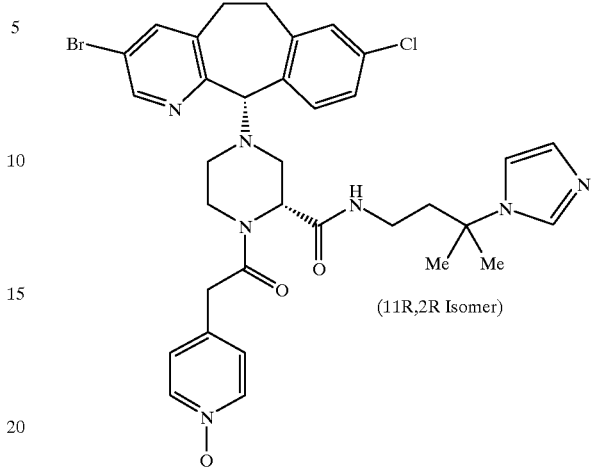

(11R,2R Isomer)

A solution of the title compound from Preparative Example 8 (0.10 g, 0.17 mmol) (11S,2R(−)-isomer) in DMF (1.0 mL) was treated with 4-pyridylacetic acid N-oxide (0.039 g, 1.5 eq.), NMM (0.03 mL, 1.5 eq), DEC (0.049 g, 1.5 eq.), and HOBT (0.034 g, 1.5 eq.) and the resulting solution stirred at room temperature overnight. The reaction mixture was quenched by the addition of saturated NaHCO$_3$ (10 mL) and extracted with CH$_2$Cl$_2$ (4×50 mL). The combined organics were dried over MgSO$_4$, filtered, and concentrated in vacuo. The crude residue was purified by Preparative TLC using a 15% (10% NH$_4$OH in MeOH) solution in CH$_2$Cl$_2$ as eluent to yield the 11S,2R isomer (0.044 g, 39% yield). mp=115–117° C.; LCMS: MH$^+$=706.

By essentially the same procedure, except using the racemate or 11R,2R isomer from Preparative Example 8, one can obtain the corresponding racemate or 11R,2R isomer product.

EXAMPLES 7–9

By essentially the same procedure as that set forth in Example 6, the compounds of the formula

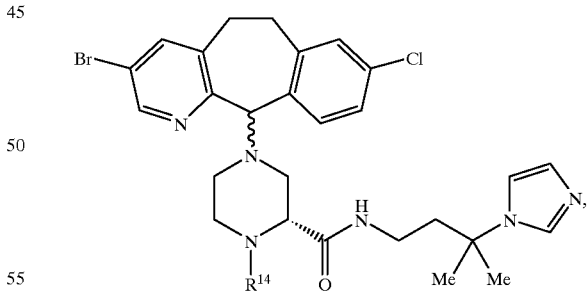

wherein $R^{14}$ is as defined in Table 6 below, were obtained.

TABLE 6

| EX. | $R^{14}$ = | MP (° C.) | Mass Spec |
|---|---|---|---|
| 7 | 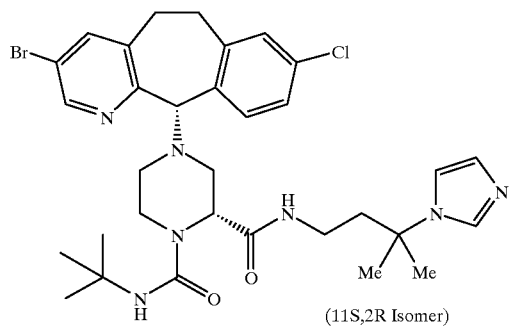 11R, 2R isomer | 148–150 | LCMS: $MH^+$ = 706 |
| 8 |  11S, 2R isomer | 123–127 | LCMS: $MH^+$ = 739 |
| 9 |  11R, 2R isomer | 150–153 | LCMS: $MH^+$ = 739 |

EXAMPLE 10

A solution of the title compound from Preparative Example 8 (11S,2R-isomer) (0.080 g, 0.14 mmol) in $CH_2Cl_2$ (2.0 mL) was treated with t-BuNCO (0.080 mL, 5.0 eq). The resulting solution was stirred at room temperature overnight and concentrated under reduced pressure. The crude product was purified by preparative TLC using a 10% (10% $NH_4OH$ in MeOH) solution in $CH_2Cl_2$ as eluent to give the title compound (0.045 g, 48% yield). mp=139–142° C.; LCMS: $MH^+$=670.

EXAMPLE 11

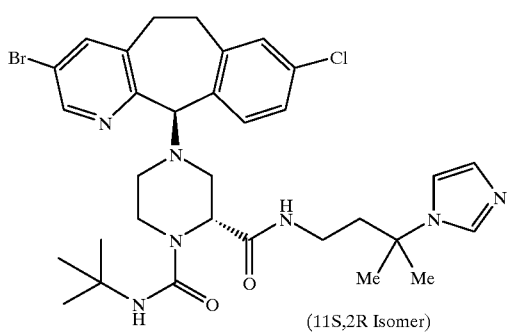

The title compound was prepared by essentially the same procedure as that set forth in Example 10, but substituting the 11R,2R-isomer from Preparative Example 8. mp=157–159° C.; LCMS: $MH^+$=670.

EXAMPLES 12–14

By essentially the same procedure as that set forth in Example 10, except the title compounds from Preparative Example 9 are used, the compounds of the formula

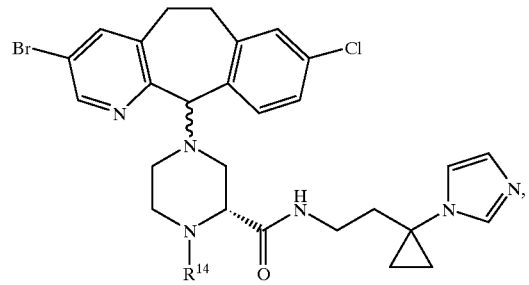

wherein $R^{14}$ is as defined in Table 7 below, were obtained.

TABLE 7

| EX. | R = | MP (° C.) | Mass Spec |
|---|---|---|---|
| 12 | 11S, 2R isomer | 136–139 | LCMS: $MH^+$ = 668 |
| 13 | 11R, 2R isomer | 106–110 | LCMS: $MH^+$ = 668 |
| 14 | 11R/S, 2R isomers | 133–139 | LCMS: $MH^+$ = 654 |

EXAMPLE 15

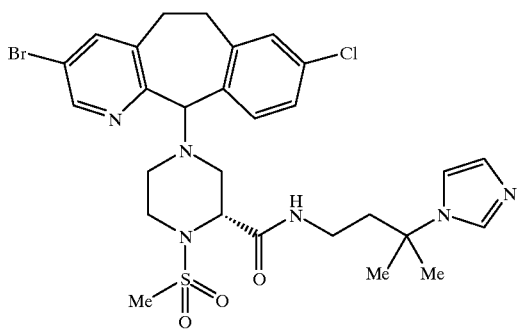

To a solution of the title compound (11-racemate) from Preparative Example 8 (0.072 g, 0.12 mmol) and TEA (0.010 mL, 1.1 eq.) in $CH_2Cl_2$ (4 mL) was added $MeSO_2Cl$ (0.01 mL, 1.1 eq.) and the resulting solution was stirred at room temperature overnight. The reaction mixture was quenched by the addition of saturated $NaHCO_3$ (5 mL), separated and extracted with $CH_2Cl_2$ (2×50 mL).

The combined organics were dried over $Na_2SO_4$ and concentrated in vacuo. The crude residue was purified by preparative TLC using a 10% (10% $NH_4OH$ in MeOH) solution in $CH_2Cl_2$ as eluent (44 mg, 63% yield). mp=107–110° C.; LCMS: $MH^+$=649.

By essentially the same procedure, the 11R,2R or 11S,2R isomers can be obtained by using the 11R,2R or 11S,2R isomer, respectively, title compounds from Preparative Example 8.

EXAMPLES 16–18

By essentially the same procedure as that set forth in Example 15, compounds of the formula:

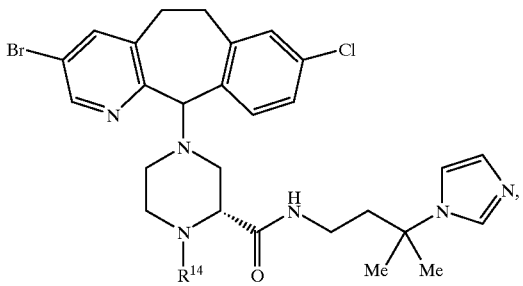

wherein $R^{14}$ is as defined in Table 8, were obtained.

TABLE 8

| EX. | R = | MP (° C.) | Mass Spec |
|---|---|---|---|
| 16 | (11S, 2R isomer) | 109–111 | LCMS: $MH^+$ = 657 |

TABLE 8-continued

| EX. | R = | MP (° C.) | Mass Spec |
|---|---|---|---|
| 17 | (11R, 2R isomer) | 107–108 | LCMS: $MH^+$ = 657 |
| 18 | (11R/S, 2R isomers) | 139–142 | LCMS: $MH^+$ = 642 |

EXAMPLE 19

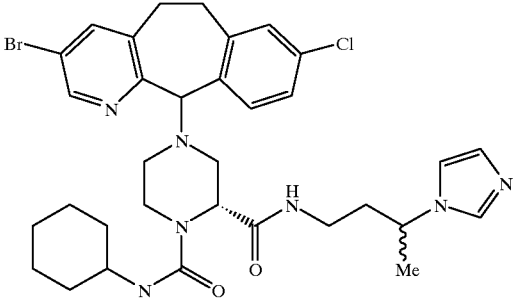

By essentially the same procedure as that set forth in Example 1, except using the title compound from Preparative Example 7.3, the title compound was obtained. mp=133–138° C.; LCMS: $MH^+$=682.

EXAMPLE 20

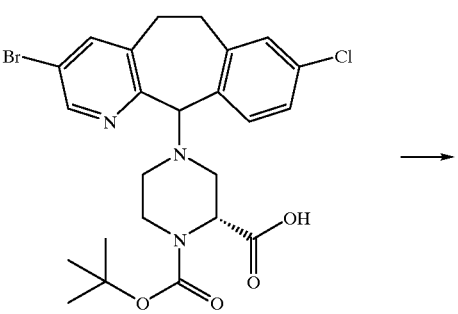

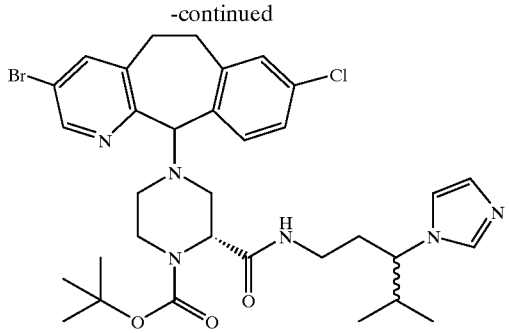

The title compound from Preparative Example 4 (0.211 g, 1.4 eq.) found in Table 1 was added to a solution of acid from Preparative Example 51 (0.487 g, 0.90 mmol), DEC (0.201 g, 1.2 eq.), HOBT (0.73 g, 6.0 eq.), and NMM (0.60 mL, 6.0 eq.) in DMF (6.0 mL). The resulting solution was stirred at room temperature 3 days. The crude product was precipitated from the reaction mixture by the addition of water and filtered. The residue was purified by flash chromatography using a gradient of 0.5% to 3% by 0.5% increments (10% $NH_4OH$ in MeOH) solution in $CH_2Cl_2$ as eluent to give the title compound (0.411 g, 67% yield). mp=178–179° C.; $MH^+$=685.

EXAMPLE 21

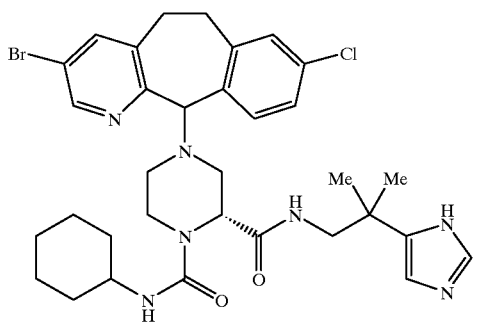

The title compound was prepared by essentially the same procedure as that set forth in Example 110, but substituting the title compound from Preparative Example 11 Step C. mp=150–154° C.; $MH^+$=682.

EXAMPLE 22

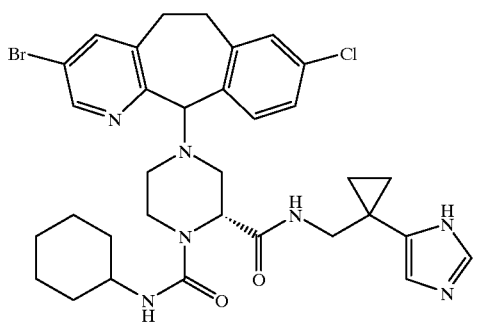

The title compound was prepared by essentially the same procedure as that set forth in Example 110, but substituting for the title compound from Preparative Example 102 Step C the amine prepared by the method described in Preparative Example 11 Steps A–C only substituting dichloroethane for methyl iodide in Preparative Example 11 Step A. mp=156–158° C.; $MH^+$=680.

EXAMPLE 24

Step A

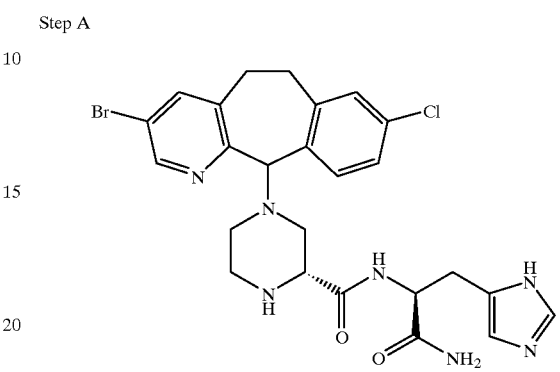

The title compound from Preparative Example 12 (0.23 g, 0.49 mmol) in $CH_2Cl_2$ (5.0 mL) and TFA (3.0 mL) was stirred at room temperature 2 hours and concentrated in vacuo. The residue was dissolved in $CH_2Cl_2$ (5.0 mL) and treated with TEA (0.45 mL, 20 eq.) and chloride

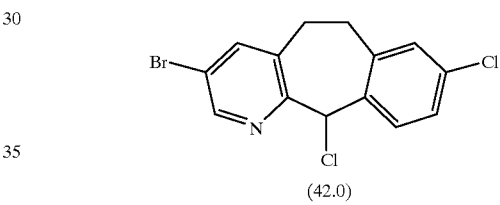

(42.0)

(0.056 g, 0.33 eq.) and stirred at room temperature 48 hours. The reaction mixture was diluted with saturated $NaHCO_3$ (5.0 mL), water (15 mL), and extracted with $CH_2Cl_2$ (2×50 mL). The combined organics were dried over $Na_2SO_4$ and concentrated under reduced pressure. The crude product was purified by flash chromatography using a 15% (10% $NH_4OH$ in MeOH) solution in $CH_2Cl_2$ as eluent (0.063 g, 67% yield). mp=157° C.(dec.); FABMS: $MH^+$=572.

Step B

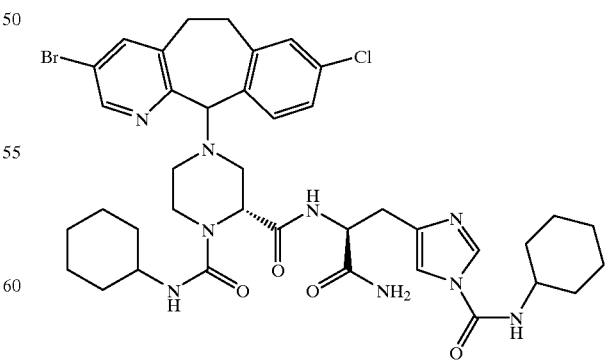

The title compound from Step A (0.058 g, 0.101 mmol) in $CH_2Cl_2$ (3 mL) was treated with excess cyclohexyl isocyanate and stirred at room temperature for one hour. The reaction mixture was concentrated in vacuo and purified by flash chromatography using an 8% MeOH in CH$_2$Cl$_2$ solution as eluent to give the title compound (0.062 g, 75% yield). mp=164—167° C.; FABMS: MH$^+$822.

EXAMPLE 25

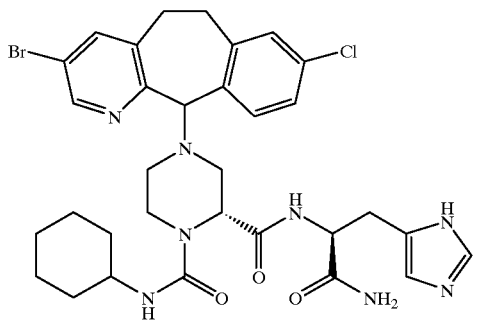

The title compound from Example 24 (0.045 g, 0.0547 mmol) was stirred in concentrated NH$_4$OH (3.0 mL) and MeOH (3.0 mL) overnight. The resulting solution was concentrated in vacuo and the residue purified by flash chromatography using a 15% MeOH in CH$_2$Cl$_2$ solution as eluent to give the title compound (0.022 g, 58% yield). mp=164–169° C.; FABMS: MH$^+$=697.

EXAMPLE 26

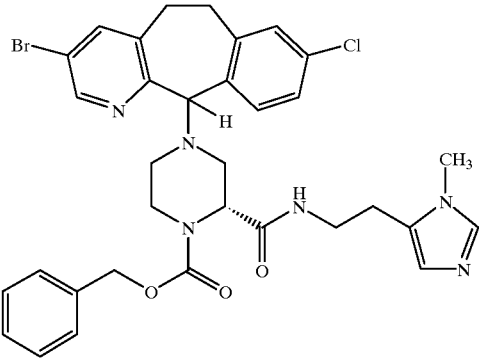

Step A

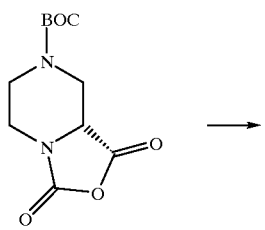

-continued

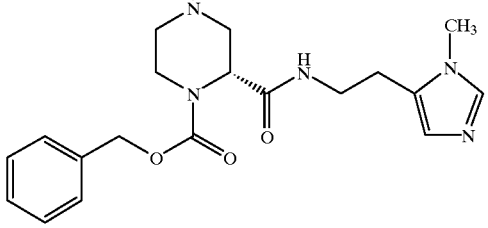

Dissolve 2.99 g (15.09 mmol) of the 3-methylhistamine hydrochloride in 100 mL of methylene chloride followed by 3.21 g (31.70 mmole) of triethylamine. Stir under nitrogen for 30 min then add, in small portions, 4.83 g (18.87 mmol) of anhydride from Preparative Example 44 and stir under nitrogen for 30 min. Add 4.14 g (16.60 mmol) of benzyl chloroformate and stir over night. Dilute with 100 mL of methylene chloride and wash with aqueous NaHCO$_3$ solution. Dry the organic layer over MgSO$_4$ and concentrate in vacuo. Flash chromatograph on 650 g of silica gel using 97% CH$_2$Cl$_2$ (NH$_4$OH)—3% methanol to give the product as a white solid, mp=51.8–63.2° C.

Step B

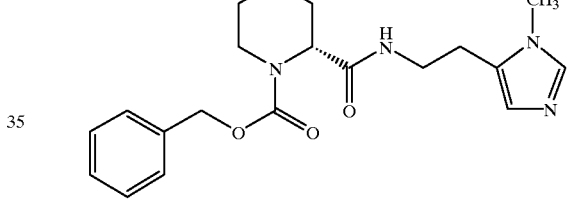

Dissolve 4.9 g of the product from Step A in 30 mL of methylene chloride and add 13 mL of trifluoroacetic acid. Stir overnight under nitrogen then concentrate in vacuo. The residue was triturated with ether then dried in vacuo giving the product as a clear oil.

Step C

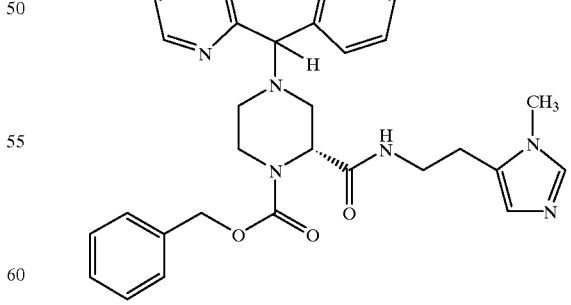

Dissolve 10.01 g (11.04 mmol) of the product of Step B in 50 mL of DMF containing 5.6 g (55.19 mmol) of triethylamine. Add dropwise a solution of the chloride

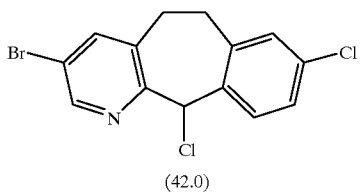

(42.0)

in 70 mL of DMF and stir under nitrogen overnight. Concentrate under vacuo and dissolve the residue in 50 mL of methylene chloride. Wash with aqueous $NaHCO_3$ solution, dry the organic layer over $MgSO_4$ and concentrate in vacuo. Flash chromatograph the residue on 640 g of silica gel using 97% $CH_2Cl_2$ ($NH_4OH$)—3% methanol to give the product as a tan solid, mp=111.8–114.5° C., $MH^+$=677 (FAB).

EXAMPLE 27

Step A

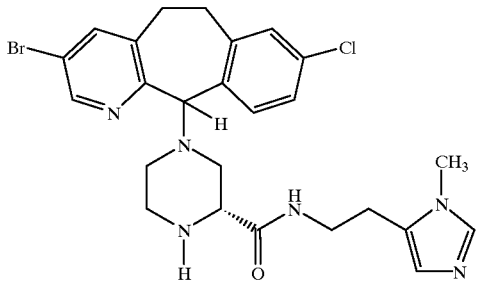

Dissolve 4.61 g (6.8 mmol) of the product of Example 26, Step C, in 6 mL of acetic acid 9 mL of a 5.7 M (33%) solution of HBr in acetic. After 3 hr the reaction was complete by silica gel tlc (95% $CH_2Cl_2$ ($NH_4OH$)—5% methanol). Add 25 mL of diethyl ether and filter the resulting precipitate under nitrogen giving 5.8 g of a tan solid. Chromatograph on a Chiralpack AD, 5 cm×50 cm column (Chiral Technologies) using 25% 2-propanol/-hexane+0.2% diethylamine, and a flow rate of 80 mL/min to give the two diastereomers.

Diastereomer A: Mp=122.2–130.2° C., $MH^+$=543 (FAB).

Diastereomer B: Mp=122.1–130.2° C., $MH^+$=543 (FAB).

Step B

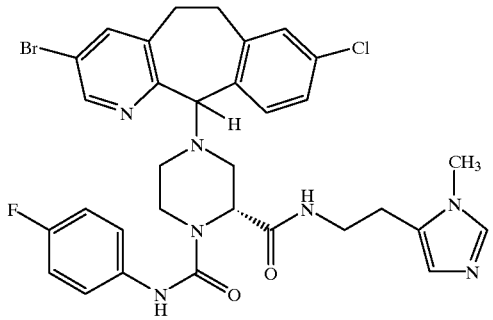

Dissolve 0.07 g (0.129 mmol) of Diastereomer A of Step A in 2 mL of methylene chloride followed by 0.021 g (0.155 mmol) of 4-fluorophenylisocyanate and stir over night under nitrogen. Dilute with 20 mL of methylene chloride and wash with aqueous $NaHCO_3$ solution, dry the organic layer over $MgSO_4$ and concentrate under vacuo. Chromatograph the residue by preparative silica gel TLC using 95% $CH_2Cl_2$ ($NH_4OH$)—5% methanol to give 0.0179 g of the product as a white solid. Diastereomer A: Mp=143.1–145.2° C., $MH^+$=680 (FAB).

In a similar manner react 0.07 g (0.129 mmol) of Diastereomer B from Step A with 4-fluorophenylisocyanate to obtain 0.018 g of the Diastereomer B product as a white solid. Diastereomer B: Mp=140.1–149.4° C., $MH^{30}$ =680 (FAB).

EXAMPLE 28

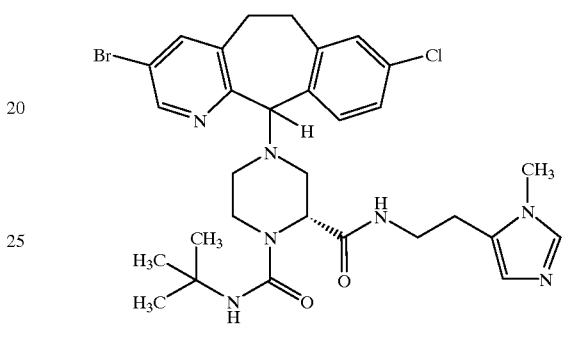

Following the procedure of Example 27, react 0.07 g (0.129 mmol) of Diastereomer A from Example 27, Step A, with tert-butylisocyanate to obtain 0.065 g of the Diastereomer A product as a white solid. Mp=125.1–133.5° C., $MH^+$=642 (FAB).

Following the above procedure, but using Diastereomer B from Example 27, Step A, obtain 0.052 g of the Diastereomer B product as a white solid. Mp=128.1–135.2° C., $MH^+$=642 (FAB).

EXAMPLE 29

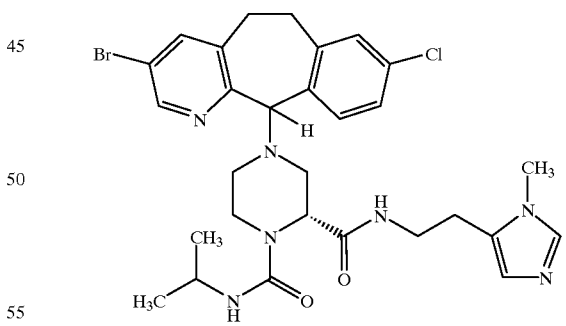

Following the procedure of Example 27, react 0.10 g (0.184 mmol) of Diastereomer A from Example 27, Step A, with isopropylisocyanate to obtain 0.041 g of the Diastereomer A product as a white solid. Mp=128.1–133.3° C., $MH^+$=628 (FAB).

Following the above procedure, but using Diastereomer B from Example 27, Step A, obtain 0.040 g of the Diastereomer B product as a white solid. Mp=128.1–133.4° C., $MH^+$=628 (FAB).

EXAMPLE 30

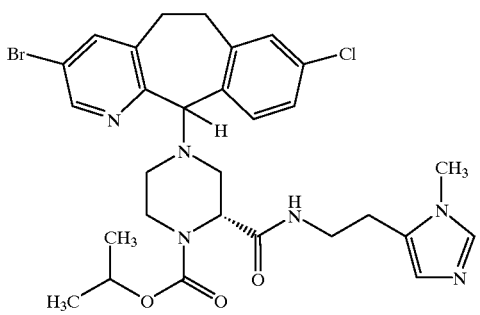

Dissolve 0.116 g (0.202 mmol) of Diastereomer A of Example 27, Step A, in 2 mL of methylene chloride followed by 0.02 g (0.202 mmol) of triethyl amine and 0.24 mL (0.24 mmol) of a 1.0M solution of isopropyl chloroformate in toluene and stir overnight under nitrogen. Dilute with 20 mL of methylene chloride and wash with aqueous NaHCO₃ solution, dry the organic layer over MgSO₄ and concentrate under vacuo. Chromatograph the residue by preparative silica gel TLC using 95% $CH_2Cl_2$ ($NH_4OH$)—5% methanol to give 0.044 g of the Diastereomer A product as a white solid.

Following the above procedure, but using Diastereomer B from Example 27, Step A, obtain 0.038 g of the Diastereomer B product as a white solid.

Diastereomer A: Mp=120.5–125.5° C., MH⁺=629 (FAB).

Diastereomer B: Mp=120.3–126.1° C., MH⁺=629 (FAB).

EXAMPLE 31

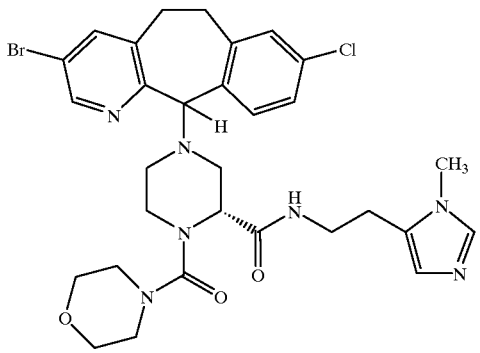

Following the procedure of Example 30, react 0.07 g (0.128 mmol) of Diastereomer A from Example 27, Step A, with 0.021 g (0.142 mmol) of 4-morpholinecarbonyl chloride and 0.035 g (0.256 mmol) triethylamine to obtain 0.024 g of the Diastereomer A product as a white solid.

Following the above procedure, but using Diastereomer B from Example 27, Step A, obtain 0.019 g of the Diastereomer B product as a white solid.

Diastereomer A: Mp=137.9–138.9° C., MH⁺=656 (FAB).

Diastereomer B: Mp=136.4–138.6° C., MH⁺=656 (FAB).

EXAMPLE 32

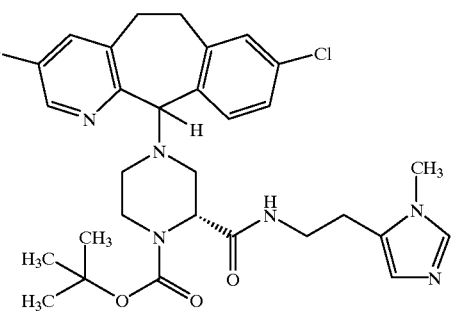

Dissolve 0.07 g (0.129 mmol) of Diastereomer A of Example 27, Step A, in 0.5 mL of methylene chloride followed by 0.033 g (0.152 mmol) di-tert-butyldicarbonate and stir overnight under nitrogen. Dilute with 20 mL of methylene chloride and wash with aqueous NaHCO₃ solution, dry the organic layer over MgSO₄ and concentrate under vacuo. Chromatograph the residue by preparative silica gel TLC using 95% $CH_2Cl_2$ ($NH_4OH$)—5% methanol to give 0.024 g of the Diastereomer A product as a white solid.

Following the above procedure, but using Diastereomer B from Example 27, Step A, obtain 0.026 g of the Diastereomer B product as a white solid.

Diastereomer A: Mp=127.1–128.4° C., MH⁺=643 (FAB).

Diastereomer B: Mp=134.9–137.5° C., MH⁺=643 (FAB).

EXAMPLE 33

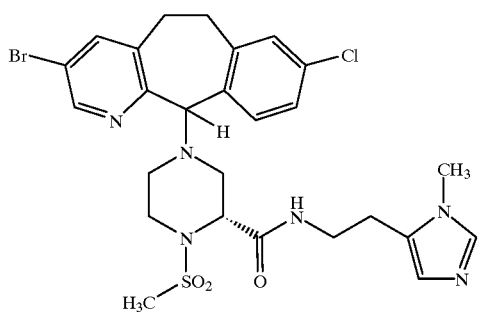

Following the procedure of Example 30, react 0.05 g (0.092 mmol) of Diastereomer A from Example 27, Step A, with 1.1 g (0.10 mmol) of methanesulfonyl chloride and 0.019 g (0.183 mmol) triethylamine in 1.5 mL of methylene chloride to obtain 0.011 g of the Diastereomer A product as a white solid.

Following the above procedure, but using Diastereomer B from Example 27, Step A, obtain 0.032 g of the Diastereomer B product as a white solid.

Diastereomer A: Mp=138.1–144.6° C., MH⁺=621 (FAB).

Diastereomer B: Mp=139–145.1° C., MH⁺=621 (FAB).

EXAMPLE 34

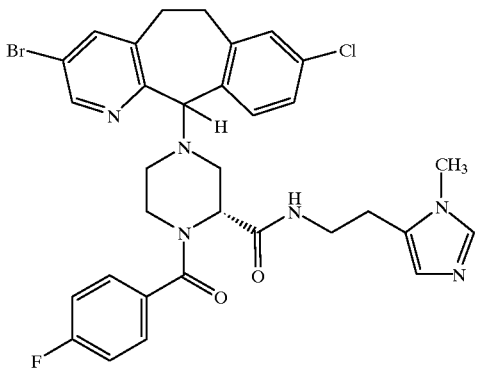

Dissolve 0.07 g (0.129 mmol) of Diastereomer A of Example 27, Step A, in 1.0 mL of DMF followed by 0.023 g (0.167 mmol) 4-fluorobenzoic acid, 0.032 g (0.167 mmol) DEC, 0.0225 g (0.167 mmol) HOBT and 0.018 mL (0.167 mmol) N-methylmorpholine and stir overnight under nitrogen. Concentrate in vacuo and dissolve the residue in 20 mL of methylene chloride. Wash with aqueous 1N NaOH, dry the organic layer over $MgSO_4$ and concentrate in vacuo. Flash chromatograph on silica gel using 93% $CH_2Cl_2$ ($NH_4OH$)—7% methanol to give 0.060 g of the Diastereomer A product as a white solid.

Following the above procedure, but using Diastereomer B from Example 27, Step A, obtain the Diastereomer B product as a white solid.

Diastereomer A: Mp=141.5–145.8° C., $MH^+$=665 (FAB).

Diastereomer B: Mp=144.9–148.7° C., $MH^+$=665 (FAB).

EXAMPLE 35

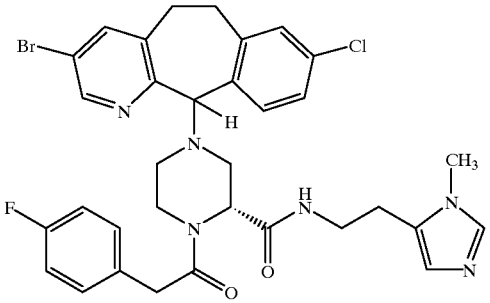

Following the procedure of Example 34, use 4-fluorophenylacetic acid instead of 4-fluorobenzoic acid to obtain the Diastereomer A product as a white solid. Mp=132.8–140.1° C., $MH^+$=679 (FAB).

Following the above procedure obtain the Diastereomer B product as a white solid. Mp=132.5–139.7° C., $MH^+$=679 (FAB).

EXAMPLE 36

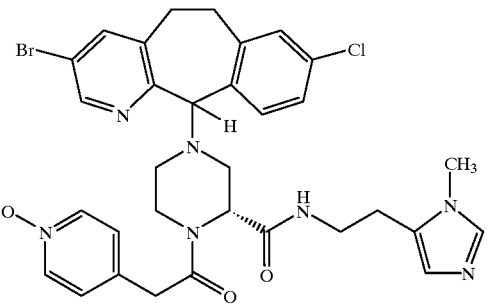

Following the procedure of Example 34, use 4-pyridylacetic acid N-oxide instead of 4-fluorobenzoic acid to obtain the Diastereomer A product as a white solid, and the Diastereomer B product as a white solid. Diastereomer A: Mp=168.5–172.4° C., $MH^+$=678 (FAB). Diastereomer B: Mp=168.9–172.3° C., $MH^+$=678 (FAB).

EXAMPLE 37

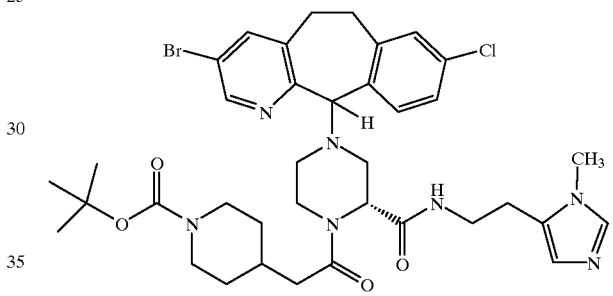

Following the procedure of Example 34, use N-t-butoxycarbony-4-piperidinacetic acid instead of 4-fluorobenzoic acid to obtain the Diastereomer A product as a white solid, and the Diastereomer B product as a white solid. Diastereomer A: Mp=135.1–142.1° C., $MH^+$=768 (FAB). Diastereomer B: Mp=141.7–143.2° C., $MH^+$=768 (FAB).

EXAMPLE 38

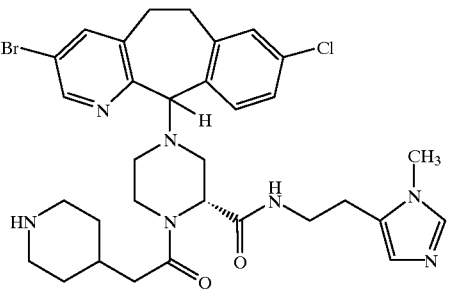

Dissolve 0.23 g (0.31 mmol) of the Diastereomer A product of Example 37 in 3 mL of methylene chloride and 3 mL of trifluoroacetic acid and stir under nitrogen for 3.5 hr. Concentrate under vacuo and dissolve the residue in 20 mL methylene chloride and wash with 1.0 N aqueous NaOH. Concentrate the organic layer in vacuo and chromatograph the residue by preparative silica gel TLC using 80% CH₂Cl₂ (NH₄OH)—20% methanol to give 0.113 g of the Diastereomer A product as a white solid.

Following the above procedure, but using the Diastereomer B product of Example 37, Step A, obtain the Diastereomer B product as a white solid.

Diastereomer A: Mp=136.1–139.5° C., MH⁺=668 (FAB).
Diastereomer B: MH⁺=6668 (FAB).).

EXAMPLE 39

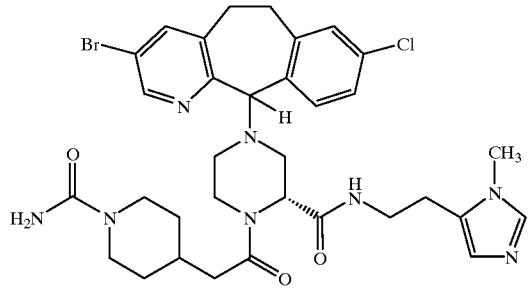

Dissolve 0.073 g (0.11 mmol) of the Diastereomer A product from Example 38 in 3 mL methylene chloride containing 0.013 g (0.121 mmol) of trimethylsilyl isocyanate and stir under nitrogen overnight. Dilute with 5 mL methylene chloride and wash with 10 mL sat aqueous NaHCO₃. Dry the organic layer over MgSO₄ and concentrate in vacuo. Chromatograph the residue by preparative silica gel TLC using 90% CH₂Cl₂ (NH₄OH)—10% methanol to give 0.032 g of the Diastereomer A product as a white solid.

Following the above procedure, but using the Diastereomer B product of Example 38, obtain the Diastereomer B product as a white solid.

Diastereomer A: Mp=148.2–151.3° C., MH⁺=711 (FAB).
Diastereomer B: Mp=148.1–150.4° C., MH⁺=711 (FAB).).

EXAMPLE 40

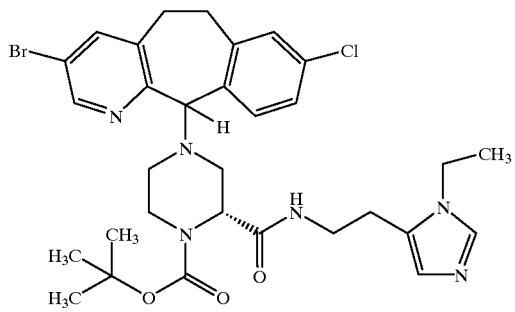

Dissolve the carboxylic acid from Preparative Example 51 (0.32 g, 0.596 mmol), the product from Preparative Example 13 (0.108 g, 0.775 mmol), DEC (0.149 g, 0.775 mmol), HOBT (0.105 g, 0.775 mmol) and 0.13 mL of N-methylmorpholine in 5 mL of DMF and stir overnight. Concentrate in vacuo and dissolve the residue in 20 mL of methylene chloride. Wash with satd. NaHCO₃ solution, dry over MgSO₄ and flash chromatograph on silica gel using 97% CH₂Cl₂ (NH₄OH)—3% methanol to give 0.2 g of the product as a white solid. Separate the diastereomers by preparative chiral chromatography (Chiralpack AD, 5 cm×50 cm column, flow rate 100 mL/min., 15% 2-propanol/hexane+0.2% diethylamine).

Diastereomer A: Mp=54–58° C., MH⁺=657 (FAB).
Diastereomer A: Mp=64–58° C., MH⁺=657 (FAB).

EXAMPLE 41

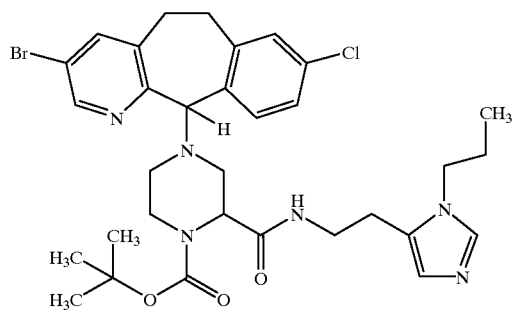

Following the procedure of Example 40, use the product from Preparative Example 14 instead of Preparative Example 13 to obtain the product as a white solid. Mp=116–123° C., MH⁺=671 (FAB).

EXAMPLE 42

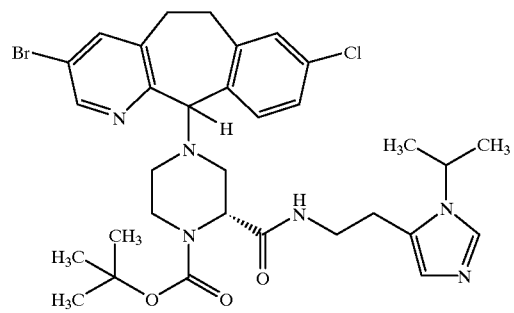

Following the procedure of Example 40, use the product from Preparative Example 15 instead of Preparative Example 13 to obtain the product as a white solid.

Diastereomer A: Mp=115–120° C., MH⁺=671 (FAB).
Diastereomer A: Mp=98–101° C., MH⁺=671 (FAB).

EXAMPLE 43

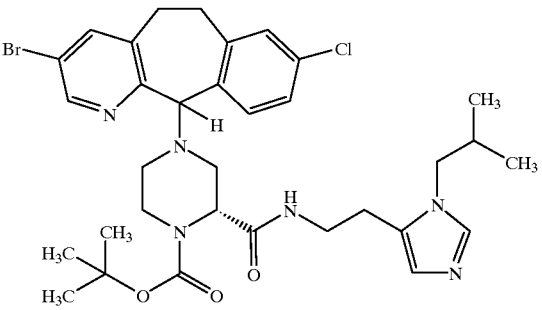

Following the procedure of Example 40, use the product from Preparative Example 16 instead of Preparative Example 13 to obtain the product as a white solid. Mp=120–122° C., MH+=685 (FAB).

EXAMPLE 44

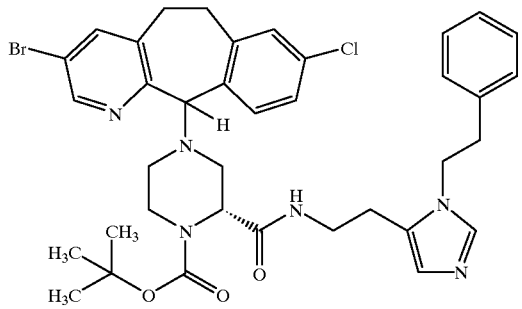

Following the procedure of Example 40, use the product from Preparative Example 17 instead of Preparative Example 13 to obtain the product as a white solid. Mp=101–103° C., MH+=733 (FAB).

EXAMPLES 45–59

Following the procedure of Example 40, use the amines from Preparative Examples 18–26 instead of Preparative Example 13 to obtain the compounds

[structure of general product with R27 group attached to piperazine-carbonyl, bearing Br-pyridine tricyclic system and N-Boc group]

wherein $R^{27}$ is defined in Table 9.

TABLE 9

| Ex. | Prep. Ex. (amine) | Product $R^{27}=$ | Melting Point (° C.) | Mass Spec MH+ |
|---|---|---|---|---|
| 45 | 18 | [benzyl-N(CH3)-CH2CH2-imidazole, Isomer A] | 128–133 | 719 |
| 46 | 18 | [benzyl-N(CH3)-CH2CH2-imidazole, Isomer B] | 129–132 | 719 |
| 47 | 19 | [benzyl-N(CH3)-CH2CH2-(N-CH3-imidazole), Isomer A] | 106–112 | 733 |
| 48 | 19 | [benzyl-N(CH3)-CH2CH2-(N-CH3-imidazole), Isomer B] | 105–111 | 733 |
| 49 | 20 | [neopentyl-N(CH3)-CH2CH2-(N-CH3-imidazole), Isomer A] | 115–117 | 713 |
| 50 | 20 | [neopentyl-N(CH3)-CH2CH2-(N-CH3-imidazole), Isomer B] | 108–110 | 713 |

TABLE 9-continued

| Ex. | Prep. Ex. (amine) | Product R²⁷ = | Melting Point (° C.) | Mass Spec MH⁺ |
|---|---|---|---|---|
| 51 | 21 | 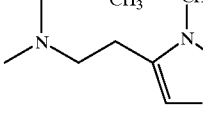 Isomer A | 86–89 | 699 |
| 52 | 21 | 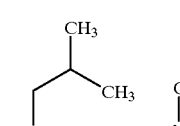 Isomer B | 58–86 | 699 |
| 53 | 22 | 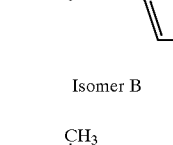 Isomer A | 106–111 | 685 |
| 54 | 22 | 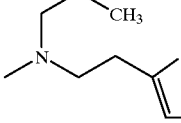 Isomer B | 110–114 | 685 |
| 55 | 23 | 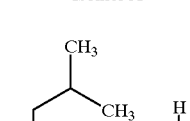 Isomer A | 98–111 | 739 |
| 56 | 23 | 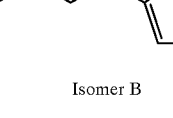 Isomer B | 99–111 | 739 |
| 57 | 24 | 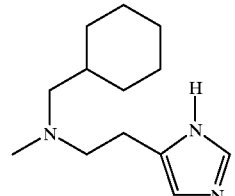 | 136–144 | 725 |
| 58 | 25 | 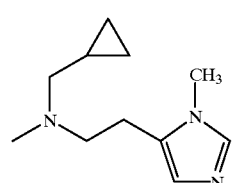 | 101–103 | 697 |
| 59 | 26 | 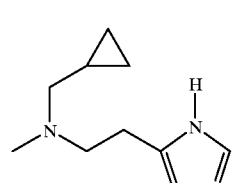 | 128–133 | 683 |

EXAMPLE 60

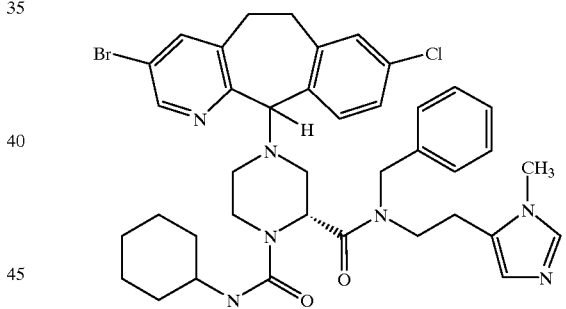

Step A

Dissolve the product of Example 47 (0.148 g, 0.202 mmol) in 0.78 mL of methylene chloride and add 0.45 mL of trifluoroacetic acid and stir under nitrogen for 2 hr. Concentrate under vacuum. Dissolve the residue in 20 mL of methylene chloride and wash with aqueous NaHCO₃, dry the organic layer over MgSO₄, and concentrate under vacuum to give the amine as a white solid.

Step B

Dissolve the product of Step A (0.05 g, 0.078 mmol) in 2 mL of methylene chloride and add 0.015 g, 0.118 mmol of cyclohexyl isocyanate. Stir overnight then concentrate under vacuum. Flash chromatograph the residue on silica gel using 99% CH₂Cl₂ (NH₄OH)—1% methanol giving the Isomer A product as a white solid. Mp=138–142° C., MH⁺=758 (FAB).

Follow the above procedure, but use the product of Example 48 instead of Example 47 in Step A, to obtain the Isomer B product as a white solid. Mp=130–139° C., MH⁺=758 (FAB).

EXAMPLE 61

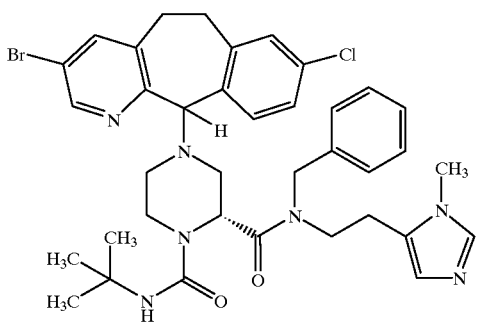

Step A
Using the product of Example 47, follow the procedure of Example 60, but use t-butyl isocyanate instead of cyclohexyl isocyanate in Step B, to obtain the Isomer A product as a white solid. Mp=127–132° C., MH$^+$=732 (FAB).

Step B
Follow the procedure of Example 60, but use the product of Example 48 instead of Example 47 in Step A and t-butyl isocyanate instead of cyclohexyl isocyanate in Step B to obtain the Isomer B product as a white solid. Mp=127–130° C., MH$^+$=732 (FAB).

EXAMPLE 62

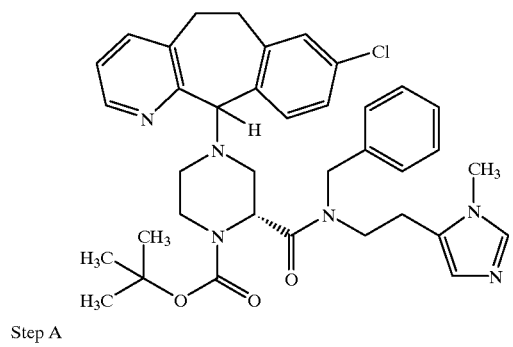

Step A

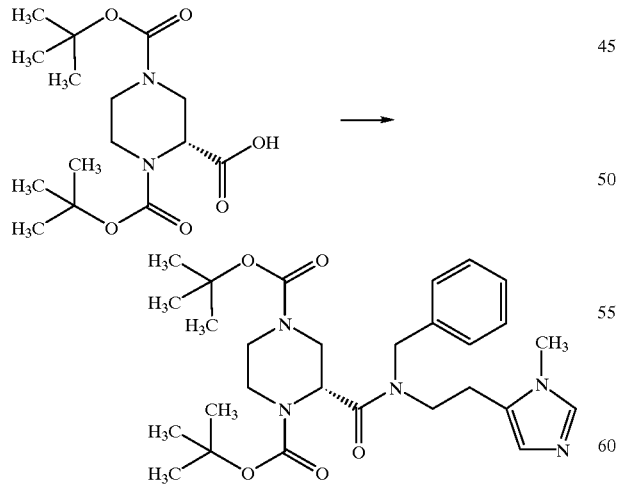

Dissolve the acid from Preparative Example 43 (0.37 g, 1.12 mmol), the product from Preparative Example 19 (0.29 g, 1.35 mmol), DEC (0.289 g, 1.46 mmol), HOBT (0.197 g, 1.46 mmol), N-methylmorpholine (0.25 mL, 2.24 mmol) in 20 mL of DMF and stir under nitrogen over night. Concentrate under vacuum. Dissolve the residue in 50 mL of methylene chloride, wash with sat. NaHCO$_3$ soln., dry the organic layer over MgSO$_4$ and concentrate under vacuum. Flash chromatograph the residue on silica gel using 100% CH$_2$Cl$_2$ (NH$_4$OH) giving a white solid.

Step B

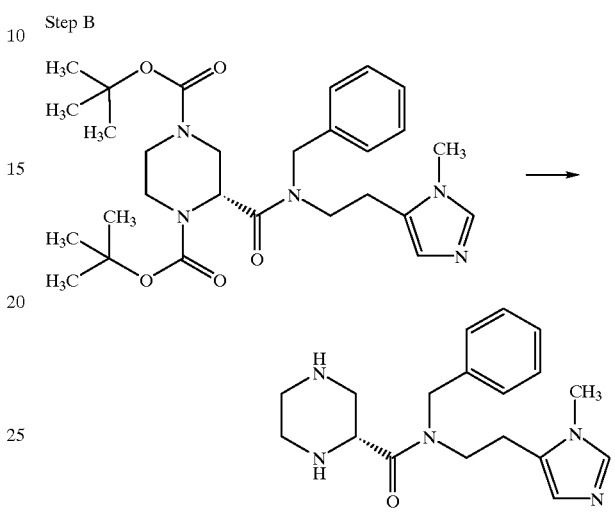

Dissolve the product of Step A (0.59 g, 1.048 mmol) in 3 mL of methylene chloride and add 2.5 mL of trifluoroacetic acid. Stir overnight and concentrate under vacuum.

Step C

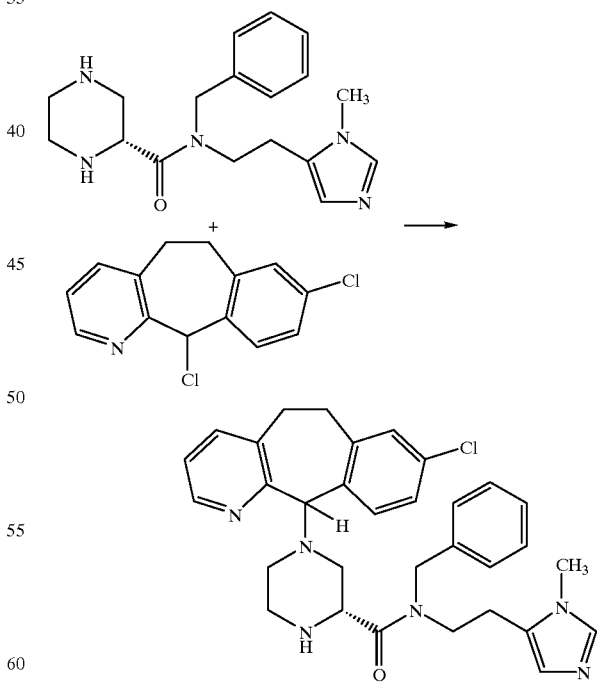

Dissolve the product of Step B (0.5 g, 1.048 mmol), the 8-Cl-tricyclic chloride (0.359 g, 1.048 mmol) and triethyl amine (2.19 mL, 15.72 mmol) in 5 mL of methylene chloride and stir overnight. Concentrate under vacuum and flash chromatograph the residue on silica gel using 95% CH$_2$Cl$_2$ Step D

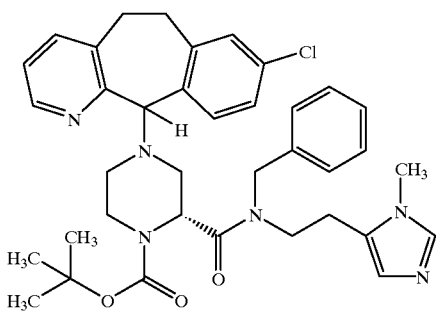

Dissolve the product of Step C (0.27 g, 0.486 mmol) in 2 mL of methylene and add di-tert-butyldicarbonate (0.125 g, 0.57 mmol) and stir for 2 hr. Concentrate under vacuum and separate the diastereomers by preparative chiral chromatography (Chiralpack AD, 5 cm×50 cm column, flow rate 100 mL/min., 5% 2-propanol/hexane+0.2% diethylamine) giving the products as white solids.

Diastereomer A: Mp=93.1–99.8° C., MH$^+$=655 (FAB).

Diastereomer B: Mp=93.1–99.8° C., MH$^+$=655 (FAB).

EXAMPLE 63

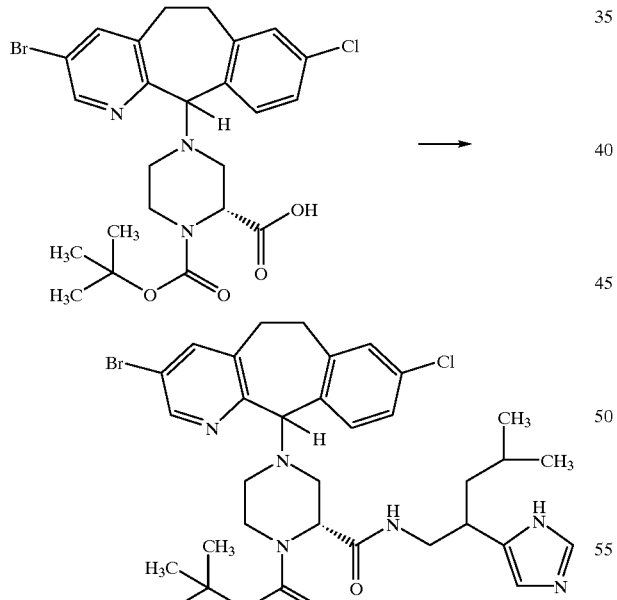

Following the procedure of Example 40, use the product from Preparative Example 27 instead of Preparative Example 13 to obtain the products as white solids.

Isomer mix 1: Mp=148–151° C., MH$^+$=687 (FAB).

Isomer mix 2: Mp=110–114° C., MH$^+$=687 (FAB).

EXAMPLE 64

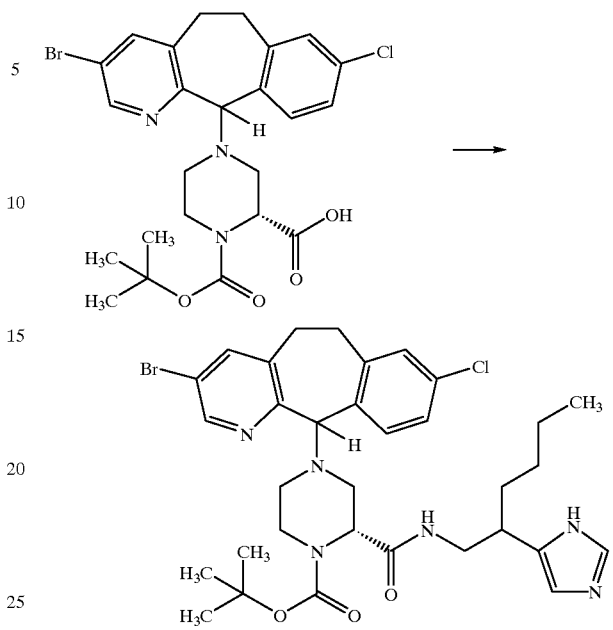

Following the procedure of Example 40, use the product from Preparative Example 28 instead of Preparative Example 13 to obtain the product as a white solid: Mp=131–138° C. decomp., MH$^+$=687 (FAB).

EXAMPLE 65

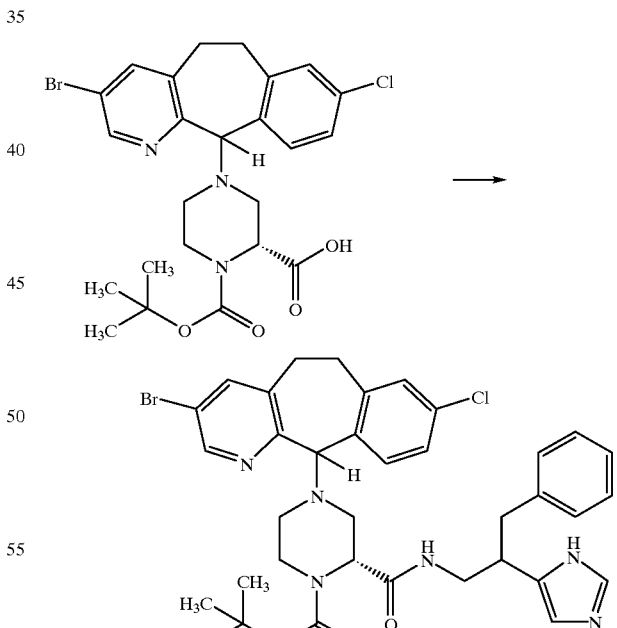

Following the procedure of Example 40, use the product from Preparative Example 29 instead of Preparative Example 13 to obtain the products as white solids.

Isomer mix 1: Mp=148–157° C., MH$^+$=721 (FAB).

Isomer mix 2: Mp=120–126° C., MH$^+$=721 (FAB).

EXAMPLE 66

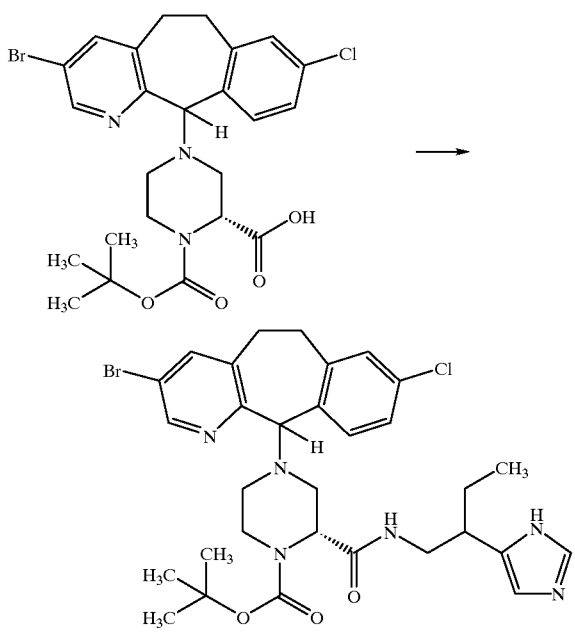

Following the procedure of Example 40, use the product from Preparative Example 30 instead of Preparative Example 13 to obtain the products as white solids.

Isomer mix 1: Mp=146–154° C., MH$^+$=657 (FAB).
Isomer mix 2: Mp=122–127° C., MH$^+$=657 (FAB).

EXAMPLE 67

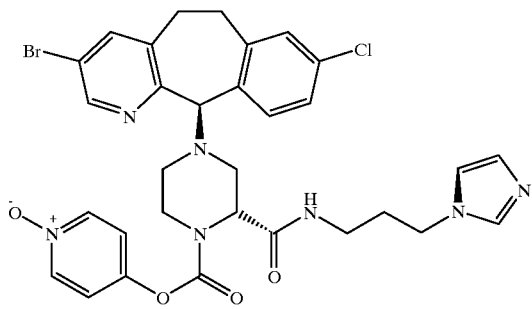

The 11R,2R(−)-diastereoisomer from Preparative Example 34 (0.25 g, 0.46 mmoles), 4-pyridylacetic acid N1-oxide (0.0915 g, 0.598 mmoles) (see Preparative Example 61 of U.S. Pat. No. 5,719,148 issued Feb. 17, 1998), DEC (0.1146 g, 0.598 mmoles), HOBt (0.0807 g, 0.598 mmoles) and 4-methyl-morpholine (0.0657 mL, 0.598 mmoles) were dissolved in anhydrous DMF (9 mL) and the mixture was stirred under argon at 25° C. for 96 h. The reaction was worked up as described in Preparative Example 40, Step A above, and chromatographed on a silica gel column using 5% (10% conc. NH$_4$OH in methanol)-dichloromethane as the eluant to give the title compound: (Yield: 0.2434 g, 78%); FABMS: m/z 678.0 (MH$^+$); $\delta_C$(CDCl$_3$) 30.1, 30.3, 30.9, 36.5, 38.5, 44.1, 44.3, 50.7, 52.5; CH: 53.4, 78.3, ~119.1, 126.2, 127.3, 127.3, ~129.1, 130.6, 132.3, ~137.1, 138.6, 138.6, 141.1, 146.9; C: 120.1, 134.2, 134.6, 134.8, 137.1, 140.8, 155.1, 169.2, 169.8; $\delta_H$ (CDCl$_3$) 4.31 (1H, s, H$_{11}$), 4.97 (1H, broad s, CHCO), 6.74 (1H, broad s, Im-H$_5$), 6.91 (1H, broad s, Im-H$_4$), 7.02 (1H, broad s, Ar—H), 7.07–7.17 (5H, m, CONHCH$_2$ and Ar—H), 7.38 (1H, broad s, Im-H$_2$), 7.56 (1H, s, Ar—H), 8.08, (1H, d, Ar—H), 8.10 (1H, d, Ar—H) and 8.35 ppm (1H, s, Ar—H$_2$); [a]$_D^{23.2°}$+44.4° (c=10.64 mg/2 mL, methanol).

EXAMPLE 68

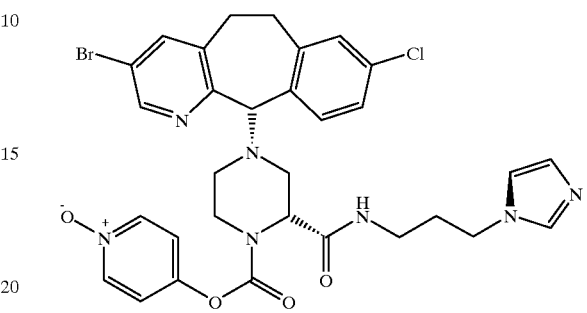

The 11S,2R(−)-diastereoisomer from Preparative Example 34 (0.3 g, 0.552 mmoles), 4-pyridylacetic acid N1-oxide (0.110 g, 0.718 mmoles) (U.S. Pat. No. 5,719,148, Feb. 17, 1998), DEC (0.1375 g, 0.718 mmoles), HOBt (0.0969 g, 0.718 mmoles) and 4-methylmorpholine (0.0788 mL, 0.718 mmoles) were dissolved in anhydrous DMF (9 mL) and the mixture was stirred under argon at 25° C. for 19 h. The reaction was worked up as described in Preparative Example 40, Step A above, and chromatographed on a silica gel column using 6% (10% conc. NH$_4$OH in methanol)-dichloromethane as the eluant to give the title compound: (Yield: 0.2847 g, 80%); FABMS: m/z 678.0 (MH$^+$); $\delta_C$ (CDCl$_3$) 30.1, 30.6, 30.8, 36.5, 38.5, 44.0, 44.4, 51.1, 52.7; CH: 53.4, 78.5, ~119.0, 126.2/126.3, 127.2/127.3, 127.2/127.3, ~129.2, 130.3, 132.4/132.6, ~137.1, 138.7, 138.7, 141.2/141.5, 147.0/147.2; C: 120.1, 134.2/134.4, 134.3, 134.9, 136.9, 141.5, 154.4/154.7, 168.8/169.2, 169.0/169.9; $\delta_H$ (CDCl$_3$) 4.30 (1H, s, H$_{11}$), 4.96 (1H, broad s, CHCO), 6.64 (1H, broad s, CONHCH$_2$), 6.89–7.02 (3H, broad overlap, Im-H$_5$, Im-H$_4$ and Ar—H), 7.10–7.18 (4H, m, Ar—H), 7.33 (1H, broad s, Im-H$_2$), 7.59 (1H, s, Ar—H), 8.08, (1H, d, Ar—H), 8.10 (1H, d, Ar—H) and 8.37 ppm (1H, s, Ar—H$_2$); [a]$_D^{23.4°}$+6.9° (c=10.48 mg/2 mL, methanol).

EXAMPLE 69

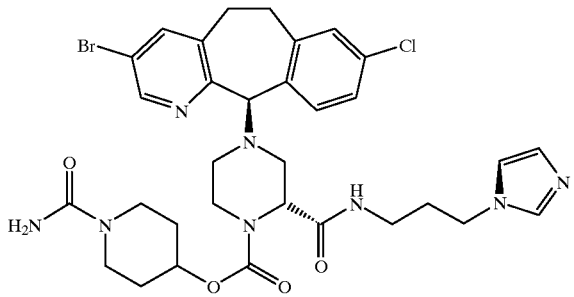

The 11R,2R(−)-diastereoisomer from Preparative Example 34 (0.3 g, 0.552 mmoles), 1-aminocarbonyl-4-piperidinylacetic acid (0.1335g, 0.718 mmoles) (Preparative Example 33), DEC (0.1375 g, 0.718 mmoles), HOBt (0.0969 g, 0.718 mmoles) and 4-methylmorpholine (0.157 mL, 1.436 mmoles) were dissolved in anhydrous DMF (7 mL) and the mixture was stirred under argon at 25° C. for 68 h. The reaction was worked up as described in Preparative Example 40, Step A above, and chromatographed on a silica gel column using 6% (10% conc. NH$_4$OH in methanol)-dichloromethane as the eluant to give the title compound: (Yield: 0.3547 g, 90%); LCMS: m/z 711.2 (MH$^+$); $\delta_C$ (CDCl$_3$): 30.3, 30,4, 31.2, 32.0, 32.0, 36.6/37.2, 39.3/39.6, 43.9, 44.4, 44.4, 44.4, 51.0, 51.8; CH: 32.9, 53.0, 78.7, 118.9, 126.2, 129.7, 130.5/130.7, 132.3, 137.3, 141.3, 147.0; C: 120.3, 134.3, 135.1, 137.3, 141.1, 155.1, 157.9, 170.0, 171.9; $\delta_H$ (CDCl$_3$) 4.30 (1H, s, H$_{11}$), 4.89 (2H, s, NCONH$_2$), 4.98 (1H, s, CHCO), 6.92 (1H, broad s, Im-H$_5$), 6.99 (1H, broad s, Im-H$_4$), 7.07–7.14 (3H, m, Ar—H), 7.41 (1H, broad s, Im-H$_2$), 7.57 (1H, s, Ar—H), 7.59 (1H, broad s, CONHCH$_2$) and 8.35 ppm (1H, s, Ar—H$_2$); [a]$_D^{20.0°}$+ 35.5° (c=9.40 mg/2 mL, methanol).

EXAMPLE 70

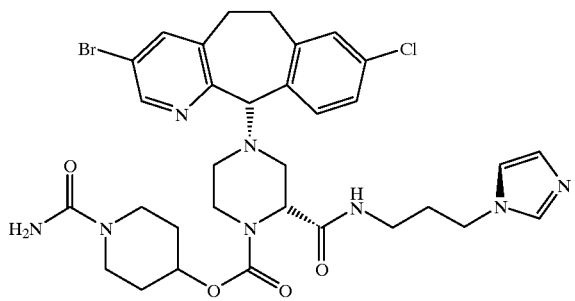

Following the procedure of Example 69, except using the 11S,2R(−)-diastereoisomer from Preparative Example 34 instead of the 11R,2R(−)-diastereoisomer, and stirring under argon for 96 h instead of 68 h, the title compound was obtained: (Yield: 0.3241 g, 83%); LCMS: m/z 711.2 (MH$^+$); $\delta_C$ (CDCl$_3$): 30.2, 30.6, 31.1, 32.0, 32.0, 36.5/36.8, 39.6/39.7, 43.8, 44.4, 44.4, 44.4, 51.3, 51.6; CH: 32.9, 53.0, 78.8, 119.0, 126.3/126.4, 129.4, 130.4/130.6, 132.5/132.6, 137.1, 141.5, 147.1; C: 120.2, 134.3, 135.0, 137.1, 141.5, 155.1, 158.1, 170.3, 172.4; $\delta_H$ (CDCl$_3$) 4.29 (1H, s, H$_{11}$), 4.55 (2H, s, NCONH$_2$), 4.98 (1H, s, CHCO), 6.23 (1H, t, CONHCH$_2$), 6.92 (1H, broad s, Im-H$_5$), 7.03 (1H, broad s, Im-H$_4$) 7.10–7.17 (3H, m, Ar—H), 7.43 (1H, broad s, Im-H$_2$), 7.59 (1H, s, Ar—H) and 8.37 ppm (1H, s, Ar—H$_2$); [a]$_D^{23.1°}$+1.0° (c=10.00 mg/2 mL, methanol).

EXAMPLE 71

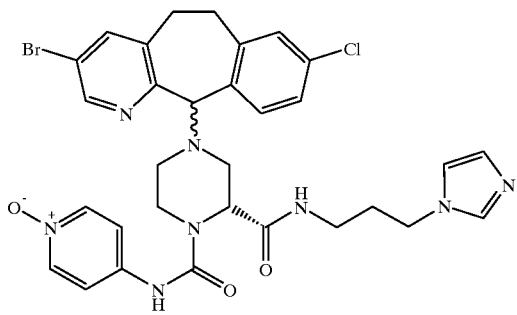

Pyridine-4-acylazide N1-oxide (*J. Med. Chem.*, 1998, 41, 877–893) (0.346 g, 2.30 mmoles) was dissolved in dry toluene (30 mL) and the solution was heated under reflux in an argon atmosphere at 110° C. for 1 h. The solution was cooled to room temperature and the C$_{11}$-Racemic title compound from Preparative Example 141 (0.250 g, 0.46 mmoles) was added. The mixture was stirred at 25° C. for 22 h. The solution was evaporated to dryness and the residue was chromatographed on a silica gel column using 4% (10% conc. NH$_4$OH in methanol)-dichloro-methane as the eluant to give the title compound: (Yield: 0.1265 g, 32%); LCMS: m/z 679.2 (MH$^+$); $\delta_C$ (CDCl$_3$) CH$_2$: 30.3, 30.6, 31.0/31.1, 36.7/36.8, 42.6, 44.6, 51.0/51.3, 52.4/52.6; CH: 55.1/55.2, 78.8, 115.8, 115.8, 119.2, 126.3, 129.1, 130.5/130.6, 132.7, 137.2, 138.6, 138.6, 141.4, 147.0/147.2; C: 120.2, 134.2, 134.3, 134.9, 136.9, 141.3, 155.0, 155.2, 170.4; $\delta_H$ (CDCl$_3$) 4.34 (1H, s, H$_{11}$), 4.67 (1H, s, CHCO), 6.89 (1H, d, Im-H$_5$), 6.99 (1H, d, Im-H$_4$), 7.10–7.15 (3H, m, Ar—H), 7.46 (2H, d, Ar—H), 7.59 (1H, s, Im-H$_2$), 7.90 (2H, d, Ar—H), 8.39 (1H, s, Ar—H$_2$) and 9.77 ppm (1H, broad s, NCONH).

EXAMPLE 72

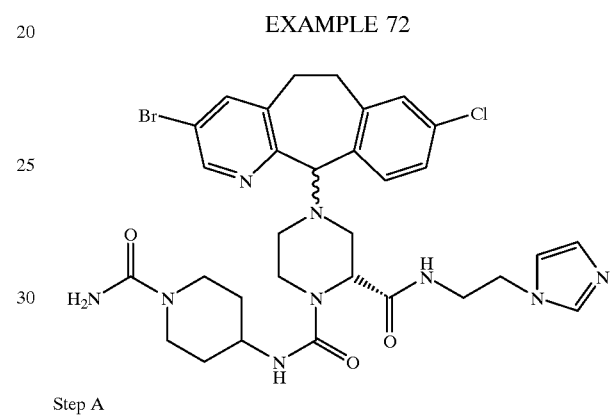

Step A

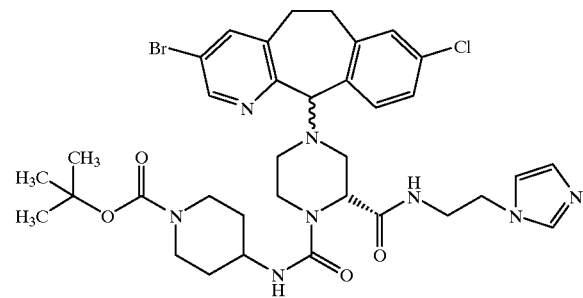

1-N-t-Butoxycarbonylpiperidine-3-acylazide (Preparative Example 35, Step B above) (1.177 g, 4.63 mmoles), was dissolved in dry toluene (150 mL) and the solution was heated under reflux in an argon atmosphere at 110° C. for 1 h. The solution was cooled to room temperature and added in three portions (1.47 mmoles at 0h; 2.21 mmoles at 69 h and 0.95 mmoles at 93 h) to a solution of the C$_{11}$-Racemic title compound from Preparative Example 141 (0.4 g, 0.735 mmoles) in anhydrous dichloromethane (26 mL). The mixture was stirred at 25° C. for 117 h. The solution was evaporated to dryness and the residue was chromatographed on a silica gel column using 4% (10% conc. NH$_4$OH in methanol)-dichloromethane as the eluant to give the title compound: (Yield: 0.1265 g, 32%); LCMS: m/z 679.2 (MH$^+$); $\delta_C$ (CDCl$_3$) CH$_3$: 28.5, 28.5, 28.5; CH$_2$: 30.5, 30.6, 31.2/31.3, 32.5, 32.5, 36.6, 41.8, 42.7, 42.7, 44.6, 50.9/51.1, 51.9/52.2; CH: 48.2, 54.9/55.0, 78.9/79.0, ~119.0, 126.4/126.5, ~129.6, 130.5/130.6, 132.8, ~137.1, 141.3/141.4, 147.1/147.3; C: 79.6, 120.3, 134.5, 134.7, 136.9, 141.1, 154.7, 154.8, 157.6, 171.0; δ$_H$(CDCl$_3$) 1.46 (9H, s, CH$_3$), 4.33 (1H, s, H$_{11}$), 4.41 (1H, broad s, CHCO), 5.18 (1H, d, NCONH), 6.55 (1H, broad m, CONHCH$_2$), 6.92 (1H, broad s, Im-H$_5$), 7.08 (1H, broad s, Im-H$_4$), 7.10–7.15 (3H, m, Ar—H), 7.50 (1H, broad s, Im-H$_2$), 7.59 (1H, d, Ar—H) and 8.40 ppm (1H, s, Ar—H$_2$).

Step B

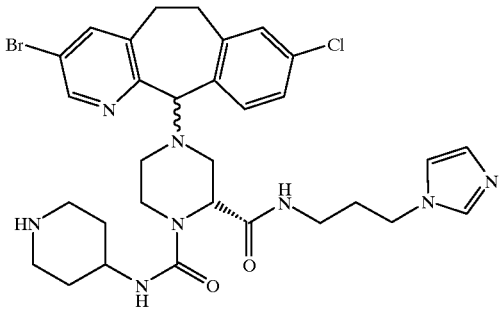

The title compound from Step A above (0.2361 g, 0.307 mmoles) was dissolved in methanol (1.61 mL) and a 10% (v/v) solution of conc. H$_2$SO$_4$ in dioxane (4.18 mL) was added. The mixture was stirred under argon at 25° C. for 1 h. The mixture was passed over a bed of BioRad® AG 1-X8 (OH$^{31}$) resin and the resin was washed with methanol. The combined eluates were evaporated to dryness and the residue was chromatographed on a silica gel column using 20% (10% conc. NH$_4$OH in methanol)-dichloromethane as the eluant to give the title compound: (Yield: 0.1984 g, 97%); LCMS: m/z 669.2 (MH$^+$); δ$_C$ (CDCl$_3$) CH$_2$: 30.3, 30.5, 30.9, 31.6, 31.6, 36.3/36.4, 42.3, 42.3, 42.3, 44.3, 50.8/51.2, 52.1/52.4; CH: 47.2/47.3, 54.8, 78.9, 119.1, 126.3, 129.0, 130.5/130.6, 132.7, 137.5, 141.3, 147.0/147.1; C: 120.1, 134.2/134.3, 134.9, 136.9, 141.2, 155.2, 157.7/157.8, 171.2; δ$_H$ (CDCl$_3$) 4.29 (1H, s, H$_{11}$), 4.61 (1H, broad s, CHCO), 5.72 (1H, broad m, NCONH), 6.85 (1H, m, CONHCH$_2$), 6.92 (1H, broad s, Im-H$_5$), 6.99 (1H, broad s, Im-H$_4$), 7.10–7.15 (3H, m, Ar—H), 7.57 (1H, s, Ar—H), 7.66 (1H, broad s, Im-H$_2$) and 8.37 ppm (1H, s, Ar—H$_2$).

Step C

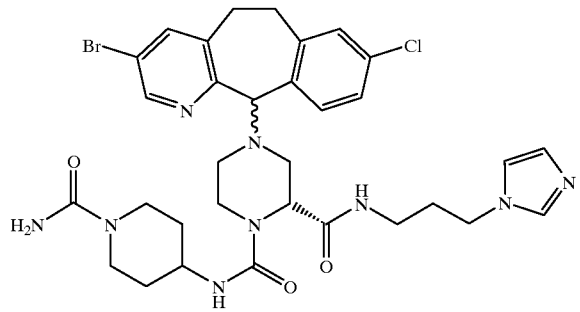

The title compound from Step B above (0.195 g, 0.291 mmoles) was dissolved in anhydrous dichloromethane (10 mL) and trimethylsilyl isocyanate (0.394 mL, 2.91 mmoles) was added. The mixture was stirred under argon at 25° C. for 20 h. Additional trimethylsilyl isocyanate (0.188 mL, 0.873 mmoles) was added and the mixture was stirred for a total of 23 h. The mixture was diluted with dichloromethane (900 mL) and washed with saturated aqueous sodium bicarbonate, dried (MgSO$_4$), filtered and evaporated to dryness. The product was chromatographed on a silica gel column using 4% (10% conc. NH$_4$OH in methanol)-dichloromethane as the eluant to give the title compound: (Yield: 0.1325 g, 64%); LCMS: m/z 712.2 (MH$^+$), δ$_C$ (CDCl$_3$) CH$_2$: 30.3/30.4, 30.6, 31.0/31.1, 32.4, 32.4, 36.5, 42.0, 43.4, 43.4, 44.4, 50.9/51.2, 52.4/52.6; CH: 48.1, 54.9/55.0, 78.9, 119.0, 126.3/126.4, 129.4, 130.5/130.6, 132.7, 137.3, 141.3/141.4, 147.1/147.2; C: 120.2, 134.2/134.3, 135.1, 136.9, 141.2, 155.1, 157.8/157.9, 158.1, 171.4/171.5; δ$_H$: (CDCl$_3$) 4.31 (1H, s, H$_{11}$), 4.53 (1H, broad s, CHCO), 4.75 (2H, broad s, NCONH$_2$), 5.73 (1H, d, NCONH), 6.65 (1H, t, CONHCH$_2$), 6.92 (1H, broad s, Im-H$_5$), 7.04 (1H, broad s, Im-H$_4$), 7.10–7.15 (3H, m, Ar—H), 7.46 (1H, s, Ar—H), 7.58 (1H, broad s, Im-H$_2$) and 8.38 ppm (1H, s, Ar—H$_2$)

EXAMPLE 73

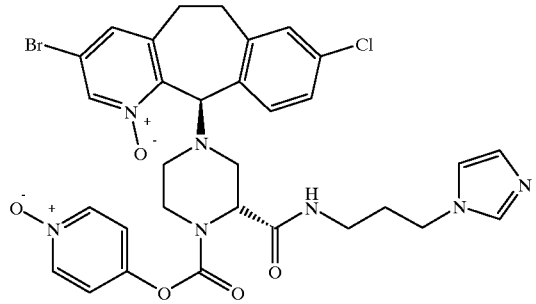

The 11R,2R(+)-diastereoisomer from Preparative Example 38, Step D above (0.1647 g, 0.294 mmoles), 4-pyridylacetic acid N1-oxide (0.0586 g, 0.382 mmoles), DEC (0.0733 g, 0.382 mmoles), HOBt (0.0517 g, 0.382 mmoles) and 4-methyl-morpholine (0.042 mL, 0.382 mmoles) were dissolved in anhydrous DMF (5 mL) and the mixture was stirred under argon at 25° C. for 25 h. The reaction was worked up as described in Preparative Example 40, Step A above, and chromatographed on a silica gel column using 2% increasing to 6% (10% conc. NH$_4$OH in methanol)-dichloromethane as the eluant to give the title compound: (Yield: 0.1048 g, 51%); SIMS: m/z 694.5 (MH$^+$); δ$_C$ (CDCl$_3$) 30.0, 30.4, 31.0, 36.7, 38.5, 44.1, 44.5, 50.5, 51.3; CH: 53.6, 63.6, 119.1, 126.4, 127.4, 127.4, ~129.1, 130.7, 130.8, 133.4, ~137.2, 138.4/138.6, 138.7, 138.7; C: 118.5, 133.3, 134.6, 134.9, 140.4, 141.4, 147.4, 169.2, 169.9; δ$_H$(CDCl$_3$) 4.98 (1H, broad s, CHCO), 5.70 (1H, s, H$_{11}$), 6.92/6.97 (1H, broad s, Im-H$_5$), 7.01 (1H, broad s, Im-H$_4$), 7.08–7.18 (5H, m, Ar—H), 7.43/7.51 (1H, broad s, Im-H$_2$), 7.79 (1H, t, CONHCH$_2$), 8.05 (1H, d, Ar—H), 8.09 (2H, d, Ar—H), 8.26/8.31 ppm (1H, s, Ar—H$_2$); $[a]_D^{20.0°}$+82.8° (c=9.11 mg/2 mL, methanol).

EXAMPLE 74

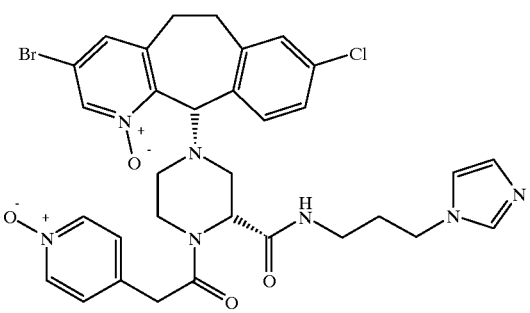

The 11S,2R(−)-diastereoisomer from Preparative Example 38, Step D above (0.1576 g, 0.281 mmoles), 4-pyridylacetic acid N1-oxide (0.0560 g, 0.366 mmoles), DEC (0.0702 g, 0.366 mmoles), HOBt (0.0495 g, 0.366 mmoles) and 4-methyl-morpholine (0.040 mL, 0.366 mmoles) were dissolved in anhydrous DMF (5 mL) and the mixture was stirred under argon at 25° C. for 26 h. The reaction was worked up as described in Preparative Example 40, Step A above, and chromatographed on a silica gel column using 2% increasing to 6% (10% conc. NH$_4$OH in methanol)-dichloromethane as the eluant to give the title compound: (Yield: 0.1017 g, 50%); SIMS: m/z 694.5 (MH$^+$); δ$_C$ (CDCl$_3$) 29.7, 30.5, 30.8, 36.5, 38.4, 44.2, 44.3, 50.1, 52.3; CH: 53.4, 63.6, ~119.0, 126.4, 127.4, 127.4, ~129.1, 130.3, 130.9, 133.3, ~137.3, 138.3/138.7, 138.7, 138.7; C: 118.4, 133.3, 134.6, 134.8, 140.1, 141.6, 147.4, 169.2, 169.9; δ$_H$(CDCl$_3$) 4.97 (1H, broad s, CHCO), 5.71 (1H, s, H$_{11}$), 6,58 (1H, t, CONHCH$_2$), 6.88 (1H, broad s, Im-H$_5$), 6.98/7.03 (1H, broad s, Im-H$_4$), 7.09–7.21 (5H, m, Ar—H), 7.34/7.41 (1H, broad s, Im-H2), 8.09 (1H, d, Ar—H), 8.10 (2H, d, Ar—H), 8.27/8.28 ppm (1H, s, Ar—H$_2$); [a]$_D^{20.0°}$ −12.7° (c=10.08 mg/2 mL, methanol).

EXAMPLE 75

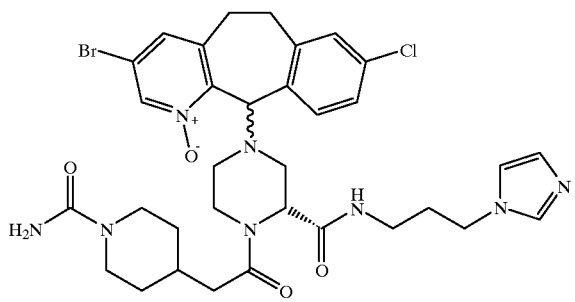

3Bromo-8,11-dichloro-6,11-dihydro-5H-benzo[5,5] cyclohepta[1,2-b]pyridine N1-oxide (Preparative Example, 38 Step C) (0.2656 g, 0.74 mmoles) in anhydrous dichloromethane (3.8 mL) was added to 1-[2-[N-[3-(1H-imidazol-1-yl)propyl]-2(R)-piperazinecarboxamide]-2-oxoethyl-1-piperidinecarboxamide (Preparative Example 40, Step B above) (0.3 g, 0.74 mmoles) and triethylamine (1.0316 mL, 7.40 mmoles) in anhydrous dichloromethane (6 mL) and the mixture was stirred at 25° C. under argon for 19 h. The solution was directly chromatographed on a silica gel column using 3.5% (10% conc. NH$_4$OH in methanol)-dichloromethane as the eluant to give the title compound: (Yield: 0.3727 g, 69%); LCMS: m/z 727.2 (MH$^+$); δ$_C$ (CDCl$_3$) CH$_2$: 29.9/30.1, 30.4/30.5, 31.1/31.2, 32.0, 32.0, 36.5/36.6, 39.6, 44.0/44.4; 44.0/44.4, 44.4, 44.4, 50.5/50.7/51.1, 52.1; CH: 32.9, 53.0/53.1, 63.8, ~119.2, 126.4/126.5, ~129.4, 130.5/130.7, 130.9, 133.4, ~137.2, 138.4; C: 118.5, 133.3/133.4, 134.8/134.9, 140.2/140.5, 141.4/141.6, 147.6/147.8, 158.1, 169.3/170.2, 171.4/172.0; δ$_H$ (CDCl$_3$) 4.60 (1H, s, NCONH$_2$), 4.98 (1H, broad s, CHCO), 5.69 (1H, s, H$_{11}$), 6.29/6.53 (1H, t, CONHCH$_2$, S(−) and R(+) isomers at C$_{11}$ respectively), 6.92 (1H, broad s, Im-H$_5$), 7.05 (1H, broad s, Im-H$_4$), 7.14 (2H, m, Ar—H), 7.18 (1H, m Ar—H), 7.20 (1H, m, Ar—H), 7.56 (1H, broad s, Im-H$_2$) and 8.27 ppm (1H, s, Ar—H$_2$).

EXAMPLE 76

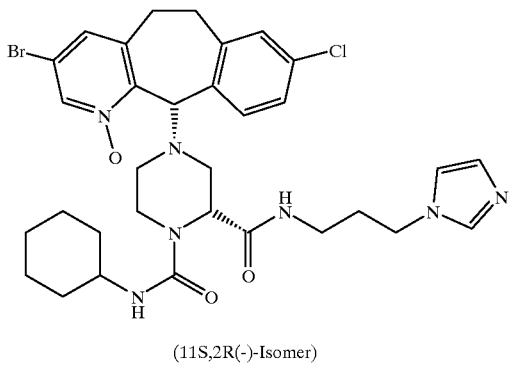

(11S,2R(−)-Isomer)

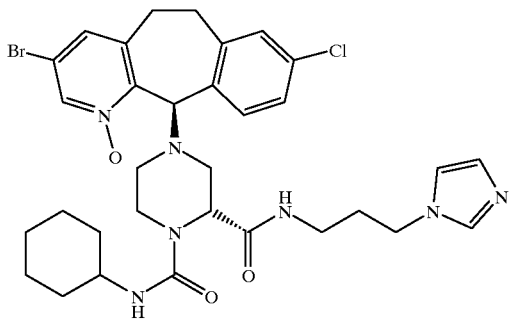

(11S,2R(+)-Isomer)

Method 1

3-Bromo-8,11-dichloro-6,11-dihydro-5H-benzo[5,5]cyclohepta[1,2-b]pyridine N1-oxide (Preparative Example 38, Step C) (0.2818 g, 0.785 mmoles) in anhydrous dichloromethane (4 mL) was added to N1-cyclohexyl-N2-[3-(1H-imidazol-1-yl)propyl]-1,2(R)-piperazinedicarboxamide (below) (0.2844 g, 0.785 mmoles) and triethylamine (1.094 mL, 7.85 mmoles) in anhydrous dichloromethane (4.5 mL) and the mixture was stirred at 25° C. under argon for 67 h. The solution was directly chromatographed on a silica gel column using 3% (10% conc. NH$_4$OH in methanol)-dichloromethane as the eluant to give the racemic mixture of the title compounds: (Yield: 0.4664 g, 87%). The mixture was subjected to preparative HPLC on a Chiralpak AD® column (50×5 cm) using 65% hexane—35% isopropyl alcohol—0.2% diethylamine as the eluant to give in the order of elution the 11S,2R(−)-diastereoisomer and the 11R,2R(+)-diastereoisomer.

11S,2R(−)-diastereoisomer: (Yield: 0155.5 g); LCMS: m/z 684.2 (MH$^+$); δ$_C$ (CDCl$_3$) 25.0, 25.1, 25.6, 30.1, 30.5, 31.1, 33.7, 33.7, 36.4, 42.4, 44.5, 50.2, 51.5; CH: 49.9, 54.8, 64.1, 119.1, 126.5, 129.3, 130.5, 130.8, 133.5, 137.2, 138.4; C: 118.4, 133.1, 134.9, 140.2, 141.4, 147.8, 157.6, 171.2; δ$_H$ (CDCl$_3$) 4.53 (1H, broad s, C<u>H</u>CO), 4.91 (1H, d, NCON<u>H</u>), 5.68 (1H, s, H$_{11}$), 6.62 (1H, t, CON<u>H</u>CH$_2$), 6.94 (1H, broad s, Im-H$_5$), 7.08 (1H, broad s, Im-H$_4$), 7.15 (1H, m, Ar—H), 7.17 (1H, s, Ar—H), 7.21 (1H, s, Ar—H), 7.23 (1H, m, Ar—H), 7.55 (1H, broad s, Im-H$_2$) and 8.27 ppm (1H, s, Ar—H$_2$); [a]$_D^{20.0°}$-33.1° (c=8.76 mg/2 mL, methanol).

11R,2R(+)-diastereoisomer: (Yield: 0.1890 g); LCMS: m/z 684.2 (MH$^+$); δ$_C$ (CDCl$_3$) 25.1, 25.1, 25.6, 30.3, 30.7, 31.1, 33.7, 33.7, 36.5, 42.3, 44.7, 50.2, 50.7; CH: 50.0, 55.0, 64.2, 119.1, 126.3, 128.8, 130.6, 130.9, 133.5, 137.2, 138.5; C: 118.5, 133.1, 134.7, 140.4, 141.4, 147.5, 157.5, 171.1; δ$_H$ (CDCl$_3$) 4.52 (1H, broad s, C<u>H</u>CO), 4.95 (1H, d, NCON<u>H</u>), 5.69 (1H, s, H$_{11}$), 6.97 (1H, t, CON<u>H</u>CH$_2$), 6.97 (1H, broad s, Im-H$_5$), 7.10 (1H, broad s, Im-H$_4$), 7.13 (1H, m, Ar—H), 7.18 (2H, s, Ar—H), 7.21 (1H, m, Ar—H), 7.69 (1H, broad s, Im-H$_2$) and 8.27 ppm (1H, s, Ar—H$_2$); [a]$_D^{20.0°}$+49.9° (c=10.23 mg/2 mL, methanol).

The starting reactant N1-cyclohexyl-N2-[3-(1H-imidazol-1-yl)propyl]-1,2(R)-piperazinedicarboxamide is obtained following the procedure of Preparative Example 5, except that

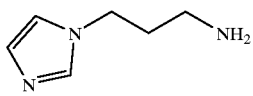

is used instead of

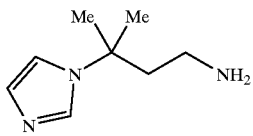

The resulting BOC protected compound is deprotected with TFA following the procedure in Preparative Example 8, Step B.

Method 2

The 11S,2R(−)-diastereoisomer (Preparative Example 38, Step D above) (1 mg, 0.00179 mmoles) was dissolved in anhydrous dichloromethane (0.05 mL) and cyclohexylisocyanate (0.0023 mL, 0.0179 mmoles) was added. The mixture was stirred at 25° C. for 0.5 h under argon. The solution was evaporated to dryness to give the title compound which was identical on chiral HPLC to the 11S,2R(−)-diastereoisomer prepared in Method 1 above.

EXAMPLE 77

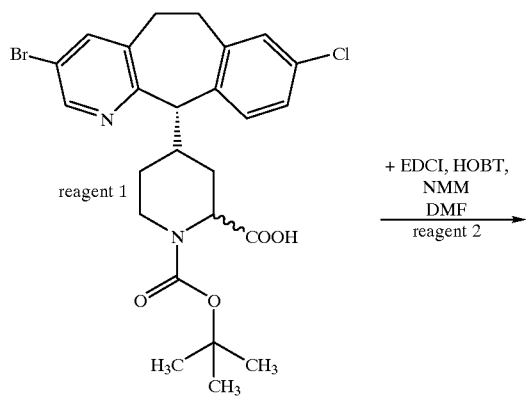

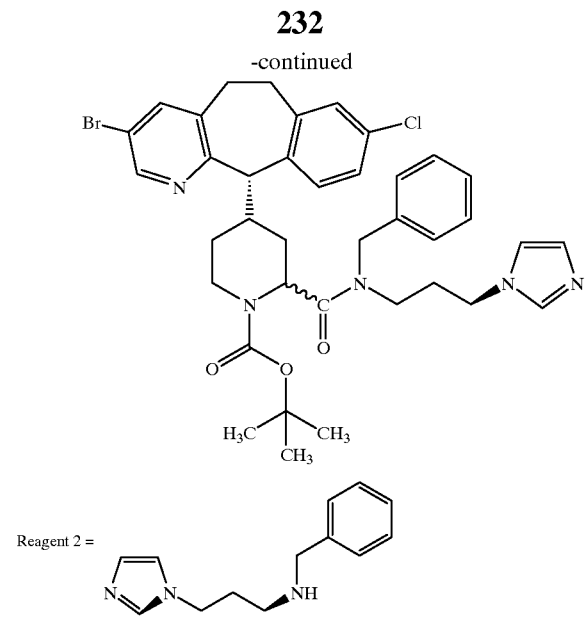

Reagent 2 =

The imidazole from Preparative Example 74 (Reagent 2), (250 mg, 1.16 mmol), was added to a solution of the BOC-acid (Reagent 1, see Preparative Example 41), (0.45 g, 0.842 mmol), EDCI (200 mg, 1.043 mmol), HOBT (130 mg, 0.962 mmol),and N-methyl morpholine (0.2 ml, 1.81 mmol) in DMF (anhydrous, 2 ml) at room temperature (20° C.). The resultant solution was stirred overnight at 20° C. The solvent was evaporated, water (70 ml) and EtOAC (120 ml) were added. The organic layer was separated, and washed with 10% Na$_2$CO$_3$ solution (50 ml), then dried over MgSO$_4$, filtered and evaporated solvent yielding an oil, which chromatographed on silica gel eluting with 100% EtOAC yielding the product as a white solid (300 mg). Mixture of 4 isomers A,B,C,D.

Mass Spec: High Resolution(ES) Estimated(MH$^+$) 732.2316 Observed 732.2332

EXAMPLE 78

Step A

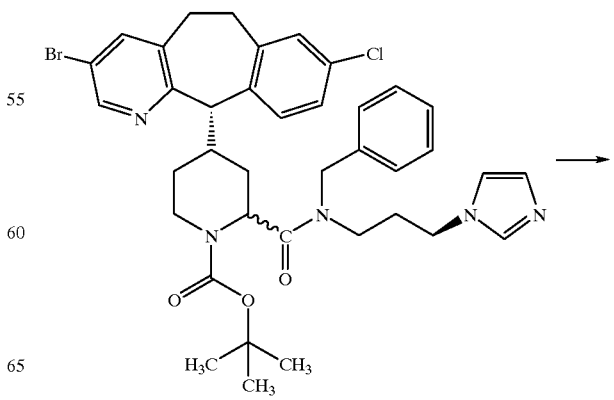

-continued

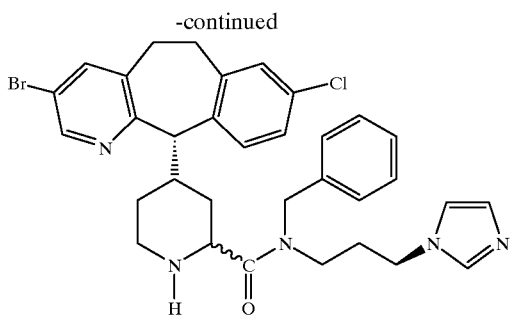

A solution of the title compound from Example 77, (Isomers A, B, C and D), (150 mg, 0.205 mmol) in 50% trifluoro-acetic acid-CH$_2$Cl$_2$ was stirred at 20° C. for 3 hours. The solvent was evaporated, water (25 ml) and 10% NaOH (4 ml) were added, then extracted with CH$_2$Cl$_2$ (2×100 ml). The organic layer was separated, dried over MgSO$_4$, and solvent evaporated yielding a solid which was purified by chromatography on silica gel eluting with 3% MeOH—CH$_2$Cl$_2$ containing 2% NH$_4$OH yielding the product as a white solid (70 mg, 54% yield).

The product was obtained as a mixture of 2 Isomers (C and D). (Product 1) Mass Spec FABS (MH) 632.

Further elution yielded a white solid (25 mg, 20% yield). This product was a mixture of 2 Isomers (A and B) (Product 2) Mass Spec FABS (MH$^+$) 632.

Product 2 was separated into single isomers on a Chiralcell AD column eluting with 40% IPA-Hexanes yielding Isomer A as a white solid FABS (MH$^+$) 632. Further elution yielded Isomer B as a white solid, FABS MH$^+$) 632.

Product 1 was derivatised and separated into constituent Isomers C and D as shown in Step B below.

Step B

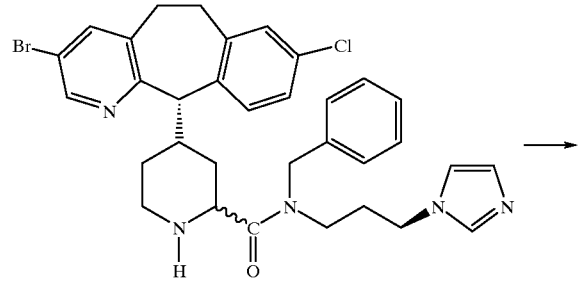

A solution of di-tert-butyldicarbonate (65 mg, 0.29 mmol) in CH$_2$Cl$_2$ (2 ml) was added to a solution of Product 1 (Step A, Isomers C and D) (150 mg, 0.237 mmol) in CH$_2$Cl$_2$ (10 ml), at 0° C., then stirred at 20° C. for 10 minutes. The reaction was cooled to 0° C., water (5 ml), 10% NaOH (2 ml) and CH$_2$Cl$_2$ (10 ml) were added. The organic layer was separated, dried over MgSO$_4$, filtered and solvent evaporated yielding an oil, which was chromatographed on silica gel, eluting with 3% v/v MeOH: CH$_2$Cl$_2$ yielding the product as a white solid (150 mg) as a mixture of 2 isomers, which were separated on Chiralcell AD column, eluting with 30% IPA-Hexanes/0.2% Diethylamine yielding Isomer C 60 mg. Mass Spec (FABS, MH$^+$) Calculated (C$_{38}$H$_{44}$N$_5$O$_3$BrCl:734.2296) Measured: 734.2304. Further elution yielded Isomer D 70 mg. Mass Spec (FABS, MH$^+$) CALC MH (734.2296) Measured: (734.2305).

EXAMPLE 79

Step A

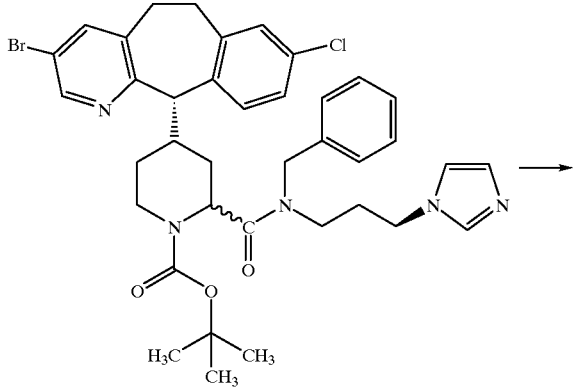

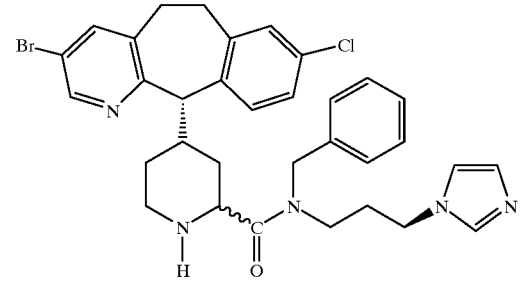

Following the procedure of Example 78 Step A, the BOC group of the Isomer C product of Step B was removed to produce the Isomer C title product as a white solid (Mass Spec, MH$^+$) FABS (632).

Step B

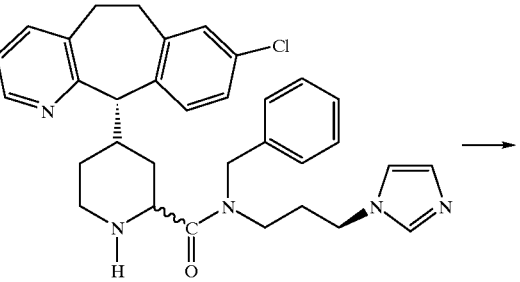

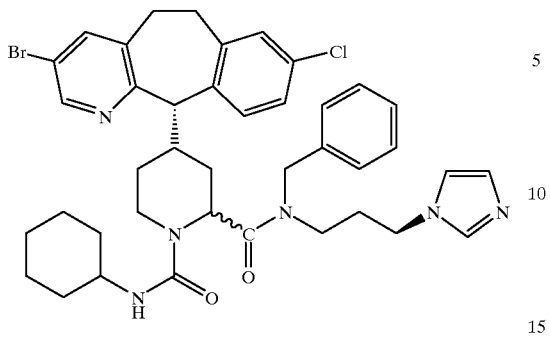

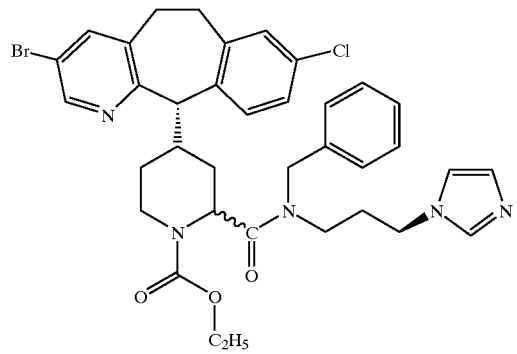

Cyclohexyl isocyanate (0.025 ml, 0.19 mmol) was added to a solution of Isomer A (Example 78, Step A) (25 mg, 0.039 mmol), in $CH_2Cl_2$ (3 ml) at 0° C., then stirred at 20° C. for 30 minutes. Methylene chloride (20 ml) and water (20 ml) were added. The organic layer was separated, dried over $MgSO_4$, filtered and solvent was evaporated yielding a residue, which chromatographed on silica gel, eluting with 2% v/v MeOH: $CH_2Cl_2$, yielding the product (Isomer A) as a white solid (25 mg). High resolution Mass Spec (ES) Calculated: $C_{40}H_{47}O_2N_6ClBr$ (757.2632)(Br=79) Measured: 757.2643.

Following the above procedure, but substituting an equivalent quantity of Isomer B (Example 78, Step A) for Isomer A, the title product (Isomer B) was obtained. Mass Spec (FABS, HRMS) Calculated 759.2612 (Br=81) Measured 759.2626

Following the above procedure, but substituting an equivalent quantity of Isomer C (Example 79, Step A) for Isomer A, the title product Isomer C was obtained. Mass Spec (ES, $MH^+$) 757 (Br=79)

Following the above procedure, except using the mixture of Isomers C and D (Product 1 from Example 78 Step A), yields the C and D isomer mixture of the title compound Mass Spec (ES,$MH^+$) 757

EXAMPLE 80

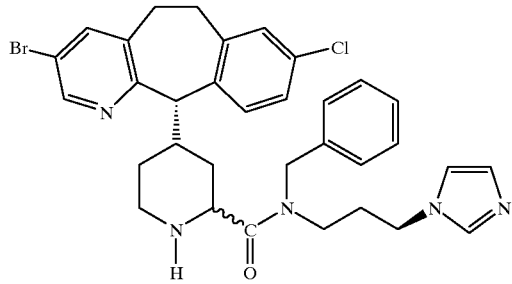

Ethyl chloroformate (0.1 ml, 1.04 mmol) was added to a solution of the Isomer A (Example 78, Step A) (20 mg, 0.03 mmol) in $CH_2Cl_2$ (2 ml) at 20° C. Triethylamine (0.1 ml, 0.7 mmol) was added, and the solution was stirred for 30 minutes at 20° C. The solvent was evaporated, and the residue chromatographed on silica gel, eluting with 3% v/v MeOH: $CH_2Cl_2$ containing 2% $NH_4OH$, yielding the Isomer A product as a white solid (20 mg). Mass Spec (ES, $MH^+$) 704.

Following the above procedure, but substituting an equivalent quantity of the Isomer B (Example 78, Step A) for Isomer A, the Isomer B product was obtained. Mass Spec (ES, $MH^+$) 704: HRMS (ES) Calculated (704.2003) (Br=79) Measured (704.2012).

EXAMPLES 81–85

Follow the procedure of Examples 127 and 80, but use the title compounds from Preparative Examples 9.1 or 111.1 with the appropriate isocyanate or chloroformate to obtain compounds of the formula:

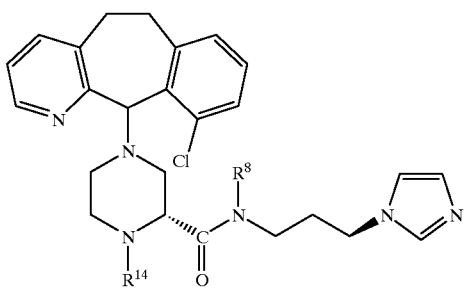

wherein $R^8$ and $R^{14}$ are defined in Table 10 below are obtained.

TABLE 10

| Ex. | R⁸ | R¹⁴ | Isomer | MS |
|---|---|---|---|---|
| 81 (Product of Prep. Ex. 9.1 and di-t-butyldicarbonate) | H | *t-butyl carbonate group* | A and B (R,S) | Fabs (MH) 565 |
| 82 (Product of Prep. Ex. 111.1 and di-t-butyldicarbonate) | benzyl | *t-butyl carbonate group* | A and B (R,S) | ES (MH) 655 |
| 83 (Product of Prep. Ex. 111.1 and di-t-butyldicarbonate) | benzyl | *t-butyl carbonate group* $[\alpha]_D^{20} = +2.5°$ | A (R(+)) | ES (MH) 655 |
| 84 (Product of Prep. Ex. 111.1 and di-t-butyldicarbonate) | benzyl | *t-butyl carbonate group* $[\alpha]_D^{20} = -34.9°$ | B (S(−)) | ES (MH) 655 |
| 85 (Product of Prep. Ex. 111.1 and cyclohexyl isocyanate) | benzyl | cyclohexyl-NH-C(O)- | A and B (R,S) | ES (MH) 680 |

The compounds of Examples 83 and 84 were separated on Chiralcell AD column.

EXAMPLE 86

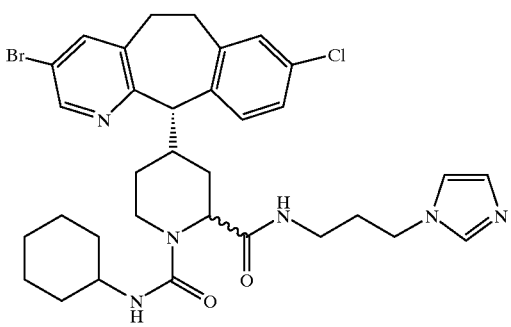

11S Isomer

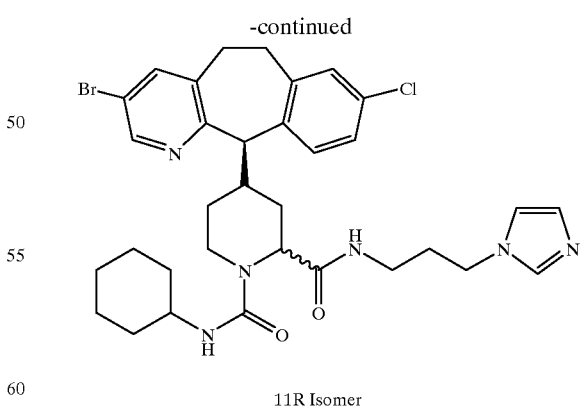

11R Isomer

Following the procedures of Examples 77–79, but substituting an equivalent quantity of 1-(3-aminopropyl) imidazole for the N-benzyl substituted imidazole from Preparative Example 74 in Example 77, the title compounds are obtained.

11S-Isomer: Mass Spec: Fabs (MH⁺) 667(Br=79) HRMS Calc (MH) $C_{33}H_{41}N_6O_2Cl(81)Br$ 669.2142 Measured 669.2151

11R-Isomer: FABS (MH⁺) 667.

EXAMPLE 86A

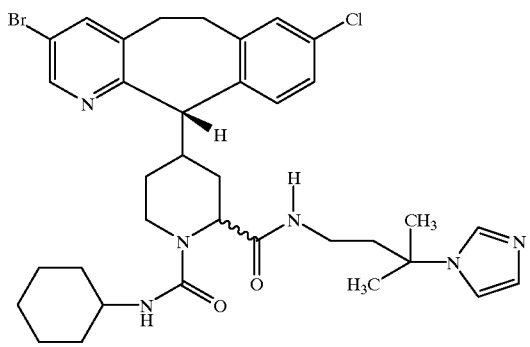

Use the imidazole from Preparative Example 1 Step D and follow the procedure of Example 77 and Example 79 Step A to obtain the compound

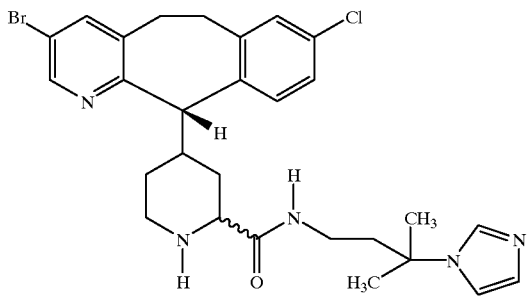

which is then reacted with cyclohexyl isocyanate according to the procedure set forth in Example 79 Step B. Mass Spec: Fabs (MH) 695 (Br=79) 669.2142.

EXAMPLES 87–97

Following the procedures set forth in Examples 77–80, but using the 11(R)-isomer, compounds of the formula:

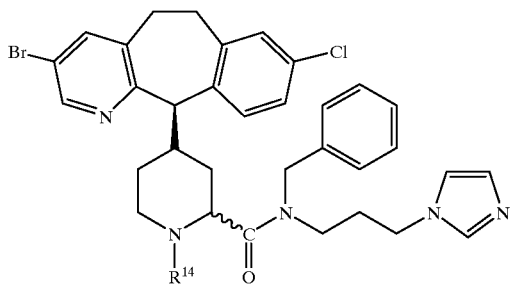

are obtained. $R^{14}$ is defined in Table 11.

TABLE 11

| Ex. | $R^{14}$ | Isomer | Mass Spec Observed (Estimated) |
|---|---|---|---|
| 87 | | A, B, C, D | 732.2343 (732.2316) |
| 88 | | A | 732.2332 (732.2316) |
| 89 | | B | 734.2305 (743.2296) |
| 90 | | A | 757.2641 (757.2632) |
| 91 | | B | 759.2618 (759.2612) |
| 92 | | C | 734.2296 (732.2296) |
| 93 | | D | 734.2297 (734.2296) |
| 94 | | C, D | 734.2318 (734.2296) |

TABLE 11-continued

| Ex. | R[14] | Isomer | Mass Spec Observed (Estimated) |
|---|---|---|---|
| 95 | 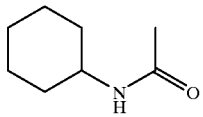 | C | 759.2611 (759.2612) |
| 96 | 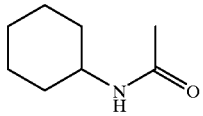 | D | 759.2618 (759.2612) |
| 97 | 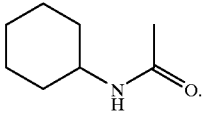 | C, D | 759.2626 (759.2612) |

EXAMPLE 98

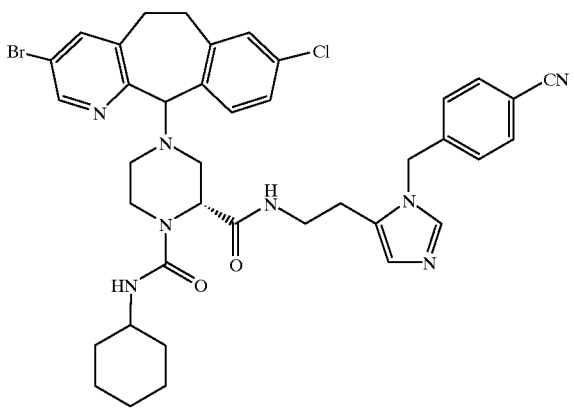

The product of Preparative Example 45 (0.6 gm) was dissolved in 6 ml of dichloromethane and 6 ml of trifluoroacetic acid was added and the reaction mixture stirred for 2 hours. After 2 hours the reaction mixture was evaporated to an oil. The oil was dissolved in N,N,-dimethylformamide and triethyl amine (0.445 mL, 3 eq.) was added and 3-bromo-8,11-dichloro-6,11-dihydro-5H-benzo[5,6]cyclohepta[1,2-b]pyridine (0.39 gm, 113 mmol.) was added and the reaction mixture stirred for 24 hours. The reaction mixture was added to brine and the product extracted with ethylacetate 3 times to obtain a crude oil after the solvent was evaporated under reduced pressure, which was purified by chromatography on a silica gel column using 2% up to 4% methanol/dichloromethane as the eluent. The product containing fractions were pooled to obtain 0.34 gm of pure title compound. The compound was separated into its pure enantiomeric forms by HPLC on a Chiral Technologies AD column using 20% isopropanol/hexanes. Isomer 1: mp=148.3–157.5° C.; Isomer 2: mp=148.3–157.5° C.

EXAMPLE 99

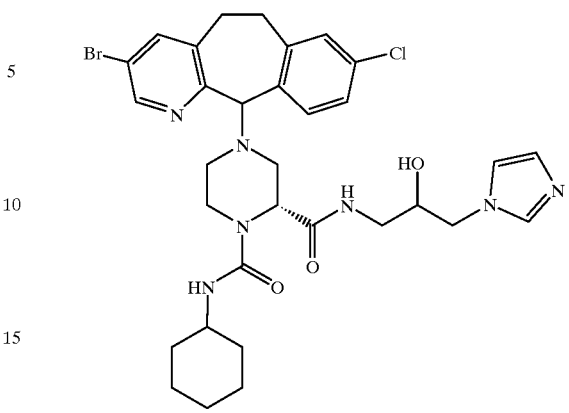

The title compound from Preparative Example 48 (0.487 gm) was dissolved in dichloromethane (3 ml) and trifluoroacetic acid (3 ml) and the reaction mixture stirred for 2 hours. The reaction mixture was evaporated to dryness and dissolved in 10 mL of N,N-dimethyl-formamide. Triethylamine (1.42 mL, 10 eq.) was added and 3-bromo-8,11-dichloro-6,11-dihydro-5H-benzo[5,6]cyclohepta[1,2-b]pyridine (Compound No. 42.0) (0.45 gm, 1.2 eq.) was added and the reaction mixture stirred for 24 hours. The reaction mixture was added to brine and the product extracted with ethylacetate 3 times to obtain a crude oil after the solvent was evaporated under reduced pressure, which was purified by chromatography on a silica gel column using 2% up to 4% methanol/dichloromethane as the eluent. The product containing fractions were pooled to obtain 0.26 gm of pure title compound as a mixture of isomers. Isomers were separated by HPLC on a Chiral Technologies AD column using 20–30% isopropanol/hexanes. Isomer 1: mp=192.7–194.3° C.; Isomer 2: mp=189.2–190.7° C.

EXAMPLE 100

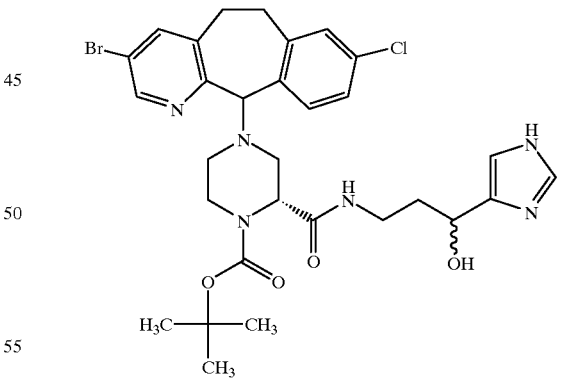

The title compound from Preparative Example 52 (0.3 gm, 0.5 mmol) was stirred in a mixture of 10 ml of dichloromethane and 15 μL of water and Dess-Martin Periodinane (0.32 gm, 1.5 eq.) was added and the reaction mixture stirred at ambient temperature. After 24 hours the reaction mixture was washed with 20% $Na_2S_2O_3$ solution followed by sodium bicarbonate solution and evaporated to dryness under vacuum. This compound was dissolved in dichloromethane and a premixed solution of 4-iodo-1-tritylimidazole (89 mg) and ethylmagnesiumbromide (3M soln in ether, 66 μL, added to the reaction mixture and stirred at ambient temperature for 4 hours. The reaction mixture was poured into saturated ammonium chloride solution and the product extracted with dichloromethane to obtain the crude product which was purified by preparative tlc to obtain 52 mg of title product after deprotection with TFA and introduction of the Boc group with (BOC)$_2$O.

EXAMPLES 101–102

Following procedures similar to those described in Examples 98–100, the following compounds are obtained:

Example 101

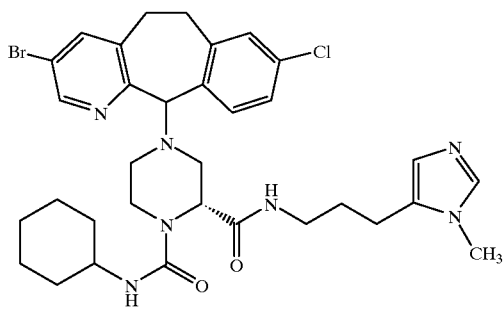

and

Example 102

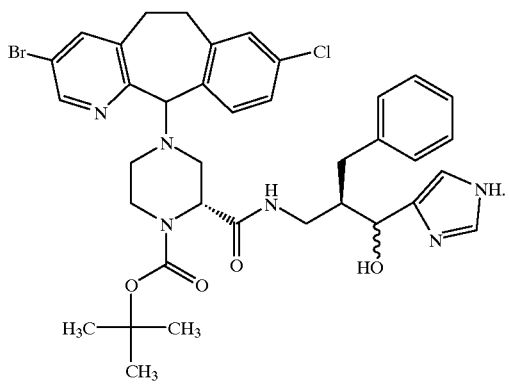

EXAMPLE 103

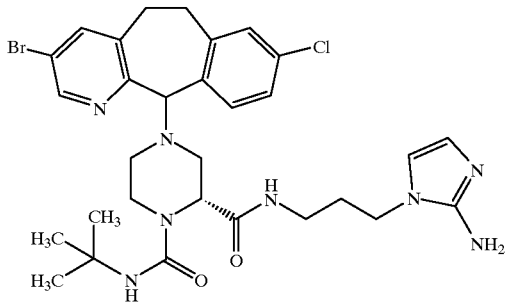

The title compound from Preparative Example 58 was dissolved in 1 ml of dichloromethane and 68 microliters of tert-butylisocyanate was added and the reaction mixture stirred. The reaction mixture was evaporated to obtain the crude product which was stirred with 33% HBr/HOAc to obtain 20 mg of the title product after addition to ether, collection of the product as a tan solid, and preparative thin layer chromatography. FABMS M+1=659.

EXAMPLE 104

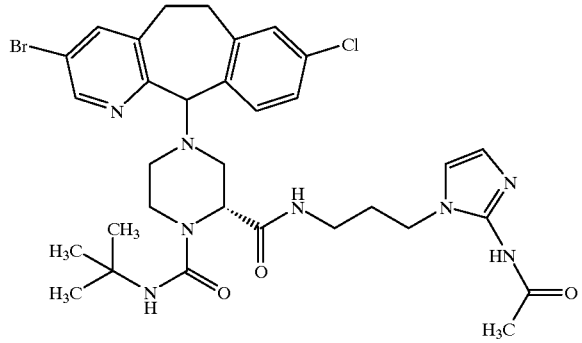

The title compound from Example 103 (50 mg) was dissolved in 5 ml of dichloromethane and 0.5 ml of acetic anhydride was added. The reaction mixture was evaporated to dryness after 18 hours and chromatographed by preparative tlc to obtain 39 mg of pure title product. FABMS MH$^+$=699.

EXAMPLE 105

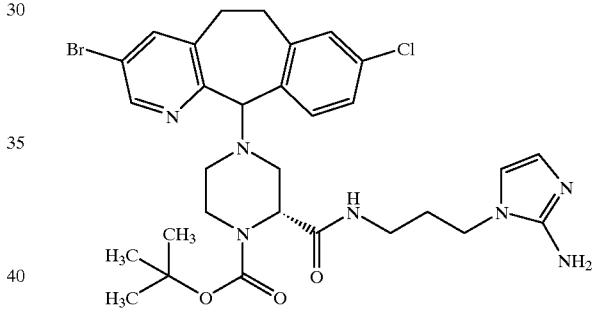

The title compound was prepared following essentially the same procedure as set forth in Preparative Example 52, but substituting 1-(3-aminopropyl)-2-aminoimidazole for 1-amino-3-propanol to obtain the title product in 65% yield. FABMS MH$^+$=660.

EXAMPLE 106

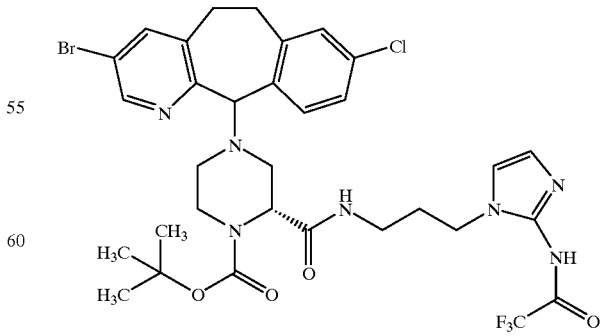

The title compound was prepared following the procedure set forth in Example 104, but using the title compound from Preparative Example 105 in place of the title compound from Example 103 and trifluoroacetic anhydride in place of acetic anhydride to obtain the pure title product. FABMS MH+=756.

EXAMPLE 107

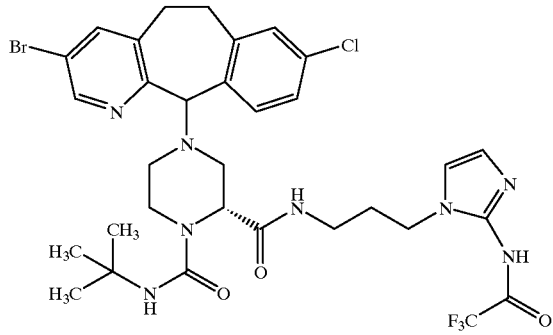

Follow the precedure set forth in Example 104, but substitute trifluoracetic anhydride for acetic anhydride to obtain the pure title product. FABMS MH+=755.

EXAMPLE 108

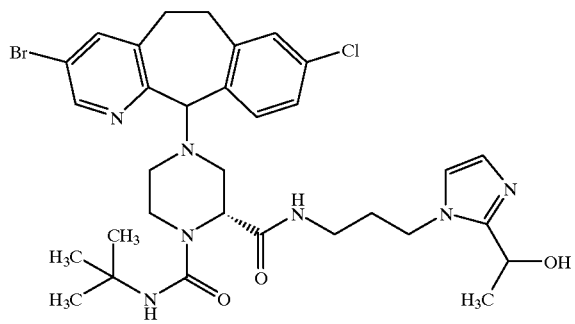

The title product was prepared following the procedure set forth in Example 110, but substituting the title compound from Preparative Example 60 for that from Preparative Example 102 Step C and tert-butyl isocyanate for cyclohexyl isocyanate to obtain the pure title product. FABMS MH+=688.

EXAMPLE 109

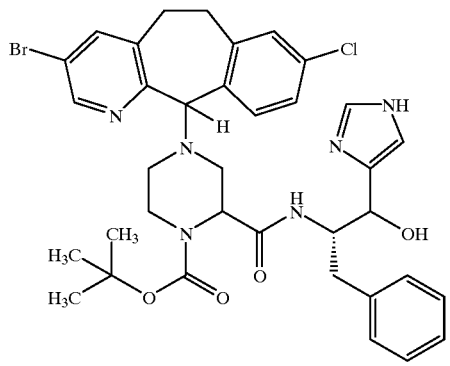

The title product was obtained following the procedure set forth in Preparative Example 52, but substituting 2-S-benzyl-3-R,S-hydroxy-histamine for 1-amino-3-propanol. FABMS (MH+)=737.

EXAMPLE 110

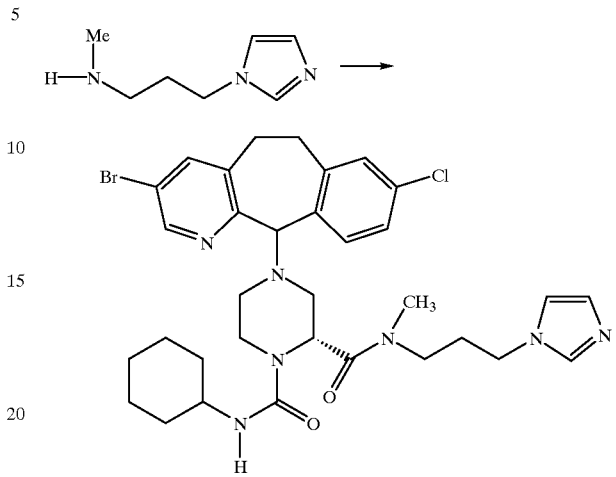

A mixture of the title compound from Preparative Example 102 Step C (0.28 g, 2 mmol), the title compound from Preparative Example 44 (0.5 g, 2 mmol) and anhydrous $CH_2Cl_2$ (5 mL) was stirred at room temperature for 15 min. Cyclohexyl-isocyanate (0.51 mL, 4 mmol) was added and the reaction mixture allowed to stir at room temperature for an additional 48 hrs. After concentrating the reaction mixture in vacuo, the residue was diluted with $CH_2Cl_2$ (10 mL) and trifluoroacetic acid (10 mL) and stirred at room temperature overnight. The resulting mixture was concentrated in vacuo, diluted with anhydrous DMF (5 mL) and to it were added N-methylmorpholine (2.2 mL, 20 mmol) and the tricyclic chloride (compound No. 42.0) (0.83 g, 2 mmol). The reaction mixture was stirred at room temperature overnight, concentrated in vacuo and purified by flash column chromatography (silica gel) using 5% MeOH-95% $CH_2Cl_2$ saturated with aqueous ammonium hydroxide to give the title compound as a mixture of diastereomers (tan solid, 95 mg, 7%, MH+=682, mp=118.4° C.).

EXAMPLE 111

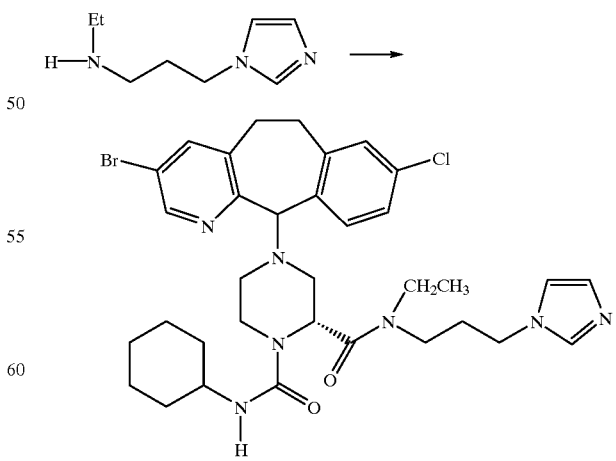

Following a similar procedure as that used for the preparation of the title compound from Example 110, but using the title compound from Preparative Example 103, the title compound was obtained as a mixture of diastereomers (brown, sticky solid, 28.7 mg, 2%, MH⁺=696, mp=79.3° C.).

EXAMPLE 112

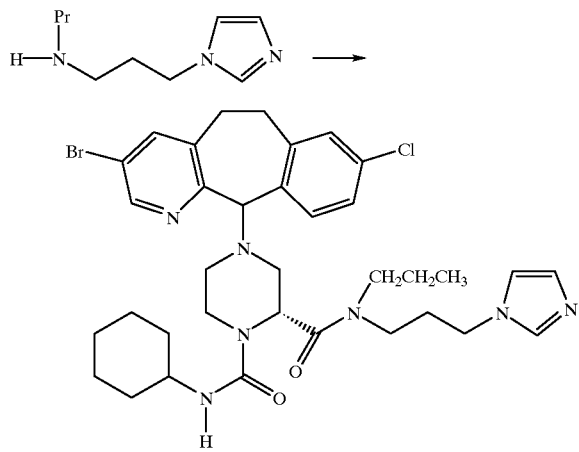

Following a similar procedure as that used for the preparation of the title compound from Example 110, but using the title compound from Preparative Example 104, the title compound was obtained as a mixture of diastereomers (tan solid, 18.5 mg, 1%, MH⁺=710, mp=63.8–67.4° C.).

EXAMPLE 113

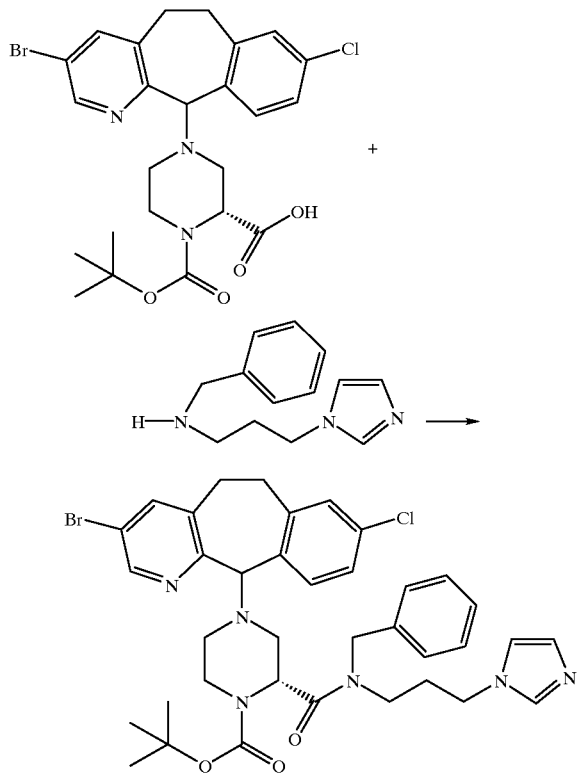

To the title compound from Preparative Example 51 (10.04 g, 19 mmol) were added HOBT (3.34 g, 25 mmol), DEC (4.79 g, 25 mmol), the title compound from Preparative Example 74 (4.32 g, 20 mmol), NMM (5.5 mL, 50 mmol) and anhydrous DMF (20 mL). The mixture was stirred at room temperature under N₂ overnight. The mixture was concentrated in vacuo, diluted with CH₂Cl₂ and washed with a saturated aqueous solution of NaHCO₃. The organic phase was dried over anhydrous MgSO₄, filtered and concentrated in vacuo. The residue was purified by flash column chromatography (silica gel) using 2% MeOH-98% CH₂Cl₂ saturated with aqueous ammonium hydroxide to give the title compound as a mixture of diastereomers (4.92 g, 36%, MH⁺=733).

EXAMPLE 114

If the procedure set forth in Example 113 is followed, but the N-substituted imidazolylalkyl amine below is used the indicated compound would be obtained.

Amine A

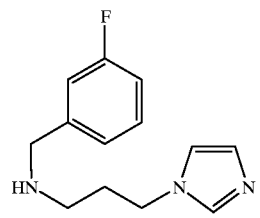

Compound A

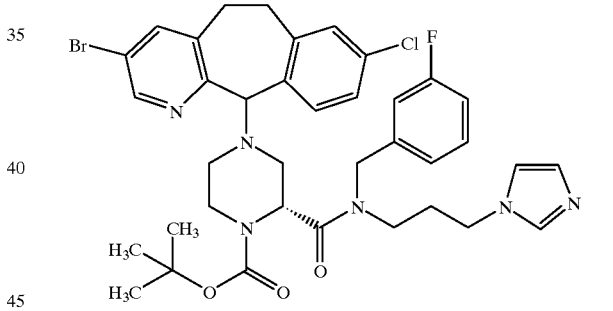

Amine B

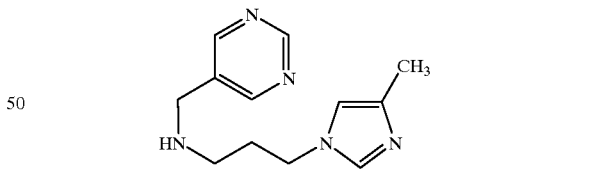

Compound B

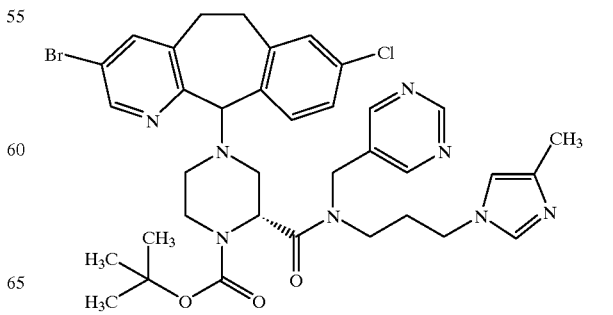

Amine C
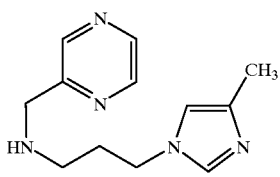
Compound C
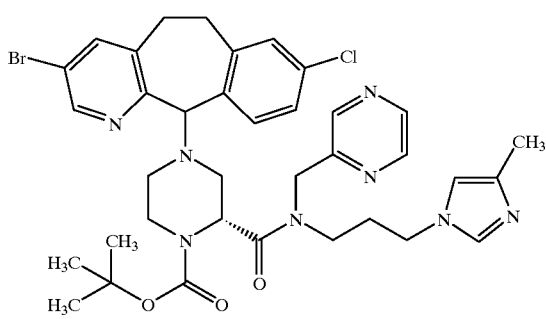
Amine D
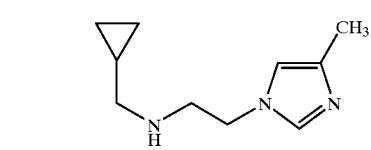
Compound D
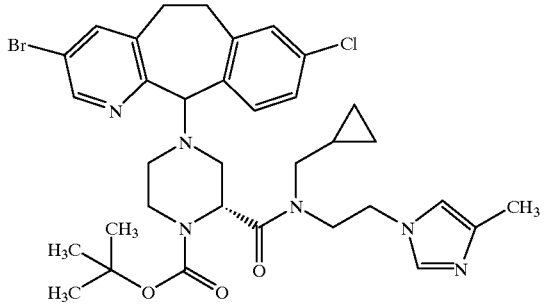
EXAMPLES 115–126
Following the procedure set forth in Example 113, but using the N-substituted imidazolylalkyl amine (Imidazole) in Table 12 and the carboxylic acid from Preparative Example 51, the Products in Table 12 were obtained.
TABLE 12
| Ex. | Amine | Product | 1. % Yield<br>2. MH+<br>3. mp (° C.) |
|---|---|---|---|
| 115 | 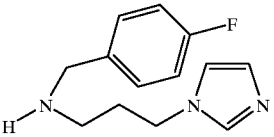 | 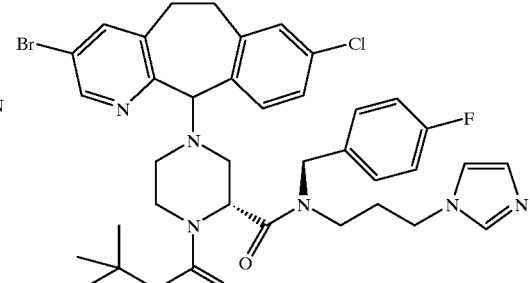 | 1. 19<br>2. 751<br>3. 105.4 |
| 116 | 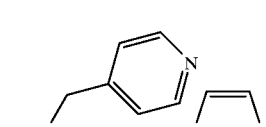 | 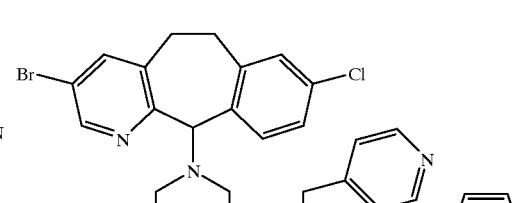 | 1. 27<br>2. 734<br>3. semi-solid |

TABLE 12-continued

| Ex. | Amine | Product | 1. % Yield<br>2. MH+<br>3. mp (° C.) |
|---|---|---|---|
| 117 | | | 1. 35<br>2. 734<br>3. semi solid |
| 118 | | | 1. 52<br>2. 749<br>3. oil |
| 119 | | | 1. 18<br>2. 763<br>3. 65–70 |
| 120 | | | 1. 48<br>2. 763<br>3. 125–130 |

TABLE 12-continued

| Ex. | Amine | Product | 1. % Yield<br>2. MH+<br>3. mp (° C.) |
|---|---|---|---|
| 121 | (3-cyanobenzyl)(3-imidazol-1-ylpropyl)amine | structure | 1. 20<br>2. 758<br>3. semi-solid |
| 122 | (3-carbamoylbenzyl)(3-imidazol-1-ylpropyl)amine | structure | 1. 19<br>2. 776<br>3. semi-solid |
| 123 | (naphth-2-ylmethyl)(3-imidazol-1-ylpropyl)amine | structure | 1. 15<br>2. 783<br>3. 85–90 |
| 124 | (cyclohexylmethyl)(3-imidazol-1-ylpropyl)amine | structure | 1. 12<br>2. 739<br>3. semi-solid |

TABLE 12-continued

| Ex. | Amine | Product | 1. % Yield<br>2. MH+<br>3. mp (° C.) |
|---|---|---|---|
| 125 | | | 1. 35<br>2. 747<br>3. (A): 86<br>(B) 84.7 |
| 126 | | | 1. 15<br>2. 719<br>3 (A): 206.7<br>(B) 121.2–130.4 |

EXAMPLE 127

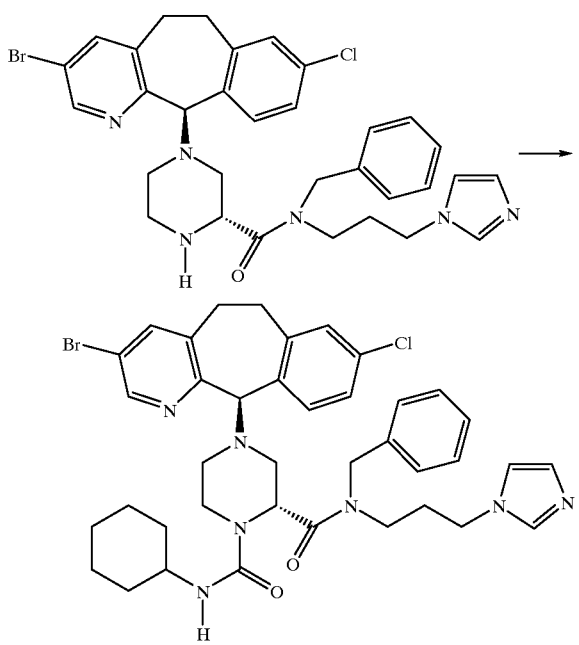

To a solution of the title compound from Preparative Example 109 (11R,2R diastereomer B, 1.7 g, 2.7 mmol) dissolved in anhydrous CH2Cl₂ (10 mL) was added cyclohexylisocyanate (0.38 mL, 2.9 mmol) and the resulting solution was stirred at room temperature under N₂ for 1.5 hrs. The solution was concentrated in vacuo and purified by flash column chromatography (silica gel) using 2% MeOH-98% CH₂Cl₂ saturated with aqueous ammonium hydroxide to give the title compound as a light yellow solid (1.98 g, 84%, MH+=758).

EXAMPLES 128–148

Following the procedure set forth for Example 127, but using the isocyanates and the compounds of the preparative examples given in Table 13 below, the Products given in Table 13 were obtained.

TABLE 13

| Ex. | Isocyanate and Prep. Ex. Compound | Product | 1. Yield (%) 2. MH+ 3. mp (° C.) |
|---|---|---|---|
| 128 | cyclohexyl-NCO<br><br>Prep. Ex. 109<br>Diastereomer A | [structure]<br><br>222421 | 1. 87<br>2. 760<br>3. 125.2 |
| 129 | t-butyl-NCO<br><br>Prep. Ex. 109<br>Diastereomer A | [structure] | 1. 61<br>2. 732<br>3. 126.6 |
| 130 | t-butyl-NCO<br><br>Prep. Ex. 109 | [structure] | 1. 100<br>2. 732<br>3. 112.3 |

TABLE 13-continued

| Ex. | Isocyanate and Prep. Ex. Compound | Product | 1. Yield (%) 2. MH+ 3. mp (° C.) |
|---|---|---|---|
| | Diastereomer B | | |
| 131 | isopropyl-NCO Prep. Ex. 109 Diastereomer A | [structure] | 1. 95 2. 718 3. 109.8 |
| 132 | isopropyl-NCO Prep. Ex. 109 Diastereomer B | [structure] | 1. 63 2. 718 3. 118.1 |
| 133 | ethyl-NCO Prep. Ex. 109 | [structure] | 1. 95 2. 704 3. 93.5 |

TABLE 13-continued

| Ex. | Isocyanate and Prep. Ex. Compound | Product | 1. Yield (%) 2. MH+ 3. mp (° C.) |
|---|---|---|---|
| | Diastereomer A | | |
| 134 | propyl-NCO<br><br>Prep. Ex. 109<br>Diastereomer B | [structure with Br, Cl, piperazine, propyl urea, imidazole] | 1. 86<br>2. 718<br>3. 98.9 |
| 135 | phenyl-NCO<br><br>Prep. Ex. 109<br>Diastereomer A | [structure with Br, Cl, piperazine, phenyl urea, imidazole] | 1. 56<br>2. 752<br>3. 81.4 |
| 136 | benzyl-NCO<br><br>Prep. Ex. 109 | [structure with Br, Cl, piperazine, benzyl urea, imidazole] | 1. 17<br>2. 766 |

TABLE 13-continued
| Ex. | Isocyanate and Prep. Ex. Compound | Product | 1. Yield (%) 2. MH+ 3. mp (° C.) |
|---|---|---|---|
| | Diastereomer A | | |
| 137 | 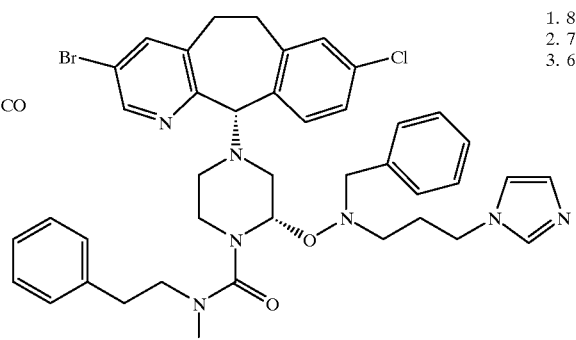<br>Prep. Ex. 109<br>Diastereomer A | | 1. 80<br>2. 780<br>3. 68.4 |
| 138 | 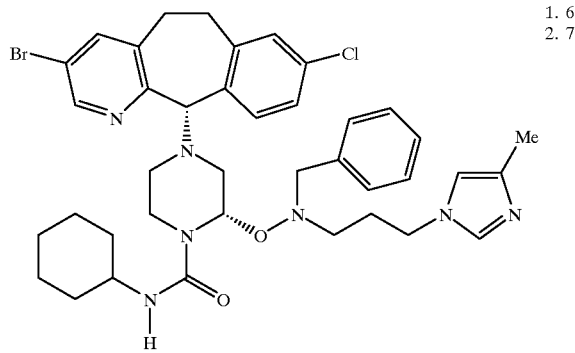<br>Prep. Ex. 131<br>Diastereomer A | | 1. 68<br>2. 772 |
| 139 | 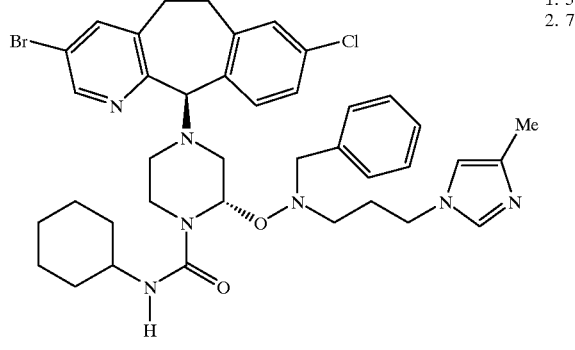<br>Prep. Ex. 131 | | 1. 53<br>2. 772 |

TABLE 13-continued

| Ex. | Isocyanate and Prep. Ex. Compound | Product | 1. Yield (%) 2. MH+ 3. mp (° C.) |
|---|---|---|---|
| | Diastereomer B | | |
| 140 | cyclohexyl-NCO | [structure] | 1. 83 2. 744 3. 143.8 |
| | Prep. Ex. 113 Diastereomer A | | |
| 141 | cyclohexyl-NCO | [structure] | 1. 96 2. 744 3. 135.4 |
| | Prep. Ex. 113 Diastereomer B | | |
| 142 | t-Bu-NCO | [structure] | 1. 77 2. 733 3. 120.8 |
| | Prep. Ex. 117 | | |

TABLE 13-continued

| Ex. | Isocyanate and Prep. Ex. Compound | Product | 1. Yield (%) 2. MH+ 3. mp (° C.) |
|---|---|---|---|
| | Diastereomer B | | |
| 143 | tBu-NCO  Prep. Ex. 117  Diastereomer A | (structure with Br, Cl, benzazepine, piperazine, O-N(benzyl)(ethyl-imidazole), t-Bu urea) | 1. 64 2. 733 3. 116.8 |
| 144 | Cyclohexyl-NCO  Prep. Ex. 111  Diastereomer B | (structure with Cl, benzazepine, piperazine, O-N(benzyl)(propyl-imidazole), cyclohexyl urea) | 1. 100 2. 680 |
| 145 | tBu-NCO  Prep. Ex. 111 | (structure with Cl, benzazepine, piperazine, O-N(benzyl)(propyl-imidazole), t-Bu urea) | 1. 79 2. 654 3. 61.3– 69.3 |

TABLE 13-continued

| Ex. | Isocyanate and Prep. Ex. Compound | Product | 1. Yield (%) 2. MH+ 3. mp (° C.) |
|---|---|---|---|
| | Diastereomer A | | |
| 146 | *tert*-butyl-NCO  Prep. Ex. 111 Diastereomer B | [structure: 8-chloro-benzocycloheptapyridine with piperazine bearing N-tert-butylcarboxamide and O-linked N-benzyl-N-(3-imidazol-1-yl-propyl)aminoxy substituent] | 1. 97 2. 654 3. 97.0 |
| 147 | cyclohexyl-NCO  Prep. Ex. 125 | [structure: benzocycloheptapyridine with piperazine bearing N-cyclohexylcarboxamide and O-linked N-benzyl-N-(3-imidazol-1-yl-propyl)aminoxy substituent] | 1. 91 2. 645 |
| 148 | *tert*-butyl-NCO  Prep. Ex. 130 | [structure: 3-bromo-8-chloro-benzocycloheptapyridine with piperazine bearing N-tert-butylcarboxamide and O-linked N-(pyridin-2-ylmethyl)-N-(3-imidazol-1-yl-propyl)aminoxy substituent] | 1. 68 2. 735 |

EXAMPLE 149

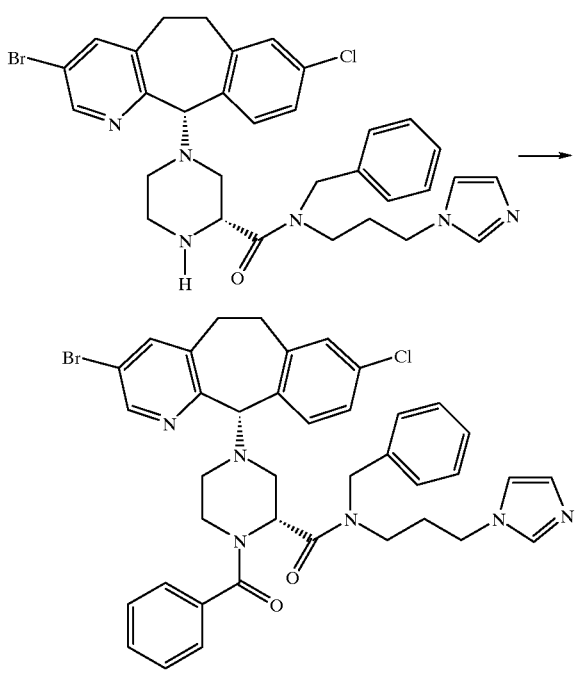

To a solution of the title compound from Preparative Example 109 (11S,2R diastereomer A, 50 mg, 0.08 mmol) dissolved in anhydrous $CH_2Cl_2$ (1 mL) was added benzoyl chloride (0.02 mL, 0.16 mmol) and triethylamine (0.03 mL, 0.2 mmol) and the resulting mixture was stirred at room temperature under $N_2$ overnight. The solution was diluted with dichloromethane, washed with 1N aqueous NaOH and dried over anhydrous $MgSo_4$. Filtration and concentration in vacuo provided a residue which was purified by preparative plate chromatography (silica gel) using 5% MeOH-95% $CH_2Cl_2$ saturated with aqueous ammonium hydroxide to give the title compound as an off-white solid (54.4 mg, 93%, $MH^+$=737). SCH

EXAMPLES 150–217

Similarly, using the procedure described for Example 149, the title compound (diastereomer A or B) from the Preparative Example given in Table 14 was treated with the corresponding acid chloride, chloroformate, carbamyl chloride, dicarbonate, anhydride or sulfonyl chloride given in Table 14 below (Electrophile column) to give the N-substituted arylalkyl or heteroarylalkyl Products listed in Table 14.

TABLE 14

| Ex. | Electrophile and Prep. Ex. Compound | Product | 1. Yield (%) 2. $MH^+$ 3. mp (20 C.) |
|---|---|---|---|
| 150 | ![acetyl chloride] Prep Ex. 109 Diastereomer A | ![product 150] | 1. 54 2. 675 3. 79.7 |
| 151 | ![acetyl chloride] Prep Ex. 109 Diastereomer B | ![product 151] | 1. 75 2. 675 3. 69.3 |

TABLE 14-continued
| Ex. | Electrophile and Prep. Ex. Compound | Product | 1. Yield (%)<br>2. MH+<br>3. mp (20 C.) |
|---|---|---|---|
| 152 | 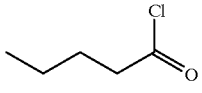<br>Prep Ex. 109<br>Diastereomer A | 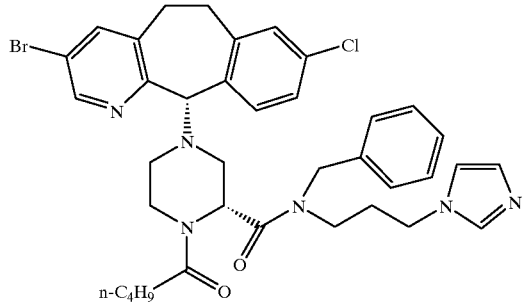 | 1. 72<br>2. 717<br>3. 86.4 |
| 153 | 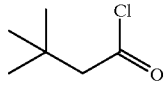<br>Prep Ex. 109<br>Diastereomer A | 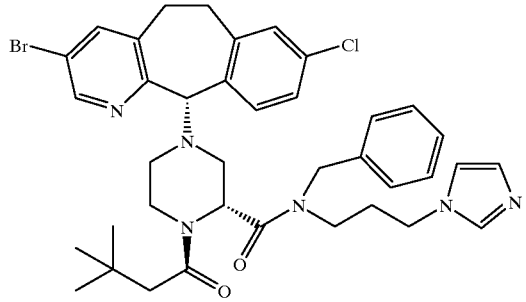 | 1. 172<br>2. 731<br>3. 85.4 |
| 154 | 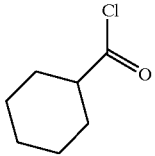<br>Prep Ex. 109<br>Diastereomer A | 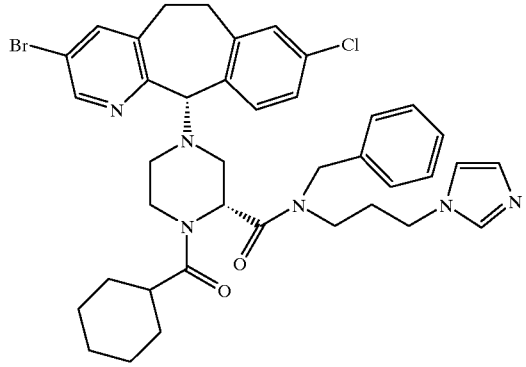 | 1. 85<br>2. 743<br>3. 100–101 |
| 155 | 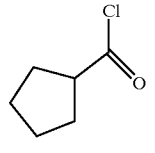<br>Prep Ex. 109<br>Diastereomer A | 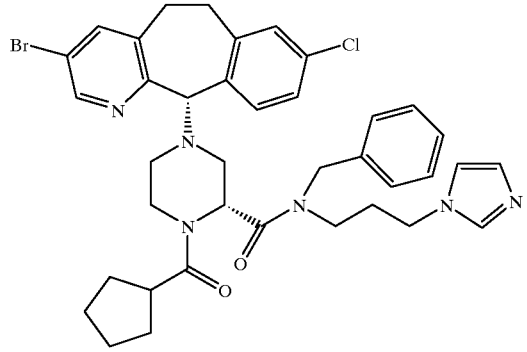 | 1. 88<br>2. 729<br>3. 101–104 |

TABLE 14-continued
| Ex. | Electrophile and Prep. Ex. Compound | Product | 1. Yield (%) 2. MH+ 3. mp (20 C.) |
|---|---|---|---|
| 156 | 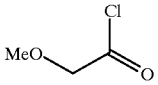 Prep Ex. 109 Diastereomer A | 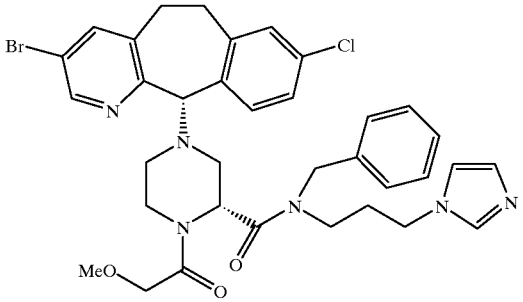 | 1. 61 2. 705 3. 102.7 |
| 157 | 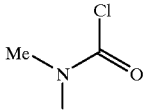 Prep No. 109 Diastereomer A | 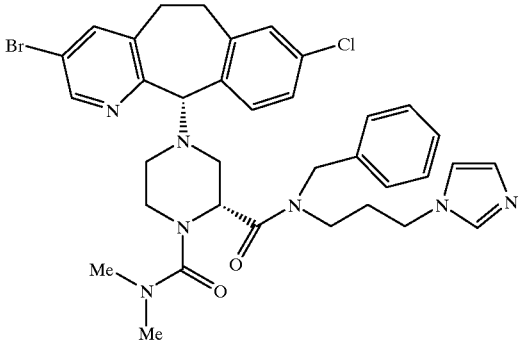 | 1. 92 2. 704 3. 114.7 |
| 158 | 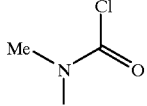 Prep No. 109 Diastereomer B | 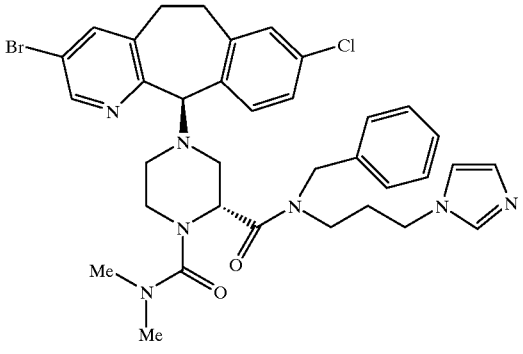 | 1. 100 2. 704 3. 110.4 |
| 159 | 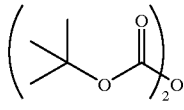 Prep Ex. 109 Diastereomer A | 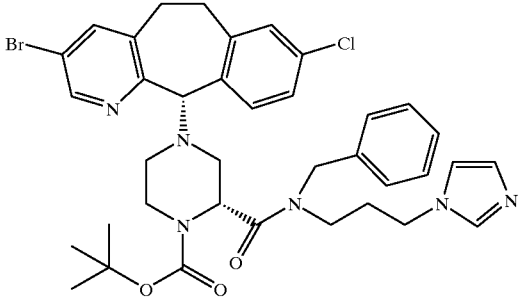 | 1. 97 2. 733 3. 103.5 |

TABLE 14-continued

| Ex. | Electrophile and Prep. Ex. Compound | Product | 1. Yield (%) 2. MH+ 3. mp (20 C.) |
|---|---|---|---|
| 160 | (Boc)₂O<br>Prep Ex. 109<br>Diastereomer B | | 1. 83<br>2. 733<br>3. 94.5 |
| 161 | isopropyl chloroformate<br>Prep Ex. 109<br>Diastereomer A | | 1. 85<br>2. 719<br>3. 95.5 |
| 162 | isobutyl chloroformate<br>Prep Ex. 109<br>Diastereomer A | | 1. 87<br>2. 733<br>3. 84.5 |
| 163 | ethyl chloroformate<br>Prep Ex. 109<br>Diastereomer A | | 1. 89<br>2. 705<br>3. 93.7 |

TABLE 14-continued
| Ex. | Electrophile and Prep. Ex. Compound | Product | 1. Yield (%) 2. MH+ 3. mp (20 C.) |
|---|---|---|---|
| 164 | 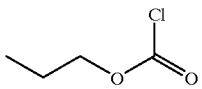<br>Prep Ex. 109<br>Diastereomer A | 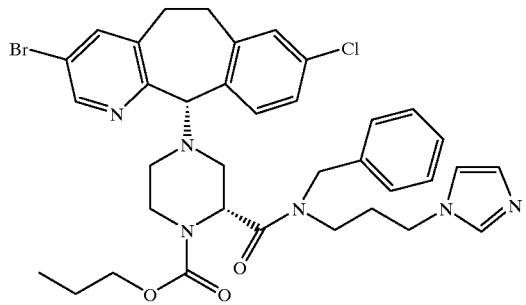 | 1. 89<br>2. 719<br>3. 79.8 |
| 165 | 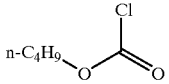<br>Prep Ex. 109<br>Diastereomer A | 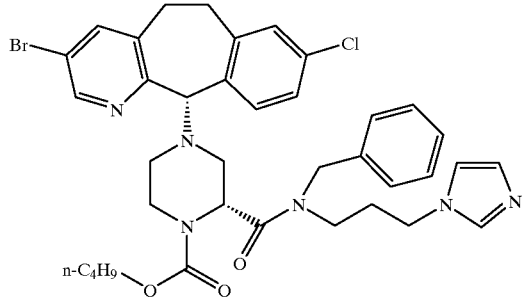 | 1. 87<br>2. 733<br>3. 70.5 |
| 166 | 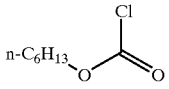<br>Prep Ex. 109<br>Diastereomer A | 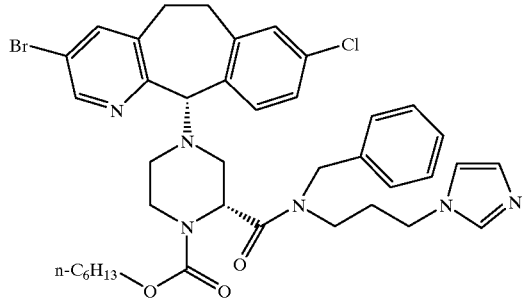 | 1. 83<br>2. 761<br>3. 60.2 |
| 167 | 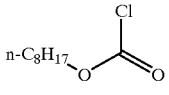<br>Prep Ex. 109<br>Diastereomer A | 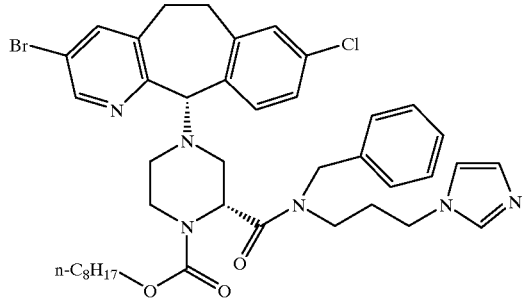 | 1. 86<br>2. 789<br>3. 63.1 |

TABLE 14-continued
| Ex. | Electrophile and Prep. Ex. Compound | Product | 1. Yield (%) 2. MH+ 3. mp (20 C.) |
|---|---|---|---|
| 168 | 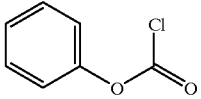<br>Prep Ex. 109<br>Diastereomer A | 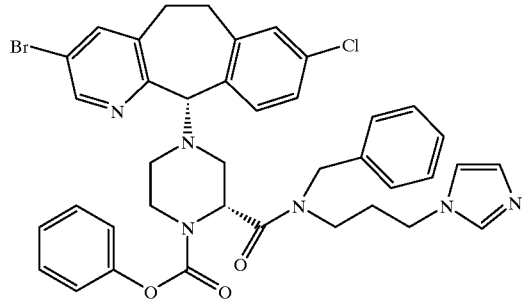 | 1. 50<br>2. 753<br>3. 91.1 |
| 169 | 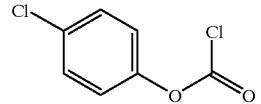<br>Prep Ex. 109<br>Diastereomer A | 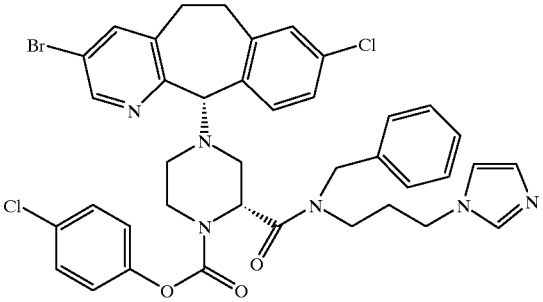 | 1. 91<br>2. 787<br>3. 87.3 |
| 170 | 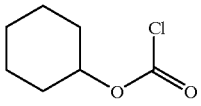 | 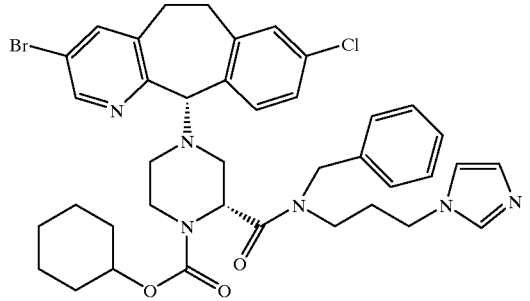 | 1. 83<br>2. 759<br>3. 78.7 |
| 171 | 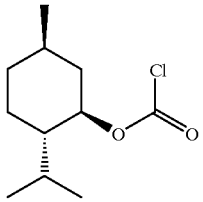<br>Prep Ex. 109<br>Diastereomer A | 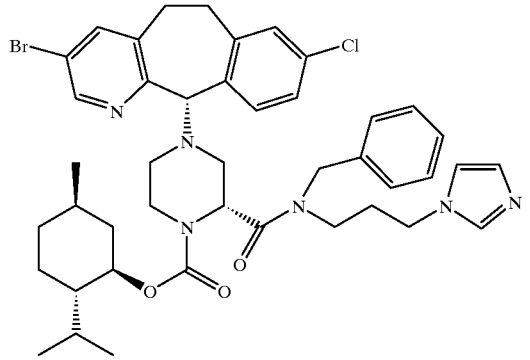 | 1. 96<br>2. 815<br>3. 96.4 |

TABLE 14-continued
| Ex. | Electrophile and Prep. Ex. Compound | Product | 1. Yield (%) 2. MH+ 3. mp (20 C.) |
|---|---|---|---|
| 172 | 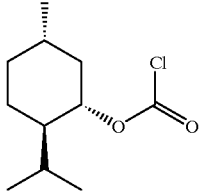<br>Prep Ex. 109<br>Diastereomer A | | 1. 88<br>2. 815<br>3. 95.8 |
| 173 | MeSO$_2$Cl<br>Prep Ex. 109<br>Diastereomer A | | 1. 68<br>2. 711<br>3. 113.6 |
| 174 | MeSO$_2$Cl<br>Prep Ex. 109<br>Diastereomer B | | 1. 83<br>2. 711<br>3. 114.6 |
| 175 | n-PrSO$_2$Cl<br>Prep Ex. 109<br>Diastereomer A | | 1. 50<br>2. 739<br>3. 86.5 |

TABLE 14-continued

| Ex. | Electrophile and Prep. Ex. Compound | Product | 1. Yield (%) 2. MH+ 3. mp (20 C.) |
|---|---|---|---|
| 176 | n-PrSO₂Cl<br>Prep Ex. 109<br>Diastereomer B | | 1. 15<br>2. 739<br>3. 93.8 |
| 177 | n-BuSO₂Cl<br>Prep Ex. 109<br>Diastereomer A | | 1. 40<br>2. 753<br>3. 87.9 |
| 178 | i-PrSO₂Cl<br>Prep Ex. 109<br>Diastereomer A | | 1. 21<br>2. 739<br>3. 93.2 |

TABLE 14-continued

| Ex. | Electrophile and Prep. Ex. Compound | Product | 1. Yield (%) 2. MH+ 3. mp (20 C.) |
|---|---|---|---|
| 179 | PhCH₂SO₂Cl Prep Ex. 109 Diastereomer A | | 1. 50 2. 787 3. 110.4 |
| 180 | (cyclobutanecarbonyl chloride) | | 1. 92 2. 715 3. 105.5 |
| 181 | (cyclopropanecarbonyl chloride) | | 1. 98 2. 701 3. 106.8 |
| 182 | (4-chlorophenyl chloroformate) Prep Ex. 109 Diastereomer B | | 1. 90 2. 787 3. 78.8 |

TABLE 14-continued
| Ex. | Electrophile and Prep. Ex. Compound | Product | 1. Yield (%) 2. MH+ 3. mp (20 C.) |
|---|---|---|---|
| 183 | 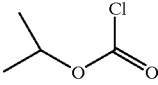<br>Prep Ex. 109<br>Diastereomer B | 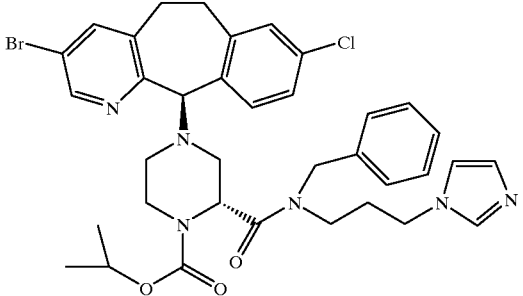 | 1. 57<br>2. 719<br>3. 95.2 |
| 184 | 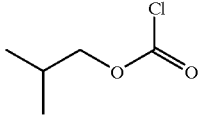<br>Prep Ex. 109<br>Diastereomer B | 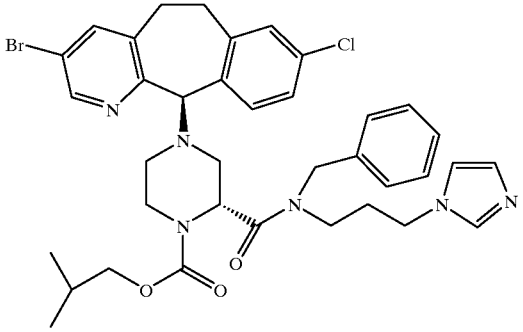 | 1. 95<br>2. 733<br>3. 84.9 |
| 185 | 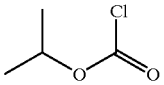<br>Prep Ex. 111<br>Diastereomer A | 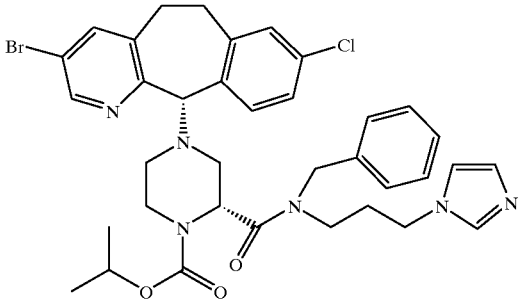 | 1. 53<br>2. 641<br>3. 89.6 |
| 186 | 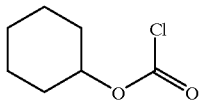<br>Prep Ex. 111<br>Diastereomer A | 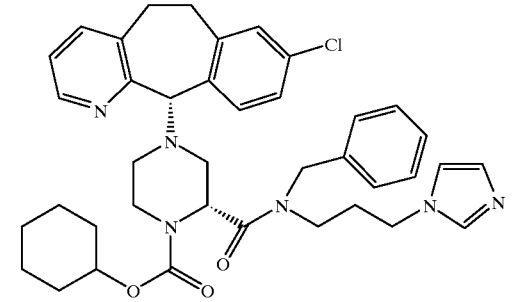 | 1. 68<br>2. 681<br>3. 101.1 |

TABLE 14-continued
| Ex. | Electrophile and Prep. Ex. Compound | Product | 1. Yield (%) 2. MH+ 3. mp (20 C.) |
|---|---|---|---|
| 187 | 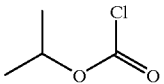<br>Prep Ex. 111<br>Diastereomer B | 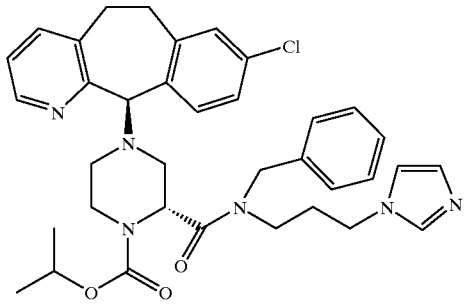 | 1. 77<br>2. 641<br>3. 68 |
| 188 | 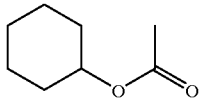<br>Prep Ex. 111<br>Diastereomer B | 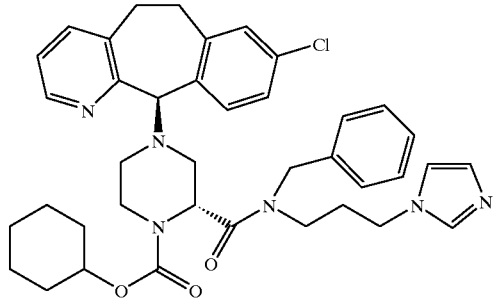 | 1. 61<br>2. 681<br>3. 87.9 |
| 189 | 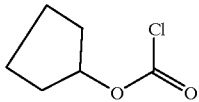<br>Prep Ex. 109<br>Diastereomer B | 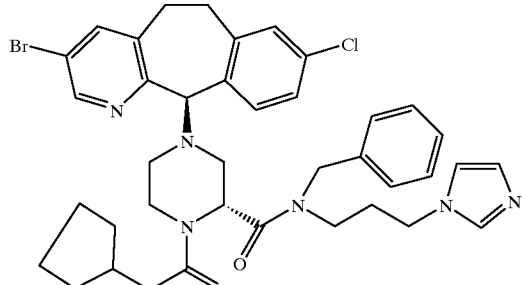 | 1. 85<br>2. 745<br>3. 94.2 |
| 190 | 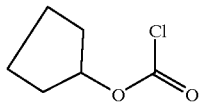<br>Prep Ex. 111<br>Diastereomer B | 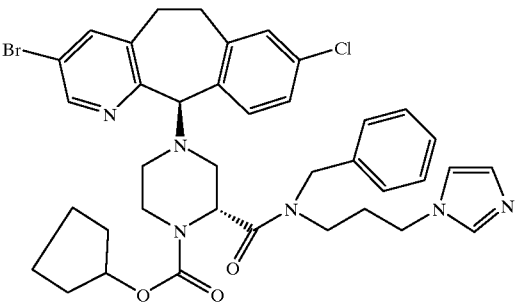 | 1. 72<br>2. 667<br>3. 97.2 |

TABLE 14-continued
| Ex. | Electrophile and Prep. Ex. Compound | Product | 1. Yield (%) 2. MH+ 3. mp (20 C.) |
|---|---|---|---|
| 191 | 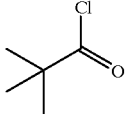<br>Prep Ex. 109<br>Diastereomer A | 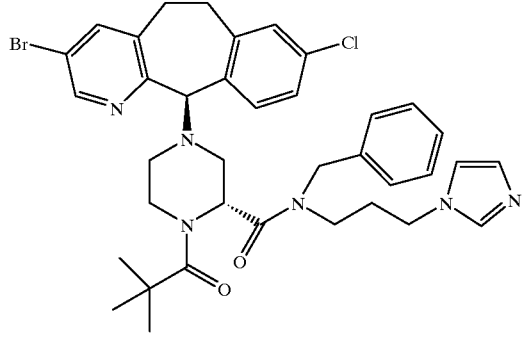 | 1. 52<br>2. 717<br>3. 91.8 |
| 192 | 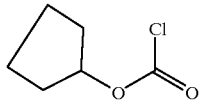<br>Prep Ex. 111<br>Diastereomer A | 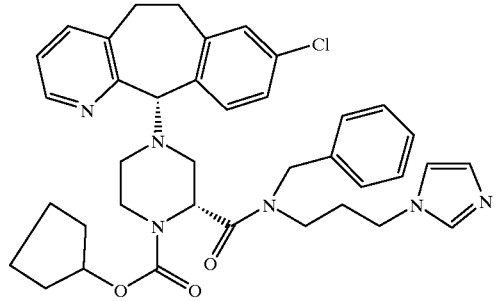 | 1. 81<br>2. 667<br>3. 85.8 |
| 193 | 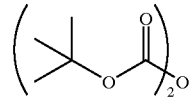<br>Prep Ex. 113<br>Diastereomer A | 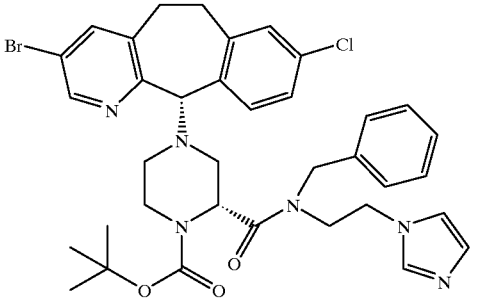 | 1. 76<br>2. 719<br>3. 206.7 |
| 194 | 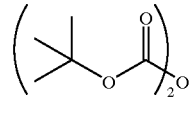<br>Prep Ex. 113<br>Diastereomer B | 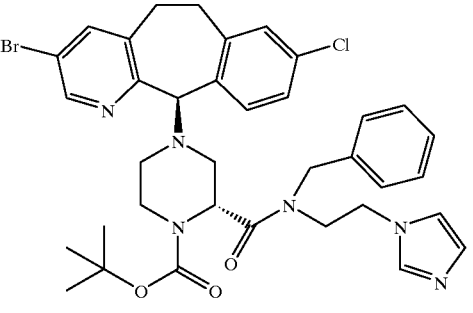 | 1. 85<br>2. 719<br>3. 121.2–130.4 |

TABLE 14-continued
| Ex. | Electrophile and Prep. Ex. Compound | Product | 1. Yield (%) 2. MH+ 3. mp (20 C.) |
|---|---|---|---|
| 195 | 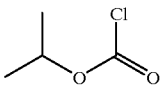<br>Prep Ex. 131<br>Diastereomer A | 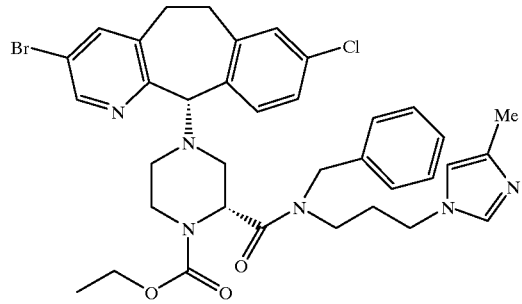 | 1. 69<br>2. 733<br>3. 96.1–120.3 |
| 196 | 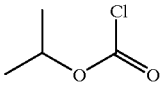<br>Prep Ex. 131<br>Diastereomer B | 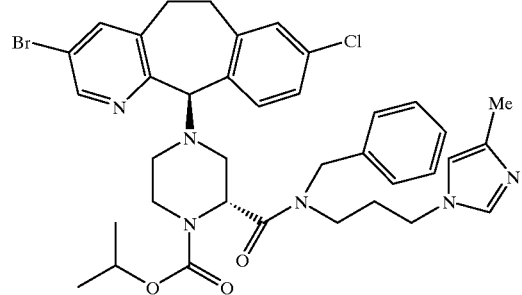 | 1. 77<br>2. 733<br>3. 105.1–114.2 |
| 197 | 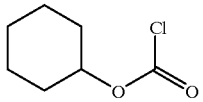<br>Prep Ex. 131<br>Diastereomer B | 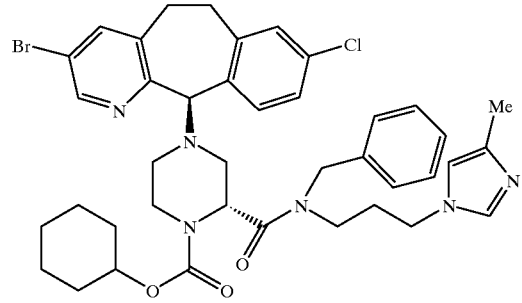 | 1. 56<br>2. 775<br>3. 100.4–108.8 |
| 198 | 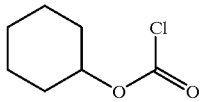<br>Prep Ex. 114<br>Diastereomer B | 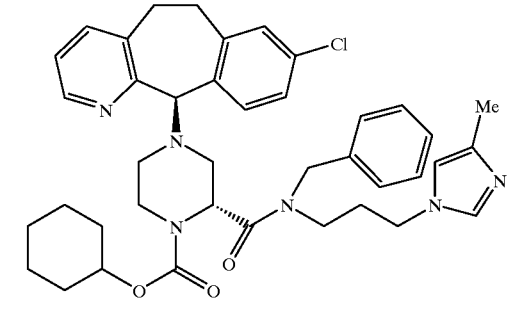 | 1. 69<br>2. 695<br>3. 82.5 |

TABLE 14-continued
| Ex. | Electrophile and Prep. Ex. Compound | Product | 1. Yield (%) 2. MH+ 3. mp (20 C.) |
|---|---|---|---|
| 199 | 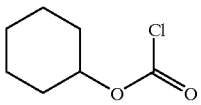<br>Prep Ex. 114<br>Diastereomer A | 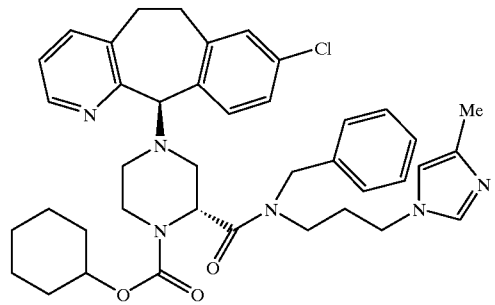 | 1. 60<br>2. 695<br>3. 83.4 |
| 200 | 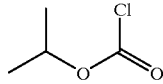<br>Prep Ex. 114<br>Diastereomer A | 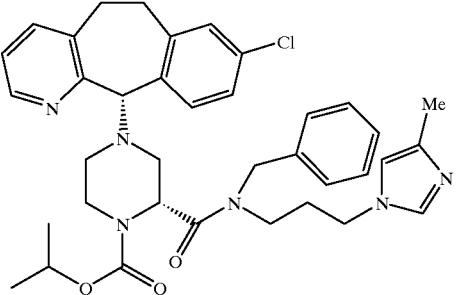 | 1. 61<br>2. 655<br>3. 83.2 |
| 201 | 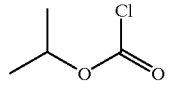<br>Prep Ex. 114<br>Diastereomer B | 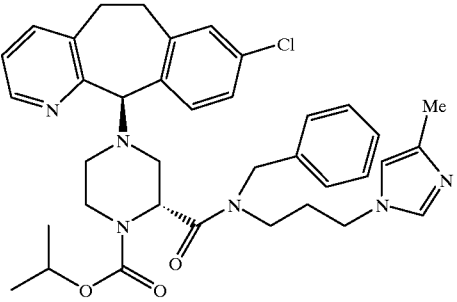 | 1. 64<br>2. 655<br>3. 81.2 |
| 202 | 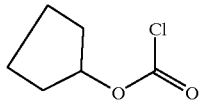<br>Prep Ex. 114<br>Diastereomer A | 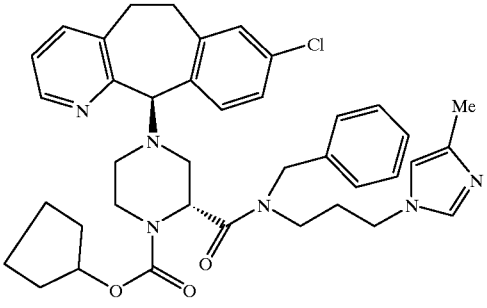 | 1. 72<br>2. 681<br>3. 98.2 |

TABLE 14-continued

| Ex. | Electrophile and Prep. Ex. Compound | Product | 1. Yield (%) 2. MH+ 3. mp (20 C.) |
|---|---|---|---|
| 203 | Prep Ex. 114 Diastereomer B | | 1. 76 2. 681 3. 94.5 |
| 204 | Prep Ex. 108 Diastereomer A | | 1. 62 2. 659 3. 97.8 |
| 205 | Prep Ex. 108 Diastereomer B | | 1. 83 2. 56.7 3. 659 |
| 206 | Prep Ex. 117 Diastereomer A | | 1. 64 2. 734 3. 114.9 |

TABLE 14-continued

| Ex. | Electrophile and Prep. Ex. Compound | Product | 1. Yield (%) 2. MH+ 3. mp (20 C.) |
|---|---|---|---|
| 207 | Prep Ex. 117 Diastereomer B | | 1. 36 2. 734 3. 124.2 |
| 208 | Prep Ex. 121 Diastereomer A | | 1. 45 2. 711 3. 95.1 |
| 208 A | Prep Ex. 121 Diastereomer A | | — |
| 209 | Prep Ex. 121 Diastereomer B | | 1. 39 2. 711 3. 101.8 |

TABLE 14-continued

| Ex. | Electrophile and Prep. Ex. Compound | Product | 1. Yield (%) <br> 2. MH+ <br> 3. mp (20 C.) |
|---|---|---|---|
| 209 A | Prep Ex. 121 Diastereomer B | | — |
| 210 | Prep Ex. 121 Diastereomer A | | 1. 49 <br> 2. 697 <br> 3. 64.3 |
| 210 A | Prep Ex. 121 Diastereomer A | | — |

TABLE 14-continued
| Ex. | Electrophile and Prep. Ex. Compound | Product | 1. Yield (%) 2. MH+ 3. mp (20 C.) |
|---|---|---|---|
| 210 B | 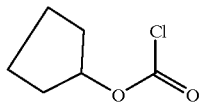 Prep Ex. 121 Diastereomer B | 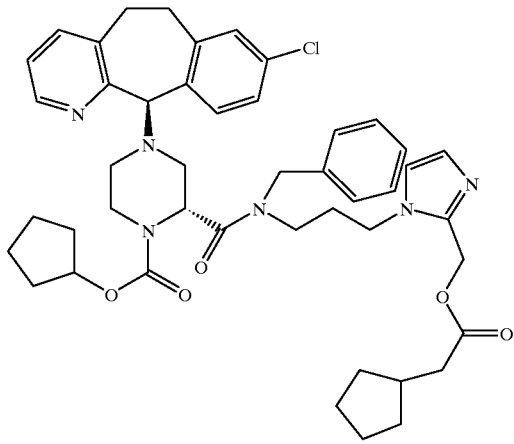 | — |
| 211 | 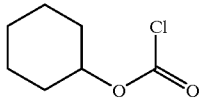 Prep Ex. 124 Diastereomer A | 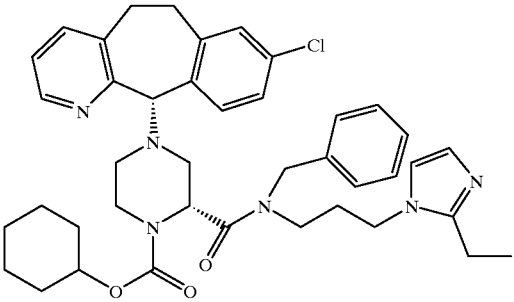 | 1. 93 2. 709 3. 83.2 |
| 212 | 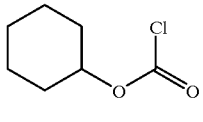 Prep Ex. 124 Diastereomer B | 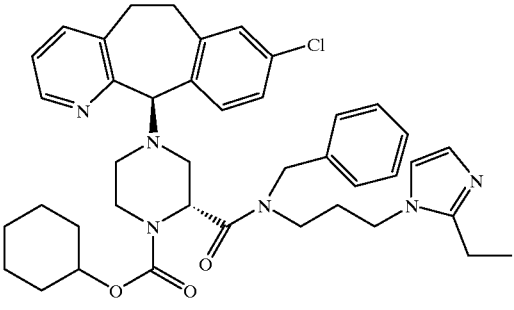 | 1. 94 2. 709 3. 83.6 |
| 213 | 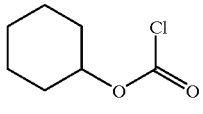 Prep Ex. 124 Diastereomer A | 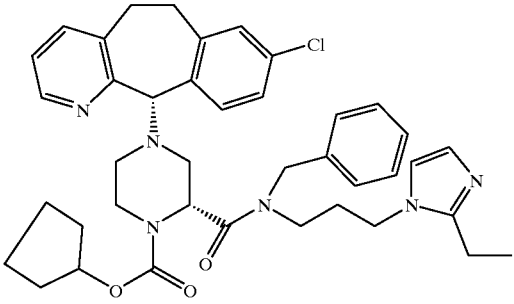 | 1. 68 2. 695 3. 88.2 |

TABLE 14-continued

| Ex. | Electrophile and Prep. Ex. Compound | Product | 1. Yield (%) 2. MH+ 3. mp (20 C.) |
|---|---|---|---|
| 214 | MeSO₂Cl Prep Ex. 125 | | 1. 81 2. 598 3. 81 |
| 215 | MeSO₂Cl Prep Ex. 11 Diastereomer A | | 1. 69 2. 633 3. 69 |
| 216 | MeSO₂Cl Prep Ex. 111 Diastereomer B | | 1. 71 2. 633 3. 106 |
| 217 | Prep Ex. 130 | | 1. 73 2. 736 |

EXAMPLE 218

If the procedure described in Example 149 were followed, the title compound from Preparative Example 109 (diastereomer A) could be reacted with

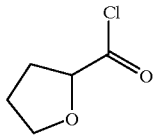

to give the compound

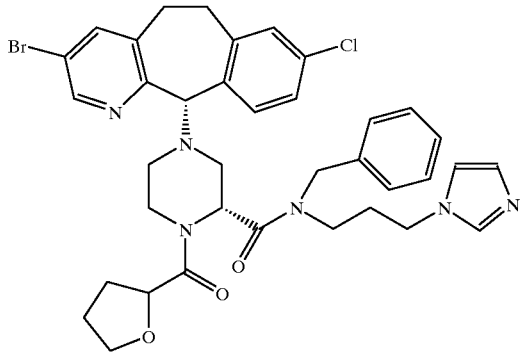

EXAMPLE 219

If the procedure described in Example 149 were followed, the title compound from Preparative Example 109 (diastereomer A) could be reacted with

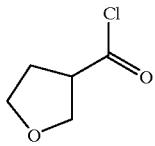

to give the compound

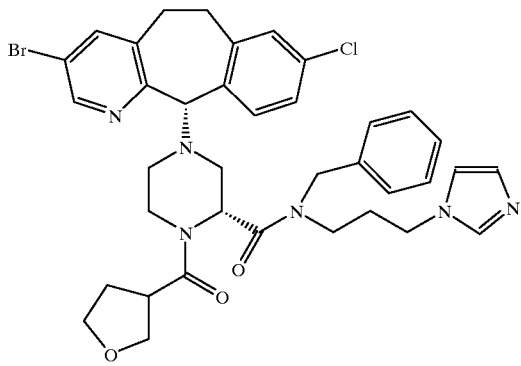

EXAMPLE 220

If the procedure set forth in Preparative Example 51 were followed, but substituting the 3,8-dichloro tricyclic alcohol

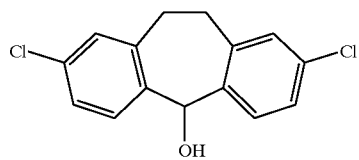

for the 3-Br-8-Cl tricyclic alcohol, the following compound could be prepared:

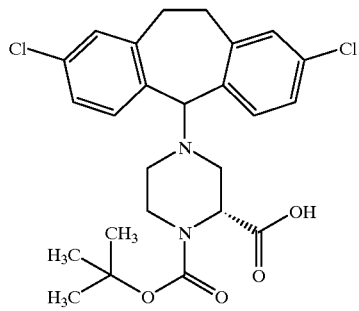

Then, if the procedure of Example 113 were followed to react the above compound with the title compound from Preparative Example 95.1 the following compound could be obtained

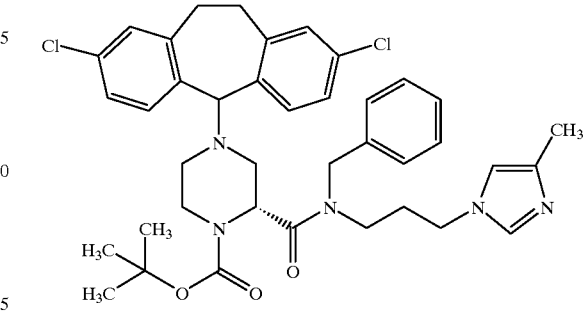

Then, if the procedure of Preparative Example 109 were followed using the above compound the following compound could be obtained:

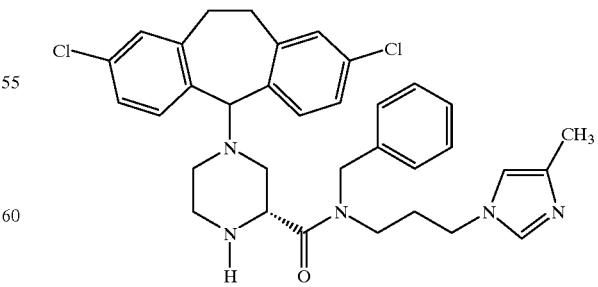

Then if the procedure of Example 149 were followed using the above compound and

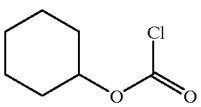

the following compound could be obtained

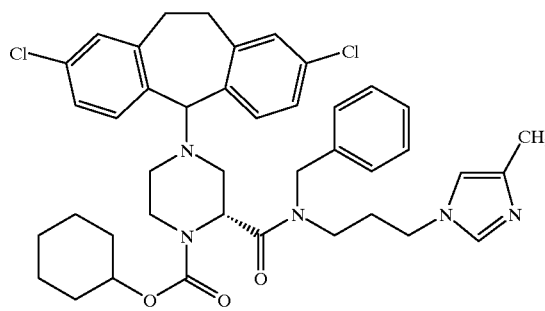

EXAMPLE 220A

If the procedure of Example 220 were followed, but the title compound from Preparative Example 90 were used instead of the title compound from Preparative Example 95.1 in the procedural step of Example 113, the following compound could be obtained

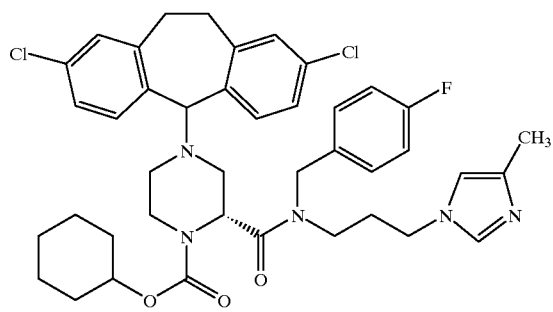

EXAMPLE 221

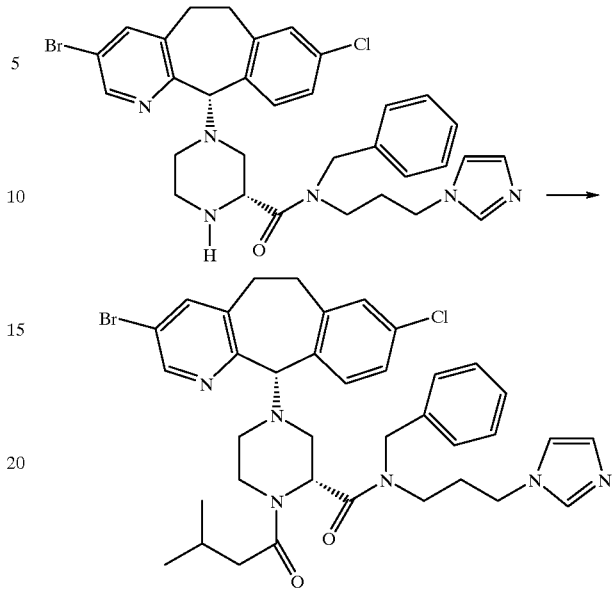

To a solution of the title compound from Preparative Example 109 (11S,2Rdiastereomer A, 75 mg, 0.12 mmol) dissolved in anhydrous DMF (1 mL) was added HOBT (32 mg, 0.24 mmol), DEC (45.4 mg, 0.24 mmol) and isovaleric acid (0.026 mL, 0.24 mmol) and the resulting solution was stirred at room temperature under $N_2$ overnight. The solution was concentrated in vacuo, diluted with dichloromethane, washed with 1N aqueous NaOH and dried over anhydrous $MgSO_4$. Filtration and concentration in vacuo provided a residue which was purified by preparative plate chromatography (silica gel) using 5% MeOH-95% $CH_2Cl_2$ saturated with aqueous ammonium hydroxide to give the title compound as an off-white solid (81.5 mg, 96%, $MH^+$=717).

EXAMPLES 222–224

Following the procedure described for Example 221, the title compound (diastereomer A or B) from Preparative Example 109 was treated with the carboxylic acid given in Table 15 to give the N-benzyl Product listed in Table 15.

TABLE 15

| Ex. | Carboxylic Acid and Diastereomer of Prep. Ex. 109 | Product | 1. Yield (%) 2. $MH^+$ 3. mp (° C.) |
|---|---|---|---|
| 222 | ![cyclohexylacetic acid] Diastereomer A | ![product 222] | 1. 74 2. 757 3. 94.7 |

TABLE 15-continued

| Ex. | Carboxylic Acid and Diastereomer of Prep. Ex. 109 | Product | 1. Yield (%) 2. MH+ 3. mp (° C.) |
|---|---|---|---|
| 223 | (cyclohexylacetic acid) Diastereomer B | (structure) | 1. 85 2. 757 3. 104.2 |
| 224 | (piperidine-carboxamide acetic acid) Diastereomer A | (structure) | 1. 59 2. 801 3. 129.3 |

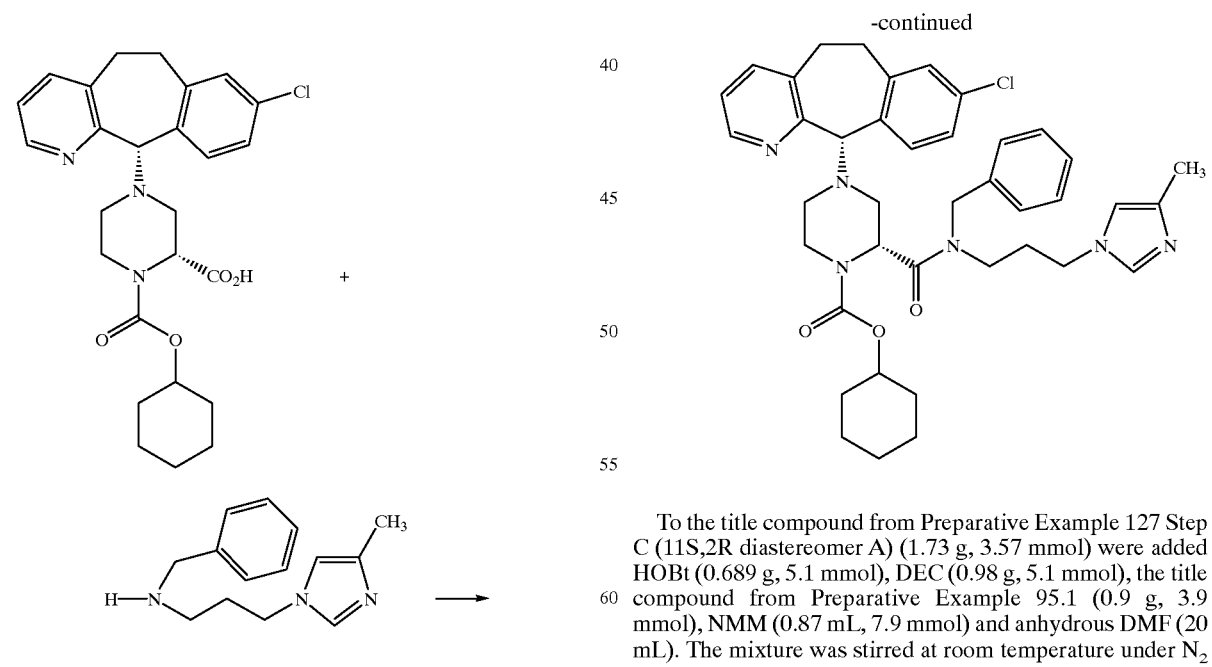

To the title compound from Preparative Example 127 Step C (11S,2R diastereomer A) (1.73 g, 3.57 mmol) were added HOBt (0.689 g, 5.1 mmol), DEC (0.98 g, 5.1 mmol), the title compound from Preparative Example 95.1 (0.9 g, 3.9 mmol), NMM (0.87 mL, 7.9 mmol) and anhydrous DMF (20 mL). The mixture was stirred at room temperature under N₂ overnight. The mixture was concentrated in vacuo, diluted with CH$_2$Cl$_2$ and washed with a saturated aqueous solution of NaHCO$_3$. The organic phase was dried over anhydrous MgSO$_4$, filtered and concentrated in vacuo. The residue was purified by flash column chromatography (silica gel) using 2% MeOH-98% CH$_2$Cl$_2$ saturated with aqueous ammonium hydroxide to give the title compound (1.7 g, 69%, MH$^+$= 695).

EXAMPLES 226–232

Following the procedure described for Example 225, the Products listed in Table 16 below were prepared using the carboxylic acid from Preparative Example 127 Step C (diastereomer A) and the appropriate N-substituted imidazolylalkyl amine purified by preparative chiral chromatography (Chiralpack AD, 5 cm×50 cm column, flow rate 80 mL/min, 5–13% IPA-Hexane +0.2% diethylamine).

TABLE 16

| Ex. | Amine of Prep Ex. No. | Product | 1. Yield (%) 2. MH$^+$ 3. mp (° C.) |
|---|---|---|---|
| 226 | 89 | | 1. 40 2. 709 3. 92.4 |
| 227 | 86 | | 1. 43 2. 696 3. 93.7 |
| 228 | 90 | | 1. 39 2. 713 3. 74.6 |

TABLE 16-continued

| Ex. | Amine of Prep Ex. No. | Product | 1. Yield (%) 2. MH+ 3. mp (° C.) |
|---|---|---|---|
| 229 | 91 | | 1. 44 2. 708 3. 85.6 |
| 230 | 93 | | 1. 29 2. 681 3. 82.2 |
| 231 | 94 | | 1. 71 2. 695 3. 79.7 |

TABLE 16-continued

| Ex. | Amine of Prep Ex. No. | Product | 1. Yield (%) 2. MH+ 3. mp (° C.) |
|---|---|---|---|
| 232 | 101 | 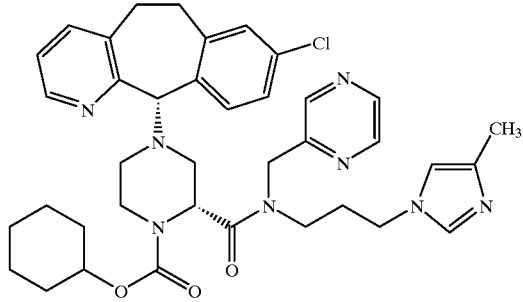 | 1. 62 2. 709 3. 85.6 |

EXAMPLE 234B

If the procedure of Example 225 were followed, but the amine from Preparative Example 101.2 was to be used, then the following compound would be obtained Example 234B

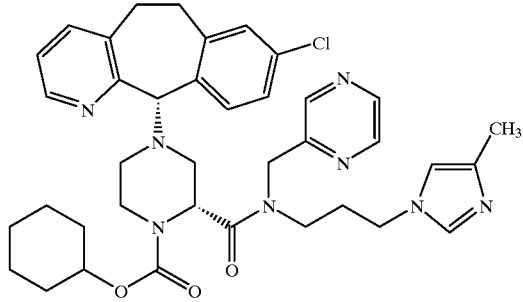

EXAMPLE 235

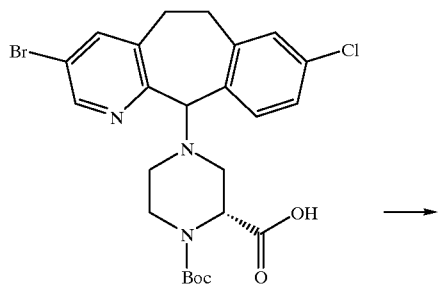

-continued

The title compound from Preparative Example 51 (0.184 g, 0.35 mmoles.) was added to a solution of the title compound from Preprative Example 132 Step C (0.2 g, 0.437 mmol), DEC (0.168 g, 0.87 mmoles.), HOBT (0.118 g, 0.87 mmoles.) and NMM (0.22 g, 2.19 mmoles.) in DMF (10 mL). The resulting solution was stirred at room temperature 24 hours. The reaction mixture was diluted with $H_2O$ until precipitation ceased and the slurry filtered. The precipitate was diluted with $CH_2Cl_2$, washed with brine, dried over $Na_2SO_4$ and concentrated. The crude product was purified by chromatography using a 5% (10% $NH_4OH$ in MeOH) solution in $CH_2Cl_2$ as eluent to give the title compound (0.18 g, 42% yield).

EXAMPLES 236–238

Following essentially the same procedure as set forth in Example 235, except using the amine given in Table 18, compounds of the formula

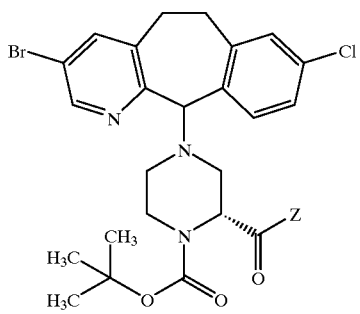

are obtained, wherein Z is as defined in Table 18.

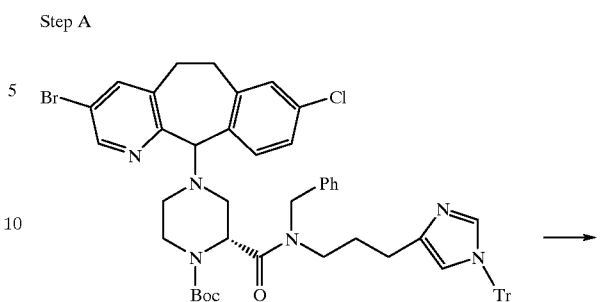

TABLE 18

| Ex. | Amine | Z |
|---|---|---|
| 236 | ![structure] | ![structure] |
|  |  | FAB: MH⁺ = 975 |
| 237 | ![structure] | ![structure] |
|  |  | FAB: MH⁺ = 747 |
| 238 | ![structure] | ![structure] |
|  |  | FAB: MH⁺ = 735 |

EXAMPLE 239

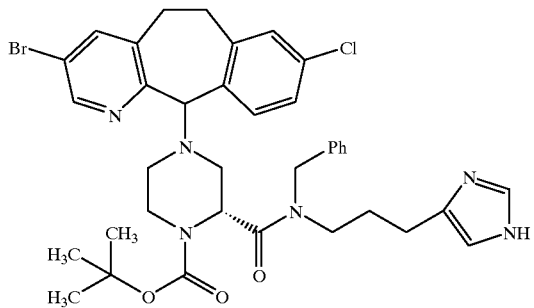

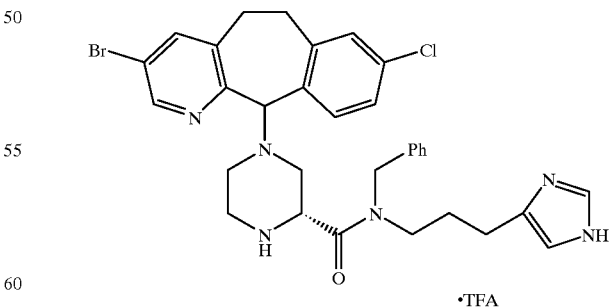

The title compound from Example 235 (0.5 g, 0.517 mmoles) in CH$_2$Cl$_2$ (50 mL) was stirred with TFA (6 mL) at room temperature overnight. The reaction mixture was evaporated to give the title compound as a TFA salt (0.743 g) which was used for following reactions.

Step B

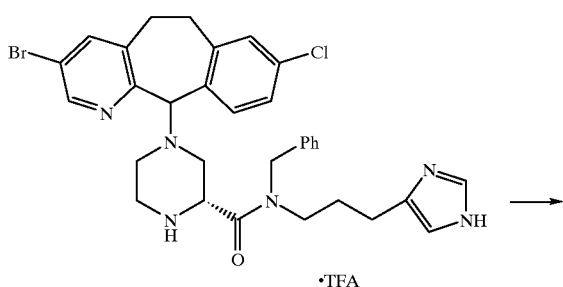

·TFA

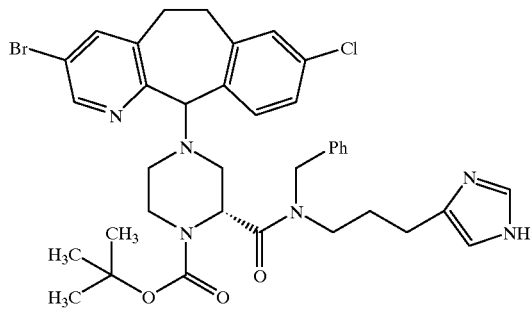

To a stirred solution of the title compound from Step A (0.102 g, 0.0936 mmoles), triethyl amine (0.0798 g, 0.798 mmoles) in CH₂Cl₂, di-tert-butyldicarbonate (0.0515 g, 0.236 mmoles) was added and stirred overnight. Evaporated to a residue which was stirred in 2N ammonia solution in methanol (2 mL) overnight and evaporated to dryness. The residue was chromatographed on silica gel using 5% (10% conc NH₄OH in methanol) to give the title compound (0.043 g).

EXAMPLES 240–243

Following essentially the same procedure as that set forth in Example 239 Step B, except using the chloroformate given in Table 19 below, compounds of the formula:

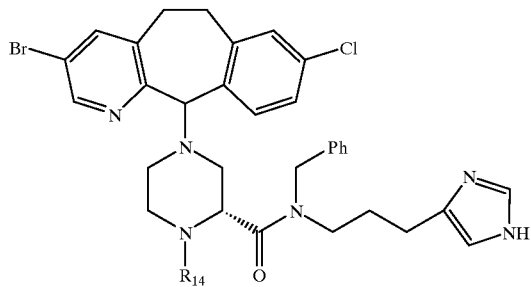

were obtained, wherein R¹⁴ is as defined in Table 19.

TABLE 19 / TABLE 19-continued

| Ex. | Chloroformate | R¹⁴ | |
|-----|---------------|-----|---|
| 240 | H₃C—C(CH₃)₂—O—C(O)Cl | H₃C—C(CH₃)₂—O—C(O)— | (R, S) FAB: MH⁺ = 733 |
| 241 | (CH₃)₂CH—O—C(O)Cl | (CH₃)₂CH—O—C(O)— | (R, S) FAB: MH⁺ = 719 |
| 242 | (CH₃)₂CHCH₂—O—C(O)Cl | (CH₃)₂CHCH₂—O—C(O)— | (R, S) FAB: MH⁺ = 733 |
| 243 | cyclohexyl—O—C(O)Cl | cyclohexyl—O—C(O)— | (R, S) FAB: MH⁺ = 759 |

EXAMPLE 244

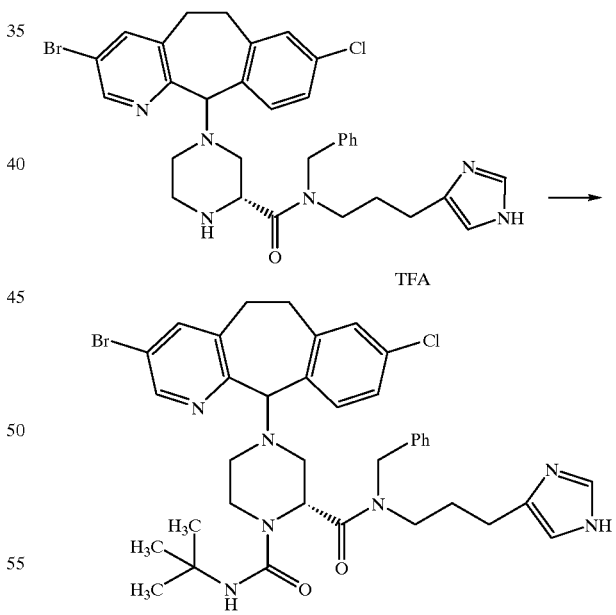

To a solution of the title compound from Step A of Example 239 (0.126 g, 0.126 mmoles), triethylamine (0.071 g, 0.726 mmoles) in CH₂Cl₂ (5 mL), t-butylisocyanate (0.018 g, 0.189 mmoles) was added. The resulting solution was stirred at room temperature overnight. Evaporated to dryness and the residue was then stirred with 2N ammonia solution in methanol (3 mL) overnight. Evaporated to dryness and the product was chromatographed on silica gel using 5% (10% conc. NH$_4$OH in methanol)-CH$_2$Cl$_2$ as the eluant to give the title compound. (0.046 g) CIMS: m/z (MH$^+$) 732.

EXAMPLES 245–254

Following the procedures set forth in Examples 77–79 and 86, but using the diastereomeric mixture A and B from Preparative Example 135 and the appropriate amido-imidazole, the following compounds were prepared:

(Example 245)

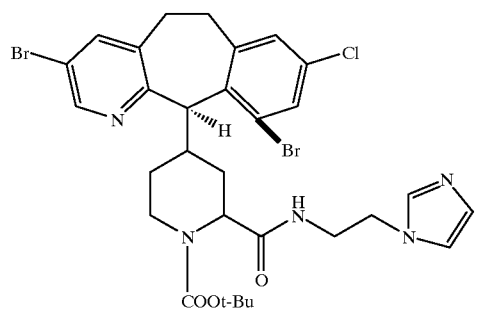

(Example 246)

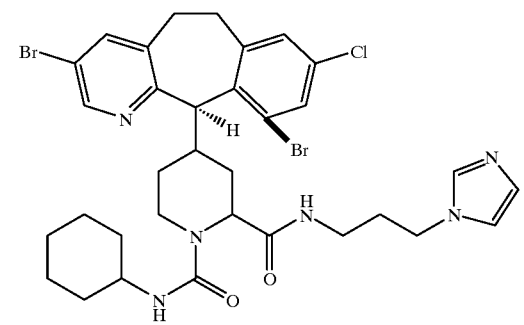

(Example 247)

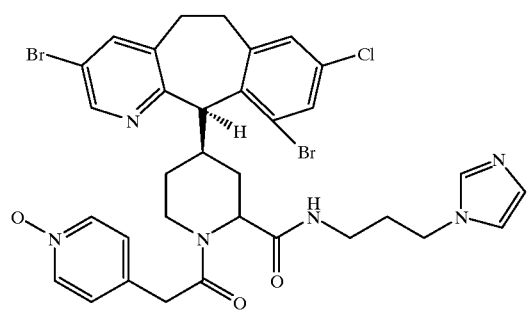

(Example 248)

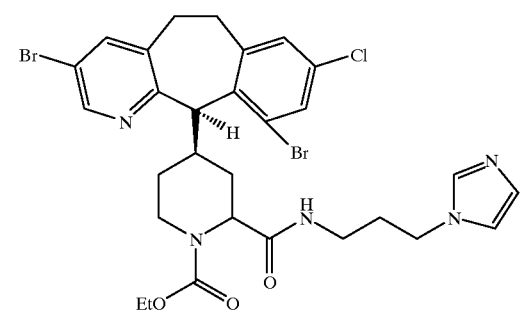

-continued (Example 249)

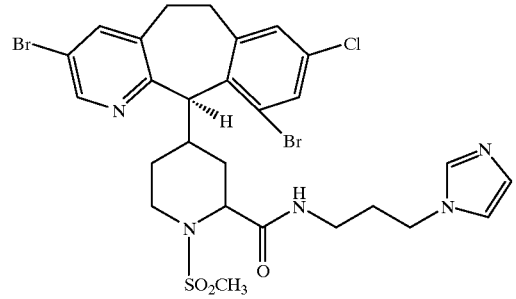

(Example 250)

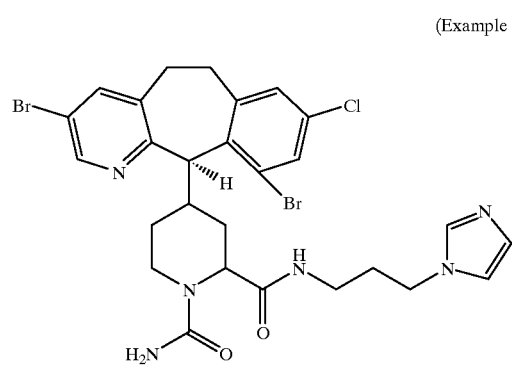

(Example 251)

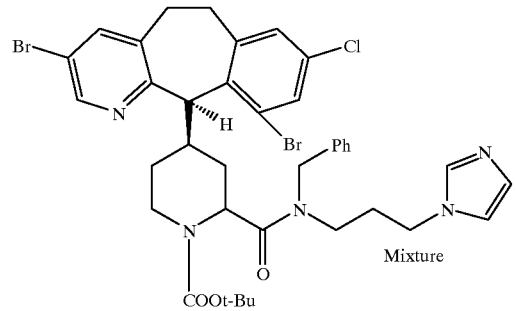

(Example 252)

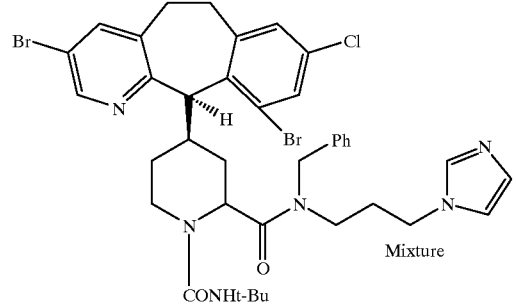

327
-continued (Example 253)

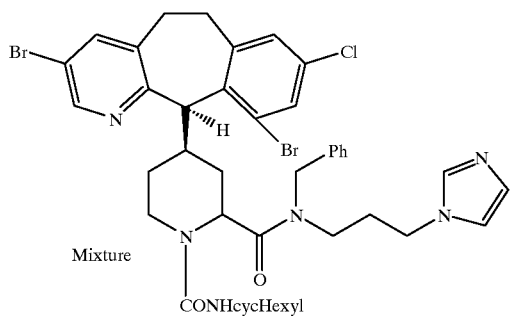

328
-continued (Example 254)

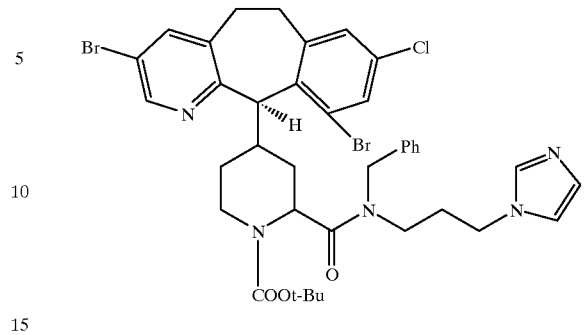

EXAMPLES 255–278

Following the procedure described for Example 127, the title compound (diastereomer A or B or A+B) from the Preparative Example indicated in Table 20 below was treated with the corresponding isocyanate to give the urea products listed in Table 20.

TABLE 20

| Ex. | Isocyanate and Prep. Ex. | Product | 1. Yield (%) 2. MH+ 3. mp (° C.) |
|---|---|---|---|
| 255 | 4-Cl-C6H4-NCO<br>139<br>diastereomer A | (A) | 1. 49<br>2. 695<br>3. 159.1 |
| 256 | t-Bu-NCO<br>139<br>diastereomer B | (B) | 1. 65<br>2. 642<br>3. 141.5 |

TABLE 20-continued
| Ex. | Isocyanate and Prep. Ex. | Product | 1. Yield (%) 2. MH⁺ 3. mp (° C.) |
|---|---|---|---|
| 257 | 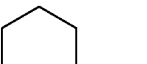<br>139<br>diastereomer A | 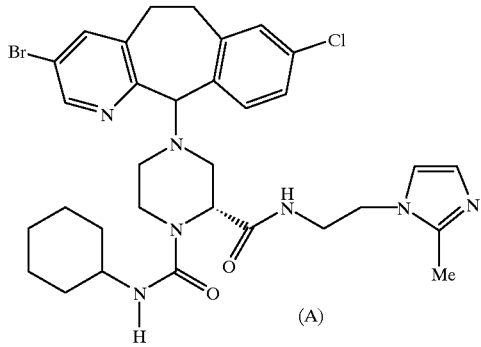<br>(A) | 1. 82<br>2. 668<br>3. 147.5 |
| 258 | <br>139<br>diastereomer B | 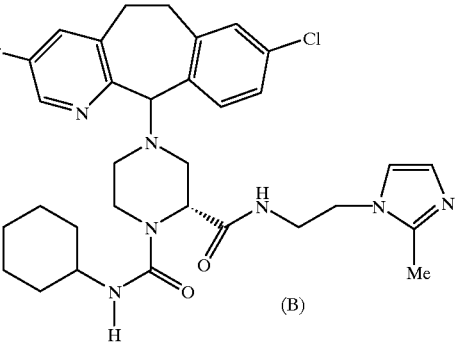<br>(B) | 1. 90<br>2. 668<br>3. 148.2 |
| 259 | 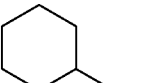<br>140<br>diastereomer A + B | 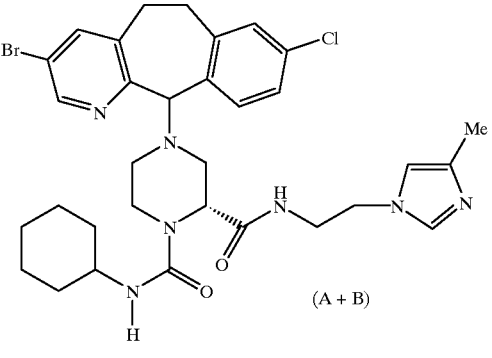<br>(A + B) | 1. 7<br>2. 668<br>3. 141.5–146.6 |
| 260 | 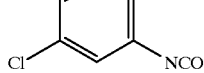<br>140<br>diastereomer A + B | 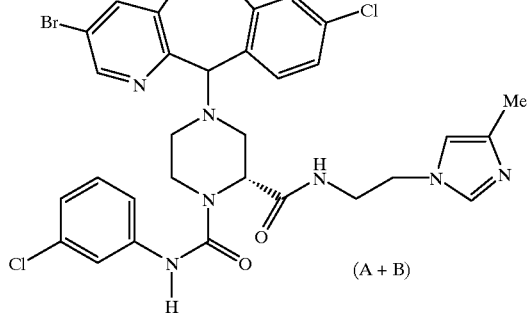<br>(A + B) | 1. 17<br>2. 696<br>3. 136.1 |

TABLE 20-continued
| Ex. | Isocyanate and Prep. Ex. | Product | 1. Yield (%)<br>2. MH+<br>3. mp (° C.) |
|---|---|---|---|
| | | 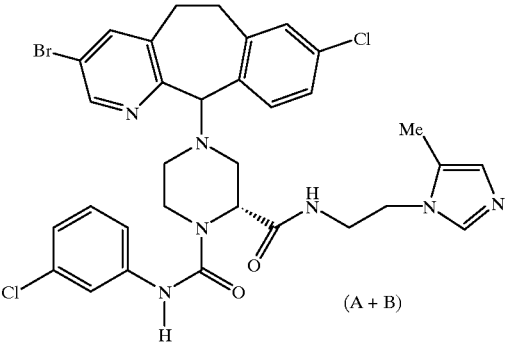 (A + B) | |
| 261 | 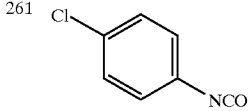<br>140<br>diastereomer<br>A + B | 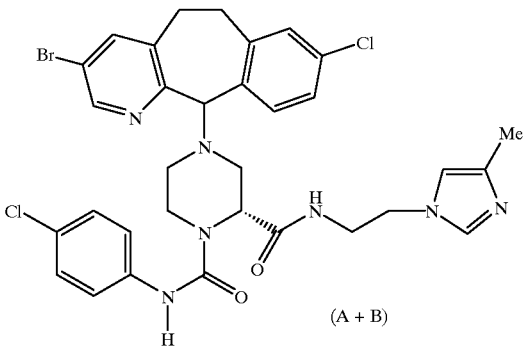 (A + B) | 1. 15<br>2. 696<br>3. 140.8 |
| 262 | 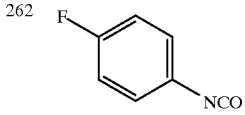<br>140<br>diastereomer<br>A + B | 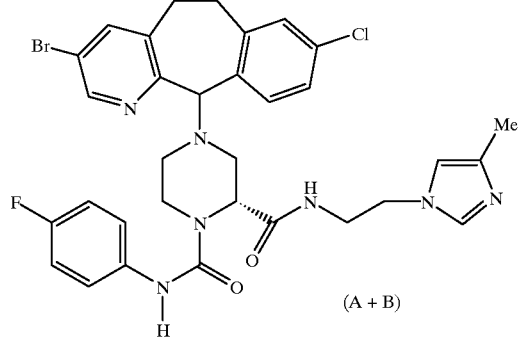 (A + B) | 1. 12<br>2. 680<br>3. 130.3 |

TABLE 20-continued

| Ex. | Isocyanate and Prep. Ex. | Product | 1. Yield (%) 2. MH⁺ 3. mp (° C.) |
|---|---|---|---|
| | | (A + B) | |
| 263 | TMS-NCO 142 | (A + B) | 1. 25 2. 711 3. 165.5 |
| | | (A + B) | |
| 264 | cyclohexyl-NCO 152 | (A) | 1. 34 2. 682 3. 131.6 |

TABLE 20-continued
| Ex. | Isocyanate and Prep. Ex. | Product | 1. Yield (%) 2. MH+ 3. mp (° C.) |
|---|---|---|---|
| 265 | 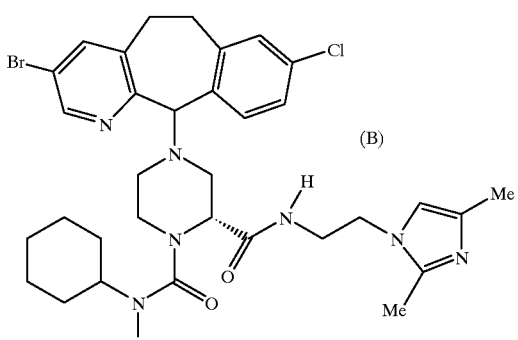 153 | 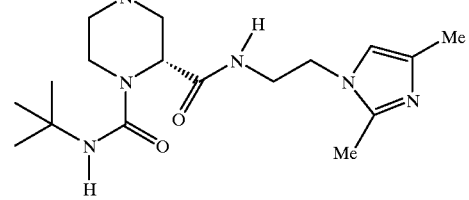 (B) | 1. 71 2. 682 3. 120.6 |
| 266 | 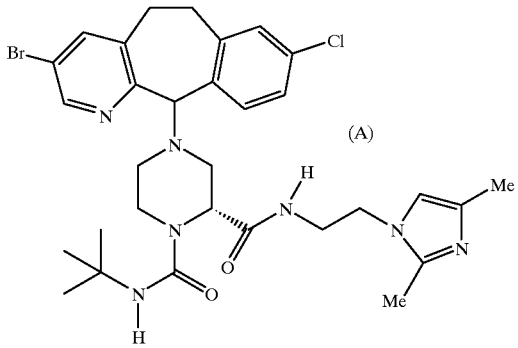 152 | 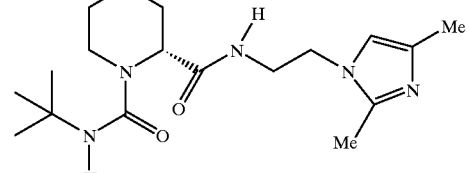 (A) | 1. 65 2. 656 3. 143.6 |
| 267 | 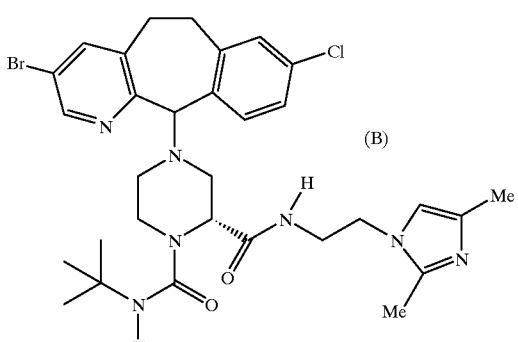 153 | 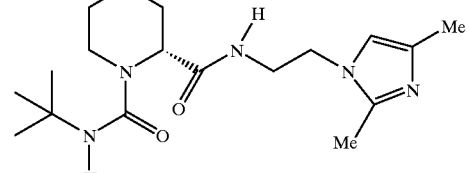 (B) | 1. 64 2. 656 3. 142.9 |
| 268 | 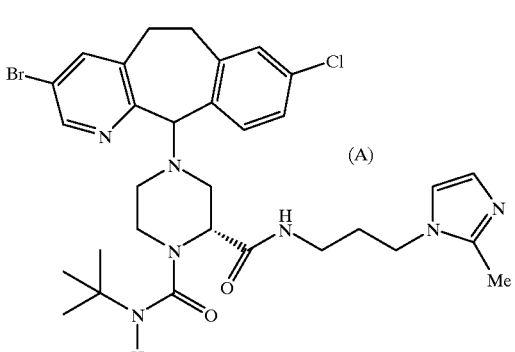 154 diastereomer A | 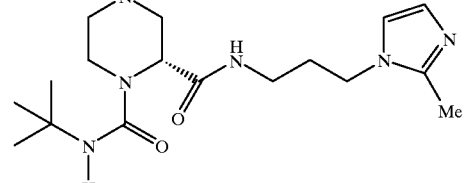 (A) | 1. 83 2. 656 3. 142.8 |

TABLE 20-continued
| Ex. | Isocyanate and Prep. Ex. | Product | 1. Yield (%) 2. MH+ 3. mp (° C.) |
|---|---|---|---|
| 269 | 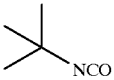 154 diastereomer B | 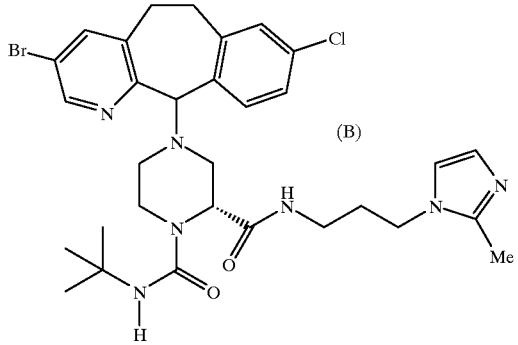 (B) | 1. 89 2. 656 3. 146.8 |
| 270 | 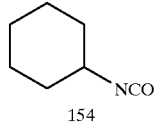 154 diastereomer A + B | 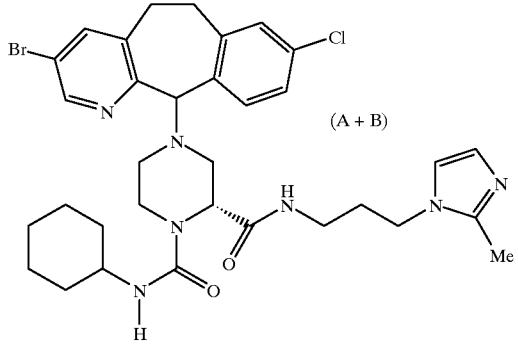 (A + B) | 1. 43 2. 682 3. 144.6 |
| 271 | 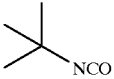 158 diastereomer A + B | 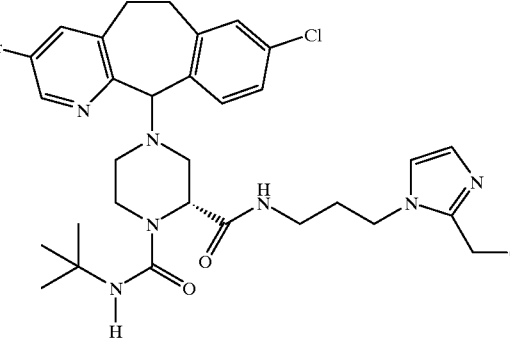 | 1. 52 2. 672 3. 122.5–143.6 |
| 272 | 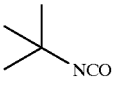 158 diastereomer A + B | 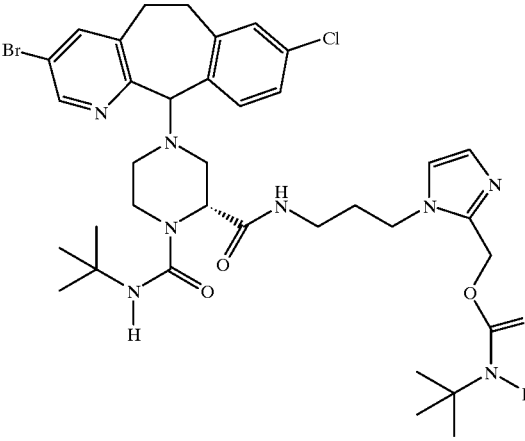 | 1. 21 2. 769 3. 141.0 |

TABLE 20-continued
| Ex. | Isocyanate and Prep. Ex. | Product | 1. Yield (%) 2. MH+ 3. mp (° C.) |
|---|---|---|---|
| 273 | 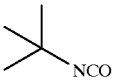 159 diastereomer A + B | 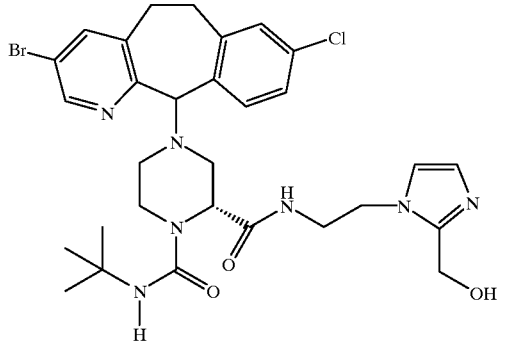 | 1. 61 2. 658 3. 151.7 |
| 274 | 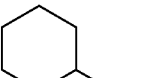 159 diastereomer A + B | 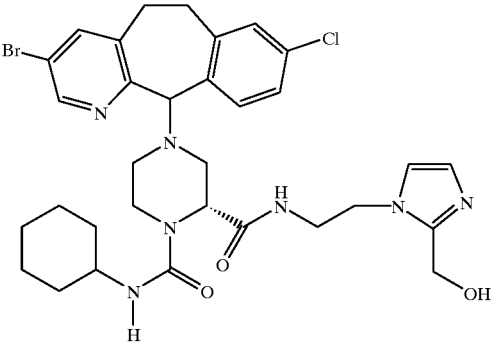 | 1. 48 2. 683 3. 133.1 |
| 275 | 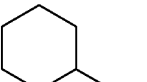 159 diastereomer A + B | 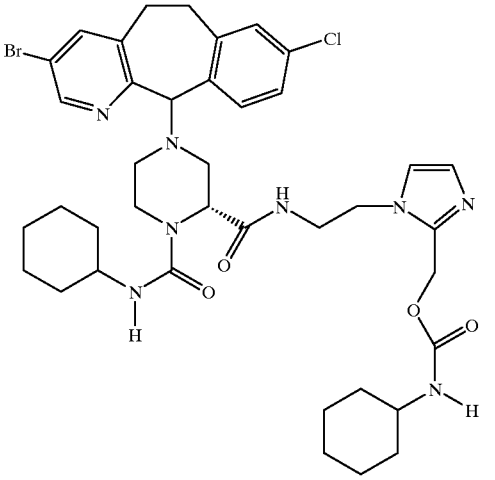 | 1. 46 2. 809 3. 131.2 |

TABLE 20-continued

| Ex. | Isocyanate and Prep. Ex. | Product | 1. Yield (%) 2. MH+ 3. mp (° C.) |
|---|---|---|---|
| 276 | 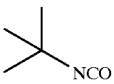 160 diastereomer A + B | 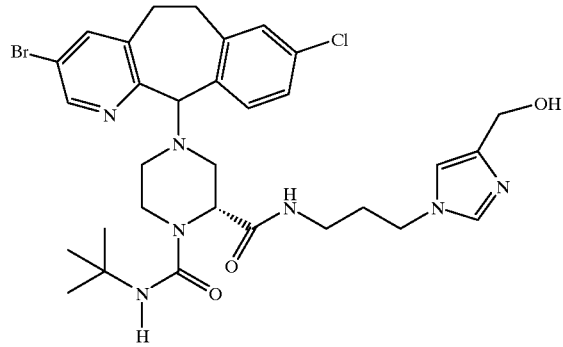 | 1. 52 2. 672 3. 130.8 |
| 277 | 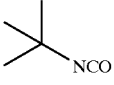 160 diastereomer A + B | 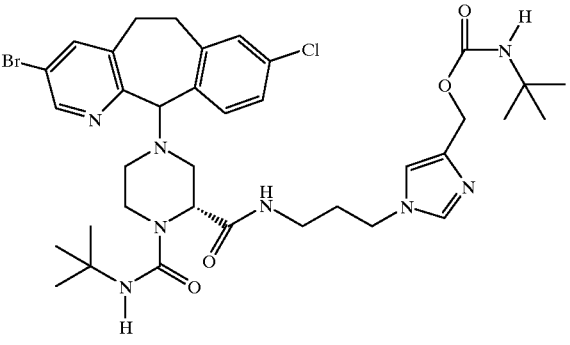 | 1. 38 2. 771 3. 144.6 |
| 278 | 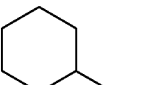 158 diastereomer A + B | 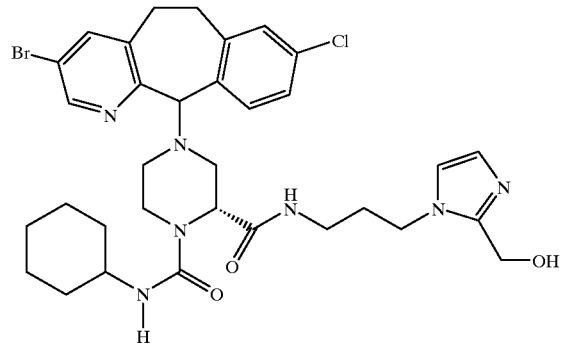 | 1. 75 2. 698 3. 141.2 |

EXAMPLES 279–286

Following the procedure described for Example 149, the title compound (diastereomer A or B or A+B) from the Preparative Example indicated in Table 21 below was treated with the corresponding acid chloride, chloroformate, carbamyl chloride, dicarbonate, anhydride or sulfonyl chloride to give the products listed in the Table 21.

TABLE 21

| Ex. | Electrophile and Prep. Exam. | Product | 1. Yield (%) 2. MH+ 3. mp (° C.) |
|---|---|---|---|
| 279 | PhCH₂SO₂Cl 139 diastereomer A | (A) | 1. 66 2. 697 3. 148.5 |
| 280 | CH₃SO₂Cl 140 diastereomer A + B | (A+B) (A + B) | 1. 10 2. 621 3. 134.8 |
| 281 | CH₃CH₂SO₂Cl 140 diastereomer A + B | (A + B) (A + B) | 1. 11 2. 635 3. 124.8 |

TABLE 21-continued
| Ex. | Electrophile and Prep. Exam. | Product | 1. Yield (%) 2. MH+ 3. mp (° C.) |
|---|---|---|---|
| 282 | CH₃CH₂COCl 140 diastereomer A + B | 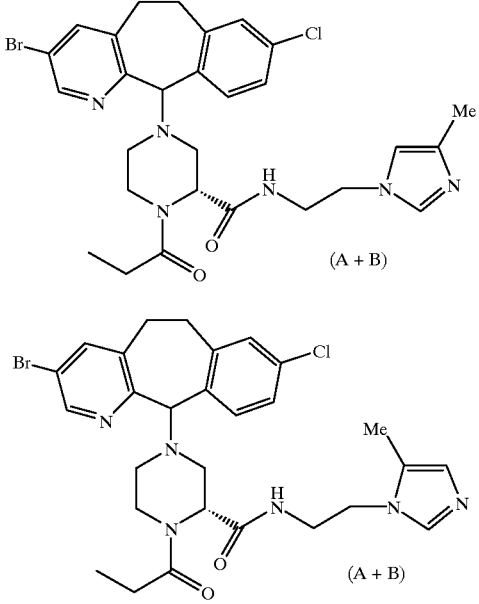 | 1. 17 2. 599 3. 93.2 |
| 283 | CH₃CH₂CH₂COCl 140 diastereomer A + B | 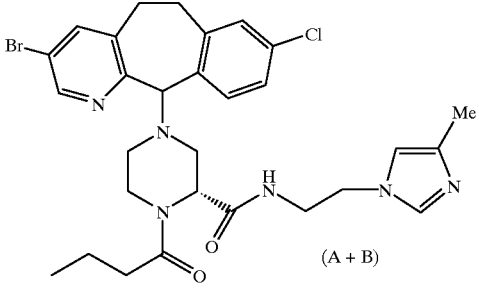 | 1. 17 2. 613 3. 85.7 |
| 284 | 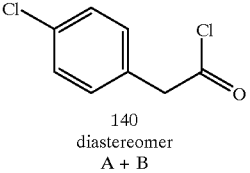 140 diastereomer A + B | 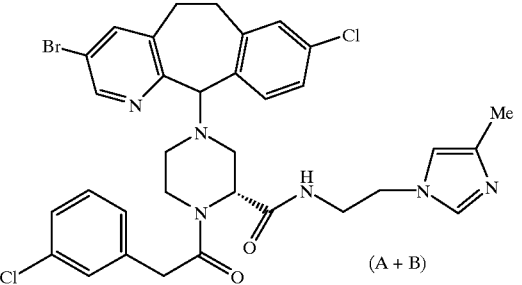 | 1. 11 2. 695 3. 128.4 |

TABLE 21-continued
| Ex. | Electrophile and Prep. Exam. | Product | 1. Yield (%)<br>2. MH+<br>3. mp (° C.) |
|---|---|---|---|
| | | 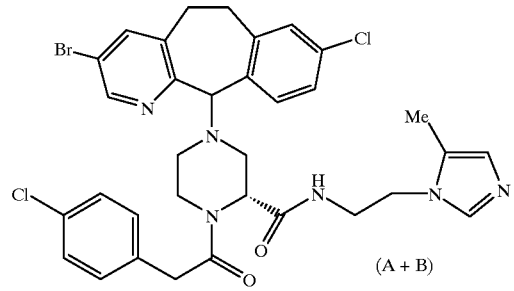 (A + B) | |
| 285 | 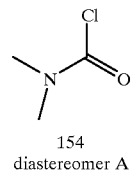<br>154<br>diastereomer A | 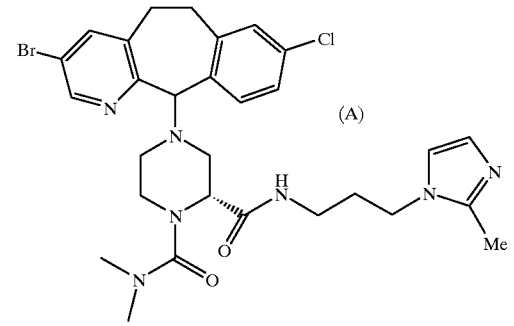 (A) | 1. 55<br>2. 628<br>3. 108.9 |
| 286 | 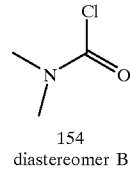<br>154<br>diastereomer B | 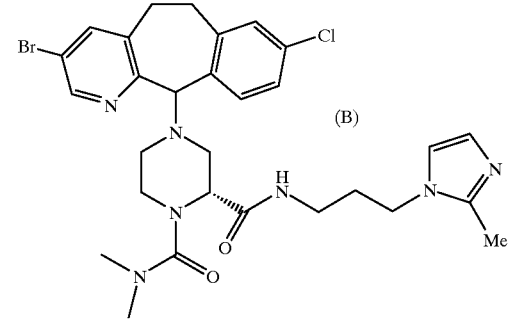 (B) | 1. 23<br>2. 628<br>3. 109.3 |
| 286 A | 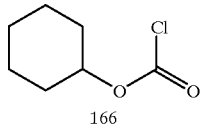<br>166 | 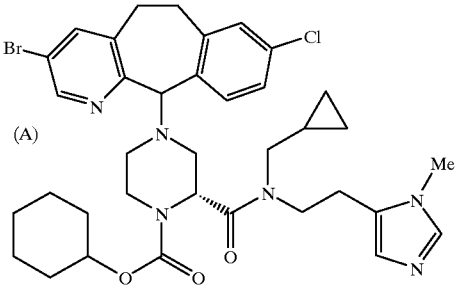 (A) | 1. 70<br>2. 725<br>3. 88–96 |

TABLE 21-continued

| Ex. | Electrophile and Prep. Exam. | Product | 1. Yield (%)<br>2. MH+<br>3. mp (° C.) |
|---|---|---|---|
| 286 B | 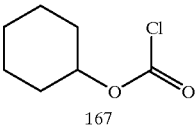<br>167 | 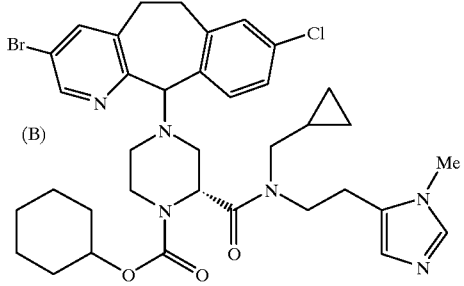<br>(B) | 1. 60<br>2. 725<br>3. 89–96 |

EXAMPLES 287–289

Following the procedure described for Example 221, the title compound (diastereomer A or B or A+B) from the Preparative Example indicated in Table 22 below was treated with the corresponding carboxylic acid to give the products listed in Table 22.

TABLE 22

| Ex. | Carboxylic Acid and Prep. Ex. | Product | 1. Yield (%)<br>2. MH+<br>3. mp (° C.) |
|---|---|---|---|
| 287 | 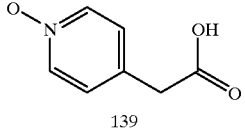<br>139<br>diastereomer A | 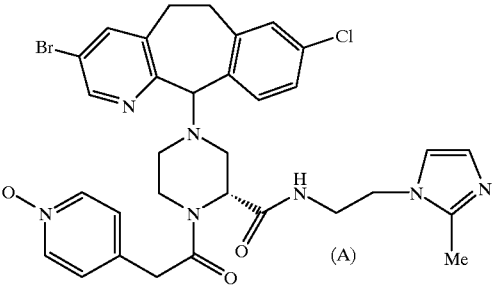<br>(A) | 1. 71<br>2. 678<br>3. 139.5 |
| 288 | 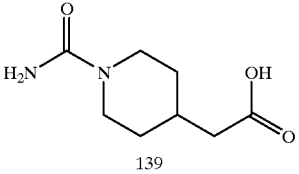<br>139<br>diastereomer A | 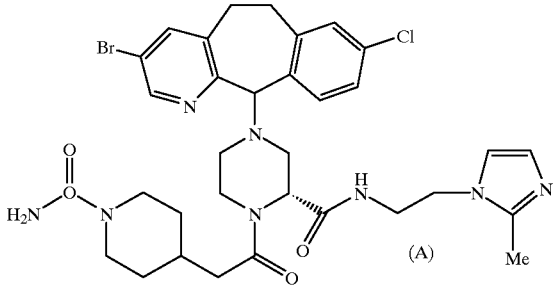<br>(A) | 1. 39<br>2. 711<br>3. 136.1 |

TABLE 22-continued

| Ex. | Carboxylic Acid and Prep. Ex. | Product | 1. Yield (%) 2. MH+ 3. mp (° C.) |
|---|---|---|---|
| 289 | 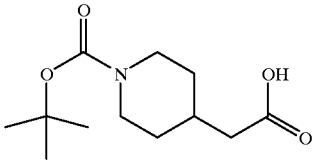<br>140<br>diastereomer<br>A + B | 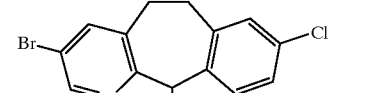 (A + B)<br>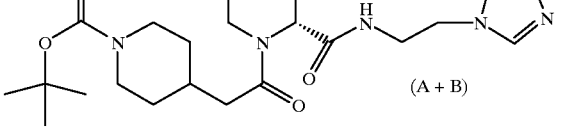 (A + B) | 1. 21<br>2. 768<br>3. 115.5 |

EXAMPLE 290

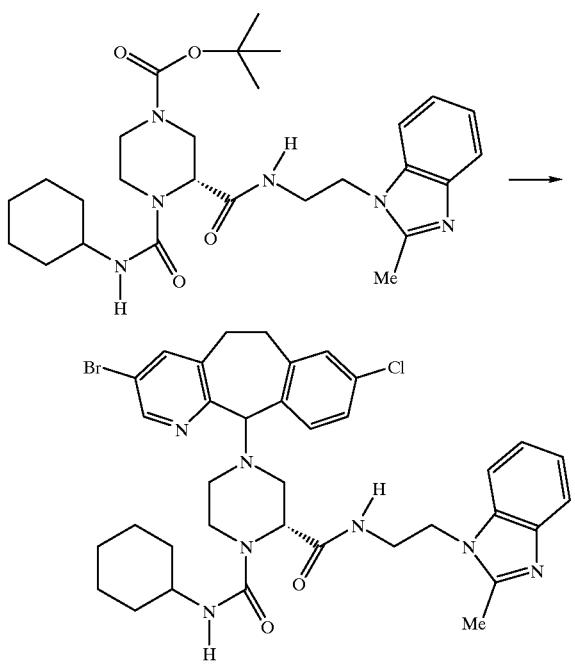

A solution of the title compound from Preparative Example 143 (0.59 g, 1.15 mmol) dissolved in anhydrous dichloromethane (10 ml) and trifluoroacetic acid (2 ml) was stirred at room temperature for 3 hrs. The resulting solution was concentrated in vacuo, then the residue was combined with anhydrous dichloromethane (10 ml), the tricyclic chloride (compound No. 42.0) (0.474 g, 1.38 mmol) and triethylamine (1.61 mL, 11.5 mmol) and allowed to stir at 25–40° C. for 12 h. The reaction mixture was concentrated in vacuo and purified by flash column and preparative plate chromatography (silica gel) using 1–4% MeOH—CH$_2$Cl$_2$ saturated with aqueous ammonium hydroxide to afford the title compounds (457 mg, 55%, MH+=718).

EXAMPLES 291–297

Following the procedure described for Preparative Example 290 and the BOC-protected piperazines listed in Table 23 below, the tricyclic compounds in Table 23 were prepared as diastereomeric mixtures. The diastereomers that were separated, were separated by preparative chiral chromatography (Chiralpack AD, 5 cm×50 cm column, flow rate 80 mL/min., 7–12% IPA-Hexane+0.2% diethylamine) to give diastereomer A and diastereomer B.

TABLE 23

| Ex. | BOC-Piperazine | Product |
|---|---|---|
| 291 | | 1. Yield: 44%<br>2. MH+ = 705<br>3. mp = 132–135° C. |
| 292 | | 1. Yield: 14%<br>2. MH+ = 705<br>3. mp = 127–132° C. |
| 293 | | For (A): 1. Yield: 38%; 2. MH+ = 691; 3. mp = 107.5° C.<br>For (B): 1. Yield: 36%; 2. MH+ = 691; 3. mp = 82.2° C. |

TABLE 23-continued

| Ex. | BOC-Piperazine | Product |
|---|---|---|
| 294 | | |
| | | 1. Yield: 36% |
| | | 2. MH+ = 722 |
| | | 3. mp = 173.8° C. |
| 295 | | (A + B) |

For (A):

1. Yield: 30%
2. MH+ = 682

For (B):

1. Yield: 25%
2. MH+ = 682

For (C):

1. Yield: 10%
2. MH+ = 682

For (D):

1. Yield: 13%
2. MH+ = 682

TABLE 23-continued

| Ex. | BOC-Piperazine | Product |
|---|---|---|
| 296 | | |
| 297 | | |

296: 1. Yield: 75%  2. MH+ – 698  3. mp = 141.2° C.

297: 1. Yield: 13%  2. MH+ = 670  3. mp = 182.1–219.4° C.

EXAMPLE 299

Step A

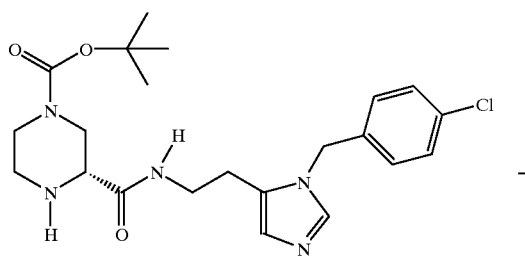

Step B

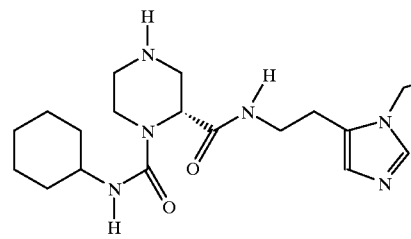

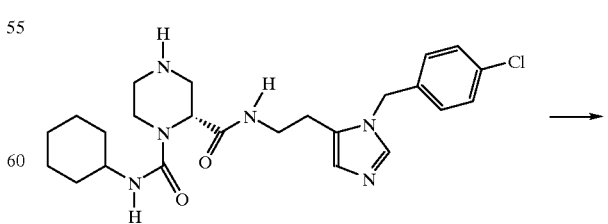

To a solution of the title compound from Preparative Example 155 Step F (0.30 g, 0.67 mmol) dissolved in anhydrous dichloromethane (3 ml) was added cyclohexylisocyanate (0.09 mL, 0.7 mmol) and the resulting solution was stirred at room temperature for 30 min, then concentrated in vacuo. The resulting residue was diluted with dichloromethane (3 ml) trifluoroacetic acid (3 ml). The solution was stirred at room temperature overnight, then concentrated in vacuo, diluted with dichloromethane and washed with 1N NaOH (aq). The organic phase was dried over anhydrous MgSO$_4$, filtered, and concentrated in vacuo to afford a yellow foam (0.319 g, 100%, MH+=473).

359
-continued

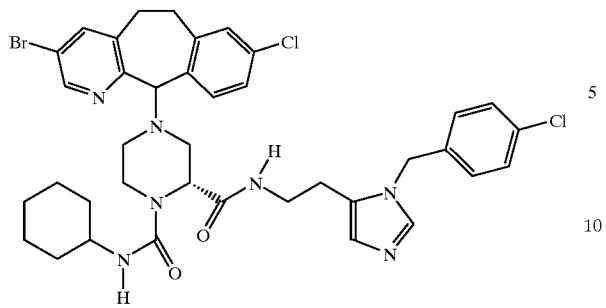

To a solution of the title compound from Step A above (0.212 g, 0.45 mmol) dissolved in anhydrous dichloromethane (10 ml) was added the tricyclic chloride (compound # 42.0) (0.154 g, 0.45 mmol) and triethylamine (0.32 mL, 2.25 mmol) and allowed to stir at 25° C. for 48 h. The reaction mixture was concentrated in vacuo and purified by preparative plate chromatography (silica gel) using 5% MeOH—CH$_2$Cl$_2$ saturated with aqueous ammonium hydroxide to afford the title compounds (125 mg, 35%, mp=114.8° C., MH$^+$=778).

EXAMPLE 300

Following the procedure described for Example 299 Steps A–B, the product listed in Table 24 below was prepared using the corresponding piperazine from the indicated Preparative Example.

360
-continued

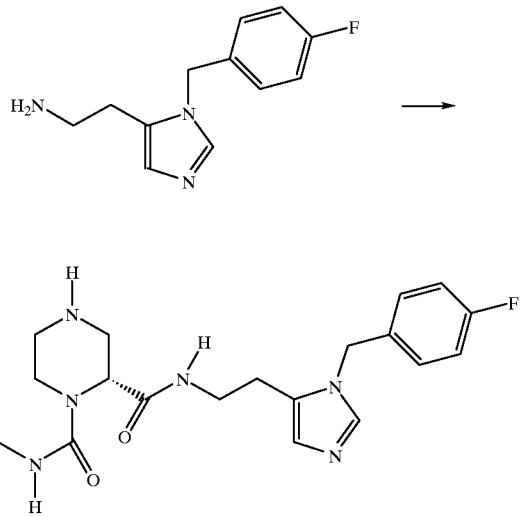

A mixture of the title compound from Preparative Example 162 (400 mg, 1.86 mmol), the anhydride from Preparative Example 44 (561 mg, 2.19 mmol) and anhydrous CH$_2$Cl$_2$ (10 mL) was stirred at 25° C. for 3 hrs before

TABLE 24

| Ex. | Prep. Ex. | Product | 1. Yield (%)<br>2. MH$^+$<br>3. mp (° C.) |
|---|---|---|---|
| 300 | 156 | 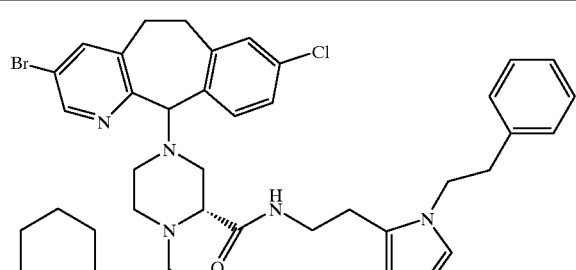 | 1. 38<br>2, 758<br>3. 117.3 |

EXAMPLE 302

Step A

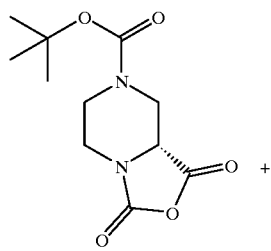 + tert-butylisocyanate (0.26 mL, 2.19 mmol) was added. After 12 h, the mixture was concentrated in vacuo, diluted with CH$_2$Cl$_2$ and washed with water. The organic phase was dried over anhydrous Na$_2$SO$_4$, filtered and concentrated. The resulting foam was diluted with anhydrous CH$_2$Cl$_2$ (10 mL) and trifluoroacetic acid (10 ml) and stirred for 3 h. Concentration in vacuo, redilution with CH$_2$Cl$_2$ and washing with 1N NaOH (0.5 M, aq) provided an organic solution which was dried over anhydrous Na$_2$SO$_4$, filtered, concentrated and used without further purification (181 mg, 27%, MH$^+$= 431.5).

Step B

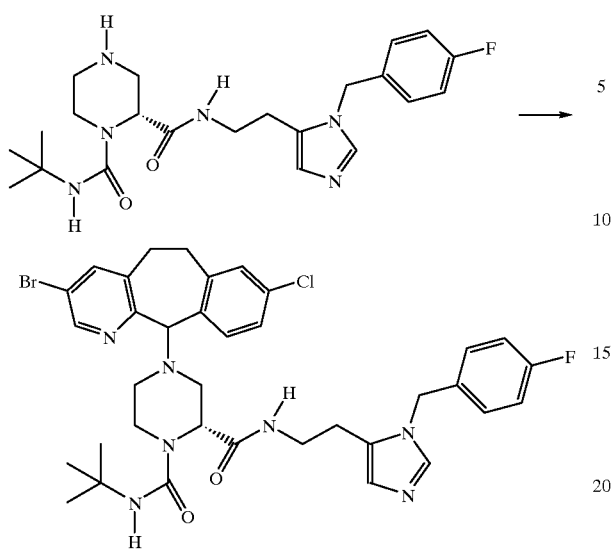

To a solution of the title compound from Step A (170 mg, 0.39 mmol) dissolved in anhydrous dichloromethane (10 ml) was added the tricyclic chloride (compound No. 42.0) (175 mg, 0.51 mmol) and triethylamine (71 μL, 0.51 mmol) and allowed to stir at 25° C. for 48 h. The reaction mixture was concentrated in vacuo and purified by preparative plate chromatography (silica gel) using 5% MeOH—CH$_2$Cl$_2$ saturated with aqueous ammonium hydroxide to afford the title compounds (oil, 24 mg, 8%, MH$^+$=736).

EXAMPLE 303

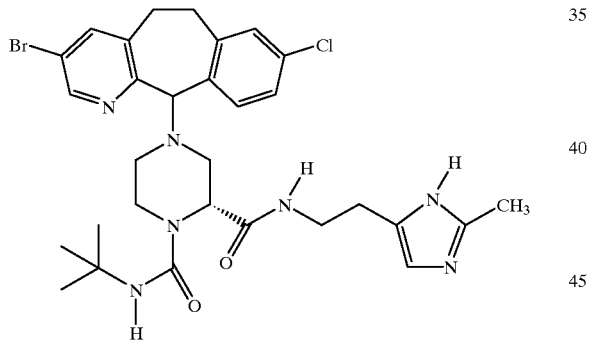

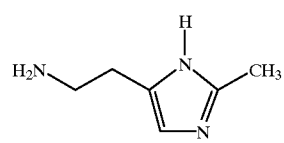

instead of the title compound from Preparative Example 162, the title compound would be obtained.

EXAMPLE 304

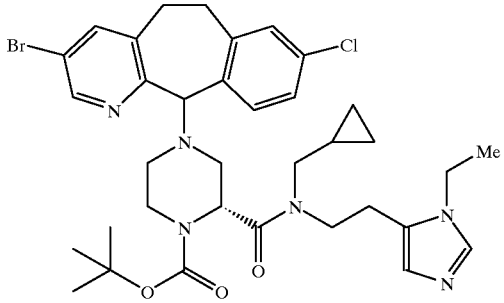

Following the procedure described for Example 58, except using the title compound from Preparative Example 165 instead of the title compound from Preparative Example 25, the title compound was prepared (51%, MH$^+$=711, mp=103.7–107.5).

EXAMPLE 305

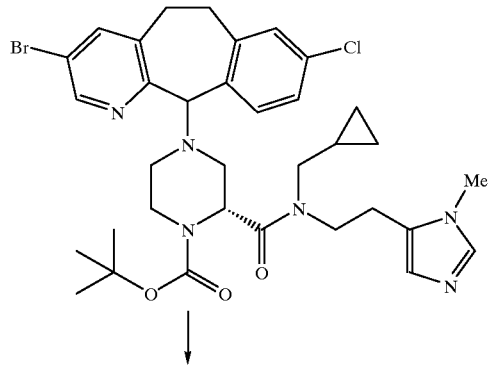

-continued

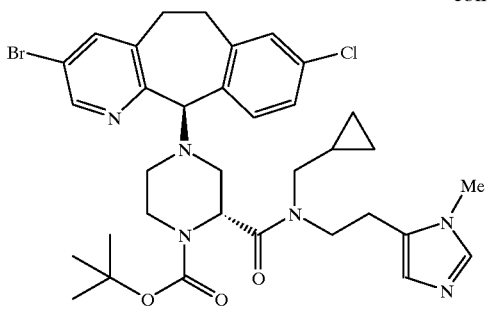
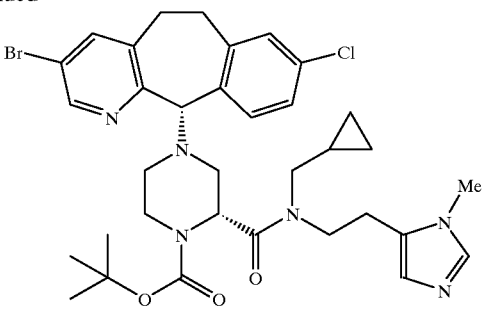

The title compound from Example 58 was separated into its two diastereomers by HPLC (Chiracel AD column) using 10% isopropanol—90% hexane—0.2% diethylamine to give the 11(R),2(R) and 11(S),2(R) isomers.

Diastereomer A: MH+=697; mp=103–108° C.

Diastereomer B: MH+=697; mp=101–107° C.

EXAMPLE 306

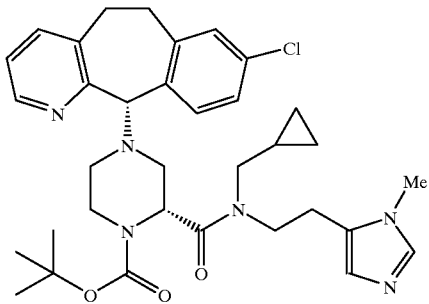

Following the procedure described for Example 58, except using the 11(S),2(R) diastereomer from Preparative Example 164 instead of the title compound from Preparative Example 51, the title compound was prepared (59%, MH$^+$=619, mp=100–114° C.).

EXAMPLE 307

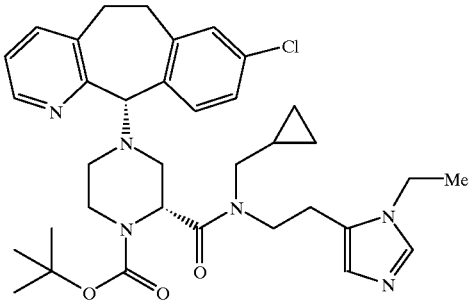

Following the procedure described for Example 306, except using the title compound from Preparative Example 165 instead of the title compound from Preparative Example 25, the title compound was prepared (73%, MH$^+$=633, mp=89.1–96.5° C.).

EXAMPLE 308

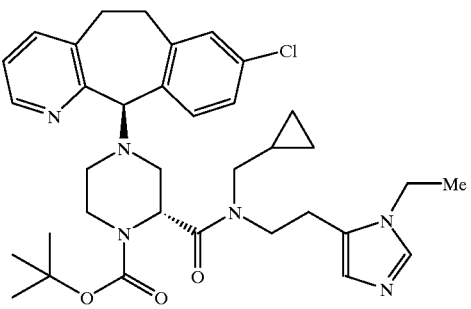

Following the procedure described for Example 58, except using the 11(R),2(R) diastereomer from Preparative Example 164 Step C instead of the title compound from Preparative Example 51, and using the title compound from Preparative Example 165 instead of the title compound from Preparative Example 25, the title compound was prepared (65%, MH$^+$=633, mp=89.1–96.5).

EXAMPLE 309

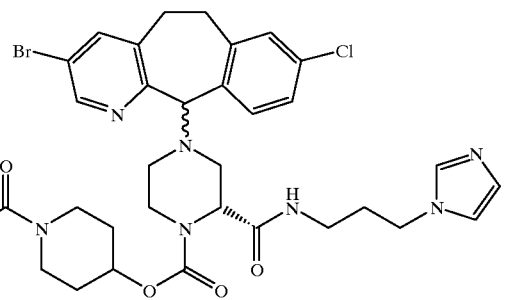

The racemic product from Preparative Example 141 (0.2 g, 0.368 mmoles), 4-(4-nitrophenyloxycarbonyl)piperidine-1-carboxamide (0.1706 g, 0.552 mmoles) (Preparative Example 36, Step B) and isopropanol (10 mL) were heated under reflux and under argon at 87° C. for 24 h. The solution was evaporated to dryness and the residue was taken up in dichloromethane and washed with satd. aqueous NaHCO$_3$, water, dried (MgSO$_4$), filtered and evaporated to dryness. The residue was chromatographed on a silica gel column using 3%–6%–10% (10% conc. NH$_4$OH in methanol)-dichloromethane as the eluant to give the title compound (0.057 g, 22%): FABMS; m/z 712.9 (MH$^+$); δ$_C$ (CDCl$_3$) CH$_2$: 30.3, 30.5, 30.6, 30.6, 31.1, 36.7; 41.3, 41.3, 42.2, 44.5, 50.7/51.1, 52.3; CH: 55.4, 71.0, 78.8, ~118.9, 126.3, 129.4, 130.5, 132.5, 137.0, 141.4, 147.1; C: 120.2, 134.3, 135.0, 137.0, 141.3, 155.2, 155.2, 158.0, 170.2; $\delta_H$ (CDCl$_3$) 4.31/4.32 (1H, s, H$_{11}$), 4.56 (2H, broad s, NCONH$_2$), 6.93 (1H, broad s, Im-H$_5$), 7.07 (1H, broad s, Im-H$_4$), 7.10–7.16 (3H, m, Ar—H), 7.48 (1H, m, Ar—H), 7.60 (1H, broad s, Im-H$_2$) and 8.30 ppm (1H, s, Ar—H$_2$).

EXAMPLES 310–342

Following the procedure described for Example 225, the Products listed in Table 25 were prepared using the carboxylic acid (diastereomer A or B) from Preparative Example 127 Step C and the appropriate N-substituted imidazolylalkyl amine.

TABLE 25

| Ex. | Amine of Prep. Ex. No. Carboxylic acid diastereomer A or B | Product | 1. Yield (%) 2. MH$^+$ 3. mp (° C.) |
|---|---|---|---|
| 310 | 94 diastereomer A | 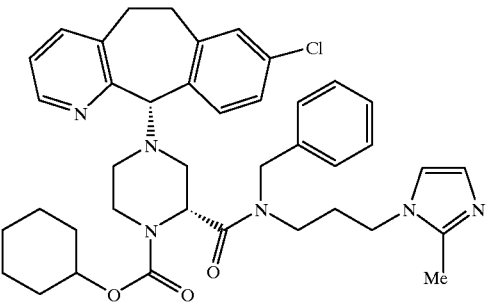 | 1. 71 2. 695 3. 79.7 |
| 311 | 93 diastereomer A | 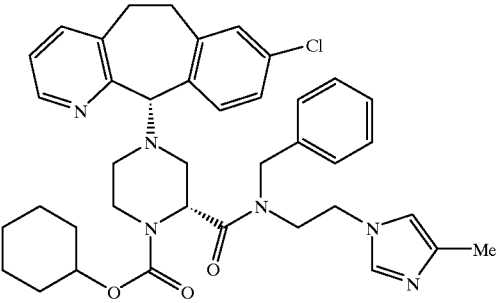 | 1. 29 2. 681 3. 82.2 |
| 312 | 89 diastereomer B | 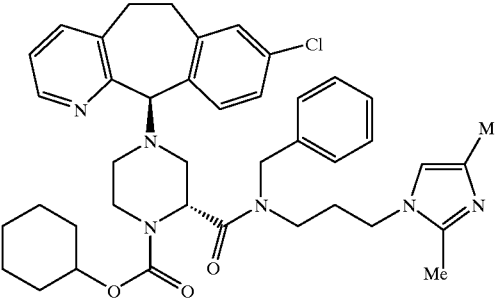 | 1. 43 2. 709 3. 88.4 |
| 313 | 94 diastereomer B | 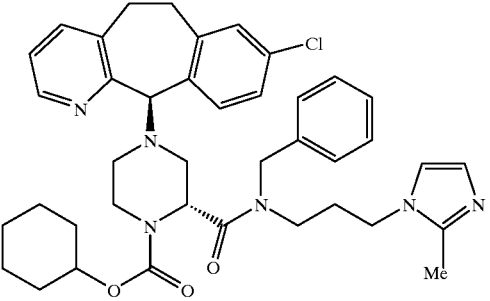 | 1. 47 2. 695 3. 86.3 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 314 | 101 diastereomer B | | 1. 52 2. 709 3. 89.1 |
| 315 | 179 diastereomer A | | 1. 14 2. 756 3. semi-solid |
| 316 | 172 diastereomer A | | 1. 65 2. 711 3. 122.2 |
| 317 | 173 diastereomer A | | 1. 27 2. 712 3. 62.9– 88.2 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 318 | 174 diastereomer A | | 1. 19 2. 679 3. 78.3 |
| 319 | 199 Step B diastereomer A | | 1. 20 2. 712 3. 135.7 |
| 320 | 91 diastereomer B | | 1. 32 2. 709 3. 94.6 |
| 321 | 95.1 diastereomer A | | 1. 4 2. 695 3. 76.7 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 322 | 176 diastereomer A | | 1. 37 2. 729 2. 78– 83 |
| 323 | 177 diastereomer A | | 1. 50 2. 729 3. 96– 101 |
| 324 | 178 diastereomer A | | 1. 45 2. 729 3. 87– 92 |
| 325 | 85 (B) diastereomer A | | 1. 55 2. 695 3. 88– 93 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 326 | 180 diastereomer A | | 1. 53 2. 709 3. 87.7 |
| 327 | 183 diastereomer A | | 1. 63 2. 645 3. 103.6 |
| 328 | 181 diastereomer A | | 1. 40 2. 723 3. 86.5– 95.2 |
| 329 | 184 diastereomer A | | 1. 16 2. 697 3. 95– 100 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 330 | 182 diastereomer A | | 1. 7 2. 712 3. semi-solid |
| 331 | 165 Diastereomer A | | 1. 52 2. 660 3. 90.7–101.7 |
| 332 | 165 Diastereomer B | | 1. 69 2. 660 3. 91.6–102.8 |
| 333 | 185 Diastereomer A | | 1. 29 2. 660 3. 75.9–82.8 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 334 | 186 Diastereomer A | | 1. 90 2. 646 3. 83–89.7 |
| 335 | 133 diastereomer A | | 1. 63 2. 696 |
| 336 | 133 diastereomer B | | 1.59 2. 696 |
| 337 | 171 diastereomer A | | 1. 15 2. 698 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 338 | 171 diastereomer B | | 1. 36 2. 698 |
| 339 | 171 diastereomer A | | 1. 26 2. 698 |
| 340 | 171 diastereomer A | | 1. 42 2. 698 |
| 341 | 171 diastereomer B | | 1. 57 2. 698 |

TABLE 25-continued

| Ex. | Amine of Prep. Ex. No. Carboxylic acid diastereomer A or B | Product | 1. Yield (%) 2. MH+ 3. mp (° C.) |
|---|---|---|---|
| 342 | 171 diastereomer B | (structure shown) (2) | 1. 21 2. 698 |

EXAMPLES 343–361

Following the procedure described for Example 40, the Products listed in Table 26 were prepared using either the mixture or the pure isomers of the carboxylic acids (diastereomer A and/or B) from Preparative Example 51 and the appropriate N-substituted imidazolylalkyl amine instead of the amine from Preparative Example 13. The resulting Products were separated by HPLC (Chiracel, AD column, 85/15 Hexane/IPA).

TABLE 26

| Ex | Amine of Prep. Ex. No. | Product | 1. Yield (%) 2. MH+ 3. mp (° C.) |
|---|---|---|---|
| 343 and 344 | 89 | (structure shown) Isomer A (Ex. 343) And Isomer B (Ex. 344) | For (A): 1. 27 2. 761 3. 99.3 For (B): 1. 30 2. 761 3. 92.3 |
| 345 and 346 | 177 | (structure shown) Isomer A (ex. 345) | For (A): 1. 16 2. 761 3. 92.4 For (B): |

TABLE 26-continued
| Ex | Amine of Prep. Ex. No. | Product | 1. Yield (%) 2. MH+ 3. mp (° C.) |
|---|---|---|---|
| | | And Isomer B (ex. 346) | 1. 17 2. 761 3. 96.5 |
| 347 and 348j | 101 | 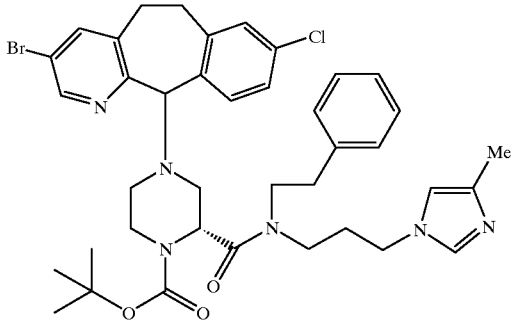 Isomer A (Ex. 347) And Isomer B (Ex. 348) | For (A): 1. 25 2. 761 For (B): 1. 30 2. 761 |
| 349 and 350 | 94 | 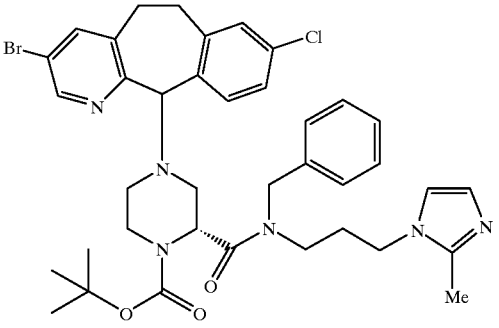 Isomer A (Ex. 349) And Isomer B (Ex. 350) | For (A): 1. 24 2. 747 For (B): 1. 26 2. 747 |
| 351 | 185 diastereomer A | 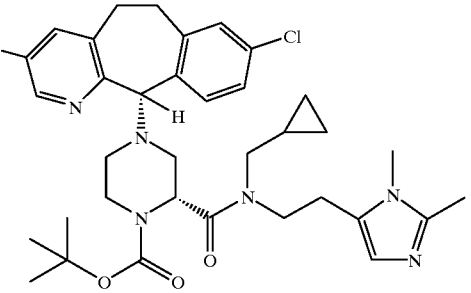 | 1. 55 2. 713 3. 102.9–107.5 |

TABLE 26-continued

| Ex | Amine of Prep. Ex. No. | Product | 1. Yield (%) 2. MH+ 3. mp (° C.) |
|---|---|---|---|
| 352 | 187 diastereomer B | | 1. 67 2. 724 3. — |
| 353 | 187 diastereomer A | | 1. 66 2. 724 3. — |
| 354 | 188 diastereomer B | | 1. 18 2. 783 3. 98–108 |
| 355 | 188 diastereomer A | | 1. 28 2. 783 3. 98–105 |

TABLE 26-continued

| Ex | Amine of Prep. Ex. No. | Product | 1. Yield (%) 2. MH+ 3. mp (° C.) |
|---|---|---|---|
| 356 | 171 diastereomer A | | 1. 54 2. 751 |
| 357 | 171 diastereomer B | | 1. 55 2. 751 |
| 358 | 171 diastereomer A | | 1. 17 2. 751 |
| 359 | 171 diastereomer A | | 1. 12 2. 751 |

TABLE 26-continued

| Ex | Amine of Prep. Ex. No. | Product | 1. Yield (%) 2. MH+ 3. mp (° C.) |
|---|---|---|---|
| 360 | 171 diastereomer B | 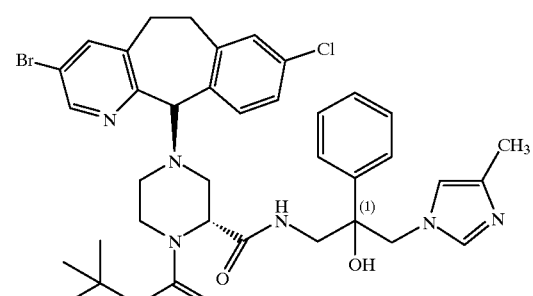 | 1. 62 2. 751 |
| 361 | 171 diastereomer B | 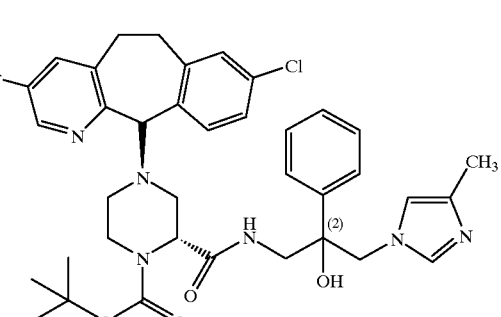 | 1. 25 2. 751 |

EXAMPLES 362–366

Following the procedure described for Example 225, except using the (11S, 2R(+))-carboxylic acid from Preparative Example 164 instead of that from Preparative Example 127 Step C, and using the substituted amine from the indicated Preparative Example in Table 27 instead of that from Preparative Example 95.1, the product listed in Table 27 was prepared.

TABLE 27

| Ex. | Amine of Prep. Ex. No. | Product | 1. Yield (%) 2. MH+ 3. mp (° C.) |
|---|---|---|---|
| 362 | 183 | 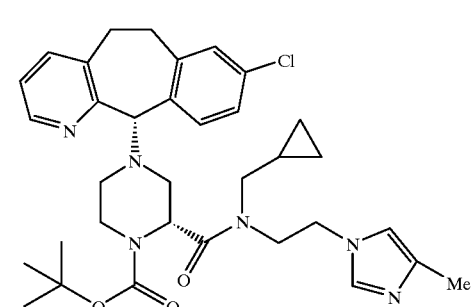 | 1. 69 2. 619 3. 98.8 |

TABLE 27-continued

| Ex. | Amine of Prep. Ex. No. | Product | 1. Yield (%) 2. MH+ 3. mp (° C.) |
|---|---|---|---|
| 363 | 89 | 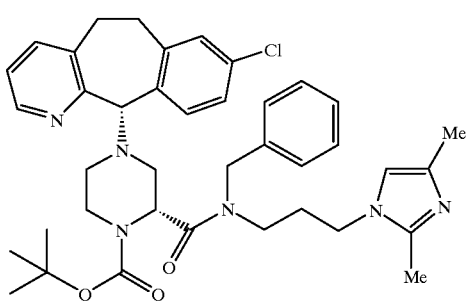 | 1. 44  2. 683  3. 91.7 |
| 364 | 95.1 | 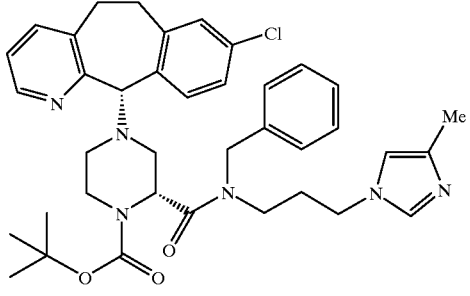 | 1. 42  2. 609  3. 83.5 |
| 365 | 185 | 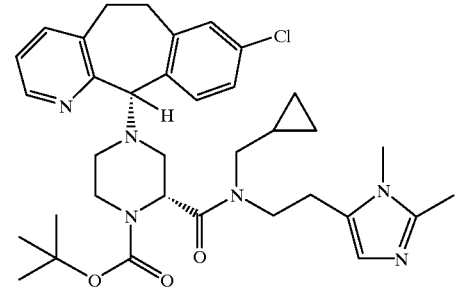 | 1. 57  2. 634  3. 92.1–102.7 |
| 366 | 186 | 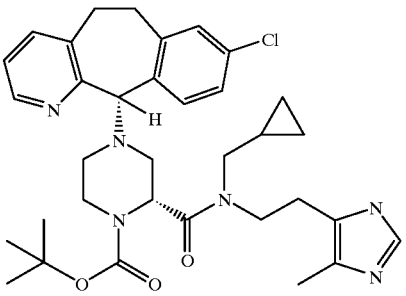 | 1. 71  2. 620  3. 130.2–140.2 |

EXAMPLES 367–374

Following the procedure described for Example 225, the Products listed in Table 28 were prepared using the Carboxylic acid (diastereomer A or B) from Preparative Example listed in Table 28 below instead of the carboxylic acid from Preparative Example 127 Step C, and the appropriate imidazolylalkyl amine (Amine).

TABLE 28
| Ex. | 1. Prep. Ex. No. of Carboxylic acid 2. Prep. Ex. No. of Amine | Product | 1. Yield (%) 2. MH+ 3. mp (° C.) |
|---|---|---|---|
| 367 | 1. 200 diastereomer A 2. 95.1 | 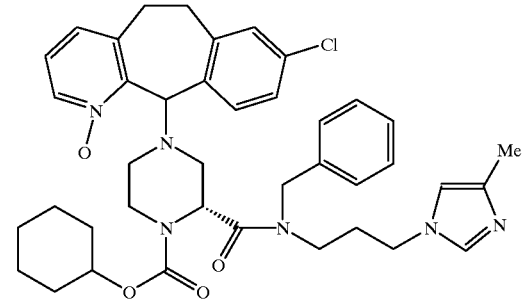 Isomer A | 1. 46 2. 711 3. 90–95 |
| 368 | 1. 200 diastereomer B 2. 95.1 | 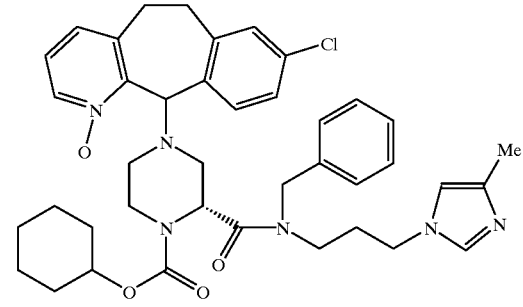 Isomer B | 1. 30 2. 711 3. 65–70 |
| 369 | 1. 200 diastereomer A 2. 172 | 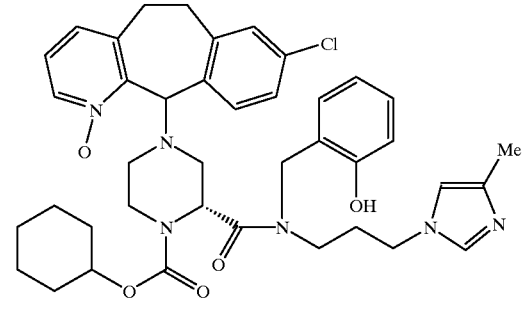 Isomer A | 1. 61 2. 727 3. 128.5 |
| 370 | 1. 200 diastereomer B 2. 169 | 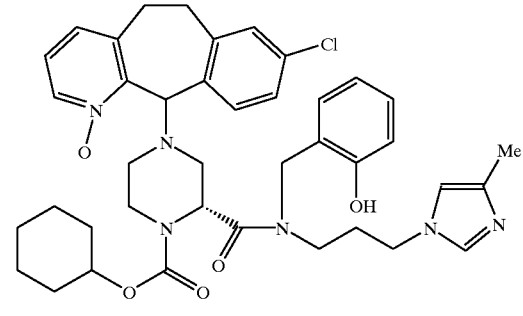 Isomer B | 1. 66 2. 727 3. 133.9 |

TABLE 28-continued

| Ex. | 1. Prep. Ex. No. of Carboxylic acid 2. Prep. Ex. No. of Amine | Product | 1. Yield (%) 2. MH+ 3. mp (° C.) |
|---|---|---|---|
| 371 | 1. 200 diastereomer B 2. 199 Step B | Isomer B | 1. 16 2. 728 3. 135.7 |
| 372 | 1. 201 Step B diastereomer A 2. 95.1 | Isomer A | 1. 35 2. 661 3. oil |
| 373 | 1. 201 Step B diastereometer B 2. 95.1 | Isomer B | 1. 49 2. 661 3. oil |
| 374 | 1. 202 2. 95.1 |  | 1. 41 2. 660 3. 80.1–88.5 |

EXAMPLES 375–382

Similarly, using the procedure described for Example 149, the title compound (diastereomer A or B) from the Preparative Example given in Table 29 was treated with cyclohexyl chloroformate to give the products listed in the Table 29.

TABLE 29
| Ex. | Prep. Ex. No. | Product | 1. Yield (%) 2. MH+ 3. mp (° C.) |
|---|---|---|---|
| 375 | 190 | 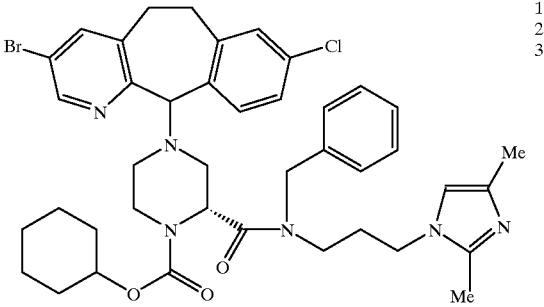 Isomer A | 1. 76 2. 787 3. 94.7 |
| 376 | 191 | 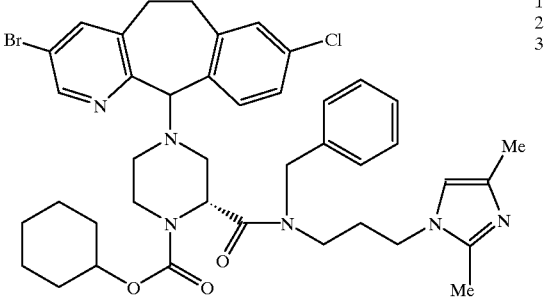 Isomer B | 1. 67 2. 787 3. 92.3 |
| 377 | 192 | 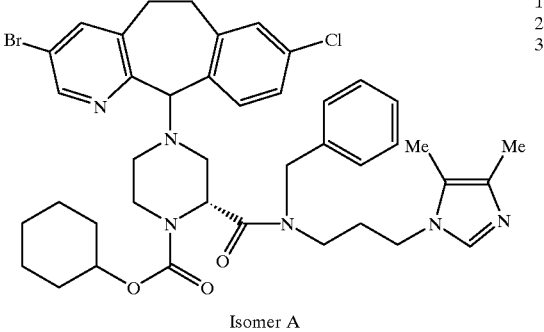 Isomer A | 1. 87 2. 787 3. 90.8 |
| 378 | 193 | 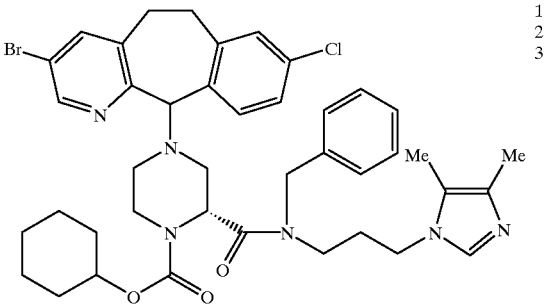 Isomer B | 1. 85 2. 787 3. 84.2 |

TABLE 29-continued
| Ex. | Prep. Ex. No. | Product | 1. Yield (%) 2. MH+ 3. mp (° C.) |
|---|---|---|---|
| 379 | 194 | 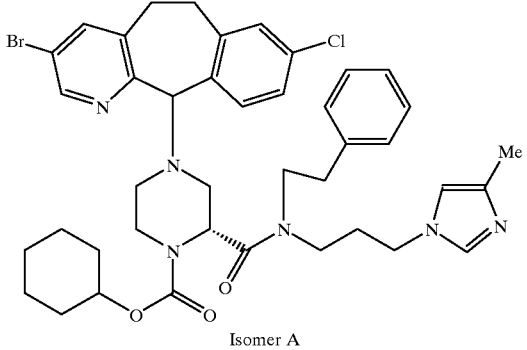 Isomer A | 1. 72 2. 787 3. 89.7 |
| 380 | 195 | 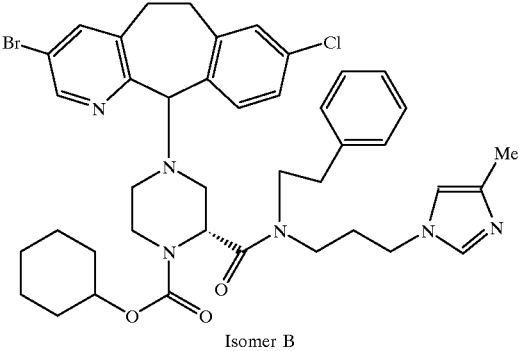 Isomer B | 1. 62 2. 787 3. 89.7 |
| 381 | 196 | 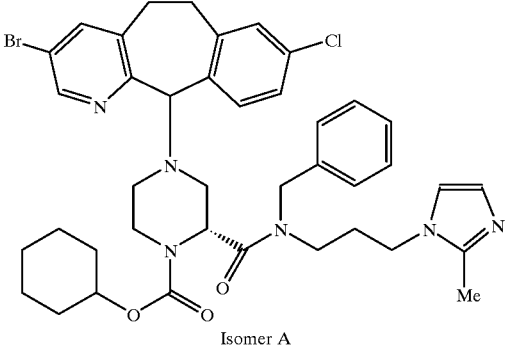 Isomer A | 1. 74 2. 773 3. 83.9 |
| 382 | 197 | 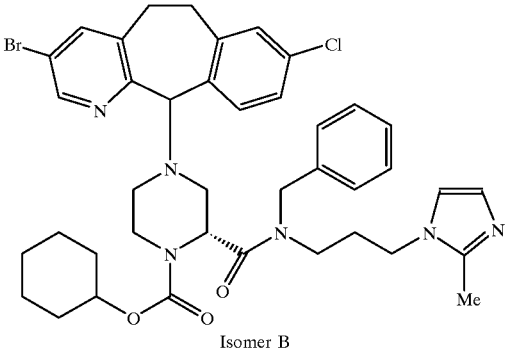 Isomer B | 1. 73 2. 773 3. 89.8 |

EXAMPLES 383–392

Following essentially the same procedure described for Example 149, the title compound (diastereomer A or B) from Preparative Example 170 was treated with the appropriate acylating agent (i.e cyclohexylchloroformate, or Boc dicarbonate, or cyclohexylisocyanate, or tert-butyl isocyanate or isobutyl chloroformate) to give the products of the formula:

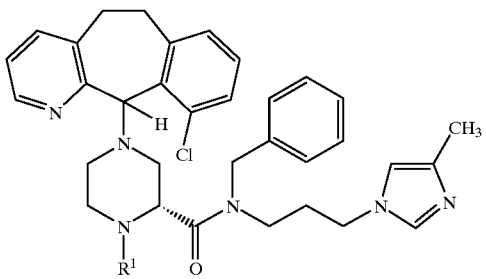

wherein $R^1$ is as defined in column 2 of Table 30.

TABLE 30

| Ex. | $R_1$ | Isomer | Mass HRMS (FABS, MH) | $[\alpha]_D^{20}$ |
|---|---|---|---|---|
| 383 | ![cyclohexyl carbonate] | A | 695.3473 | −29.2° c = 0.107 |
| 384 | ![cyclohexyl carbonate] | B | 695.3473 | +19.5° c = 0.1295 |
| 385 | —COOC(CH₃)₃ | A | 669.3366 | −42.5° c = 0.89 |
| 386 | —COOC(CH₃)₃ | B | 669.3322 | — |
| 387 | ![cyclohexyl urea] | A | 694.3629 | −51.0° c = 0.2575 |
| 388 | ![cyclohexyl urea] | B | 694.3642 | — |
| 389 | ![tert-butyl urea] | A | 668.3480 | −41.0° c = 0.19 |
| 390 | ![tert-butyl urea] | B | 668.3488 | — |//

TABLE 30-continued

| Ex. | $R_1$ | Isomer | Mass HRMS (FABS, MH) | $[\alpha]_D^{20}$ |
|---|---|---|---|---|
| 391 | ![isobutyl carbonate] | A | 669.3322 | −56.3° c = 0.3005 |
| 392 | ![isobutyl carbonate] | B | 669.3330 | — |

EXAMPLE 393

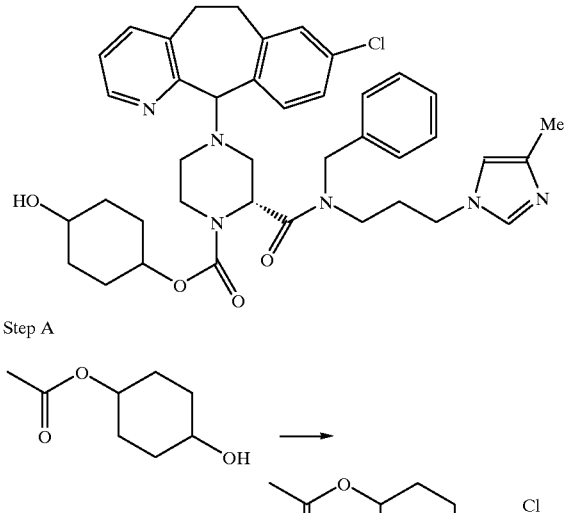

Step A

If the commercially available acetoxycyclohexanol were treated with phosgene the chloroformate would be obtained.

Step B

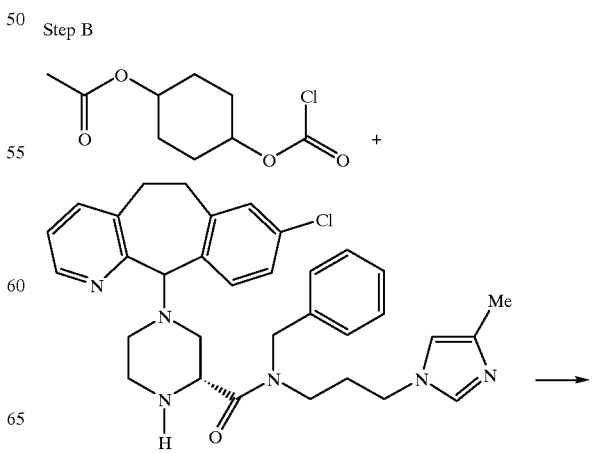

-continued

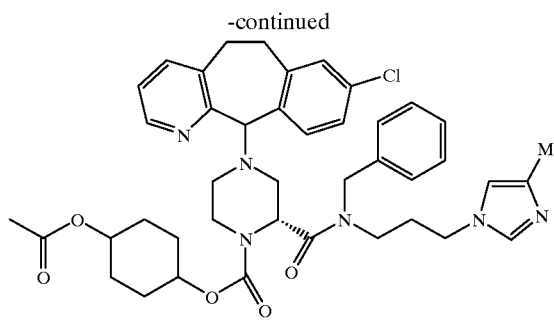

If the chloroformate from Step A were combined with the piperazine amine shown above according to the procedure described for Example 149 then the acetate would be obtained.

Step C

If the product of Step B were treated with potassium carbonate in MeOH the title compound would be obtained.

EXAMPLE 394

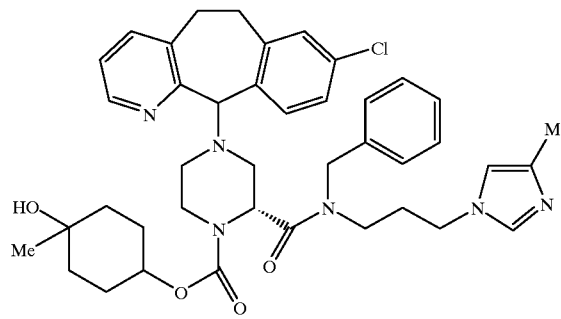

Step A

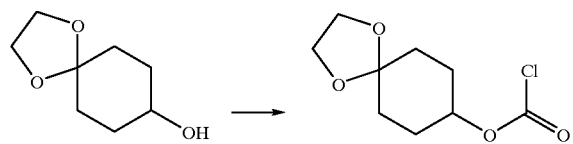

If the commercially available cyclohexanol were treated with phosgene the chloroformate would be obtained.

Step B

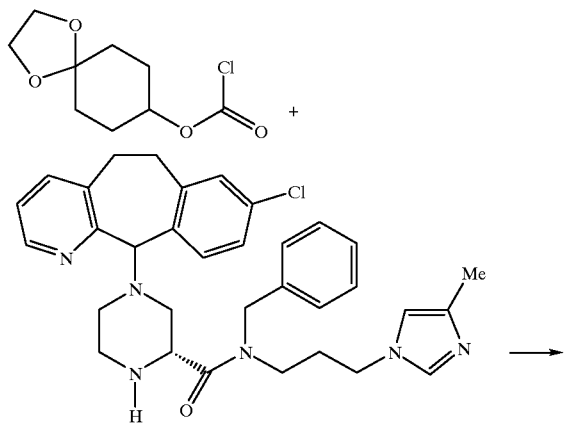

-continued

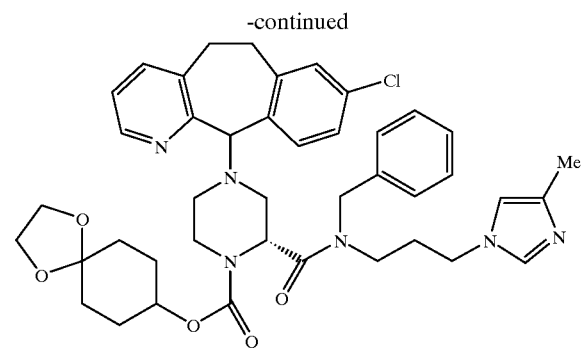

If the chloroformate from Step A were combined with the piperazine amine shown above according to the procedure described for Example 149 then the ketal would be obtained.

Step C

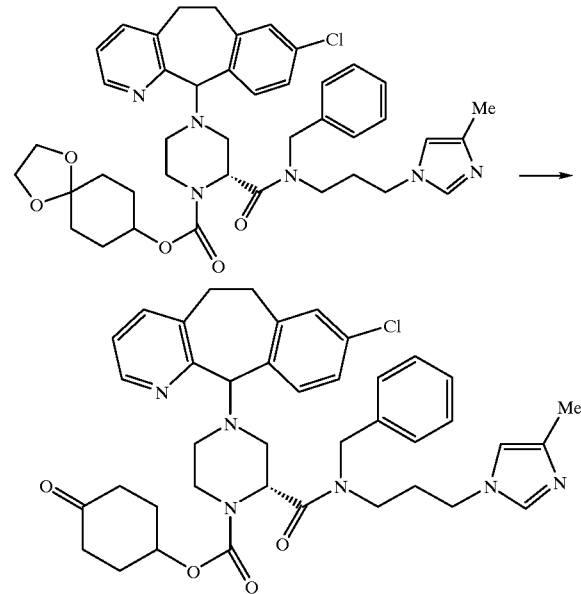

If the product of Step B were treated with aqueous acid the ketone would be obtained.

Step D

If the product of Step C were treated with MeMgBr or MeLi the title product would be obtained.

EXAMPLE 395

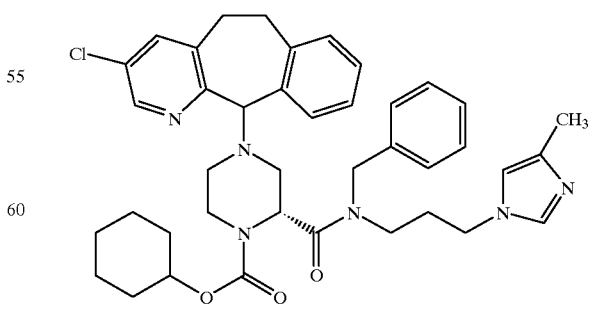

By essentially the same procedure set forth in Example 225 (coupling), only substituting the title compound from Preparative Example 212 for the acid from Preparative Example 127 Step C, the title compound was obtained. Mp 91–107° C., LCMS MH$^+$=695.

EXAMPLE 397

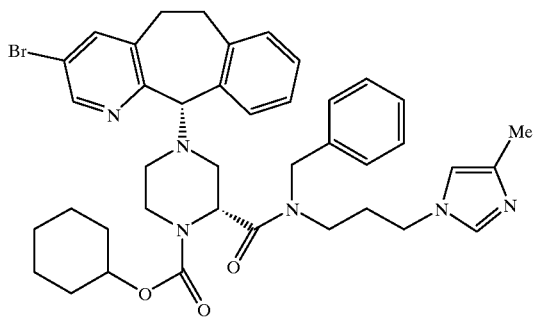

and

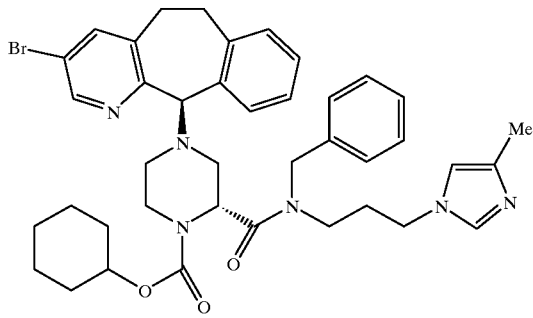

Step A

If the 3-bromotricyclic chloride from Preparative Example 209 were used instead of the chloride in Preparative Example 127 Step C then the carboxylic acid

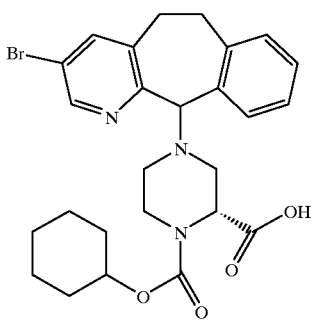

would be obtained.

Step B

If the carboxylic acid from Step A was used in essentially the same procedure as that used for Example 225 then the title compound would be prepared. Separation of isomers could be made using chiral HPLC (AD column) using IPA-Hexane as eluent.

EXAMPLE 398

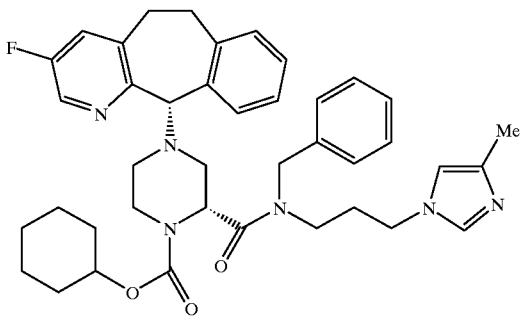

and

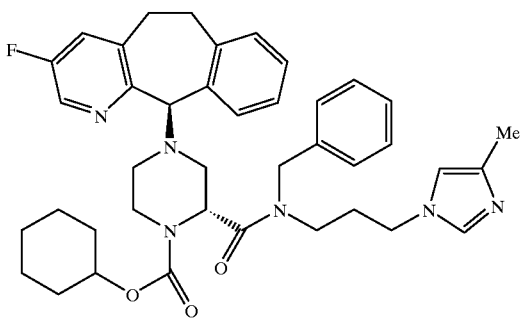

Step A

If the 3-fluorotricyclic chloride from Preparative Example 211 were used instead of the chloride in Preparative Example 127 Step C then the carboxylic acid

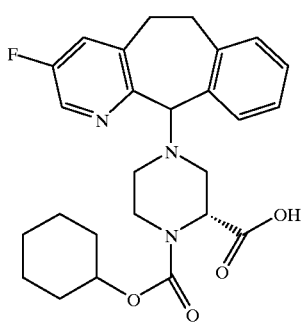

would be obtained.

Step B

If the carboxylic acid from Step A was used in essentially the same procedure as that used for Example 225 then the title compound would be prepared. Separation of isomers could be made using chiral HPLC (AD column) using IPA-Hexane as eluent.

EXAMPLE 399

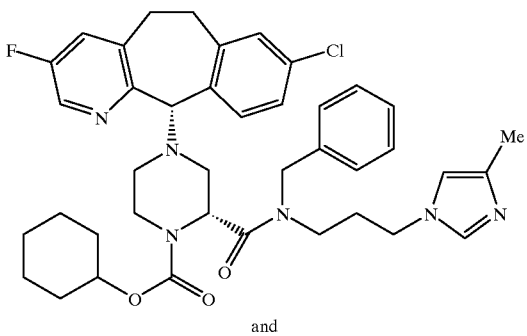

and

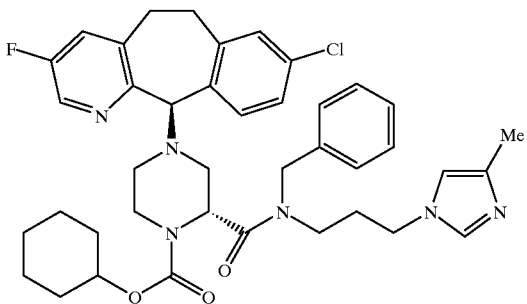

Step A

If the 3-fluoro-8-chlorotricyclic chloride from Preparative Example 204 were used instead of the chloride in Preparative Example 127 Step C then the carboxylic acid

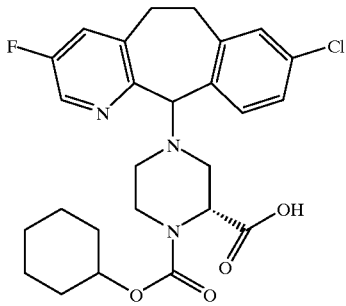

would be obtained.

Step B

If the carboxylic acid from Step A was used in essentially the same procedure as that used for Example 225 then the title compound would be prepared. Separation of isomers could be made using chiral HPLC (AD column) using IPA-Hexane as eluent.

ASSAYS

FPT $IC_{50}$ (inhibition of farnesyl protein transferase, in vitro enzyme assay) and COS Cell $IC_{50}$ (Cell-Based Assay) were determined following the assay procedures described in WO 95/10516, published Apr. 20, 1995. GGPT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10–16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

The compounds of Examples 1–19, 21–25, 67–71, 72 Step B, 72 Step C, 73–77, 78 Step B (Isomer C), 78 Step B (Isomer D), 79 Step B (Isomers A, B, and C), 80 Isomers A and B), 81–86, 86A, 87, 88, 93–104, 106, 108, 110–113, 115–211, 214–217, 221–228, 236–238, 236–238, 241–244, 255–286, 286A, 286B, 287–297, 299 Step B, 300, 302 Step B, 305 and 309 had an FPT $IC_{50}$ within the range of <0.05 nM to 20%@170 nM.

The compounds of Examples 1, 2, 6–13, 15–17, 19, 78 Step B (Isomer D), 80 (Isomer A), 67–71, 72 Step B, 72 Step C, 73, 76, 81–86, 87, 88, 93, 95–101, 103, 106, 108, 110, 111, 113, 115–118, 121, 122, 124, 125 (Isomer A), 127–134, 137, 142, 144–146, 148, 151–153, 155–157, 161–162, 164, 166, 168, 173–175, 177, 180–187, 189–192, 195–196, 198–208, 210–211, 216–217, 221, 222, 225, 237, 238, 242–245, 247–263, 265, 268–286, 286A, 286B, 288–289, 292, 295–296, 299 Step B, 300, 302 StepB, 305, 309, 310–342, 343–373 and 375–382 had an FPT $IC_{50}$ within the range of <0.04 nM to 6.7 nM.

The compounds of Examples 11, 16, 78 Step B (Isomers C and D), 79 Step B (Isomer A), 80 (Isomer A), 88 (Isomer A), 93 (Isomer D), 99, 100, 225, 243, 367 and 368 had an FIT $IC_{50}$ within the range of <0.04 nM to 2.7 nM. The compound of Example 225 had an FPT $IC_{50}$ of 0.36 nM.

The compounds of Examples 1, 2, 8, 25, 86, 100, had a Cos Cell $IC_{50}$ within the range of <10–920 nM. The compounds of Examples 98, 101, 103, 104, 106, 108, 258, 259, 261, and 262 had a Cos Cell $IC_{50}$ within the range of <5 to >500 nM. The compounds of Examples 245–250 had a Cos Cell $IC_{50}$ within the range of 100%@0.01 to 0.087 $\mu$M. The compounds of Examples 100, 101, 103 and 259 had a Cos Cell $IC_{50}$ within the range of <5 nM to 35 nM.

The compounds of Examples 1, 2, 3, 7, 8, 10–16, 21, 25, 67–69, 70, 81, 82 86 (11R,2R Isomer), 88–95, 97, 110, 111–113, 115–119, 121–176, 178–184, 186–200, 202–204, 206–211, 214–217, 221–225, 256, 258, 259, 261, 262, 268–271, 273–274, 276, 278, 280–286, 289, 292, 295–296, 299 Step B, 305, 309–346, 351–373 and 375–382 had a Soft Agar $IC_{50}$ within the range of <5 to >500 nM.

The compounds of Examples 116, 117, 160, 170, 184, 186–188, 196–200, 202–204, 206–208, 217, 225, 305 (11s, 2R isomer), 316, 321, 322, 324, 325, 335, 339, 365, 364, 372, 373, 375, and 382 had a Soft Agar $IC_{50}$ within the range of 2 to 10 nM.

The compounds of Examples 11, 16, 79 Step B (Isomer A), 80 (Isomer A), 88 (Isomer A), 93 (Isomer D), and 225 had a Soft Agar $IC_{50}$ within the range of 2 to 300 nM. The compound of Example 225 had a Soft Agar $IC_{50}$ of 2 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

(Example 225)

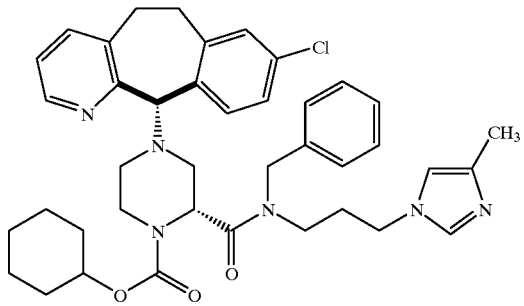

2. A compound selected from:

(Example 393)

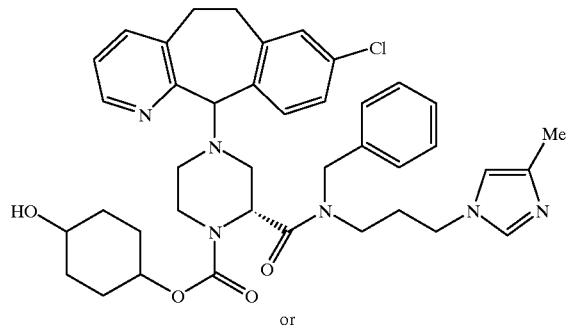

or (Example 394)

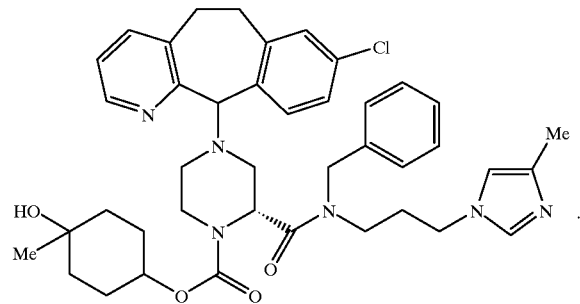

3. A method of inhibiting the abnormal growth of cells wherein said cells are selected from: pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cell, melanoma, breast tumor cells or prostate tumor cells in a patient in need thereof by the inhibition of farnesyl protein transferase comprising administering to the patient an effective amount of a compound of claim 1.

4. A method of inhibiting farnesyl protein transferase in a patient in need thereof comprising administering to the patient an effective amount of the compound of claim 1.

5. A pharmaceutical composition comprising an effective amount of compound of claim 1 in combination with a pharmaceutically acceptable carrier.

6. A compound selected from:
Example 374
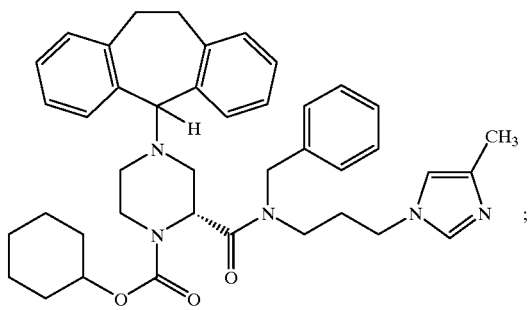
Example 220
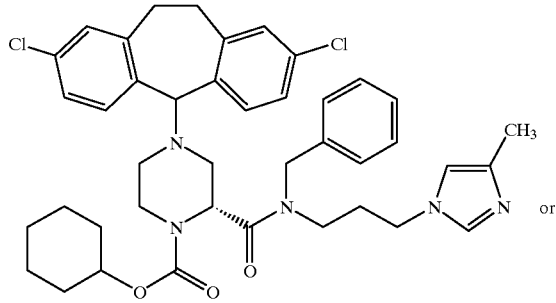
or
Example 220A
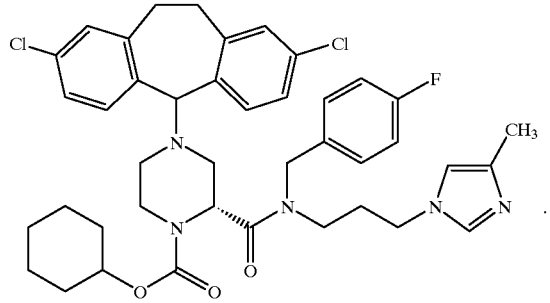
7. A compound selected from:
Example 367 (Isomer A)
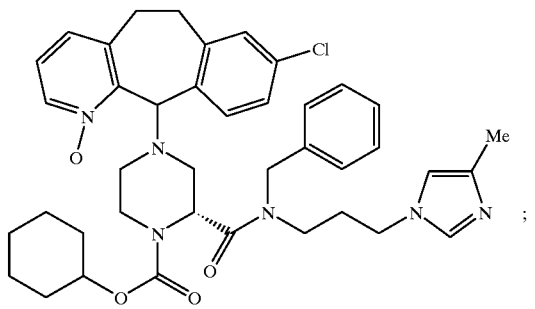
Example 368 (Isomer B)
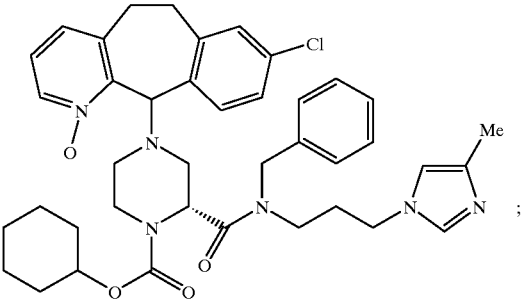
Example 369 (Isomer A)
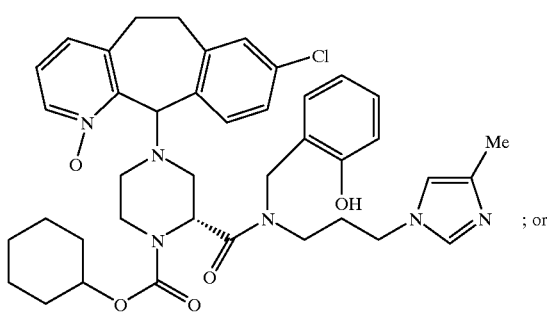
; or
Example 370 (Isomer B)
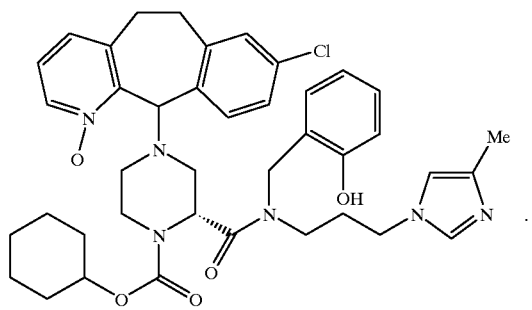
8. A compound selected from:
Example 186
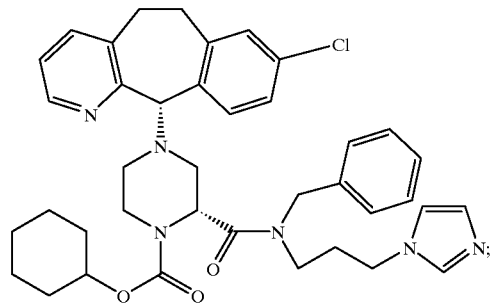

Example 188
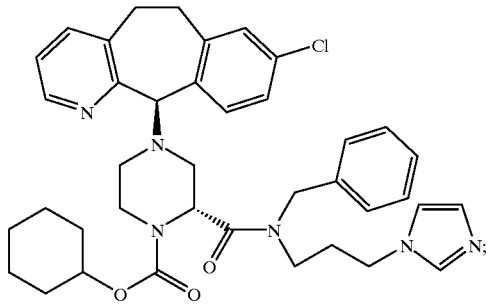
Example 197
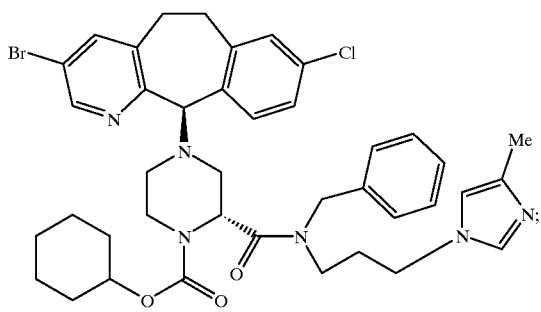
Example 198
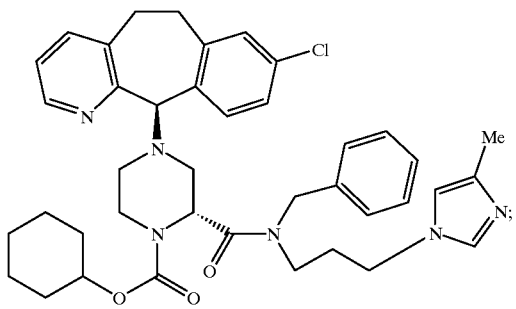
Example 199
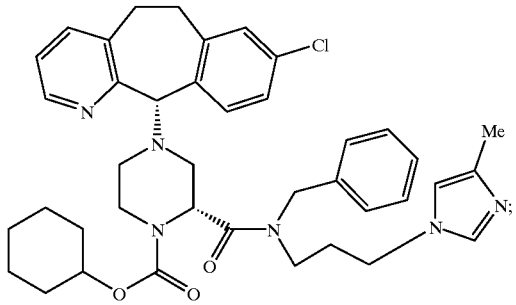
Example 208
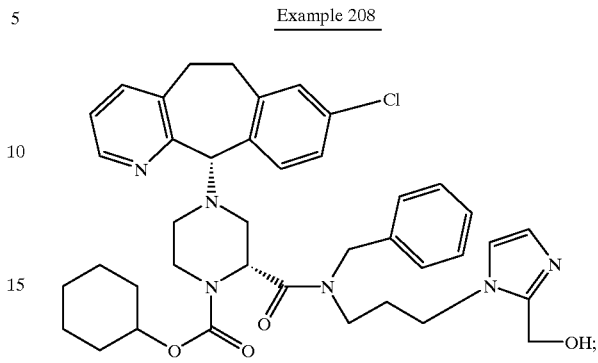
Example 208A
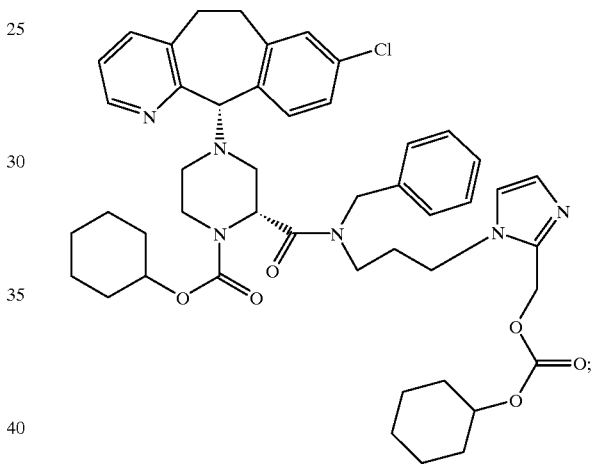
Example 209
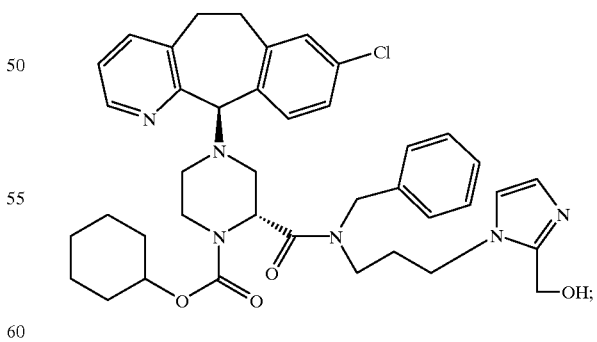

Example 209A
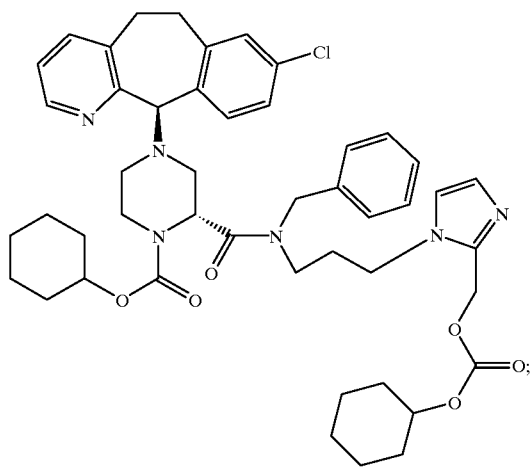
Example 211
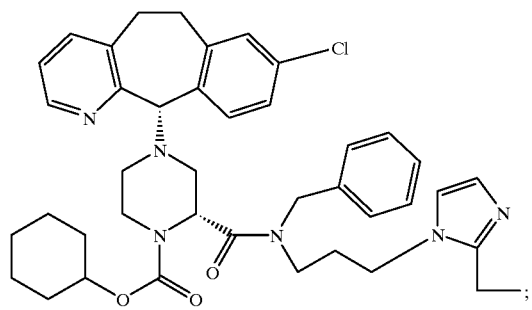
Example 212
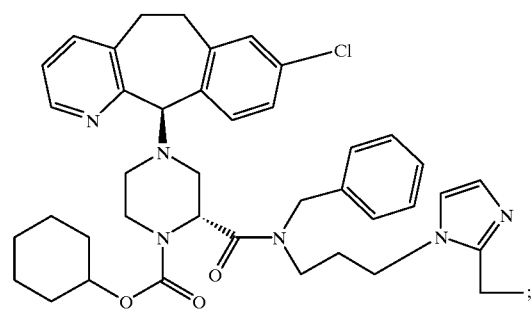
Example 226
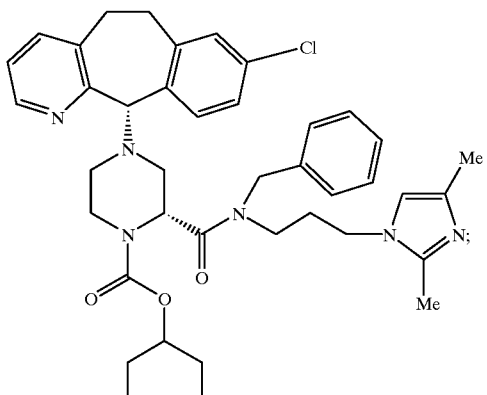
Example 228
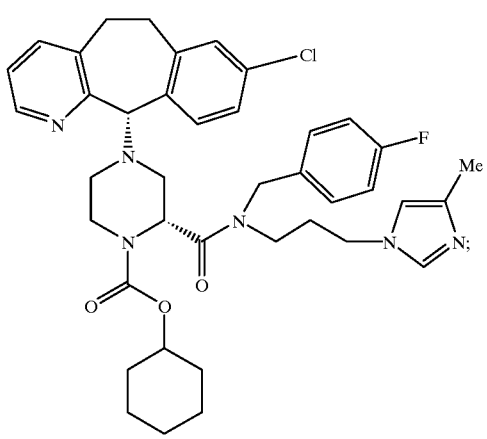
Example 229
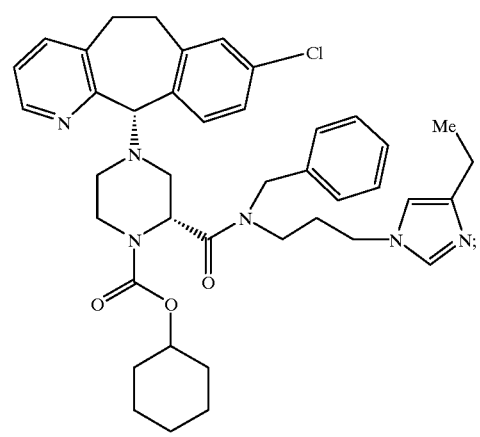

Example 230
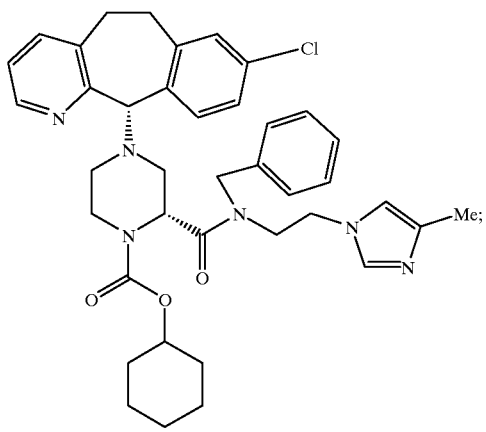
Example 231
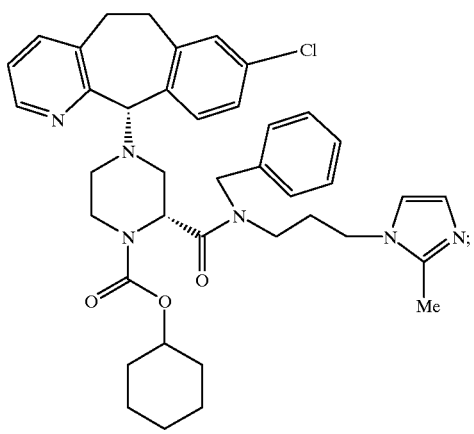
Example 232
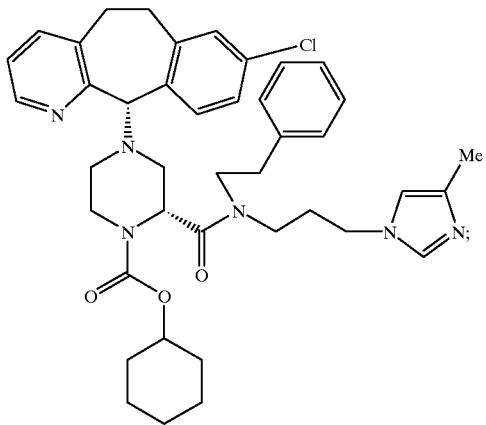
Example 243
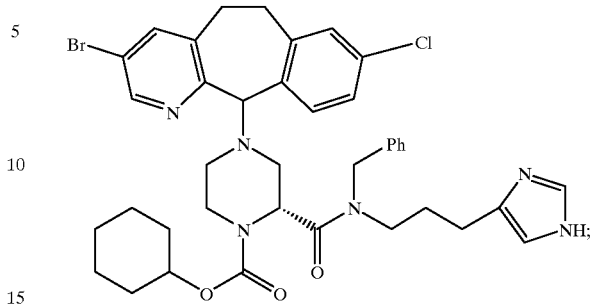
Example 310
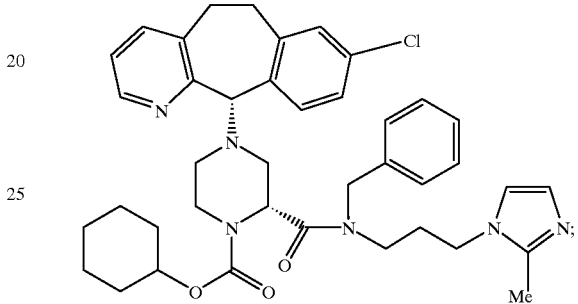
Example 311
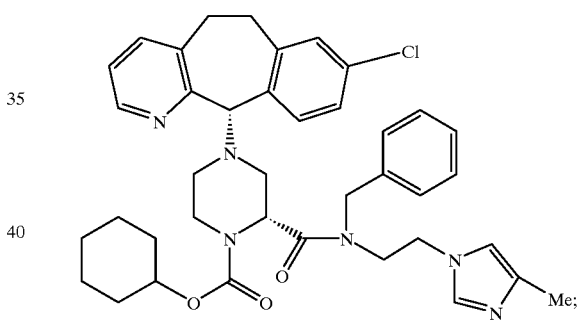
Example 312
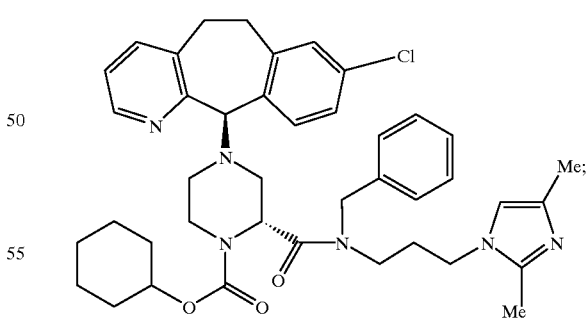

Example 313
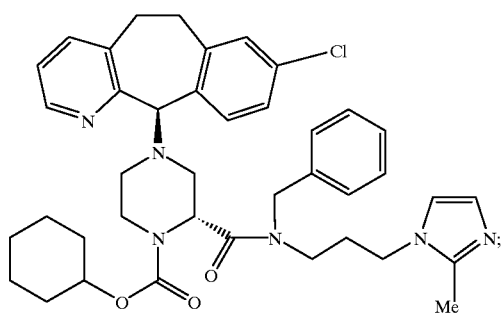
Example 321
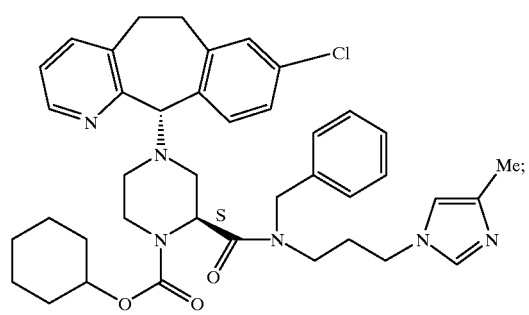
Example 314
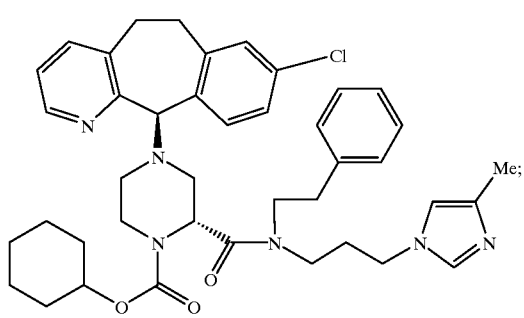
Example 322
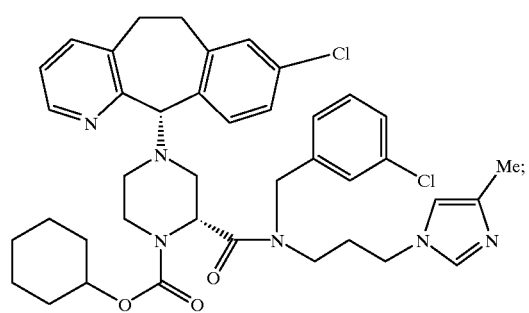
Example 316
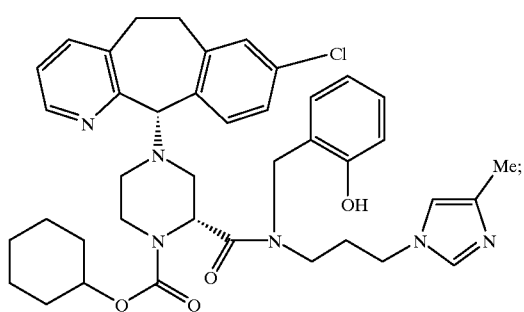
Example 323
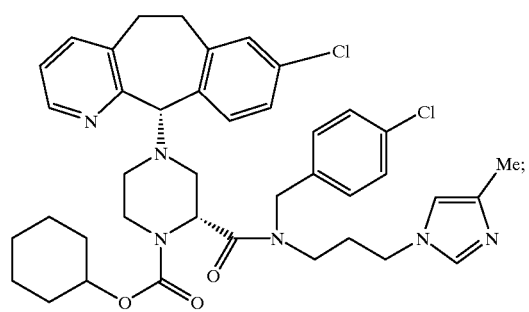
Example 320
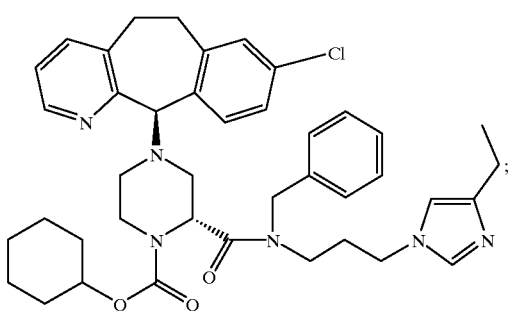
Example 324
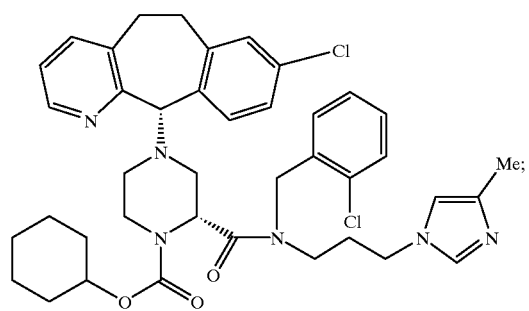

Example 325
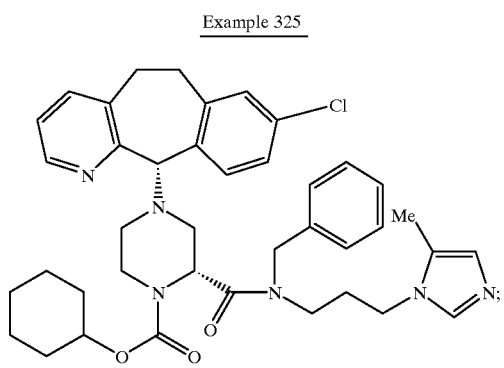
Example 326
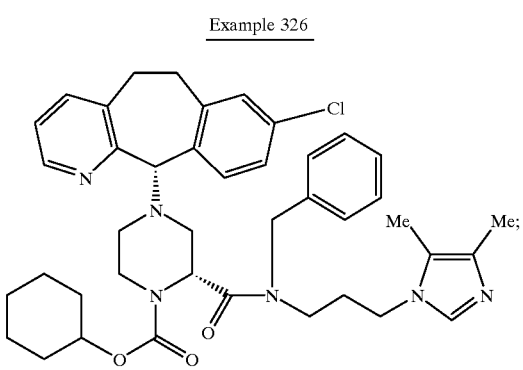
Example 328
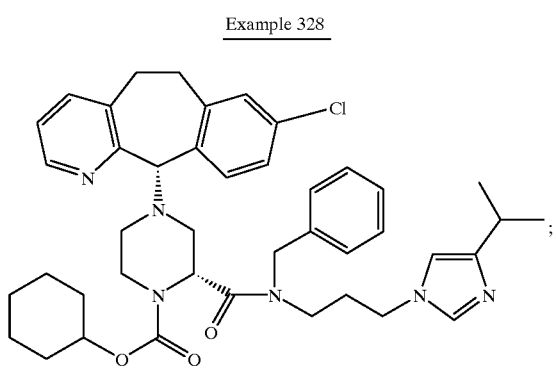
Example 335
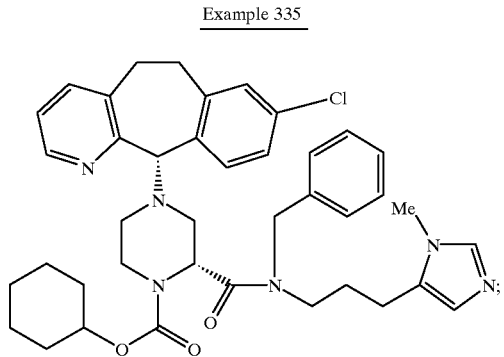
Example 336
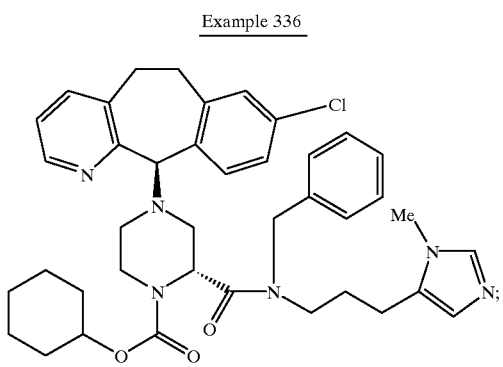
Example 372 (Isomer A)
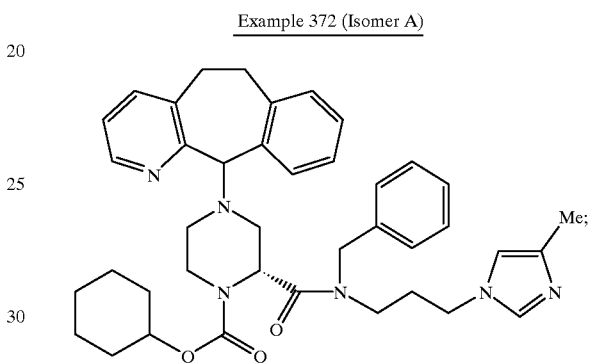
Example 373 (Isomer B)
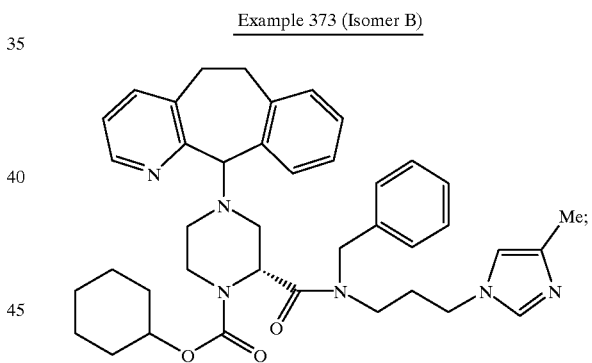
Example 375 (Isomer A)
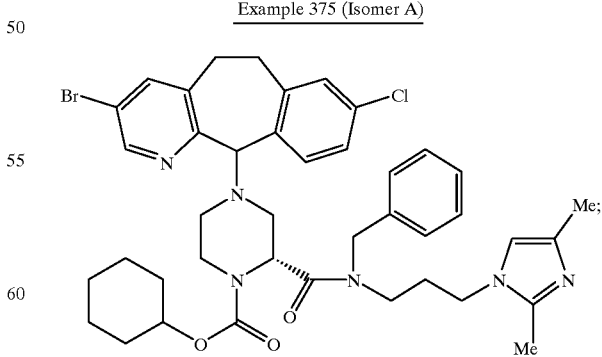

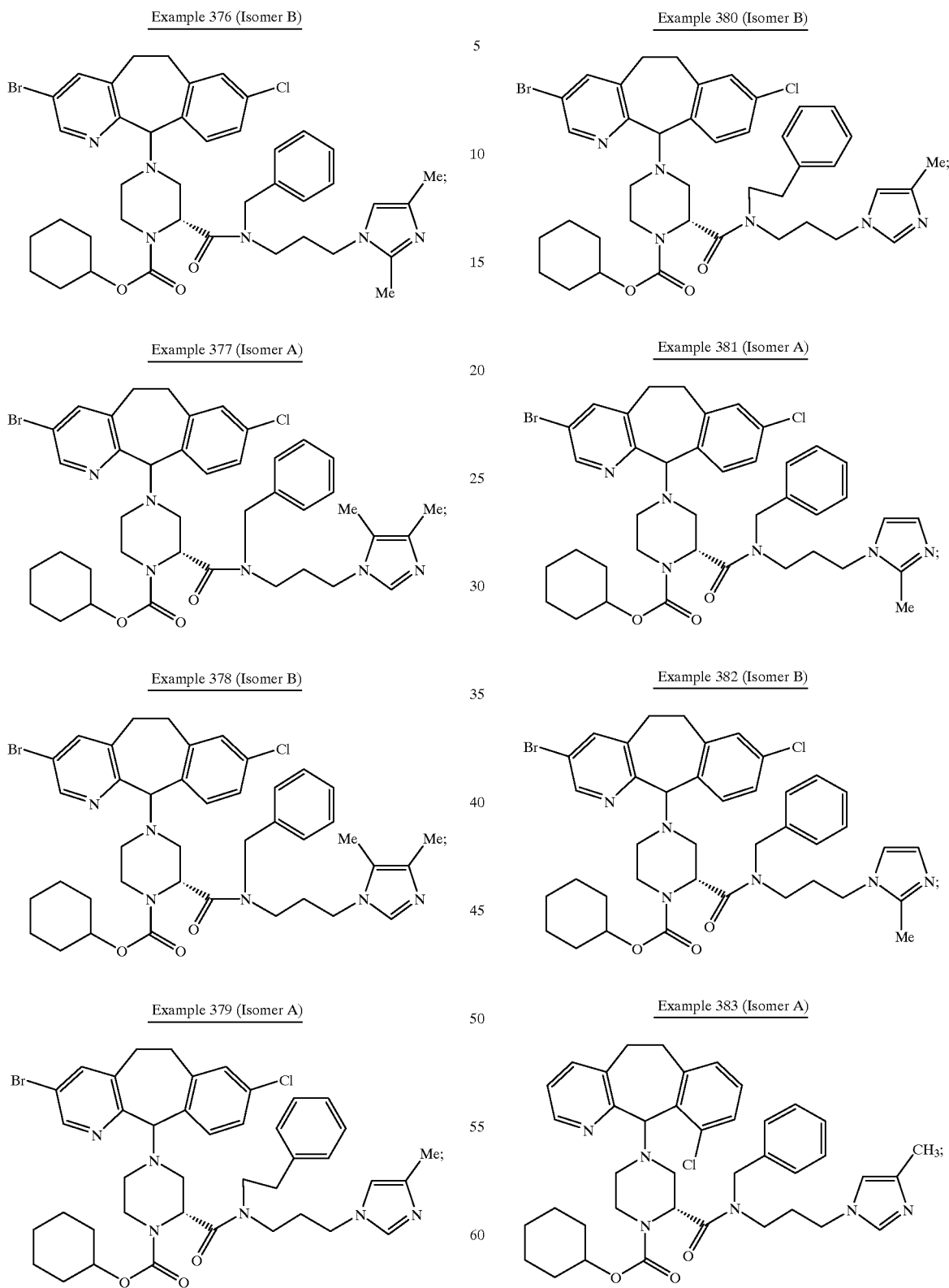

Example 384 (Isomer B)
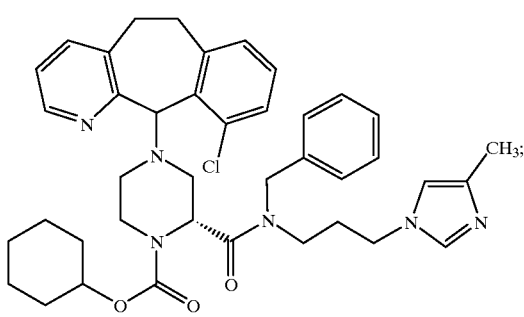
Example 395
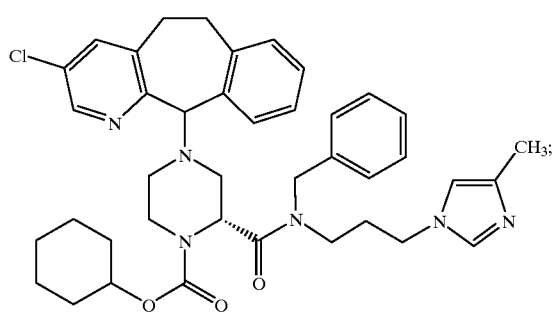
Example 397
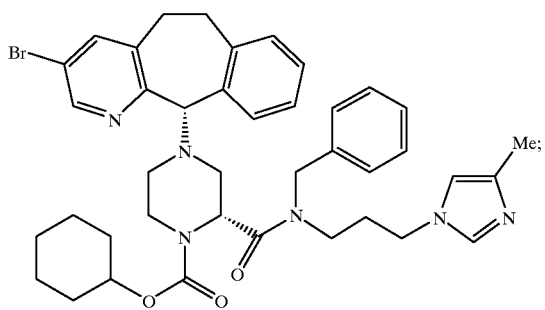
Example 397
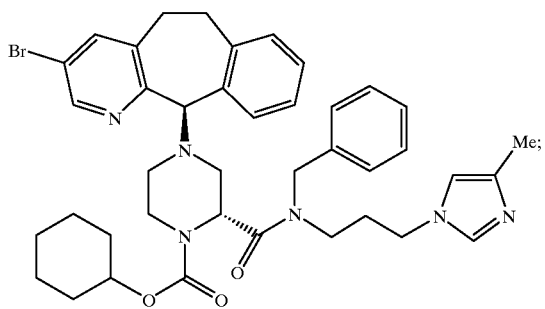
Example 398
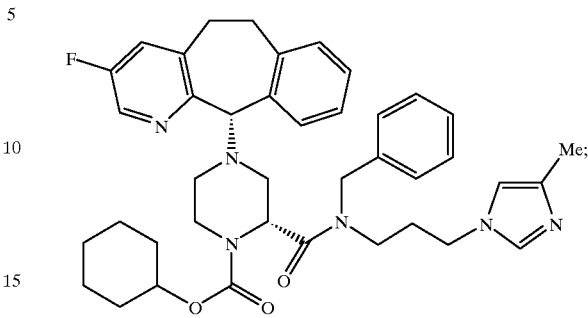
Example 398
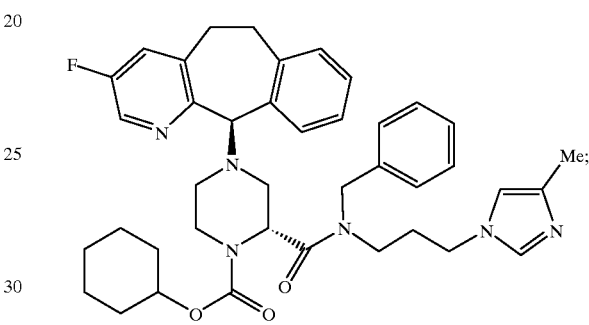
Example 399
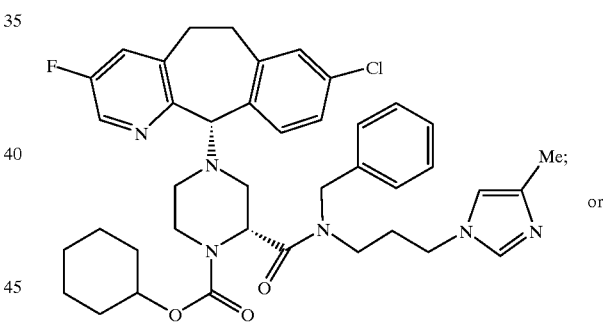
or
Example 399
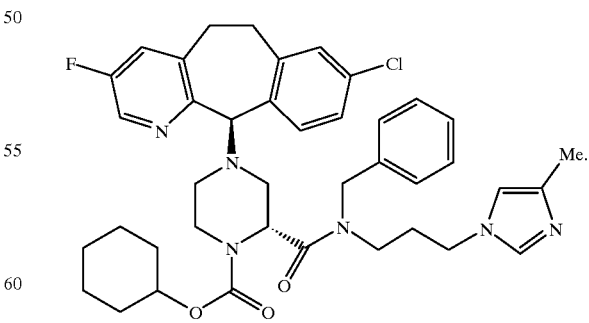

9. A method of inhibiting the abnormal growth of cells wherein said cells are selected from: pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, melanoma, breast tumor cells or prostate tumor cells in a patient in need thereof by the inhibition of farnesyl protein transferase comprising administering to the patient an effective amount of a compound of claim 2.

10. A method of inhibiting farnesyl protein transferase in a patient in need thereof comprising administering to the patient an effective amount of the compound of claim 2.

11. A pharmaceutical composition comprising an effective amount of compound of claim 2 in combination with a pharmaceutically acceptable carrier.

12. A method of inhibiting the abnormal growth of cells wherein said cells are selected from: pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, melanoma, breast tumor cells or prostate tumor cells in a patient in need thereof by the inhibition of farnesyl protein transferase comprising administering to the patient an effective amount of a compound of claim 6.

13. A method of inhibiting farnesyl protein transferase in a patient in need thereof comprising administering to the patient an effective amount of the compound of claim 6.

14. A pharmaceutical composition comprising an effective amount of compound of claim 6 in combination with a pharmaceutically acceptable carrier.

15. A method of inhibiting the abnormal growth of cells wherein said cells are selected from: pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, melanoma, breast tumor cells or prostate tumor cells in a patient in need thereof by the inhibition of farnesyl protein transferase comprising administering to the patient an effective amount of a compound of claim 7.

16. A method of inhibiting farnesyl protein transferase in a patient in need thereof comprising administering to the patient an effective amount of the compound of claim 7.

17. A pharmaceutical composition comprising an effective amount of compound of claim 7 in combination with a pharmaceutically acceptable carrier.

18. A method of inhibiting the abnormal growth of cells wherein said cells are selected from: pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, melanoma, breast tumor cells or prostate tumor cells in a patient in need thereof by the inhibition of farnesyl protein transferase comprising administering to the patient an effective amount of a compound of claim 8.

19. A method of inhibiting farnesyl protein transferase in a patient in need thereof comprising administering to the patient an effective amount of the compound of claim 8.

20. A pharmaceutical composition comprising an effective amount of compound of claim 8 in combination with a pharmaceutically acceptable carrier.

* * * * *